US011753653B2

(12) United States Patent
Krisky et al.

(10) Patent No.: US 11,753,653 B2
(45) **Date of Patent: *Sep. 12, 2023**

(54) HIGH-TRANSDUCING HSV VECTORS

(71) Applicant: PeriphaGen, Inc., Pittsburgh, PA (US)

(72) Inventors: David M. Krisky, Pittsburgh, PA (US); James B. Wechuck, Pittsburgh, PA (US); James R. Goss, Pittsburgh, PA (US)

(73) Assignee: Periphagen, Inc., Pittsburgh, PA (US)

( * ) Notice: Subject to any disclaimer, the term of this patent is extended or adjusted under 35 U.S.C. 154(b) by 541 days.

This patent is subject to a terminal disclaimer.

(21) Appl. No.: 16/088,393

(22) PCT Filed: Mar. 24, 2017

(86) PCT No.: PCT/US2017/024092

§ 371 (c)(1), (2) Date: Sep. 25, 2018

(87) PCT Pub. No.: WO2017/165813

PCT Pub. Date: Sep. 28, 2017

(65) Prior Publication Data

US 2020/0199618 A1 Jun. 25, 2020

Related U.S. Application Data

(60) Provisional application No. 62/313,391, filed on Mar. 25, 2016.

(51) Int. Cl.

*C12N 15/86* (2006.01)
*A61K 48/00* (2006.01)
*C12N 7/00* (2006.01)

(52) U.S. Cl.

CPC .......... *C12N 15/86* (2013.01); *A61K 48/0025* (2013.01); *C12N 7/00* (2013.01); *C12N 2710/16621* (2013.01); *C12N 2710/16643* (2013.01); *C12N 2710/16662* (2013.01); *C12N 2830/008* (2013.01)

(58) Field of Classification Search

CPC ................................ C12N 15/86; C12N 7/00; C12N 2710/16621; C12N 2710/16643; C12N 2710/16662; C12N 2830/008; C12N 2710/16641; A61K 48/0025

See application file for complete search history.

(56) References Cited

U.S. PATENT DOCUMENTS

| | | | |
|---|---|---|---|
| 5,763,217 A | 6/1998 | Cynader et al. | |
| 5,849,571 A | 12/1998 | Glorioso et al. | |
| 5,879,934 A | 3/1999 | DeLuca | |
| 10,301,600 B2 | 5/2019 | Coffin | |
| 10,799,560 B2 * | 10/2020 | Krisky | A61P 25/28 |
| 2001/0026799 A1 | 10/2001 | DeLuca | |
| 2002/0098170 A1 | 7/2002 | Wechsler et al. | |
| 2005/0092374 A1 | 5/2005 | Kim et al. | |
| 2008/0289058 A1 | 11/2008 | Cascio et al. | |
| 2008/0289059 A1 * | 11/2008 | Cascio et al. | C12N 15/873 800/18 |
| 2009/0156638 A1 | 6/2009 | Khanna | |
| 2014/0363469 A1 | 12/2014 | Meyers et al. | |

FOREIGN PATENT DOCUMENTS

| | | | | |
|---|---|---|---|---|
| CN | 1705438 | A | 12/2005 | |
| CN | 103667175 | A | 3/2014 | |
| WO | WO 98/015637 | A1 | 4/1998 | |
| WO | WO 2003/105750 | A2 | 12/2003 | |
| WO | WO-2005092374 | A2 * | 10/2005 | A61K 39/12 |
| WO | WO 2013/109604 | A1 | 7/2013 | |
| WO | WO-2017/165806 | A1 | 9/2017 | |
| WO | WO-2017/165813 | A1 | 9/2017 | |

OTHER PUBLICATIONS

Liu et al. "ICP0 antagonizes ICP4-dependent silencing of the herpes simplex virus ICP0 gene." PLoS One 5.1 (2010) (Year: 2010).*

Watson et al. "Sequence and comparative analysis of the genome of HSV-1 strain McKrae." Virology 433.2 (2012): 528-537 (Year: 2012).*

International Preliminary Report on Patentability for Application No. PCT/US2017/024092, dated Oct. 4, 2018.

International Preliminary Report on Patentability for Application No. PCT/US2017/024083, dated Oct. 4, 2018.

Extended European Search Report dated Aug. 16, 2019 for Application No. EP 17771265.0.

Extended European Search Report dated Aug. 22, 2019 for Application No. EP 17771260.1.

Burton et al., Multiple applications for replication-defective herpes simplex virus vectors. Stem Cells. Jan. 2001;19(5):358-77.

Chattopadhyay et al., Long-term neuroprotection achieved with latency-associated promoter-driven herpes simplex virus gene transfer to the peripheral nervous system. Mol Ther. Aug. 2005;12(2):307-13.

Chattopadhyay et al., Protective effect of herpes simplex virus-mediated neurotrophin gene transfer in cisplatin neuropathy. Brain. Apr. 2004;127(4):929-39.

DeLuca et al., Isolation and characterization of deletion mutants of herpes simplex virus type 1 in the gene encoding immediate-early regulatory protein ICP4. J Virol. Nov. 1985;56(2):558-70.

Goss et al., Herpes simplex-mediated gene transfer of nerve growth factor protects against peripheral neuropathy in streptozotocin-induced diabetes in the mouse. Diabetes. Jul. 2002;51(7):2227-32.

(Continued)

*Primary Examiner* — Janet L Epps-Smith
*Assistant Examiner* — Alexander W Nicol
(74) *Attorney, Agent, or Firm* — Wolf, Greenfield & Sacks, P.C.

(57) ABSTRACT

Disclosed herein are high transducing replication defective herpes simplex virus (HSV) vectors of McKrae strain.

14 Claims, 110 Drawing Sheets

Specification includes a Sequence Listing.

(56) References Cited

OTHER PUBLICATIONS

Goss et al., PGN-503, aherpes simplex virus based vector expressing neurotrophin-3, prevents and reverses neuropathy in a mouse model of paclitaxel-induced peripheral neuropathy. Mol Ther. May 2016;24(Suppl. 1):S72.
MacDonald et al., Genome sequence of herpes simplex virus 1 strain McKrae. J Virol. Sep. 2012;86(17):7540-1.
Shepard et al., Activities of heterodimers composed of DNA-binding- and transactivation-deficient subunits of the herpes simplex virus regulatory protein ICP4. J Virol. Jan. 1991;65(1):299-307.
Wang et al., HSV-1 strain McKrae is more neuroinvasive than HSV-1 KOS after corneal or vaginal inoculation in mice. Virus Res. Jan. 20, 2013;173(2):436-40.
Watson et al., Sequence and comparative analysis of the genome of HSV-1 strain McKrae. Virology. Nov. 2012;433(2):528-37. Epub Sep. 25, 2012.
Accession No. I3TCD6, Transcriptional Regulator ICP4 [Human Alphaherpesvirus 1], 1 pages, Sep. 5, 2012 [Retrieved Jul. 10, 2017] URL: <https://www.ncbi.nlm.nih.gov/protein/388524993?report=genbank&log$=prottop&blast_rank=1 &RID=PCWCCB3C014>.
International Search Report for PCT/US2017/024083, 4 pages (dated Jul. 13, 2017).
International Search Report for PCT/US2017/024092, 4 pages (dated Aug. 1, 2017).
Liu, M et al. ICP0 Antagonizes ICP4-Dependent Silencing of the Herpes Simplex Virus ICP0 Gene, PLoS One, 5(1): e8837 1-16 (2010).
Written Opinion for PCT/US2017/024083, 9 pages (dated Jul. 13, 2017).
Written Opinion for PCT/US2017/024092, 9 pages (dated Aug. 1, 2017).
Fink et al., Gene therapy for pain: results of a phase I clinical trial. Ann Neurol. Aug. 2011;70(2):207-12. doi: 10.1002/ana.22446. Epub Jul. 27, 2011. Author Manuscript, 12 pages.
Johnson et al., Cytotoxicity of a replication-defective mutant of herpes simplex virus type 1. J Virol. May 1992;66(5):2952-65. doi: 10.1128/JVI.66.5.2952-2965.1992.
Kolb et al., Sequence variation in the herpes simplex virus U(S)1 ocular virulence determinant. Invest Ophthalmol Vis Sci. Jun. 28, 2011;52(7):4630-38. doi: 10.1167/iovs.10-7032.
Krisky et al., Deletion of multiple immediate-early genes from herpes simplex virus reduces cytotoxicity and permits long-term gene expression in neurons. Gene Ther. Dec. 1998;5(12):1593-603. doi: 10.1038/sj.gt.3300766.
Lau et al., Herpes simplex virus vector-mediated expression of interleukin-10 reduces below-level central neuropathic pain after spinal cord injury. Neurorehabil Neural Repair. Sep. 2012;26(7):889-97. doi: 10.1177/1545968312445637. Epub May 15, 2012.
Wu et al., Prevention of diabetic neuropathy by regulatable expression of HSV-mediated erythropoietin. Mol Ther. Feb. 2011;19(2):310-7. doi: 10.1038/mt.2010.215. Epub Oct. 5, 2010.
U.S. Appl. No. 16/088,408, filed Sep. 25, 2018, Krisky et al.
EP 17771265.0, Aug. 16, 2019, Extended European Search Report.
EP 17771260.1, Aug. 22, 2019, Extended European Search Report.

* cited by examiner

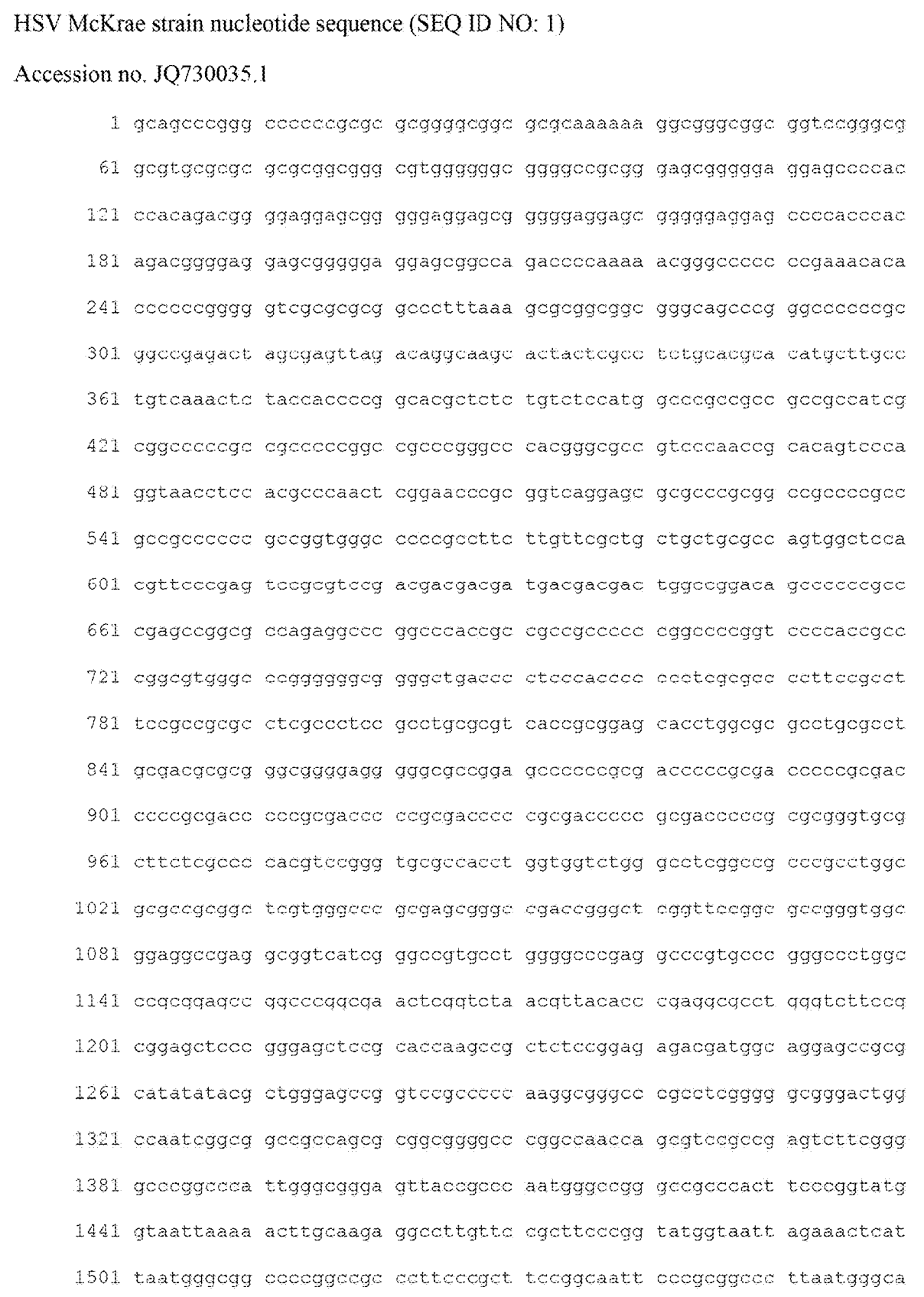

HSV McKrae strain nucleotide sequence (SEQ ID NO: 1)

Accession no. JQ730035.1

```
   1 gcagcccggg cccccgcgc gcggggcggc gcgcaaaaaa ggcgggcggc ggtccgggcg
  61 gcgtgcgcgc gcgcggcggg cgtgggggc ggggccgcgg gagcgggga ggagccccac
 121 ccacagacgg ggaggagcgg gggaggagcg ggggaggagc gggggaggag ccccacccac
 181 agacggggag gagcggggga ggagcggcca gaccccaaaa acgggccccc ccgaaacaca
 241 cccccgggg gtcgcgcgcg gccctttaaa gcgcggcggc gggcagcccg ggcccccgc
 301 ggccgagact agcgagttag acaggcaagc actactcgcc tctgcacgca catgcttgcc
 361 tgtcaaactc taccaccccg gcacgctctc tgtctccatg gcccgccgcc gccgccatcg
 421 cggccccgc cgcccccggc cgcccgggcc cacgggcgcc gtcccaaccg cacagtccca
 481 ggtaacctcc acgcccaact cggaacccgc ggtcaggagc gcgcccgcgg ccgccccgcc
 541 gccgcccccc gccggtgggc ccccgccttc ttgttcgctg ctgctgcgcc agtggctcca
 601 cgttcccgag tccgcgtccg acgacgacga tgacgacgac tggccggaca gcccccgcc
 661 cgagccggcg ccagaggccc ggcccaccgc cgccgccccc cggccccggt ccccaccgcc
 721 cggcgtgggc ccgggggcg gggctgaccc ctcccacccc ccctcgcgcc ccttccgcct
 781 tccgccgcgc ctcgccctcc gcctgcgcgt caccgcggag cacctggcgc gcctgcgcct
 841 gcgacgcgcg ggcggggagg gggcgccgga gcccccgcg acccccgcga cccccgcgac
 901 ccccgcgacc cccgcgaccc ccgcgacccc cgcgaccccc gcgaccccg cgcgggtgcg
 961 cttctcgccc cacgtccggg tgcgccacct ggtggtctgg gcctcggccg cccgcctggc
1021 gcgccgcggc tcgtgggccc gcgagcgggc cgaccgggct cggttccggc gccgggtggc
1081 ggaggccgag gcggtcatcg ggccgtgcct ggggcccgag gcccgtgccc gggccctggc
1141 ccgcggagcc ggcccggcga actcggtcta acgttacacc cgaggcgcct gggtcttccg
1201 cggagctccc gggagctccg caccaagccg ctctccggag agacgatggc aggagccgcg
1261 catatatacg ctgggagccg gtccgccccc aaggcgggcc cgcctcgggg gcgggactgg
1321 ccaatcggcg gccgccagcg cggcggggcc cggccaacca gcgtccgccg agtcttcggg
1381 gcccggccca ttgggcggga gttaccgccc aatgggccgg gccgcccact tcccggtatg
1441 gtaattaaaa acttgcaaga ggccttgttc cgcttcccgg tatggtaatt agaaactcat
1501 taatgggcgg ccccggccgc ccttcccgct tccggcaatt cccgcggccc ttaatgggca
```

FIGURE 9

1561 accccggtat tccccgcctc ccgcgccgcg cgtaaccact ccccgtgggt tccgggttat
1621 gctaattgct tttttggcgg aacacacggc ccctcgcgca ttggcccgcg ggtcgctcaa
1681 tgaacccgca ttggtcccct ggggttccgg gtatggtaat gagtttcttc gggaaggcgg
1741 gaagccccgg ggcaccgacg caggccaagc ccctgttgcg tcggcgggag gggcatgcta
1801 atggggttct ttgggggaca ccgggttggt cccccaaatc gggggccggg ccgtgcatgc
1861 taatgatatt ctttgggggc gccgggttgg tccccgggga cggggccgcc ccgcggtggg
1921 cctgcctccc ctgggacgcg cggccattgg gggaatcgtc actgccgccc ctttggggag
1981 gggaaaggcg tggggtataa gttagccctg gcccgacggt ctggtcgcat ttgcacctcg
2041 gcactcggag cgagacgcag cagccaggca gactcgggcc gccccctctc cgcatcacca
2101 cagaagcccc gcctacgttg cgacccccag ggaccctccg tccgcgaccc tccagccgca
2161 tacgaccccc atggagcccc gccccggagc gagtacccgc cggcctgagg gccgccccca
2221 gcgcgaggtg aggggccggg cgccatgtct ggggcgccat attgggggc gccatgttgg
2281 gggacccccg acccttaccc tggaaccggc ccccatgttg gggggacccccc actcatacac
2341 gggagccggg cgccatgttg ggcgccatg ttagggggcg tggaaccccg tgacactata
2401 tatacaggga ccgggggcgc catgttaggg ggcgcggaac cccctgaccc tatatataca
2461 gggaccgggg tcgccctgtt gggggtcgcc atgtgacccc ctgactttat atatacagac
2521 ccccaacaca tacacatggc ccctttgact cagacgcagg gcccggggtc gccgtgggac
2581 cccctgactc atacacagag acacgccccc acaacaaaca cacagggacc ggggtcgccg
2641 tgttgggggc gtggtcccca ctgactcata cgcaggcccc ccttactcac acgcatctag
2701 gggggtgggg aggagccgcc cgccatattt gggggacgcc gtgggacccc cgactccggt
2761 gcgtctggag ggcgggagaa gagggaagaa gaggggtcgg gatccaaagg acggacccag
2821 accacctttg gttgcagacc cctttctccc ccctcttccg aggccagcag gggggcagga
2881 ctttgtgagg cgggggggga gagggggaac tcgtgggcgc tgattgacgc gggaaatccc
2941 cccccattct tacccgcccc ccttttttcc ccttagcccg ccccggatgt ctgggtgttt
3001 ccctgcgacc gagacctgcc ggacagcagc gactctgagg cggagaccga agtggggggg
3061 cggggggacg ccgaccacca tgacgacgac tccgcctccg aggcggacag cacggacacg
3121 gaactgttcg agacggggct gctggggccg cagggcgtgg atggggggc ggtctcgggg
3181 gggagccccc cccgcgagga agaccccggc agttgcgggg gcgccccccc tcgagaggac

FIGURE 9 (Continued)

3241 gggggagcg acgagggcga cgtgtgcgcc gtgtgcacgg atgagatcgc gccccacctg 3301 cgctgcgaca ccttcccgtg catgcaccgc ttctgcatcc cgtgcatgaa aacctggatg 3361 caattgcgca acacctgccc gctgtgcaac gccaagctgg tgtacctgat agtgggcgtg 3421 acgcccagcg ggtcgttcag caccatcccg atcgtgaacg acccccagac ccgcatggag 3481 gccgaggagg ccgtcagggc gggcacggcc gtggacttta tctggacggg caatcagcgg 3541 ttcgccccgc ggtacctgac cctgggggg cacacggtga gggccctgtc gcccacccac 3601 ccggagccca ccacggacga ggatgacgac gacctggacg acggtgaggc gggggcggc 3661 aaggaccctg gggaggagg aggagggagg aatgggcggg cgggcgagga aagggcgggc 3721 cggggagggg gcgtaacctg atcgcgcccc ccgttgtctc ttgcagcaga ctacgtcccg 3781 cccgcccccc gccggacgcc ccgcgccccc ccacgcagag gcaccgccgc gcccccgtg 3841 acgggcgggg cgtctaacgc agcccccag ccggccgcgg ctcggacagc gccccctcg 3901 gcgcccatcg ggccacacgg cagcagtaac accaacacca ccaccaacag cagcggcggc 3961 ggcggctccc gccagtcgcg agccgcggcg ccgcgggggg cgtctggccc ctccgggggg 4021 gttggggttg gggttggggt tgttgaagcg gaggcggggc ggccgagggg ccggacgggc 4081 ccccttgtca acagacccgc ccccttgca aacaacagag accccatagt gatcagcgac 4141 tcccccccgg cctctcccca caggcccccc gcggcgccca tgccaggctc cgcccccgc 4201 cccgggcccc ccgcgtcctc ggccgcgtcg ggacccgcgc gcccccgcgc ggccgtggcc 4261 ccgtgcgtgc gagcgccgcc tccggggccc ggcccccgcg ccccggcccc cggggcggag 4321 ccggccgccc gccccgcgga cgcgcgccgt gtgccccagt cgcactcgtc cctggctcag 4381 gccgcgaacc aagaacagag tctgtgccgg gcgcgtgcga cggtggcgcg cggctcgggg 4441 gggccgggcg tggagggtgg gcacgggccc tcccgcggcc gcaccccctc cggcgccgcc 4501 ccgctcccct ccgccgtctc tgtcgagcag gaggcggcgg tgcgtccgag gaagaggcgc 4561 gggtcgggcc aggaaaaccc ctcccccag tccacgcgtc ccccctcgc gccggcaggg 4621 gccaagaggg cggcgacgca ccccccctcc gactcagggc cgggggggcg cggccagggt 4681 gggcccggga cccccctgac gtcctcggcg gcctccgcct cttcctcctc tgcctcttcc 4741 tcctcggccc cgaccccgc gggggccgcc tcttccgccg ccggggccgc gtcctcctcc 4801 gcttccgcct cctcgggcgg ggccgtcggt gccctgggag ggagacaaga ggaaacctcc 4861 ctcggccccc gcgctgcttc tgggccgcgg gggccgagga agtgtgcccg gaagacgcgc FIGURE 9 (Continued)

4921 cacgcggaga cttccggggc cgtccccgcg ggcggcctca cgcgctacct gcccatctcg 4981 ggggtctcta gcgtggtcgc cctgtcgcct tacgtgaaca agactatcac gggggactgc 5041 ctgcccatcc tggacatgga gacggggaac atcggggcgt acgtggtcct ggtggaccag 5101 acgggaaaca tggcgacccg gctgcgggcc gcggtccccg gctggagccg ccgcaccctg 5161 ctccccgaga ccgcgggtaa ccacgtgatg ccccccgagt acccgacggc cccccgcgtcg 5221 gagtggaaca gcctctggat gacccccgtg gggaacatgc tgttcgacca gggcacccta 5281 gtgggcgccc tggacttccg cagcctgcgg tctcggcacc cgtggtccgg ggagcagggg 5341 gcgtcgaccc gggacgaggg aaaacaataa gggacgcccc ccgtgtttgt ggggaggggg 5401 gtcgggtgct gggtggtctc tggccgcgcc cactacacca gccaatccgt gtcggggagg 5461 ggaaagtgaa agacacgggc accacacacc agcgggtctt tagtgttggc cctaataaaa 5521 aactcagggg atttttgctg tctattggga aataaaggtt tacttttgta tcttttccct 5581 gtctgtgttg gatggatctt gggggtgcgt gggagtgggg gtgcgtggga gtgggggtgc 5641 gtgggagtgg gggtgcgtgg gagtgggggt gcgtgggagt gggggtgcgt gggagtgggg 5701 gtgcgtggga gtgggggtgc gtgggagtgg gggtgcgtgg gagtgggggt gcgtgggagt 5761 gggggtgcgt gggagtgggg gtgcgtggga gtgggggtgc gtgggagtgg gggtgccatg 5821 ttgggcaggc tctggtgtta accacagagc cgcggcccgg gctgcctgac caccgatccc 5881 cgaaagcatc ctgccactgg catggagcca gaaccacagt gggctgggtg tgggtgttaa 5941 gtttccgcga gcgcctgccc gcccggactg acctggcctc tggccgccac aaagggcggg 6001 gggggggtta actacactat agggcaacaa aggacgggag ggtggcgggg acggggcgcc 6061 caaaaggggg tcggccacac cacagacgtg ggtgttgggg ggtggggcgg aggggtgggg 6121 gggagacaga aacaggaaca tagttagaaa acaagaatgc ggtgcagcca gagaatcaca 6181 ggagacgagg ggatgggcgt gttggttacc aacccacacc caggcatgct cggtggtatg 6241 aaggaggggg ggcggtgctt cttagagacc gccgggggac gtggggttgg tgtgcaaagg 6301 cacgcgcacc cgcgtcggcc aggtgggccg gtaccccatc ccccccctccc ccgaccccttc 6361 ccccccccgcg tgccagagat cacccccgtc ccccggcacc cgccactcct ccatatcctc 6421 gctttaggaa caactttggg gggggggtac acacgcgccg tgcatttcct tccacacccc 6481 ccctccccccg catccccccc cccaggcagt aagacccaag catagagagc caggcacaaa 6541 aacacaggcg ggtgggaca catgccttct tggagtacgt gggtcattgg cgtgggggt FIGURE 9 (Continued)

6601 tacagcgaca ccggccgacc ccctggcggt cttccagccg gcccttagat aagggggcag 6661 ttggtggtcg gacgggtaag taacagagtc tgactaaggg tgggaggggg ggaaaagaac 6721 gggctggtgt gctgtaacac gagcccaccc gcgagtggcg tggccgacct tagcctctgg 6781 ggcgccccct gtcgtttggg tccccccccc tctattgggg agaagcaggt gtctaaccta 6841 cctggaaacg cggcgtcttt gttgaacgac accggggcgc cctcgacgag tgggataacg 6901 ggggaggaag ggagggagga gggtactggg ggtgaagaag gggggggga agaagcgaga 6961 acaggaaagg cgacggagcc cggcagaaca ccgaggaaaa aaaaaacaca gcgcatgcgc 7021 cgggccgttg tggggccccg ggccggggcc ccttgggtcc gccggggccc cgggccgggc 7081 cgccacgggg gccggccgtt ggcggtaacc ccgattgttt atctcaggcc ccgggccggg 7141 aacccggaaa agcctccggg gggccttttt cgcgtcgcgt gccggcgagc gggcccggac 7201 ggggcccgga ccgccgcggt cgggggcccc tcgtcccggg ccgtacgcgg ccttcgcccc 7261 gtgaggggcc gaacgaacga aacatcccgg cgacggaacg aaaaacaccc cagacgggtt 7321 taaaaaacag aaaccgtaac cccccccacc cccgaaacgg ggaaaacaaa aaacagacca 7381 gcggccggcc ggcgcttagg gggaggatgt cgccgacgcc ccttggccgc cccggctgca 7441 gggggggccg gagagccgcg gcacccggac gcgcccggaa agtctttcgc accacccgcg 7501 atcggcacgg ccgcgccccc gcttttataa aggctcagat gacgcagcaa aaacaggcca 7561 cagcaccacg tgggtaggtg atgtaatttt attttcctcg tctgcggcct aatggatttc 7621 cgggcgcggt gcccctgtct gcagagcact taacggattg atatctcgcg ggcacgcgcg 7681 cccttaatgg accggcgcgg ggcggggggc cggataccca cacgggcggg ggggtgtcgc 7741 gggccgtctg ctggcccgcg gccacataaa caatgactcg ggcctttct gcctctgccg 7801 cttgtgtgtg cgcgcgccgg ctctgcggtg tcggcggcgg ctgcggcggc tgcggcggcc 7861 gccgtgttcg gtctcggtag ccggccggcg ggtggactcg cggggggccg gagggtggaa 7921 ggcagggggg tgtaggatgg gtatcaggac ttccacttcc cgtccttcca tccccgttc 7981 ccctcggttg ttcctcgcct cccccaacac cccgcccgctt tccgttgggg ttgttattgt 8041 tgtcgggatc gtgcgggccg ggggtcgccg gggcaggggc gggggcgggg gtgctcgtcg 8101 atcgaccggg ctcagtgggg gcgtggggtg ggtgggaaaa ggcgaggaga ctggggtggg 8161 gggtgtcggg ggtggctgtt tttttgtggt tgtttttttgt gtctgttccc gtcccccgtc 8221 acccccctcc ctccgtcccc ccgtcgcggg tgtttgtgtt tgtttattcc gacatcggtt

FIGURE 9 (Continued)

8281 tatttaaata aacacagccg ttctgcgtgt ctgttcttgc gtgtggctgg gggcttatat 8341 gtggggtccc gggggcggga tggggtttag cggcgggggg cggcgcgccg gacggggcgc 8401 tggagataac ggcccccggg gaacggggga ccggggctgg gtctcccgcg gtgggtgggt 8461 gggcggcggt ggccgggccg ggccgggccg ggtgggcggg gtttggaaaa acgaggagga 8521 ggagaaggag gaggaggggg ggggagacgg ggggaaagca aggacacggc cccggggggg 8581 ggggagcgcg ggccgggccg cttggcaacc cccctgtttc ttccggaaac caggcttgtg 8641 gcccccacccg acatcacaag ggacctcttg tcgggcctcc cgacgtacgc cgaggctatg 8701 tcggaccacc ccccaaccta agaggggaga ggggagaggg gagaggggag aggggagagg 8761 ggagagggga ggagaggggg tatataaacc aacgaaaagc gcgggaacgg ggatacgggg 8821 cttgtgtggc acgacgtcgt ggttgtgtta ctgggcaaac acttggggac tgtaggtttc 8881 tgtggtgccg accctaggcg ctatggggat tttgggttgg gttgggctta ttgccgttgg 8941 ggttttgtgt gtgcgggggg gcttgccttc aaccgaatat gttattcgga gtcgggtggc 9001 tcgagaggtg ggggatatat taaaggtgcc ttgtgtgccg ctcccgtctg acgatcttga 9061 ttggcgctac gagacccccct cggctataaa ctatgctttg atagacggta tatttttgcg 9121 ttatcactgt cccggattgg acacggtctt gtgggatagg cacgcccaga gggcgtattg 9181 ggttaacccc tttttgtttg gggcgggttt tttggaggac ttgagtcatc ccgcgtttcc 9241 tgccgacacc caggaaacag aaacgcgctt ggccctttat aaagagatac gccaggcgct 9301 ggacagtcgc aagcaggccg ccagccacac acctgtgaag gctgggtgtg tgaactttga 9361 ctattcgcgc acccgccgct gtgtagggcg ccaggatttg ggacttacca acagaacgtc 9421 tggacggacc ccggttctgc cgtcggacga tgaagcgggc ctgcagccga agcccctcac 9481 cacgccgtcg cccatcatcg ccacgtcgga ccccaccccg cgacgggacg ccgccacaaa 9541 aagcagacgc cgacgacccc attcccggcg catctaatga tgcctcgacg gaaaaccgtc 9601 cgggtttggg gggcgaaccg gccgcctgtc gctcgtcagg gccggcgggc gctcctcgcc 9661 gccctagagg ctgtcccgct ggtgtgacgt ttcctcgtc cgcgcccccc gaccctccca 9721 tggatttaac aaacgggggg gtgtcgcctg cggcgacctc ggcgcctctg gactggacca 9781 cgtttcggcg tgtgtttctg atcgacgacg cgtggcggcc cctgttggag cctgagctgg 9841 cgaacccctt aaccgcccac ctcctggccg aatataatcg tcggtgccag accgaagagg 9901 tgctgccgcc gcgggaggat gtgttttcgt ggactcgtta ttgcaccccc gacgaggtgc

FIGURE 9 (Continued)

9961 gcgtggttat catcggccag gacccatatc accaccccgg ccaggcgcac ggacttgcgt
10021 ttagcgtgcg cgcgaacgtg ccgcctcccc cgagtcttcg gaatgtcttg gcggccgtca
10081 agaactgtta tcccgaggca cggatgagcg gccacggttg cctggaaaag tgggcgcggg
10141 acggcgtcct gttactaaac acgaccctga ccgtcaagcg cggggcggcg gcgtcccact
10201 ctagaatcgg ttgggaccgc ttcgtgggcg gagttatccg ccggttggct gcgcgccgcc
10261 ccggcctggt gtttatgctc tggggcgcac atgcccagaa tgccatcagg ccggaccctc
10321 gggtccattg cgtcctcaag ttttcgcacc cgtcgcccct ctccaaggtt ccgttcggaa
10381 catgccagca tttcctcgtg gcgaatcgat atctcgagac ccggtcgatt tcacccatcg
10441 actggtcggt ttgaaaggca tcgacgtccg gggttttcgt ctgtgggggc ttttgggtat
10501 ttccgatgaa taaagacggt taatggttaa acctctggtc tcatacgggt cggtgatgtc
10561 gggcgtcggg ggagagggag ttccctctgc gcttgcgatt ctagcctcgt ggggctggac
10621 gttcgacacg ccaaaccacg agtcagggat atcgccagat acgactcccg cagattccat
10681 tcgggggggcc gctgtggcct cacctgacca acctttacac gggggcccgg aacgggaggc
10741 cacagcgccg tctttctccc caacgcgcgc ggatgacggc ccgccctgta ccgacgggcc
10801 ctacgtgacg tttgataccc tgtttatggt gtcgtcgatc gacgaattag ggcgtcgcca
10861 gctcacggac accatccgca aggacctgcg gttgtcgctg gccaagttta gcattgcgtg
10921 caccaagacc tcctcgtttt cgggaaacgc cccgcgccac cacagacgcg gggcgttcca
10981 gcgcggcacg cgggcgccgc gcagcaacaa aagccttcag atgtttgtgt tgtgcaaacg
11041 cgccccacgcc gctcgagtgc gagagcagct tcgggtcgtt attcagtccc gcaagccgcg
11101 caagtattac acgcgatctt cggacgggcg gctctgcccc gccgtccccg tgttcgtcca
11161 cgagttcgtc tcgtccgagc caatgcgcct ccaccgagat aacgtcatgc tggcctcggg
11221 ggccgagtaa ccgccccccc cccgcgccac cctcactgcc cgtcgcgcgt gtttgatgtt
11281 aataaataac acataaattt ggctggttgt ttgttgtctt taatggaccg cccgcagggg
11341 gggtggcatt tcagtgtcgg gtgacgagcg cgatccggcc gggatcctag gaccccaaaa
11401 gtttgtctgc gtattccagg gcggggctca gttgaatctc ccgcagcacc tctaccagca
11461 ggtccgcggt gggctggaga aactcggccg tcccggggca ggcggtcgtc gggagtggag
11521 gcgcggcgcc caccccgtgt gccgcgcctg gcgtctcctc tgggggcgac ccgtaaatgg
11581 ttgcagtgat gtaaatggtg tccgcggtcc agaccacggt caaaatgccg gccgtggtgc FIGURE 9 (Continued)

11641 tccgggcgct ttcgccgcgc gaggagctga cccaggagtc gaacggatac gcgtacatat 11701 gggcgtccca cccgcgttcg agcttctggt cgctgtcccg gcctataaag cggtaggcac 11761 aaaattcggc gcgacagtcg ataatcacca acagcccaat gggggtgtgc tggataacaa 11821 cgcctccgcg cggcaggcgg tcctggcgct cccggccccg taccataatc gcgcgggtgc 11881 cgtactcaaa aacatgcacc acctgcgcgg cgtcgggcag tgcgctggtc agcgaggccc 11941 tggcgtggca taggctatac gcgatggtcg tctgtggatt ggacatctcg cggtgggtag 12001 tgagtccccc gggccgggtt cggtagaact gtaaggggac ggcgggttaa tagacaatga 12061 ccacgttcgg atcgcgcaga gccgatagta tgtgctcact aatgacgtca tcgcgctcgt 12121 ggcgctcccg gagcggattt aagttcatgc gaaggaattc ggaggaggtg gtgcgggaca 12181 tggccacgta cgcgctgttg aggcgcaggt tgccgggcgt aaagcagatg gcgaccttgt 12241 ccaggctaag gccctgggag cgcgtgatgg tcatggcaag cttggagctg atgccgtagt 12301 cggcgtttat ggccatggcc agctccgtag agtcaatgga ctcgacaaac tcgctgatgt 12361 tggtgttgac gacggacatg aagccgtgtt ggtcccgcaa gaccacgtaa ggcagggggg 12421 cctcttccag taactcggcc acgttggccg tcgcgtgccg cctccgcagc tcgtccgcaa 12481 aggcaaacac ccgtgcgtac gtgtatccca tgagcgtata attgtccgtc tgcagggcga 12541 cggacatcag cccccccgcgc ggcgagccgg tcagcatctc gcagccccgg aagataacgt 12601 tgtccacgta cgtgctaaag gggcgccttt caaatgcctc cccgaagagc tcttggagga 12661 ttcggaatct cccgaggaag gcccgcttca gcagcgcaaa ctgggtgtga acggcggcgg 12721 tggtctccgg ttccccgggg gtgtagtggc agtaaaacac gtcgagctgt tgttcgtcca 12781 gccccgcgaa aataacgtcg aggtcgtcgt cgggaaaatc gtccgggccc ccgtcccgcg 12841 gccccagttg cttaaaatca aacgcacgct cgccgggggc gcctgcgtcg gctattaccg 12901 acgcctgcgt cggcgccccc gaagatttgg ggcgcagaga cagaatctcc gccgttagtt 12961 ctcccatgcg ggcgtaggcg agggtcctct gggtcgcatc caggcccggg cgctgcagaa 13021 agttgtaaaa ggagataagc ccgctaaata tgagccgcga caggaacctg taggcaaact 13081 ccaccgaagt ctccccctga gtctttacaa agctgtcgtc acgcaacact gcctcgaagg 13141 cccggaacgt cccactaaac ccaaaaacca gttttcgcag gcgcgcggtc accgcgatct 13201 ggctgttgag gacgtaagtg acgtcgttgc gggccacgac cagctgctgt ttgctgtgca 13261 cctcgcagcg catgtgcccc gcgtcctggt cctggctctg cgagtagttg gtgatgcggc FIGURE 9 (Continued)

```
13321 tggcgttggc cgtgagccac ttttcaatag tcaggccggg ctggtgtgtc agccgtcggt
13381 attcgtcaaa ctccttgacc gacacgaacg taagcacggg gagggtgaac acgacgaact
13441 ccccctcacg ggtcaccttc aggtaggcgt ggagcttggc catgtacgcg ctcacctctt
13501 tgtgggagga gaacagccgc gtccagccgg ggaggttggc ggggttggtg atgtagcttt
13561 ccgggacgac gaagcgatcc acgaactgca tgtgctcctc ggtgatgggc aggccgtact
13621 ccagcacctt catgaggtta ccgaactcgt gctcgacgca ccgtttgttg ttaataaaaa
13681 tggcccagct atacgagagg cgggcgtact cgcgcagcgt gcggttgcag atgaggtacg
13741 tgagcacgtt ctcgctctgg cggacggaac accgcagttt ctggtgctcg aaggtcgact
13801 ccagggacgc cgtctgcgtc ggcgagccca cacacaccaa cacgggccgc aggcgggccg
13861 catactgggg ggtgtggtac agggcgttaa tcatccacca gcaatacacc acggccgtga
13921 ggaggtgacg cccaaggagc ccggcctcgt ctatgacgat cacgttgctg cgggtaaagg
13981 ccggcagcgc cccgtgggtg gccggggcca accgcgtcag ggcgccctcg gccaacccca
14041 gggtccgttc cagggcggcc agggcgcgaa actcgttccg cgactcctcg cccccggagg
14101 cggccagggc gcgcttcgtg aggtccaaaa tcacctccca gtagtacgtc agatctcgtc
14161 gctgcaggtc ctccagcgag gcggggttgc tggtcagggt gtacgggtac tgtcccagtt
14221 gggcctggac gtgattcccg cgaaacccaa attcatgaaa gatggtgttg atgggtcggc
14281 tgagaaaggc gcccgagagt ttggcgtaca tgttttgggc cgcaatgcgc gtggcgcccg
14341 tcaccacaca gtccaagacc tcgttgattg tctgcacgca cgtgctcttt ccggagccag
14401 cgttgccggt gataagatac accgcgaacg gaaactccct gaggggcagg cctgcggggg
14461 actctaaggc cgccacgtcc cggaaccact gcagacgggg cacttgcgct ccgtcgagct
14521 gttgttgcga gagctctcgg atgcgcttaa ggattggctg caccccgtgc atagacgtaa
14581 aatttaaaaa ggcctcggcc ctccctggaa cggctggtcg gtccccgggt tgctgaaggt
14641 gcggcgggcc gggtctctgt ccgtctagct ggcgctcccc gccggccgcc gccatgaccg
14701 caccacgctc gcgggccccc actacgcgtg cgcgggggga cacggaagcg ctgtgctccc
14761 ccgaggacgg ctgggtaaag gttcacccca cccccggtac gatgctgttc cgtgagattc
14821 tccacgggca gctggggtat accgagggcc agggggtgta caacgtcgtc cggtccagcg
14881 aggcgaccac ccggcagctg caggcggcga tctttcacgc gctcctcaac gccaccactt
14941 accgggacct cgaggcggac tggctcggcc acgtggcggc ccgcggtctg cagccccaac
```

FIGURE 9 (Continued)

15001 ggctggttcg ccggtacagg aacgcccggg aggcggatat cgccggggtg gccgagcggg 15061 tgttcgacac gtggcggaac acgcttagga cgacgctgct ggactttgcc cacgggttgg 15121 tcgcctgctt tgcgccgggc ggcccgagcg gcccgtcaag cttccccaaa tatatcgact 15181 ggctgacgtg cctggggctg gtccccatat tacgcaagcg acaagaaggg ggtgtgacgc 15241 agggtctgag ggcgtttctc aagcagcacc cgctgacccg ccagctggcc acggtcgcgg 15301 aggccgcgga gcgcgccggc cccgggtttt ttgagctggc gctggccttc gactccacgc 15361 gcgtggcgga ctacgaccgc gtgtatatct actacaacca ccgccggggc gactggctcg 15421 tgcgagaccc catcagcggg cagcgcggag aatgtctggt gctgtggcct cccttgtgga 15481 ccggggaccg tctggtcttc gattcgcccg tccagcggct gtttcccgag atcgtcgcgt 15541 gtcactccct ccgggaacac gcgcacgtct gccggctgcg caataccgcg tccgtcaagg 15601 tgctgctggg gcgcaagagc gacagcgagc gcggggtggc cggcgccgcg cgggtcgtta 15661 acaaggtgtt gggggaggac gacgagacca aggccgggtc ggccgcctca cgcctcgtgc 15721 ggcttatcat caacatgaag ggcatgcgcc acgtaggcga cattaacgac accgtgcgtg 15781 cctacctcga cgaggccggg gggcacctga tagacgcccc ggccgtcgac ggtaccctcc 15841 ctggattcgg caagggcgga aacagccgcg ggtctgcggg ccaggaccag gggggcgggg 15901 cgccgcagct tcgccaggcc ttccgcacgg ccgtggttaa caacatcaac ggcgtgttgg 15961 agggctatat aaataacctg tttggaacca tcgagcgcct gcgcgagacc aacgcgggcc 16021 tggcgaccca attgcaggag cgcgaccgcg agctccggcg cgcaacagcg gggccctgg 16081 agcgccagca gcgcgcggcc gacctggcgg ccgagtccgt gaccggtgga tgcggcagcc 16141 gccctgcggg ggcggacctg ctccgggccg actatgacat tatcgacgtc agcaagtcca 16201 tggacgacga catgtacgtc gccaacagct ttcagcaccc gtacatccct tcgtacgccc 16261 aggacctgga gcgcctgtcg cgcctctggg agcacgagct ggtgcgctgt tttaaaattc 16321 tgtgtcaccg caacaaccag ggccaagaga cgtcgatctc gtactccagc ggggcgatcg 16381 ccgcattcgt cgccccctac tttgaggcag tgcttcgggc cccccgggta ggcgcgccca 16441 tcacgggctc cgatgtcatc ctgggggagg aggagttatg ggatgcggtg tttaagaaaa 16501 cctgcctgca aacgtacctg acagacatcg cggccctgtt cgtcgcggac gtccagcacg 16561 cagcgctgcc cccgcccccc tccccggtcg gcgccgattt ccggcccggc gcgtccccgc 16621 ggggccggtc cagatcgcgg tcgcccggaa gaactgcgcg aggcgcaccg gaccagggcg FIGURE 9 (Continued)

16681 ggggcatcgg gcaccgggat ggccgccgcg acggccgacg atgaggggtc ggccgtcacc 16741 atcctcaagc aggccatcgc cggggaccgc agcctggtcg aggcggccga ggcgattagc 16801 cagcagacgc tgctccgcct ggcctgcgag gtgcgccagg tcggcgaccg ccagccgcgg 16861 tttaccgcca ccagcatcgc gcgcgtcgac gtcgcgcctg ggtgccggtt gcggttcgtt 16921 ctggacggga gtcccgagga cgcctatgtg acgtcggagg attactttaa gcgctgctgc 16981 ggccagtcca gttatcgcgg cttcgcggtg gcggtcctga cggccaacga ggaccacgtg 17041 cacagcctgg ccgtgccccc cctcgttctg ctgcaccggt tctccctgtt caaccccagg 17101 gacctcctgg actttgagct tgcctgtctg ctgatgtacc tggagaactg cccccgaagc 17161 cacgccaccc cgtcgacctt tgccaaggtt ctggcgtggc tcggggtcgc gggtcgccgc 17221 acgtccccat tcgaacgcgt tcgctgcctt ttcatccgca gttgccactg ggtcctaaac 17281 acactcatgt tcatggtgca cgtaaaaccg ttcgacgacg agttcgtcct gccccactgg 17341 tacatggccc ggtacctgct ggccaacaac ccgccccccg ttctctcggc cctgttctgt 17401 gccacccccga cgagctcctc attccggctg ccggggccgc ccccccgctc cgactgcgtg 17461 gcctataacc ccgccgggat catggggagc tgctgggcgt cggaggaggt gcgcgcgcct 17521 ctggtctatt ggtggctttc ggagaccccca aaacgacaga cgtcgtcgct gttttatcag 17581 ttttgttgaa ttttagtaaa taaacccggt tttgtttcta tggcctcctg acggatgcgc 17641 gtgtccttac tccgttttgg tgggtgggtg gctgtgtatg gcgtcccatc tgtgcgggga 17701 gggggcaagt cggcacgtat tcggacagac tcaagcacac acgggggagc gctcttggct 17761 cagggcaatg tttttattgg tcaaactcag gcaaacagaa acaacatctt gtcgtcaaag 17821 ggatacacaa acttcccccc ctcgccccat actcccgcca gcaccccggt aaacaccaac 17881 tcaatctcgc gcaggatttc gcgcaggtga tgagcgcagt ccacgggggg gagcacaagg 17941 ggccgcgggt atagatcgac ggggacgccg accgactccc cgcctccggg acagacacgc 18001 acgacgcgcc gccagtagtg ctctgcgtcc aacaaggcgc cgccgcggaa ggcagtgggg 18061 ggcaaggggt cgctggcctc aaagggggac acccgaacgc tccagtactc cgcgtccaac 18121 cgtttattaa acgcgtccac gataaggcgg tcgcaggcgt cctccataag gccccgggcc 18181 gtgagcgcgt cctcctccgg cacgcctgcc gttgtcaggc ccaggacccg tcgcagcgtg 18241 tcgcgtacga ccccggccgc cgtggtgtac gcgggcccgc ggagaggaaa tcccccaaga 18301 tggtcagtgt tgtcgcggga gttccagaac cacactcccg cttggctcca ggcgacggcg FIGURE 9 (Continued)

18361 tgggtgtaga cgccctcgag cgccaggcac agtgggtgcc gcagccggag gccgttggcc 18421 ataagcacgg ctcccacggc cgtctcgatg gcccgccggg cgtcctcgat caccccggaa 18481 gccgcatccg cgtcttgggg gtccacgtta aagacacccc agaacgcacc cccatcgccc 18541 ccgcagaccg cgaacttaac cgagctggcc gtctcctcaa tctgcaggca gacggcggcc 18601 atcaccccgc ccaggagctg ccgcagcgca gggcaggcgt cgcacgtgtc cgggaccagg 18661 cgctccaaga cggccccggc ccagggctct gagggagcgg ccaccaccag cgcgtccagt 18721 cttgctaggc ccgtccggcc gtggggttcc gccagcccgc tccccccgag gtcggccagg 18781 gccgccagga gctgggcgcg aagtccgggg aagcaaaacc gcgccgtcca gacgggcccg 18841 acggccgcgg gcgggtctaa cagttggatg attttagtgg cgggatgcca ccgcgccacc 18901 gcctcccgca ccgcgggcag gaggcatccg gctgccgccg aggccacgcc gggccaggct 18961 cgcgggggga ggacgaccct ggcccccacc gcgggccagg cccccaggag cgcggcgtaa 19021 gcggccgcgg ccccgcgcac caggtcccgt gccgactcgg ccgtggccgg cacggtgaac 19081 gtgggccaac ccggaaaccc caggacggca aagtacggga cgggtccccc ccggacctca 19141 aactcgggcc ccagaaaggc aaagacgggg gccagggccc cgggggcggc gtggaccgtg 19201 gtatgccact gccggaaaag ggcgacgagc gccggcgcgg agaacttctc gccggcgctt 19261 acaaagtagt cgtaatcgcg gggcagcagc acccgtgccg tgactcgttg cgggtgcccg 19321 cgtggccgca ggcccacctc gcacacctcg accaggtccc cgaacgctcc ctccttcttg 19381 atcggcggaa acgcaagagt ctggtattcg cgcgcaaata gcgcggttcc ggtggtgatg 19441 ttaacggtca gcgaagcggc ggacgcgcac tgggggggtgt cgcgaatggc cgccaggcgc 19501 gcccacgcca gccgcgcgtc gggatgctcg gcaacgcgcg ccgccagggc catagggtcg 19561 atgtcaatgt tggcctccgc gaccaggaga gcggcgcgag gggcggcggg cgggccccac 19621 gacgctctct caactttcac caccagtccc gtgcgtgggt ccgagccgat acgcagcggg 19681 gcgaacaggg ccaccggccc ggtctggcgc tccagggccg ccaggacgca cgcgtacagc 19741 gcccgccaca gagtcgggtt ctccaggggc tccagcgggg aggcggccgg cgtcgtcgcg 19801 gcgcgggcgg ccgccacgac ggcctggacg gagacgtccg cggagccgta gaaatcccgc 19861 agctccgtcg cggtgacgga gacctccgca aagcgcgcgc gaccctcccc tgcggcgttg 19921 cgacatacaa aatacaccag ggcgtggaag tactcgcgag cgcggggggg cagccatacc 19981 gcgtaaaggg taatggcgct gacgctctcc tccacccaca cgatatctgc ggtgtccatc FIGURE 9 (Continued)

20041 gcacggcccc taaggatcac gggcggtctg tgggtcccat gctgccgtgc ctggccgggc 20101 ccggtgggtc gcggaaaccg gtgacggggg ggggcggttt ttggggttgg ggtgggggtg 20161 ggaaacggcc cgggtccggg ggccaacttg gcccctcggt gcgttccggc aacagcgccg 20221 ccggtccgcg gacgaccacg taccgaacga gtgcggtccc gagacttata gggtgctaaa 20281 gttcaccgcc ccctgcatca tgggccaggc ctcggtgggg agctccgaca gcgccgcctc 20341 caggatgatg tcagcgttgg ggttggcgct ggatgagtgc gtgcgcaaac agcgcccccca 20401 cgcgggcacg cgtagcttga agcgcgcgcc cgcaaactcc cgcttgtggg ccataagcag 20461 ggcgtacagc tgcctgtggg tccggcaggc gctgtggtcg atgtggtggg cgtccaacaa 20521 ccccacgatt gtctgtttgg tgaggttttt aacgcgcccc gccccgggaa acgtctgcgt 20581 gcttttggcc atctgcacgc caaacagttc gccccagatt atcttgaaca gcgccaccgc 20641 gtggtccgtc tcgctaacgg acccgcgcgg gggacagccg cttagggcgt cggcgacgcg 20701 cttgacggct tcctccgaga gcagaagtcc gtcggttacg ttacagtggc ccagttcgaa 20761 caccagctgc atgtagcggt cgtagtgggg ggtcagtagg tccagcacgt catcggggcc 20821 gaaggtcctc ccagatcccc cggccgccga gtcccaatgc aggcgcgcgg ccatggtgct 20881 gcacaggcac aacagctccc agacgggggt tacgttcagg gtgggggggca gggccacgag 20941 ctccagctct ccggtgacgt tgatcgtggg gatgacgccc gtggcgtagt ggtcatagat 21001 ccgccgaaat atggcgctgc tgcgggtggc catgggaacg cggagacagg cctccagcaa 21061 cgccaggtaa ataaaccgcg tgcgtcccat caggctgttg aggttgcgca tgagcgcgac 21121 aatttccgcc ggcgcgacat cggaccggag gtatttttcg acgaaaagac ccacctcctc 21181 cgtctcggcg gcctgggccg gcagcgacgc ctcgggatcc cggcaccgca gctcccgtag 21241 atcgcgctgg gccctgaggg cgtcgaaatg tacgccccgc aaaaacagac agaagtcctt 21301 tggggtcagg gtatcgtcgt gtccccagaa gcgcacgcgt atgcagttta gggtcagcag 21361 catgtgaagg atgttaaggc tgtccgagag acacgccagc gtgcatctct caaagtagtg 21421 tttgtaacgg aatttgttgt agatgcgcga cccccgcccc agcgacgtgt cgcatgccga 21481 cgcgtcacag cgccccttga accggcgaca cagcaggttt gtgacctggg agaactgcgc 21541 gggccactgg ccgcaggaac tgaccacgtg gttcaggagc atgggcgtaa agacgggctc 21601 cgagcgcgcc ccggagccgt ccatgtaaat cagtagctcc cccttgcgga gggtgcgcac 21661 ccgtcccagg gactggtaca cggacaccat gtccggtccg tagttcatgg gtttcacgta FIGURE 9 (Continued)

21721 ggcgaacatg ccatcaaagt gcaggggatc gaagctgagg cccacggtta cgaccgtcgt 21781 gtatataacc acgcggtatt ggccccacgt ggtcacgtcc ccgagggggg tgagcgagtg 21841 aagcaacagc acgcggtccg taaactgacg gcagaaccgg gccacgatct ccgcgaagga 21901 gaccgtcgat gaaaaaatgc agatgttatc gcccccgcca aggcgcgctt ccagctcccc 21961 aaagaacgtg gcccccgggg cgtccggaga ggcgtccgga gacgggccgc ttggcggccc 22021 gggcgggcgc agggcagcct gcaggagctc ggtccccaga cgcgggagaa acaggcaccg 22081 gcgcgccgaa aacccgggca tggcgtactc gccgaccacc acatgcacgt ttttttcgcc 22141 ccggagaccg cacaggaagt ccaccaactg cgcgttggcg gttgcgtcca tggcgatgat 22201 ccgaggacag gtgcgcagca ggcgtagcat taacgcatcc acgcggccca gttgctgcat 22261 cgttggcgaa tagagctggc ccagcgtcga cataacctcg tccagaacga ggacgtcgta 22321 gttgttcaga aggttggggc ccacgcgatg aaggctttcc acctggacga taagtcggtg 22381 gaaggggcgg tcgttcataa tgtaattggt ggatgagaag taggtgacaa agtcgaccag 22441 gcctgactca gcgaaccgcg tcgccagggt ctgggtaaaa ctccgacgac aggagacgac 22501 gagcacactc gtgtccggag agtggatcgc ttcccgcagc cagcggatca gcgcggtagt 22561 ttttcccgac cccattggcg cgcggaccac agtcacgcac ctggccgtcg ggcgctcgc 22621 gttggggaag gtgacgggtc cgtgctgctg ccgctcgatc gttgttttcg ggtgaacccg 22681 gggcacccat tcggccaaat cccccccgta caacatccgc gctagcgata cgctcgacgt 22741 gtactgttcg cactcgtcgt ccccaatggg acgcccggcc cccagaggat cccccgactc 22801 cgcgcccccc acgaaaggca tgaccggggc gcggacggcg tggtgggtct ggtgtgtgca 22861 ggtggcgacg tttgtggtct ctgcggtctg cgtcacgggg cttctcgtcc tggcctctgt 22921 gttccgggca cggtttccct gcttttatgc cacggcgagc tcttatgccg gggtgaactc 22981 cacggccgag gtgcgcgggg gtgtagccgt gcccctcagg ttggacacgc agagccttgt 23041 gggcacttat gtaatcacgg ccgtgttgtt gttggccgcg gccgtgtatg ccgtggtcgg 23101 cgccgtgacc tcccgctacg accgcgccct ggacgcgggc cgccgtctgg ctgcggcccg 23161 catggccatg ccgcacgcca cgctgatcgc cggaaacgtc tgctcttggt tgctgcagat 23221 caccgtcctg ttgctggccc atcgcatcag ccagctggcc cacctggttt acgtcctgca 23281 ctttgcgtgt ctggtgtatt ttgcggccca tttttgcacc aggggggtcc tgagcgggac 23341 gtatctgcgt caggtgcacg gcctgatgga gccggccccg actcatcatc gcgtcgtcgg FIGURE 9 (Continued)

23401 cccggctcga gccgtgctga caaacgcctt gctgttgggc gtcttcctgt gcacggccga 23461 cgccgcggta tccctgaata ccatcgccgc gttcaacttt aatttttcgg ccccgggcat 23521 gctcatatgc ctgaccgtgc tgttcgccct tctcgtcgta tcgctgttgt tggtggtcga 23581 gggggtgttg tgtcactacg tgcgcgtgtt ggtgggcccc cacctggggg ccgtggccgc 23641 cacgggcatc gtcggcctgg cctgcgagca ctattacacc aacggctact acgttgtgga 23701 gacgcagtgg ccgggggccc agacgggagt ccgcgtcgcc ctcgccctgg tcgccgcctt 23761 tgccctcggc atggccgtgc tccgctgcac ccgcgcctat ctgtatcaca ggcggcacca 23821 caccaaattt tttatgcgca tgcgcgacac gcgacaccgc gcacattccg ccctcaggcg 23881 cgtacgcagt tccatgcgcg gatcgcgaga cggccgccac aggcccgcac ccggcagccc 23941 gcccgggatt cccgaatatg cggaagaccc ctacgcgatc tcatacggcg gccagctcga 24001 ccggtacgga gattccgacg gggagccgat ttacgacgag gtggctgacg accaaaccga 24061 cgtattgtac gccaagatac aacacccgcg gcacctgccc gacgacgagc ccatctatga 24121 caccgttggg gggtacgacc ccgagcccgc cgaggacccc gtgtacagca ccgtccgccg 24181 ttggtagctg tttggttccg ttttaataaa ccgtttgtgt ttaacccgac cgtggtgtat 24241 gtctggtgtg tggcgtccga tcccgttact atcaccgttt cccccccccc cccctcaacc 24301 ccggcgattg tgggtttttt aaaaacgaca cgcgtgcgac cgtatacaga acattgtttt 24361 ggtttttatt cgctatcgga catgggggt ggaaactggg tggcggggca ggcgcctccg 24421 ggggtccgcc ggtgagtgtg gcgcgagggg gggtccgacg aacgcaggcg ctgtctcccc 24481 ggggcccgcg taaccacgcg catatccggg ggcacgtaga aattaccttc ctcttcggac 24541 tcgatatcca cgacatcaaa gtcgtgggcg gtcagcgaga cgacctcccc gtcgtcggtg 24601 atgaggacgt tgtttcggca gcagcagggc cgggccccgg agaacgagag gcccatagct 24661 cggcgagcgt gtcgtcgaac gccaggcggc tgcttcgctg gatggcctta tagatctccg 24721 gatcgatgcg gacgggggta atgatcaggg cgatcggaac ggcctggttc gggagaatgg 24781 acgccttgct gggtcctgcg gccccgagag ccccggcgcc gtcctccagg cggaacgtta 24841 cgccctcctc cgcgctggtg cggtgcctgc cgataaacgt caccagatgc gggtgggggg 24901 ggcagtcggg gaagtggctg tcgagcacgt agccctgcac caagatctgc ttaaagttcg 24961 ggtgacgggg gttcgcgaag acgggctcgc ggcggaccag atccccggag ctccaggaca 25021 cgggggagat ggtgtggcgt ccgaggtcgg gggcgccaaa cagaagcacc tccgagacaa FIGURE 9 (Continued)

25081 cgccgctatt taactccacc aaggcccgat ccgcggcgga gcaccgcctt ttttcgcccg
25141 aggcgtgggc ctctgaccag gcctggtctt gcgtgacgag agcctcctcc gggccgggga
25201 cgcgcccggg cgcgaagtat cgcacgctgg gcttcgggat cgaccggata aatgcccgga
25261 acgcctccgg ggaccggtgt gtcatcaagt cctcgtacgc ggaggccgtg gggtcgctgg
25321 ggtccatggg gtcgaaagcg tacttggccc ggcatttgac ctcgtaaaag gccagggggg
25381 tcttggggac tggggccagg tagccgtgaa tgtcccgagg acagacgaga atatccaggg
25441 acgccccgac catccccgtg tgaccgtcca tgaggacccc acacgtatgc acgttctctt
25501 cggtgaggtc gctgggttcg tggaagataa agcgccgcgt gtcggcgccg gcctcgccgc
25561 cgtcgtccgc gcggcccacg cagtagcgaa acagcaggct tcgggccgtc ggctcgttca
25621 cccgcccgaa catcaccgcc gaagactgta catccggccg caggctggcg ttgtgcttca
25681 gccactgggg cgagaaacac ggaccctggg ggccccagcg gagggtggat gcggtcgtga
25741 ggccccgccg gagcagggcc catagctggc agtcggcctg gttttgcgtg gccgcctcgt
25801 aaaaccccat gaggggccgg ggcgccacgg cgtccgcggc ggccgggggc ccgcggcgcg
25861 tcaggcgcca taggtgccgg ccgagtccgc ggtccaccat acccgcctcc tcgaggacca
25921 cggccaggga acacagataa tccaggcggg cccagagggg accgatggcc agaggggcgc
25981 ggacgccgcg cagcaacccg cgcaggtggc gctcgaacgt ctcggctagt atatgggagg
26041 gcagcgcgtt ggggatcacc gacgccgacc acatagagtc aaggtccggg gagtcgggat
26101 cggcgtccgg gtcgcgggcg tgggtgcccc caggagatag cggaatgtct ggggtcggag
26161 gccctgaggc gtcagaaagt gccggcgacg cggcccgggg cttttcgtct gcggtgtcgg
26221 tggcgtgctg atcacgtggg gggttaacgg gcgaatggga gctcgggtcc acagctgacg
26281 tcgtctgggg tgggggggc aggggacgga aggtggttgt cagcggaaga ctgttagggc
26341 gggggcgctt ggggggctg tcggggccac gaggggtgtc ctcggccagg gcccagggac
26401 gcttagtcac ggtgcgtccc ggcggacatg ctgggcctac cgtggactcc atttccgaga
26461 cgacgtgggg gagcggtggt tgagcgcgcc gccgggtgaa cgctgattct cacgacagcg
26521 cgtgccgcgc gcacgggttg gtgtgacaca ggcgggacac cagcaccagg agaggcttaa
26581 gctcgggagg cagcgccacc gacgacagta tcgccttgtg tgtgtgctgg taatttatac
26641 accgatccgt aaacgcgcgc cgaatcttgg gattgcggag gtggcgccgg atgccctctg
26701 gtacgtcata cgccaggccg tgggtgttgg tctcggccga gttgacaaac agggctgggt FIGURE 9 (Continued)

26761 gcagcacgca gcgataggcg agcagggcca gggcgaagtc cggcgacagc tggttgttga 26821 aatactggta accgggaaac cgggtcacgg gtacgcccag gctcggggcg acgtacacgc 26881 taaccaccaa ctccagcagc gtctggccaa gggcgtacag gtcaaccgct aacccgacgt 26941 cgtgcttcag gcggtggttg gtaaattcgg cccgttcgtt gttaaggtat ttcaccaaca 27001 gctccggggg ctggttatac ccgtgaccca ccagggtgtg aaagttggct gtggttaggg 27061 cggtgggcat gccaaacatc cgggggggact tgaggtccgg ctcctggagg caaaactgcc 27121 cccgggcgat cgtggagttg gagttgaggg tgacgaggct aaagtcggcg aggacggccc 27181 gccggagcga gacggcgtcc gaccgcagca tgacgaggat gttggcgcac ttgatatcca 27241 ggtggctgat cccgcaggtg gtgtttaaaa acacaacggc gcgggccagc tccgtgaagc 27301 actggtggag ggccgtcgag accgaggggt ttgttgtgcg cagggacgcc agttggccga 27361 tatacttacc gaggtccatg tcgtacgcgg ggaacactat ctgtcgttgt tgcagcgaga 27421 acccgagggg cgcgatgaag ccgcggatgt tgtgggtgcg gccggcgcgt agagcgcact 27481 ccccgaccaa cagggtcgcg atgagctcaa cggcaaacca ctccttttcc tttatggtct 27541 taacggcaag cttatgttcg cgaatcagtt ggacgtcgcc gtatcccccca gacccccccga 27601 agcttcgggc cccggggatc tcgagggtcg tgtagtgtag ggcggggttg atggcgaaca 27661 cggggctgca tagcttgcgg atgcgcgtga gggtaaggat gtgcgagggg gacgaggggg 27721 gtgcggttaa cgccgcctgg gatctgcgca ggggcgggcg gttcagtttg gccgccgtac 27781 cgggcgtctc gggggacgcg cggcgatgag acgagcggct cattcgccat cgggatagtc 27841 ccgcgcgaag ccgctcgcgg aggccggatc ggtggcggga cccgtgggag gagcgggagc 27901 cggcggcgtc ctggagagag gggccgctgg ggcgcccgga ggccccgtgt gggttggagt 27961 gtatgtagga tgcgagccaa tccttgaagg accgttggcg tgcaccttgg gggctgaggt 28021 tagctgccac atgaccagca ggtcgctgtc tgcgggactc atccatcctt cggccaggtc 28081 gccgtctccc cacagagaag cgttggtcgc tgcttcctcg agttgctcct cctggtccgc 28141 aagacgatcg tccacggcgt ccaggcgctc accaagcgcc ggatcgaggt accgtcggtg 28201 tgcggttaga aagtcacgac gcgccgcttg ctcctccacg cgaattttaa cacaggtcgc 28261 gcgctgtcgc atcatctcta agcgcgcgcg ggactttagc cgcgcctcca attccaagtg 28321 ggccgccttt gcagccataa aggcgccaac aaaccgagga tcttgggtgc tgacgccctc 28381 ccggtgcagc tgcagggtct ggtccttgta aatctcggct cggaggtgcg tctcggccag FIGURE 9 (Continued)

28441 gcgtcggcgc agggccgcgt gggcggcatc tcggtccatt ccgccaccct gcgggcgacc 28501 cggggggtgc tctgatagtc tcgcgtgccc aaggcccgtg atcggggtac ttcgccgccg 28561 cgacccgcca cccggtgtgc gcgatgtttg gtcagcagct ggcgtccgac gtccagcagt 28621 acctggagcg cctcgagaaa cagaggcaac ttaaggtggg cgcggacgag gcgtcggcgg 28681 gcctcacaat gggcggcgat gccctacgag tgcccttttt agatttcgcg accgcgaccc 28741 ccaagcgcca ccagaccgtg gtcccgggcg tcgggacgct ccacgactgc tgcgagcact 28801 cgccgctctt ctcggccgtg gcgcggcggc tgctgtttaa tagcctggtg ccggcgcaac 28861 taaaggggcg tgatttcggg ggcgaccaca cggccaagct ggaattcctg gcccccgagt 28921 tggtacgggc ggtggcgcga ctgcggttta aggagtgcgc gccggcggac gtggtgcctc 28981 agcgtaacgc ctactatagc gttctgaaca cgtttcaggc cctccaccgc tccgaagcct 29041 ttcgccagct ggtgcacttt gtgcgggact ttgcccagct gcttaaaacc tccttccggg 29101 cctccagcct cacggagacc acgggccccc ccaaaaaacg ggccaaggtg gacgtggcca 29161 cccacggccg gacgtacggc acgctggagc tgttccaaaa aatgatcctt atgcacgcca 29221 cctactttct ggccgccgtg ctcctcgggg accacgcgga gcaggtcaac acgttcctgc 29281 gtctcgtgtt tgagatcccc ctgtttagcg acgcggccgt gcgccacttc cgccagcgcg 29341 ccaccgtgtt tctcgtcccc cggcgccacg gcaagacctg gtttctagtg cccctcatcg 29401 cgctgtcact ggcctccttt cgggggatca agatcggcta cacggcgcac atccgcaagg 29461 cgaccgagcc ggtgtttgag gagatcgacg cctgcctgcg gggctggttc ggttcggccc 29521 gagtggacca cgttaaaggg gaaaccatct ccttctcgtt tccggacggg tcgcgcagta 29581 ccatcgtgtt tgcctccagc cacaacacaa acgtaagtcc tcttttcttt cgcatggctc 29641 tcccaagggg ccccgggtcg acccgaccca cacccaccca cccacccaca tacacacaca 29701 accagacgcg ggaggaaagt ctgccccgtg ggcactgatt tttattcggg atcgcttgag 29761 gaggcccggg caacggcccg ggcaacggtg gggcaactcg tagcaaatag gcgactgatg 29821 tacgaagaga agacacacag gcgccacccg gcgctggtcg gggggatgtt gtccgcgccg 29881 caccgtcccc cgacgacctc ttgcagacgg tccgtgatgc aaggacggcg gggggcctgc 29941 agcagggtga ccgtatccac gggatggcca aagagaagcg gacacaggct agcatccccc 30001 tggaccgcca gggtacactg ggccatcttg gcccacagac acggggcgac gcagggacag 30061 gactccgtta cgacggagga gagccacagt gcgttggcgg aatcgatgtg gggcggcggg FIGURE 9 (Continued)

30121 gcgcaggact cgcagccccc cgggtggttg gtgatcctgg ccaggagcca tcccagatgg 30181 cgggccctgc ttcccggtgg acagagcgac cccaggtcgc tgtccatggc ccagcagtag 30241 atctggccgc tggggaggtg ccaccaggcc cccgggccca aggcgcagca cgcgcccggc 30301 tccggggggg tcttcgcggg gaccagatac gcgccatcca gctcgccgac cactggctcc 30361 tccgcgagct gttcggtggt tgggtcgggg gtttcctccg gggggtggc cgcccgtatg 30421 cgggcgaacg tgagggtgca caggagcggg gtcagggggt gcgtcacgct ccggaggtgg 30481 acgatcgcgc agtagcggcg ctcgcggtta aagaaaaaga gggcaaagaa ggtgttcggg 30541 ggcaaccgca gcgccttggg gcgcgtcaga tacagaaaaa tctcgcagaa gagggcgcgc 30601 ccggggtctg ggttaggaag ggccacctga cacagaggct cggtgaggac cgttagacac 30661 cgaaagatct tgagccgctc gtccgcccga acgacgcgcc acacaaagac ggagttgaca 30721 atgcgcgcga tagagtcgac gtccgtcccc aggtcgtcga ctctgtcgcg cgtgccgcga 30781 gctccggccc gggaatccgg ccggggcaag gtccccgggg gaccaggcgg cgccaggggc 30841 cgccggggtc ccagctgcgc catgccgggg gcggggggag ggcaaacccc agaggcgggg 30901 gccaacggcg cggggaggag tgggtgggcg aggtggccgg gggaaggcgc ccgctagcga 30961 gaacggccgt tcccggacga caccttgcga caaaacctaa ggacagcggc ccgcgcgacg 31021 gggtccgaga ggctaaggta ggccgcgatg ttaatggtga acgcaaagcc gccgggaaag 31081 acaactatgc cacagaggcg gcgattaaac cccaggcaga ggtaggcgta gctttccccg 31141 ggcaggtatt gctcgcagac cctgcgtggg gctgtggagg ggacggcctc catgaagcga 31201 catttactct gctcgcgttt actgacgtca ccatccatcg ccacggcgat tggacgattg 31261 ttaagccgca gcgtgtctcc gcttgtgctg tagtagtcaa aaacgtaatg gccgtcggag 31321 tcggcaaagc gggccgggag gtcgtcgccg agcgggacga cccgccgccc ccgaccgccc 31381 cgtcccccca ggtgtgccag gacggccagg gcatacgcgg tgtgaaaaaa ggagtcgggg 31441 gcggtcccct cgacggcgca catcaggttc tcgaggagaa tggggaagcg cctggtcacc 31501 tcccccaacc acgcgcgttg gtcggggcca aagtcatagc gcaggcgctg tgagattcgc 31561 gggccgccct gaagcgcggc ccggatggcc tggcccaggg cccggaggca cgccagatgt 31621 atgcgcgcgg taaaggcgac ctcggcggcg atgtcaaagg gcggcaggac ggggcgcggg 31681 tggcgcaggg gcacctcgag cgcgggaaag cgtagcagca gctccgcctg cccagcggga 31741 gacagctggt gggggcgcac gacgcgttct gcggcgcagg cctcggtcag ggccgtggcc FIGURE 9 (Continued)

31801 agcgccgagg acagcagcgg agggcgggcg cgtcgcccgc cccacgccac ggagttctcg 31861 taggagacga cgacgaagcg ctgcttggtt ccgtagtggt ggcgcaggac cacggagata 31921 gaacgacggc tccacagcca gtccggccgg tcgccgccgg ccagggcttc ccatccgcga 31981 tccaaccact cgaccagcga ccgcggcttt gcggtaccag gggtcagggt tagaacgtcg 32041 ttcaggatgt cctcgccccc gggcccgtgg ggcacggggg ccacaaagcg gcccccgcct 32101 gggggctcca gacccgccaa caccgcatct gcgtcagccg cccccatggc gcccccgctg 32161 acggcctggt gaaccagggc gccctggcgg agccccgatg caacgccaca ggccgcacgc 32221 ccggtccgag cgcggaccgg gtggcggcgg gtgacgtcct gcactgcccg ctgaaccaac 32281 gcgaggatct cctcgttctc ctgcgcgatg gacacgtcct gggccgcggt cgtgtcgccg 32341 ccgggggccg tcagctgctc ctccggggag atgggggggt cggacgcccc gacgatgggc 32401 gggtctgcgg gcgcccccgc gtggggccgg gccaagggct gcggacgcgg ggacgcgctt 32461 tcccccagac ccatggacag gtgggccgca gcctccttcg cggccggcgg ggcggcggcg 32521 ccaagcagag cgacgtagcg gcacaaatgc cgacagacgc gcatgatgcg cgtgctgtcg 32581 gccgcgtagc gcgtgttggg ggggacgagc tcgtcgtaac taaacagaat cacgcgggca 32641 cagctcgccc ccgagcccca cgcaaggcgc agcgccgcca cggcgtacgg gtcatagacg 32701 ccctgcgcgt tacacaccac gggcagggag acgaacaacc ccccggcgct ggacgcacgc 32761 ggaaggaggc cagggtgtgc cggcacgacg ggggccagaa gctcccccac cgcatccgcg 32821 ggcacgtagg cggcaaacgc cgtgcaccac ggggtacagt cgccggtggc atgagccccga 32881 gtctggattt cgacctggaa gtttgcggcc gtcccgagtc cggggtggcc gcgcatcagg 32941 gcggccagag ggattcccgc ggccgccagg cactcgctgg atatgatgac gtgaaccaaa 33001 gacgagggcc gacccgggcc gtggccgaga tcgtactgga cctcgttggc caagtgcgcg 33061 ttcatggttc gggggtgggt gtgggtgtgt aggcgatgcg ggtcccccga gtccgcggga 33121 agggcgtggg tttggcgcgc gtatgcgtat tcgccaacgg aggcgtgcgt gcttatgcgc 33181 ggcgcgtttc ttctgtctct agggaatccg aggccaggac tttaacctgc tctttgtcga 33241 cgaggccaac tttattcgcc cggatgcggt ccagacgatt atgggctttc tcaaccaggc 33301 caactgcaag attatcttcg tgtcgtccac caacaccggg aaggccagta cgagcttttt 33361 gtacaacctc cgcggggccg cagacgagct tctcaacgtg gtgacctata tatgcgatga 33421 tcacatgccg agggtggtga cgcacacaaa cgccacggcc tgttcttgtt atatcctcaa FIGURE 9 (Continued)

33481 caagcccgtt ttcatcacga tggacggggc ggttcgccgg accgccgatt tgtttctggc 33541 cgattccttc atgcaggaga tcatcggggg ccaggccagg gagaccggcg acgaccggcc 33601 cgttctgacc aagtctgcgg gggagcggtt tctgttgtac cgcccctcga ccaccaccaa 33661 cagcggcctc atggcccccg atttgtacgt gtacgtggat cccgcgttca cggccaacac 33721 ccgagcctcc gggaccggcg tcgctgtcgt cgggcggtac cgcgacgatt atatcatctt 33781 cgccctggag cacttttttc tccgcgcgct cacgggctcg gcccccgccg acatcgcccg 33841 ctgcgtcgtc cacagtctga cgcaggtcct ggccctgcat cccggggcgt ttcgcggcgt 33901 ccgggtggcg gtcgagggaa atagcagcca ggactcggcc gtcgccatcg ccacgcacgt 33961 gcacacagag atgcaccgcc tactggcctc ggagggggcc gacgcgggct cgggccccga 34021 gcttctcttc taccactgcg agcctcccgg gagcgcggtg ctgtacccct tttcctgct 34081 caacaaacag aagacgcccg cctttgaaca ctttattaaa aagtttaact ccgggggcgt 34141 catggcctcc caggagatcg tttccgcgac ggtgcgcctg cagaccgacc cggtcgagta 34201 tctgctcgag cagctaaata acctcaccga aaccgtctcc cccaacactg acgtccgtac 34261 gtattccgga aaacggaacg gcgcctcgga tgaccttatg gtcgccgtca ttatggccat 34321 ctacctcgcg gcccaggccg gacctccgca cacattcgct cctatcacac gcgtcttgtg 34381 agcgcccaat aaacacaccc aggtatgcta cgcacgacca cggtgtcgtc tgttaagggg 34441 gggggaagg gggtgttggc gggaagcgtg ggaacacggg ggattctctc acgaccggca 34501 ccagtaccac ccccctgtga acacagaaac cccaacccaa atcccataaa catacgacac 34561 acaggcatat tttggaattt cttaggtttt tatttattta ggtatgctgg ggtttctccc 34621 tggatgccca cccccacccc cccgtgggtc tagccgggcc ttagggatag cgtataacgg 34681 gggccatgtc tccggaccgc acaacggccg cgccgtcaaa ggtgcacacc cgaaccacgg 34741 gagccagggc caaggtgtct cctagttggc ccgcgtgggt cagccaggcg acgagcgcct 34801 cgtaaagcgg cagccttcgc tctccatcct gcatcagggc cggggcttcg gggtgaatga 34861 gctgggcggc ctcccgcgtg acactctgca tctgcaggag agcgttcacg tacccgtcct 34921 gggcacttag cgcaaagagc cgggggatta gcgtaaggat gatggtggtt ccctccgtga 34981 tcgagtaaac catgttaagg accagcgatc gcagctcggc gtttacggga ccgagttgtt 35041 ggacgtccgc cagcagcgag aggcgactcc cgttgtagta cagcacgttg aggtctggca 35101 gccctccggg gtttctgggg ctggggttca ggtcccggat gcccctggcc acgagccgcg FIGURE 9 (Continued)

35161 ccacgatttc gcgcgccagg ggcgatggaa gcggaacggg aaaccgcaac gtgaggtcca 35221 gcgaatccag gcgcacgtcc gtcgcttggc cctcgaacac gggcgggacg aggctgatgg 35281 ggtccccgtt acagagatct acgggggagg tgttgcgaag gttaacggtg ccggcgtggg 35341 tgaggtccac gtccaggggg caggcgacga ttcgcgtggg aagcacccgg gtgatgaccg 35401 cggggaagcg ccttcggtac gccagcaaca accccaacgt gtcgggactg acgcctccgg 35461 agacgaagga ttcgtgcgcc acgtcggcca gcgtcagttg ccggcggatg gtcggcagga 35521 ataccacccg cccttcgcag cgctgcagcg ccgccgcatc ggggcgcgag atgcccgagg 35581 gtatcgcgat gtcagtttca aagccgtccg ccagcatggc gccgatccac gcggcaggga 35641 gtgcagtggt gggtcgggtg gcgggaggag cgcggtgggg gtcagcggcg tagcagagac 35701 gggcgaccaa cctcgcatag gacgggggt gggtcttagg gggttgggag gcgacaggga 35761 ccccagagca tgcgcgggga ggtctgtcgg gcccagacgc accgagagcg aatccgtccg 35821 cggagtcccg gcttgggttt tatggggccc ggccctcgga atcgcggctt gtcggcgggg 35881 acaaaggggg cggggctagg ggcttgcgga aacagaagac gcgtgggata aaagaatcgc 35941 actaccccaa ggaagggcgg ggcggtttat tacagagcca gtcccttgag cggggatgcg 36001 tcatagacga gatactgcgc gaagtgggtc tcccgcgcgt gggcttcccc gttgcgggcg 36061 ctgcggagga gggcggggtc gctggcgcag gtgagcgggt aggcctcctg aaacaggcca 36121 cacgggtcct ccacgagttc gcggcacccc ggggggcgct taaactgtac gtcgctggcg 36181 gcggtggccg tggacaccgc cgaacccgtc tccacgatca ggcgctccag gcagcgatgt 36241 ttggcggcga tgtcggccga cgtaaagaac ttaaagcagg ggctgagcac cggcgaggcc 36301 ccgttgaggt ggtaggcccc gttatagagc aggtccccgt acgaaaatcg ctgcgacgcc 36361 cacgggttgg ccgtggccgc gaaggcccgg gacgggtcgc tctggccgtg gtcgtacatg 36421 agggcggtga catccccctc cttgtccccc gcgtaaacgc ccccggcggc gcgtccccgg 36481 gggttgcagg gccggcggaa gtagttgacg tcggtcgaca cgggggtggc gataaactca 36541 cacacggcgt cctggccgtg gtccatccct gcgcgccgcg gcacctgggc gcacccgaac 36601 acggggacgg gctgggccgg ccccaggcgg tttcccgcca cgaccgcgtt ccgcaggtac 36661 acggctgccg cgttgtccag gagaggggga gccccgcggc ccaggtaaaa gttttgggga 36721 aggttgccca tgtcggtgac ggggttgcgg acggttgccg tggccacgac ggcggtgtag 36781 cccacgccca ggtccacgtt cccgcgcggc tgggtgagcg tgaagtttac ccccccgcca FIGURE 9 (Continued)

36841 gtttcgtgcc gggccacctg gagctggccc aggaagtacg cctccgacgc gcgctccgag 36901 aacagcacgt tctcagtcac aaagcggtcc tgtcggacga cggtgaaccc aaacccggga 36961 tggaggcccg tcttgagctg atgatgcaag gccacgggac tgatcttgaa gtaccccgcc 37021 atgagcgcgt aggtcagcgc gttctccccg gccgcgctct cgcggacgtg ctgcacgacg 37081 ggctgtcgga tcgacgaaaa gtagttggcc cccagagccg gggggaccag ggggacctgc 37141 cgcgacaggt cgcgcagggc cgggggggaaa ttgggcgcgt tcgccacgtg gtcggccccg 37201 gcgaacagcg cgtggacggg gagggggtaa aaatagtcgc cattttggat ggtatggtcc 37261 agatgctggg gggccatcag caggattccg gcgtgcaacg ccccgtcgaa tatgcgcatg 37321 ttggtggtgg acgcggtgtt ggcgcccgcg tcgggcgccg ccgagcagag cagcgccgtt 37381 gtgcgttcgg ccatgttgtg ggccagcacc tgcagcgtga gcatggcggg cccgtccact 37441 accacgcgcc cgttgtgaaa catggcgttg accgtgttgg ccaccagatt ggccgggtgc 37501 agggggtgcg cggggtccgt cacggggtcg ctggggcact cctcgccggg ggcgatctcc 37561 gggaccacca tgttctgcag ggtggcgtat acgcggtcga agcgaacccc cgcggtgcag 37621 cagcggcccc gcgagaaggc gggcaccatc acgtagtagt aaatcttgtg gtgcacggtc 37681 cagtccgccc cccggtgcgg ccggtcatcc gcggcgtccg cggctcgggc ctgggtgttg 37741 tgcagcagct ggccgtcgtt gcggttgaag tccgcggtcg ccacgttaca tgccgccgcg 37801 tacacggggt cgtggccccc cgcgctaacc cggcagtcgc gatggcggtc cagggccgcg 37861 cgccgcatca gggcgtcaca gtcccacacg aggggtggca gcagcgccgg gtctcgcatt 37921 aggtgattca gctcggcttg cgcctgcccg cccagctccg ggccggtcag ggtaaagtca 37981 tcaaccagct gggccagggc ctcgacgtgc gccaccaggt cccggtacac ggccatgcac 38041 tcctcgggaa ggtctccccc gaggtaggtc acgacgtacg agaccagcga gtagtcgttc 38101 acgaacgccg cgcaccgcgt gttgttccag tagctggtga tgcactggac cacgagccgg 38161 gccagggcgc agaagacgtg ctcgctgccg tgtatggcgg cctgcagcag gtaaaacacc 38221 gccgggtagt tgcggtcgtc gaacgccccg cgaacggcgg cgatggtggc gggggccatg 38281 gcgtggcgtc ccaccccccag ctccaggccc cgggcgtccc ggaacgccgc cggacatagc 38341 gccaggggca agttgccgtt caccacgcgc caggtggcct ggatctcccc cgggccggcc 38401 gggggaacgt cccccccgg cagctccacg tcggccaccc ccacaaagaa gtcgaacgcg 38461 gggtgcagct caagagccag gttggcgttg tcgggctgca taaactgctc cggggtcatc FIGURE 9 (Continued)

38521 tggccttccg cgacccatcg gacccgcccg tgggccaggc gctgcccccca ggcgttcaaa 38581 aacagctgct gcatgtctgc ggcggggccg gccggggccg ccacgtacgc cccgtacgga 38641 ttggcggctt cgacggggtc gcggttaagg cccccgaccg ccgcgtcaac gttcatcagc 38701 gaagggtggc acacggtccc gatcgcgtgt tccagagaca ggcgcagcac ctggcggtcc 38761 ttccccccaaa aaaacagctg gcggggcggg aaggcgcggg gatccgggtg gccgggggcg 38821 gggactaggt ccccggcgtg cgcggcaaac cgttccatga ccggattgaa caggcccagg 38881 ggcaggacga acgtcaggtc catggcgccc accagggggt agggaacgtt ggtggcggcg 38941 tagatgcgct tctccagggc ctccagaaag accagcttct cgccgatgga caccagatcc 39001 gcgcgcacgc gcgtcgtctg gggggcgctc tcgagctcgt ccagcgtctg ccggttcagg 39061 tcgagctgct cctcctgcat ctccagcagg tggcggccca cgtcgtccag acttcgcacg 39121 gccttgccca tcacgagcgc cgtgaccagg ttggccccgt tcaggaccat ctcgccgtac 39181 gtcaccggca cgtcggcttc ggtgtcctcc gctttcagga aggactgcag gaggcgctgt 39241 ttgatcgggg cggtggtgac gagcaccccg tcgaccggcc gcccgcgcgt gtcggcatgc 39301 gtcagacggg gcacggccac ggagggctgc gtggccgtgg tgaggtccac gagccaggcc 39361 tcgacggcct cccggcggtg gcccgccttg cccaggaaaa agctcgtctc gcagaagctt 39421 cgctttagct cggcgaccag ggtcgcccgg gccaccctgg tggccaggcg gccgttgtcc 39481 aggtatcgtt gcatcggcaa caacaaagcc aggggcggcg ccttttccag cagcacgtgc 39541 agcatctggt cggccgtgcc gcgctcaaac gccccgagga cggcctggac gttgcgagcg 39601 agctgttgga tggcgcgcaa ctggcgatgc gcgccgatac ccgtcccgtc cagggcctcc 39661 cccgtgagca gggcgatggc ctcggtggcc aggctgaagg cggcgttcag ggcccggcgg 39721 tcgataatct tggtcatgta attgtgtgtg ggttgctcga tggggtgcgg gccgtcgcgg 39781 gcaatcagcg gctggtggac ctcgaactgt acgcgcccct cgttcatgta ggccagctcc 39841 ggaaacttgg tacacacgca cgccaccgac aacccgagct ccagaaagcg cacgagcgac 39901 agggtgttgc aatacgaccc cagcagggcg tcgaactcga cgtcgtacag gctgtttgca 39961 tcggagcgca cgcgggaaaa aaaatcgaac aggcgtcgat gcgacgccac ctcgatcgtg 40021 ctaaggaggg acccggtcgg caccatggcc gcggcatacc ggtatcccgg agggtcgcgg 40081 ttgggagctg ccatggggtc gcgtggagat cggctggatc tagcgatatt tgcccgggga 40141 ggctaagatc caccccaacg cccggccacc cgtgtacgtg cccgacggcc caaggtccac FIGURE 9 (Continued)

40201 cgaaagacac gacgggcccg gacccaaaaa ggcgggggat gctgtgtgag gggccgggtg 40261 tcggtcgggg gggaaaggca ccgggagaag gctgcggcct cgttccagga gaacccagtg 40321 tccccaacag acccggggac gtgggatccc aggccttata taccccccccc gccccacccc 40381 cgttagaacg cgacgggtgc attcaagatg gccctggtcc aaaagcgtgc caggaagaaa 40441 ttggcagagg cggcaaagct gtccgccgcc gccacccaca tcgaggcccc ggccgcgcag 40501 gctatcccca gggcccgtgt gcgcagggga tcggtgggcg gcagcatttg gttggtggcg 40561 ataaagtgga aaagcccgtc cggactgaag gtctcgtggg cggcggcgaa caaggcacac 40621 agggccgtgc ctcccaaaaa cacggacatc ccccaaaaca ctggcgccga caacggcaga 40681 cgatccctct tgatgttaac gtacaggagg agcgcccgca ccgcccacgt aacgtagtag 40741 ccgacgatgg cggccaggat acaggccggc gccaccaccc ttccggtcag cccgtaatac 40801 atgcccgctg ccaccatctc caacggcttc aggaccaaaa acgaccaaag gaacagaatc 40861 acgcgctttg aaaagaccgg ctgggtatgg ggcggaagac gcgagtatgc cgaactgaca 40921 aaaaaatcag aggtgccgta cgaggacaat gaaaactgtt cctccagcgg cagttctccc 40981 tcctcccccc cgaaggcggc ctcgtcgacc agatctcgat ccaccagagg aaggtcatcc 41041 cgcatggtca tggggtgtgc ggtggaggtg gggagaccga aaccgcaaag ggtcgcttac 41101 gtcagcagga tcccgagatc aaagacaccc gggttcttgc acaaacacca cccgggttgc 41161 atccgcggag gcgagtgttt tgataaggcc gttccgcgcc ttgatataac ctttgatgtt 41221 gaccacaaaa cccggaattt acgcctacgc cccaatgccc acgcaagatg aggtaggtaa 41281 cccccccgtg ggtgtgacgt tgcgtttagt tcattggagg ccaaggggaa aaatggggtg 41341 gggaggaaac ggaaaaccca gtaggccgtg tcgggaacac gcccggggtt gtcctcaaaa 41401 ggcagggtcc atactacgga agccgtcgtt gtattcgaga cctgcctgtg cgacgcacgt 41461 cggggttgcc tgtgtccggt tcggcccccca ccgcgtgcgg cacgcacgag gacgagtccg 41521 cgtgctttat tggcgttcca agcgttgccc tccagtttct gttgtcggtg ttcccccata 41581 cccacgccca catccaccgt agggggcctc tgggccgtgt tacgtcgccg cccgcgatgg 41641 agcttagcta cgccaccacc atgcactacc gggacgttgt gttttacgtc acaacggacc 41701 gaaaccgggc ctactttgtg tgcgggggggt gtgtttattc cgtggggcgg ccgtgtgcct 41761 cgcagcccgg ggagattgcc aagtttggtc tggtcgttcg agggacaggc ccagacgacc 41821 gcgtggtcgc caactatgta cgaagcgagc tccgacaacg cggcctgcag gacgtgcgtc FIGURE 9 (Continued)

41881 ccattgggga ggacgaggtg tttctggaca gcgtgtgtct tctaaacccg aacgtgagct 41941 ccgagctgga tgtgattaac acgaacgacg tggaagtgct ggacgaatgt ctggccgagt 42001 actgcacctc gctgcgaacc agcccgggtg tgctaatatc cgggctgcgc gtgcgggcgc 42061 aggacagaat catcgagttg tttgaacacc caacgatagt caacgtttcc tcgcactttg 42121 tgtatacccc gtccccatac gtgttcgccc tggcccaggc gcacctcccc cggctcccga 42181 gctcgctgga ggccctggtg agcggcctgt ttgacggcat ccccgcccca cgccagccac 42241 ttgacgccca caacccgcgc acggatgtgg ttatcacggg ccgccgcgcc ccacgaccca 42301 tcgccgggtc gggggcgggg tcgggggcgg cgggcgccaa gcgggccacc gtcagcgagt 42361 tcgtgcaagt caaacacatt gaccgcgtgg gccccgctgg cgtttcgccg gcgcctccgc 42421 caaacaacac cgactcgagt tccctggtgc ccggggccca ggattccgcc ccgcccggcc 42481 ccacgctaag ggagctgtgg tgggtgtttt atgccgcaga ccgggcgctg gaggagcccc 42541 gcgccgactc tggcctcacc cgcgaggagg tacgtgccgt acgtgggttc cgggagcagg 42601 cgtggaaact gtttggctcc gcgggggccc cgcgggcgtt tatcggggcc gcgttgggcc 42661 tgagccccct ccaaaagctg gccgtttact actatatcat ccaccgagag aggcgcctgt 42721 ccccttccc cgcgctagtc cggctcgtag gccggtacac acagcgccac ggcctgtacg 42781 tccctcggcc cgacgaccca gtcttggccg atgccatcaa cgggctggtt cgcgacgcgc 42841 tggcggccgg aaccacagcc gagcagctcc tcatgttcga ccttctcccc ccaaaggacg 42901 tgccggtggg aagcgacgtg caggccgaca gcaccgctct gctgcgcttt atagaatcgc 42961 aacgtctcgc cgtccccggg ggggtgatct cccccgagca cgtcgcgtac cttggtgcgt 43021 tcctgagcgt gctgtacgct ggccgcgggc gcatgtccgc agccacgcac accgcgcggc 43081 tgacaggggt gacctccctg gtgctagcgg tgggtgacgt ggaccgtctt tccgcgtttg 43141 accgcggagc ggcgggcgcg gccagccgca cgcgggccgc cgggtacctg gatgtgcttc 43201 ttaccgttcg tctcgctcgc tcccaacacg gacagtctgt gtaaaagacc ccaataaacg 43261 tatgtcgcta ctacaccctt gtgtgtcaat ggacgcctct ccgggggggg gaagggaaag 43321 caaagagggg ctgggggagc ggcaccaccg gggcctgaac aaacaaacca cagacacggt 43381 tacagtttat tcggtcgggc ggagaaacgg ccgaagccac gcccacttta ttcgcgtctc 43441 caaaaaaacg ggacacttgt ccggagaacc tttaggatgc cagccagggc ggcggtaatc 43501 ataaccacgc ccagcgcaga ggcggccaga aacccgggcg caattgcggc cacgggctgc FIGURE 9 (Continued)

43561 gtgtcaaagg ctagcaaatg aatgacggtt ccgtttggaa atagcaacaa ggccgtggac 43621 ggcacgtcgc tcgaaaacac gcttggggcg ccctccgtcg gcccggcggc gatttgctgc 43681 tgtgtgttgt ccgtatccac cagcaacaca gacatgacct ccccggccgg ggtgtagcgc 43741 ataaacacgg cccccacgag ccccaggtcg cgctggtttt gggtgcgcac cagccgcttg 43801 gactcgatat cccgggtgga gccttcgcat gtcgcggtga ggtaggttag gaacagtggg 43861 cgtcggacgt cgacgccggt gagcttgtag ccgatccccc ggggcagagg ggagtgggtg 43921 acgacgtagc tggcgctgtg ggtgatgggt accaggatcc gtggctcgac gttggcagac 43981 tgccccccgc accgatgtga ggcctcaggg acgaaggcgc ggatcagggc gttgtagtgt 44041 gcccaacgcg tcagggtcga ggcgaggccg tgggtctgct gggccaggac ttcgaccggg 44101 gtctcggatc gggtggcttg agccagcgcg tccaggataa acacgctctc gtctagatca 44161 aagcgcaggg aggccgcgca tggcgaaaag tggtccggaa gccaaaagag ggttttctgg 44221 tggtcggccc gggccagcgc ggtccggagg tcggcgttgg tcgctgcggc gacgtcggac 44281 gtacacaggg ccgaggctat cagaaggctc cggcgggcgc gttcccgctg caccgccgag 44341 gggacgccag ccaagaacgg ctgccggagg acagccgagg cgtaaaatag cgcccggtgg 44401 acgaccgggg tggtcagcac gcggccccct agaaactcgg catacagggc gtcgatgaga 44461 tgggctgcgc tgggcgccac tgcgtcgtac gccgaggggc tatccagcac gaaggccagc 44521 tgatagccca gcgcgtgtaa tgccaagctc tgttcgcgct ccagaatctc ggccaccagg 44581 tgctggagcc gagcctctag ctgcaggcgg gccgtgggat ccaagactga cacattaaaa 44641 aacacagaat ccgcggcaca gcccgcggcc ccgcgggcgg ccaacccggc aagcgcgcgc 44701 gagtgggcca aaaagcctag caggtcggag aggcagaccg cgccgtttgc gtgggcggcg 44761 ttcacgaaag caaaacccga cgtcgcgagc agccccgtta ggcgccagaa gagagggggg 44821 cgcgggccct gctcggcgcc cgcgtccccc gagaaaaact ccgcgtatgc ccgcgacagg 44881 aactgggcgt agttcgtgcc ctcctccggg tagccgccca cgcggcggag ggcgtccagc 44941 gcggagccgt tgtcggcccg cgtcagggac cctaggacaa agacccgata ccgggggccg 45001 cccgggggcc cgggaagagc ccccgggggg ttttcgtccg cggggtcccc gacccgatct 45061 agcgtctggc ccgcggggac caccatcact tccaccggag ggctgtcgtg catggatatc 45121 acgagcccca tgaattcccg cccgtagcgc gcgcgcacca gcgcggcatc gcacccgagc 45181 accagctccc ccgtcgtcca gatgcccacg ggccacgtcg aggccgacgg ggagaaatac FIGURE 9 (Continued)

45241 acgtacctac ctggggatct caacaggccc cgggtggcca accaggtcgt ggacgcgttg
45301 tgcaggtgcg tgatgtccag ctccgtcgtc gggtgccgcc gggccccaac cggcggtcgg
45361 gggggcggtg tatcacgcgg cccgctcggg tggctcgccg tcgccacgtt gtctccccgc
45421 gggaacgtca gggcctcggg gtcagggacg gccgaaaacg ttacccaggc ccgggaacgc
45481 agcaacacgg aggcggctgg attgtgcaag agacccttaa gggggcgac cgagggggga
45541 ggctgggcgg tcggctcgac cgtggtgggg gcgggcaggc tcgcgttcgg gggccggccg
45601 agcaggtagg tcttcgggat gtaaagcagc tggccggggt cccgcggaaa ctcggccgtg
45661 gtgaccaata caaaacaaaa gcgctcctcg taccagcgaa gaaggggcag agatgccgta
45721 gtcaggttta gttcgtccgg cggcgccaga aatccgcgcg gtggtttttg ggggtcgggg
45781 gtgtttggca gccacagacg cccggtgttc gtgtcgcgcc agtacatgcg gtccatgccc
45841 aggccatcca aaaaccatgg gtctgtctgc tcagtccagt cgtggacctg accccacgca
45901 acgcccaaaa taataacccc cacgaaccat aaaccattcc ccatgggga ccccgtccct
45961 aacccacggg gcccgtggct atggcagggc ttgccgcccc gacgttggct gcgagccctg
46021 ggccttcacc cgaacttggg gggtggggtg gggaaaagga agaaacgcgg gcgtattggc
46081 cccaatgggg tctcggtggg gtatcgacag agtgccagcc ctgggaccga accccgcgtt
46141 tatgaacaaa cgacccaaca cccgtgcgtt ttattctgtc tttttattgc cgtcatagcg
46201 cgggttactt ccggtattgt ctccttccgt gtttcagtta gcctccccca tctcccgggc
46261 aaacgtgcgc gccaggtcgc agatcgtcgg tatggagccg gggtggtga cgtgggtctg
46321 gaccatcccg gaggtaagtt gcagcagggc gtcccggcag ccggcgggcg attggtcgta
46381 atccaggata aagacgtgca tgggacggag gcgtttggcc aagacgtcca aggcccaggc
46441 aaacacgtta tacaggtcgc cgttgggggc cagcaactcg gggcccgaa acagggtaaa
46501 taacgtgtcc ccgatatggg gttgtgggcc cgcgttgctc tggggctcgg caccctgggg
46561 cggcacggcc gtccccgaaa gctgtcccca atcctcccgc cacgacccgc cgccctgcag
46621 ataccgcacc gtattggcaa gcagctcgta aacgcggcga atcgcggcca acatagccag
46681 gtcaagccgc tcgccggggc gctggcgttt ggccaggcgg tcgatgtgtc tgtcctccgg
46741 aagggccccc aacacgatgt ttgtgccggg caaggtcggc gggatgaggg ccacgaacgc
46801 cagcacggcc tgggggtca tgctgcccat aaggtatcgc gcggccgggt aacacaggag
46861 ggcggcgatg ggatggcggt cgaagatgag ggtgagggcc gggggcgggg catgtgagct FIGURE 9 (Continued)

46921 cccagcctcc cccccgatat gaggagccag aacggcgtcg gtcacggcat aaggcatgcc 46981 cattgttatc tgggcgcttg tcattaccac cgccgcgtcc ccggccgata tctcaccctg 47041 gtcgaggcgg tgttgtgtgg tgtagatgtt cgcgattgtc tcggaagccc ccaacacccg 47101 ccagtaagtc atcggctcgg gtacgtagac gatatcgtcg cgcgaaccca gggccaccag 47161 cagttgcgtg gtggtggttt tccccatccc gtggggaccg tctatataaa cccgcagtag 47221 cgtgggcatt ttctgctcca ggcggacttc cgtggctttt tgctgccggc gagggcgcaa 47281 cgccgtacgt cggttgttat ggccgcgaga acgcgcagcc tggtcgaacg cagacgcgtg 47341 ttgatggcag ggtacgaag ccatacgcgc ttctacaagg cgctggccga agaggtgcgg 47401 gagtttcacg ccaccaagat ctgcggcacg ctgttgacgc tgttaagcgg gtcgctgcag 47461 ggtcgctcgg tattcgaggc cacacgcgtc accttaatat gcgaagtgga cctgggaccg 47521 cgccgccccg actgcatctg cgtgttcgaa ttcgccaatg acaagacgct gggcggggtt 47581 tgtgtcatca tagaactaaa gacatgcaaa tatatttctt ccggggacac cgccagcaaa 47641 cgcgagcaac gggccacggg gatgaagcag ctgcgccact ccctgaagct cctgcagtcc 47701 ctcgcgcctc cgggtgacaa gatagtgtac ctgtgccccg tcctggtgtt tgtcgcccaa 47761 cggacgctcc gcgtcagccg cgtgacccgg ctcgtcccgc agaaggtctc cggtaatatc 47821 accgcagtcg tgcggatgct ccagagcctg tccacgtata cggtccccat tgagcctagg 47881 acccagcgag cccgtcgccg ccgcggcggc gccgcccggg ggtctgcgag cagaccgaaa 47941 aggtcacact ctggggcgcg cgacccgccc gagtcagcgg cccgccagtt accacccgcc 48001 gaccaaaccc ccgcctccac ggagggcggg ggggtgctta agaggatcgc ggcgctcttc 48061 tgcgtgcccg tggccaccaa gaccaaaccc cgagccgcct ccgaatgaga gtgtttcgtt 48121 ccttccccct ccccccgcgt cagacaaacc ctaaccaccg cttaagcggc ccccgcgagg 48181 tccgaagact catttggatc cggcgggagc cacccgacaa cagcccccgg gttttcccac 48241 gccagacgcc ggtccgctgt gccatcgcgc cccctcatcc caccccccat cttgtcccca 48301 aataaaacaa ggtctggtag ttaggacaac gaccgcagtt ctcgtgtgtt attttcgctc 48361 tccgcctctc gcagatggac ccgtactgcc catttgacgc tctggacgtc tgggaacaca 48421 ggcgcttcat agtcgccgat tcccgaaact tcatcacccc cgagttcccc cgggactttt 48481 ggatgtcgcc cgtctttaac ctcccccggg agacggcggc ggagcaggtg gtcgtcctac 48541 aggcccagcg cacagcggct gccgctgccc tggagaacgc cgccatgcag gcggccgagc FIGURE 9 (Continued)

48601 tccccgtcga tatcgagcgc cggttacgcc cgatcgaacg gaacgtgcac gagatcgcag 48661 gcgccctgga ggcgctggag acggcggcgg ccgccgccga agaggcggat gccgcgcgcg 48721 gggatgagcc ggcgggtggg ggcgacgggg gggcgccccc gggtctggcc gtcgcggaga 48781 tggaggtcca gatcgtgcgc aacgacccgc cgctacgata cgacaccaac ctccccgtgg 48841 atctgctaca catggtgtac gcgggccgcg gggcgaccgg ctcgtcgggg gtggtgttcg 48901 ggacctggta ccgcactatc caggaccgca ccatcacgga ctttcccctg accacccgca 48961 gtgccgactt tcgggacggc cggatgtcca agaccttcat gacggcgctg gtcctgtccc 49021 tgcagtcgtg cggccggctg tatgtgggcc agcgccacta ttccgccttc gagtgcgccg 49081 tgttgtgtct ctacctgctg taccgaaaca cgcacggggc cgccgacgat agcgaccgcg 49141 ctccggtcac gttcggggat ctgctgggcc ggctgccccg ctacctggcg tgcctggccg 49201 cggtgatcgg gaccgagggc ggccggccac agtaccgcta ccgcgacgac aagctcccca 49261 agacgcagtt cgcggccggc gggggccgct acgaacacgg agcgctggcg tcgcacatcg 49321 tgatcgccac gctgatgcac cacggggtgc tcccggcggc cccgggggac gtcccccggg 49381 acgcgagtac ccacgttaac cccgacggcg tggcgcacca cgacgacata aaccgcgccg 49441 ccgccgcgtt cctcagccgg ggccacaacc tattcctgtg ggaggaccag actctgctgc 49501 gggcaaccgc gaacaccata acggccctgg gcgttatcca gcggctcctc gcgaacggca 49561 acgtgtacgc ggaccgcctc aacaaccgcc tgcagctggg catgctgatc cccggagccg 49621 tcccttcgga ggccatcgcc cgtggggcct ccgggtccga ctcgggggcc atcaagagcg 49681 gagacaacaa tctggaggcg ctatgtgcca attacgtgct tccgctgtac cgggccgacc 49741 cggcggtcga gctgacccag ctgtttcccg gcctggccgc cctgtgtctt gacgcccagg 49801 cggggcggcc ggtcgggtcg acgcggcggg tggtggatat gtcatcgggg gcccgccagg 49861 cggcgctggt gcgcctcacc gccctggaac tcatcaaccg cacccgcaca aaccccaccc 49921 ccgtgggga ggttatccac gcccacgacg ccctggcgat ccaatacgaa caggggcttg 49981 gcctgctggc gcagcaggca cgcattggct tgggctccaa caccaagcgt ttctccgcgt 50041 tcaacgttag cagcgactac gacatgttgt actttttatg tctggggttc attccacagt 50101 acctgtcggc ggtttagtgg gtggtgggcg agggggagg gggcattagg gagaaagaac 50161 aagagcctcc gttgggtttt ctttgtgcct gtactcaaaa ggtcataccc cgtaaacggc 50221 gggctccagt cccggcccgg tggttggcgt gaacgcaacg gcgggagctg ggttagcgtt FIGURE 9 (Continued)

50281 tagtttagca ttcgctctcg cctttccgcc cgcccccccga ccgttgcgcc ttttttttcg 50341 tccaccaaag tctctgtggg tgcgcgcatg gcagccgatg ccccgggaga ccggatggag 50401 gagcccctgc ccgacagggc cgtgcccatt tacgtggctg ggtttttggc cctgtatgac 50461 agcggggact cgggcgagtt ggcattggat ccggatacgg tgcgggcggc cctgcctccg 50521 gataacccac tcccgattaa cgtggaccac cgcgctggct gcgaggtggg gcgggtgctg 50581 gccgtggtcg acgacccccg cgggccgttt tttgtggggc tgatcgcctg cgtgcagctg 50641 gagcgcgtcc tcgagacggc cgccagcgct gcgattttcg agcgccgcgg gccgccgctc 50701 tcccgggagg agcgcctgtt gtacctgatc accaactacc tgccctcggt ctccctggcc 50761 acaaaacgcc tgggggggcga ggcgcacccc gatcgcacgc tgttcgcgca cgtcgcgctg 50821 tgcgcgatcg ggcggcgcct cggcactatc gtcacctacg acaccggtct cgacgccgcc 50881 atcgcgccct ttcgccacct gtcgccggcg tctcgcgagg gggcgcggcg actggccgcc 50941 gaggccgaga tcgcgctgtc cgggcgcacc tgggcgcccg gcgtggaggc gctgacccac 51001 acgctgcttt ccaccgccgt taacaacatg atgctgcggg accgctggag cctggtggcc 51061 gagcggcggc ggcaggccgg gatcgccgga cacacctacc tccaggcgag cgaaaaattc 51121 aaaatgtggg gggcggagcc tgtttccgcg ccggcgcgcg ggtataagaa cggggccccg 51181 gagtccacgg acataccgcc cggctcgatc gctgccgcgc cgcagggtga ccggtgccca 51241 atcgtccgtc agcgcggggt cgccttgtcc ccggtactgc cccccatgaa ccccgttccg 51301 acatcgggca ccccggcccc cgcgccgccc ggcgacggga gctacctgtg gatcccggcc 51361 tcccattaca accagctcgt cgccggccat gccgcgcccc aaccccagcc gcattccgcg 51421 tttggtttcc cggctgcggc gggggccgtg gcctatgggc ctcacggcgc gggtctttcc 51481 cagcattacc ctccccacgt cgcccatcag tatcccgggg tgctgttctc gggacccagc 51541 ccactcgagg cgcagatagc cgcgttggtg ggggccatag ccgcggaccg ccaggcgggc 51601 ggtcagccgg ccgcgggaga ccctggggtc cgggggtcgg gaaagcgtcg ccggtacgag 51661 gcggggccgt cggagtccta ctgcgaccag gacgaaccgg acgcggacta cccgtactac 51721 cccggggagg ctcgaggcgg gccgcgcggg gtcgactctc ggcgcgcggc ccgccagtct 51781 cccgggacca acgagaccat cacggcgctg atgggggcgg tgacgtcttt gcagcaggaa 51841 ctggcgcaca tgcgggctag gaccagcgcc ccctatggga tgtacacgcc ggtggcgcac 51901 tatcgccctc aggtggggga gccggaacca acaacgaccc acccggccct ttgtcccccg FIGURE 9 (Continued)

Figure 9:
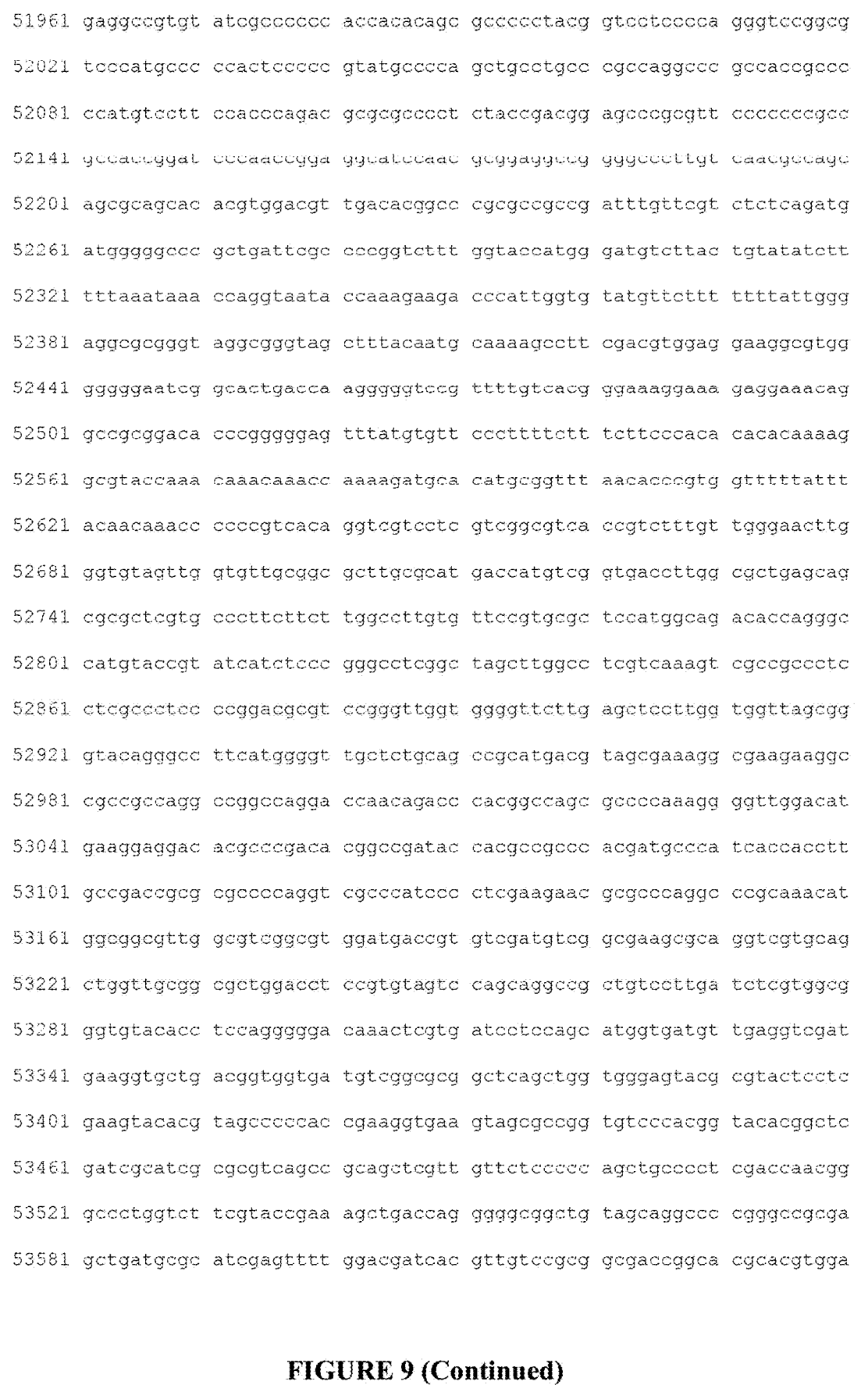

51961 gaggccgtgt atcgcccccc accacacagc gccccctacg gtcctcccca gggtccggcg 52021 tcccatgccc ccactccccc gtatgcccca gctgcctgcc cgccaggccc gccaccgccc 52081 ccatgtcctt ccacccagac gcgcgcccct ctaccgacgg agcccgcgtt cccccccgcc 52141 gccaccggat cccaaccgga ggcatccaac gcggaggccg gggcccttgt caacgccagc 52201 agcgcagcac acgtggacgt tgacacggcc cgcgccgccg atttgttcgt ctctcagatg 52261 atgggggccc gctgattcgc cccggtcttt ggtaccatgg gatgtcttac tgtatatctt 52321 tttaaataaa ccaggtaata ccaaagaaga cccattggtg tatgttcttt ttttattggg 52381 aggcgcgggt aggcgggtag ctttacaatg caaaagcctt cgacgtggag gaaggcgtgg 52441 gggggaatcg gcactgacca agggggtccg ttttgtcacg ggaaaggaaa gaggaaacag 52501 gccgcggaca cccgggggag tttatgtgtt ccctttttctt tcttcccaca cacacaaaag 52561 gcgtaccaaa caaacaaacc aaaagatgca catgcggttt aacacccgtg gtttttattt 52621 acaacaaacc ccccgtcaca ggtcgtcctc gtcggcgtca ccgtctttgt tgggaacttg 52681 ggtgtagttg gtgttgcggc gcttgcgcat gaccatgtcg gtgaccttgg cgctgagcag 52741 cgcgctcgtg cccttcttct tggccttgtg ttccgtgcgc tccatggcag acaccagggc 52801 catgtaccgt atcatctccc gggcctcggc tagcttggcc tcgtcaaagt cgccgccctc 52861 ctcgccctcc ccggacgcgt ccgggttggt ggggttcttg agctccttgg tggttagcgg 52921 gtacagggcc ttcatggggt tgctctgcag ccgcatgacg tagcgaaagg cgaagaaggc 52981 cgccgccagg ccggccagga ccaacagacc cacggccagc gccccaaagg ggttggacat 53041 gaaggaggac acgcccgaca cggccgatac cacgccgccc acgatgccca tcaccacctt 53101 gccgaccgcg cgccccaggt cgcccatccc ctcgaagaac gcgcccaggc ccgcaaacat 53161 ggcggcgttg gcgtcggcgt ggatgaccgt gtcgatgtcg gcgaagcgca ggtcgtgcag 53221 ctggttgcgg cgctggacct ccgtgtagtc cagcaggccg ctgtccttga tctcgtggcg 53281 ggtgtacacc tccaggggga caaactcgtg atcctccagc atggtgatgt tgaggtcgat 53341 gaaggtgctg acggtggtga tgtcggcgcg gctcagctgg tgggagtacg cgtactcctc 53401 gaagtacacg tagcccccac cgaaggtgaa gtagcgccgg tgtcccacgg tacacggctc 53461 gatcgcatcg cgcgtcagcc gcagctcgtt gttctccccc agctgcccct cgaccaacgg 53521 gccctggtct tcgtaccgaa agctgaccag gggcggctg tagcaggccc cgggccgcga 53581 gctgatgcgc atcgagtttt ggacgatcac gttgtccgcg gcgaccggca cgcacgtgga FIGURE 9 (Continued)

53641 gacggccatc acgtcgccga gcatccgcgc gctcacccgc cggcccacgg tggccgaggc 53701 gatggcgttg gggttcagct tgcgggcctc gttccacagg gtcagctcgt gattctgcag 53761 ctcgcaccac gcgatggcaa cgcggcccaa catatcgttg acatggcgct gtatgtggtt 53821 gtacgtaaac tgcagcctgg cgaactcgat ggaggaggtg gtcttgatgc gctccacgga 53881 cgcgttggcg ctggccccgg gcggcggggg cgtggggttt gggggcttgc ggctctgctc 53941 tcggaggtgt tcccgcacgt acagctccgc gagcgtgttg ctgagaaggg gctggtacgc 54001 gatcagaaag cccccattgg ccaggtagta ctgcggctgg cccaccttga tgtgcgtcgc 54061 gttgtacctg cgggcgaaga tgcggtccat ggcgtcgcgg gcgtccttgc cgatgcagtc 54121 ccccaggtcc acgcgcgaga gcgggtactc ggtcaggttg gtggtgaagg tggtggatat 54181 ggcgtcggag gagaatcgga aggagccgcc gtactcggag cgcagcatct cgtccacctc 54241 ctgccacttg gtcatggtgc agaccgacgg gcgctttggc acccagtccc aggccacggt 54301 gaacttgggg gtcgtgagca ggttccgggt ggtcggcgcc gtggcccggg ccttggtggt 54361 gaggtcgcgc gcgtagaagc cgtcgacctg cttgaagcgg tcggcggcgt agctggtgtg 54421 ttcggtgtgc gacccctccc ggtagccgta aaacggggac atgtacacaa agtcgccagt 54481 cgccagcaca aactcgtcgt acgggtacac cgagcgcgcg tccacctcct cgacgatgca 54541 gtttaccgtc gtcccgtacc ggtggaacgc ctccacccgc gaggggttgt acttgaggtc 54601 ggtggtgtgc cagccccggc tcgtgcgggt cgcggcgttg gccggtttca gctccatgtc 54661 ggtctcgtgg tcgtcccggt gaaacgcggt ggtctccagg ttgttgcgca cgtacttggc 54721 cgtggaccga cagacccccct tggcgttgat cttgtcgatc acctcctcga aggggacggg 54781 ggcgcggtcc tcaaagatcc ccataaactg ggagtagcgg tggccgaacc acacctgcga 54841 aacggtgacg tctttgtagt acatggtggc cttgaacttg tacggggcga tgttctcctt 54901 gaagaccacc gcgatgccct ccgtgtagtt ctgaccctcg ggccgggtcg ggcagcggcg 54961 cggctgctcg aactgcacca ccgtggcgcc cgtggggggt gggcacacgt aaaagtttgc 55021 atcggtgttc tccgccttga tgtcccgcag gtgctcgcgc agggtggcgt ggcccgcggc 55081 gacggtcgcg ttgtcgccgg cggggcgcgg cggctttggg ggtttcggtt ttttgttctt 55141 cttcggtttc gggtcccccg ttgggggggc gccaggggcg ggcggcgccg gagtggcagg 55201 gcccccgttc gccgcctggg tcgcggccgc gaccccaggc gtgccggggg aactcggagc 55261 cgccgacacc accaggaccc ccagcgtcaa ccccaagagc gcccatacga cgaaccaccg FIGURE 9 (Continued)

```
55321 gcgcccccgc gcgggggcgc cctggcgcat ggcgggacta cgggggcccg tcgtgccccc
55381 cgtcaggtag cctgggggcg aggtgctgga ggaccgagta gaggatcgag aaaacgtctc
55441 ggtcgtagac cacgaccgac cgggggccga tacagccgtc gggggcgctc tcgacgatgg
55501 ccaccagcgg acagtcggag tcgtacgtga gatatacgcc gggcgggtaa cggtaacgac
55561 cttcggaggt cgggcggctg cagtccgggc ggcgcaactc gagctccccg caccggtaga
55621 ccgaggcaaa gagtgtggtg gcgataatca gctcgcgaat atatcgccag gcggcgcgct
55681 gagtgggcgt tattccggaa atgccgtcaa aacagtaaaa cctctgaaat tcgctgacgg
55741 cccaatcagc acccgagccc cccgccccca tgatgaaccg ggcgagctcc tccttcaggt
55801 gcggcaggag ccccacgttc tcgacgctgt aatacagcgc ggtgttgggg ggctgggcga
55861 agctgtgggt ggagtgatca aagaggggcc cgttgacgag ctcgaagaag cgatgggtga
55921 tgctggggag cagggccggg tccacctggt gtcgcaggag agacgctcgc atgaaccggt
55981 gcgcgtcgaa cacgcccggc gccgagcggt tgtcgatgac cgtgcccgcg cccgccgtca
56041 gggcgcagaa gcgcgcgcgc gccgcaaagc cgttggcgac cgcggcgaac gtcgcgggca
56101 gcacctcgcc gtggacgctg acccgcagca tcttctcgag ctccccgcgc tgctcgcgga
56161 cgcagcgccc caggctggcc aacgaccgct tcgtcaggcg gtccgcgtac agccgccgtc
56221 gctcccgcac gtccgcggcc gcttgcgtgg cgatgtcccc ccacgtctcg ggcccctgcc
56281 ccccgggccc gcggcgacgg tcttcgtcct cgcccccgcc cccgggagct cccaaccccc
56341 gtgccccttc ctctacggcg acacggtccc cgtcgtcgtc ggggcccgcg ccgcccttgg
56401 gcgcgtccgc cgcgcccccc gcccccatgc gcgccagcac gcgacgcagc gcctcctcgt
56461 cgcactgttc ggggctgacg aggcgccgca agagcggcgt cgtcaggtgg tggtcgtagc
56521 acgcgcggat gagcgcctcg atctgatcgt cgggtgacgt ggcctgaccg ccgattatta
56581 gggcgtccac catatccagc gccgccaggt ggctcccgaa cgcgcgatcg aaatgctccg
56641 cccgccgccc gaacagcgcc agttccacgg ccaccgcggc ggtctcctgc tgcaactcgc
56701 gccgcgccag cgcggtcagg ttgctggcaa acgcgtccat ggtggtctgg ccggcgcggt
56761 cgccggacgc gagccagaat cgcaattcgc tgatggcgta caggccgggc gtggtggcct
56821 gaaacacgtc gtgcgcctcc agcagggcgt cggcctcctt gcggaccgag tcattctcgg
56881 gcgacgggtg gggctgcccg tcgcccccccg cggtccgggc cagcgcatgg tccaacacgg
56941 agagcgcccg cgcgcggtcg gcgtccgaca gcccggcggc gtggggcagg taccgccgca
```

FIGURE 9 (Continued)

Figure 9:
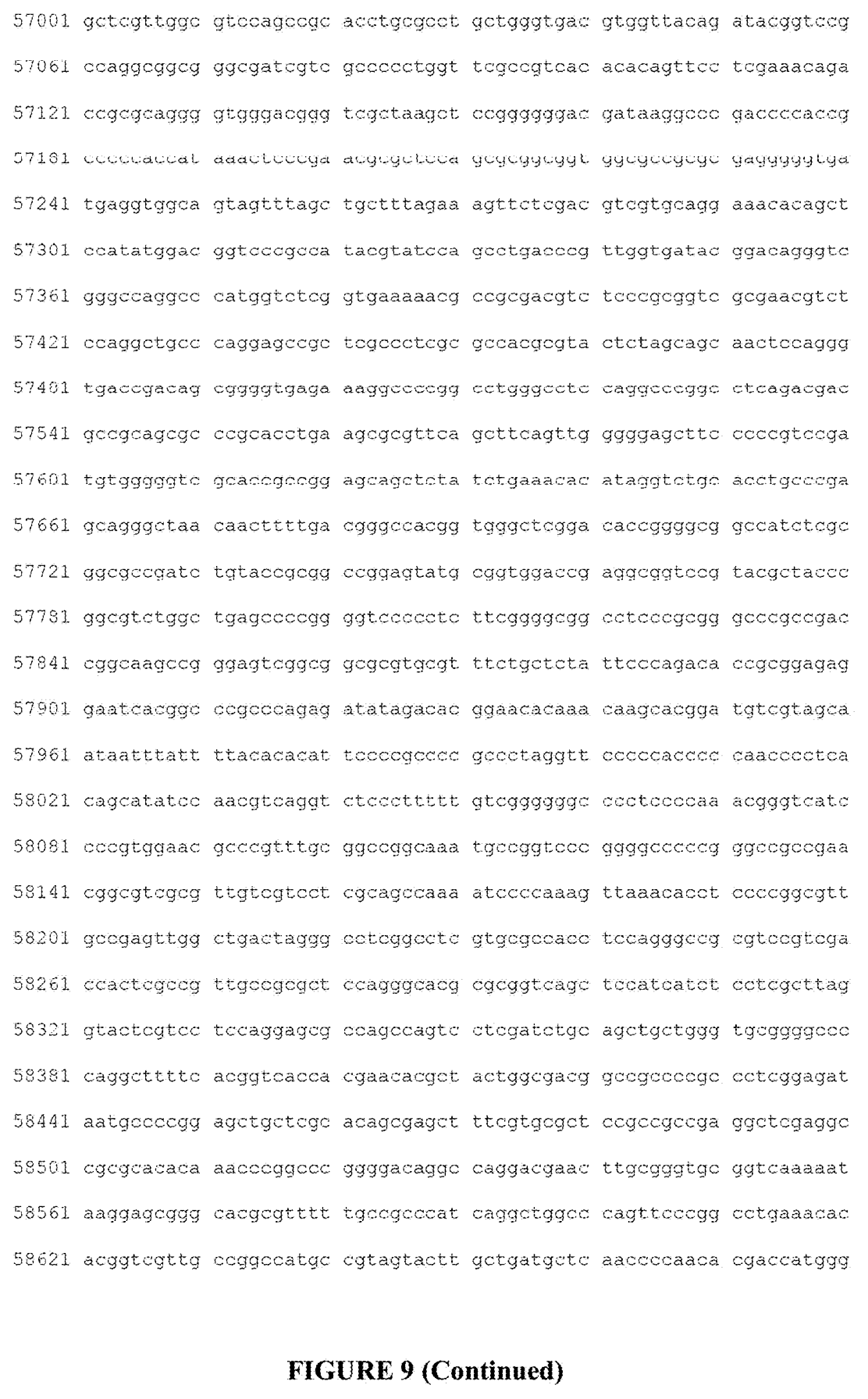

57001 gctcgttggc gtccagccgc acctgcgcct gctgggtgac gtggttacag atacggtccg 57061 ccaggcggcg ggcgatcgtc gccccctggt tcgccgtcac acacagttcc tcgaaacaga 57121 ccgcgcaggg gtgggacggg tcgctaagct ccgggggac gataaggccc gaccccaccg 57181 cccccaccat aaactcccga acgcgctcca gcgcggcggt ggcgccgcgc gagggggtga 57241 tgaggtggca gtagtttagc tgctttagaa agttctcgac gtcgtgcagg aaacacagct 57301 ccatatggac ggtcccgcca tacgtatcca gcctgacccg ttggtgatac ggacagggtc 57361 gggccaggcc catggtctcg gtgaaaaacg ccgcgacgtc tcccgcggtc gcgaacgtct 57421 ccaggctgcc caggagccgc tcgccctcgc gccacgcgta ctctagcagc aactccaggg 57481 tgaccgacag cggggtgaga aaggccccgg cctgggcctc caggcccggc ctcagacgac 57541 gccgcagcgc ccgcacctga agcgcgttca gcttcagttg ggggagcttc ccccgtccga 57601 tgtgggggtc gcaccgccgg agcagctcta tctgaaacac ataggtctgc acctgcccga 57661 gcagggctaa caacttttga cgggccacgg tgggctcgga caccggggcg gccatctcgc 57721 ggcgccgatc tgtaccgcgg ccggagtatg cggtggaccg aggcggtccg tacgctaccc 57781 ggcgtctggc tgagccccgg ggtccccctc ttcggggcgg cctcccgcgg gcccgccgac 57841 cggcaagccg ggagtcggcg gcgcgtgcgt ttctgctcta ttcccagaca ccgcggagag 57901 gaatcacggc ccgcccagag atatagacac ggaacacaaa caagcacgga tgtcgtagca 57961 ataatttatt ttacacacat tcccgcccc gccctaggtt cccccacccc caacccctca 58021 cagcatatcc aacgtcaggt ctccctttt gtcgggggc ccctccccaa acgggtcatc 58081 cccgtggaac gcccgtttgc ggccggcaaa tgccggtccc ggggccccg ggccgccgaa 58141 cggcgtcgcg ttgtcgtcct cgcagccaaa atccccaaag ttaaacacct ccccggcgtt 58201 gccgagttgg ctgactaggg cctcggcctc gtgcgccacc tccagggccg cgtccgtcga 58261 ccactcgccg ttgccgcgct ccagggcacg cgcggtcagc tccatcatct cctcgcttag 58321 gtactcgtcc tccaggagcg ccagccagtc ctcgatctgc agctgctggg tgcggggccc 58381 caggcttttc acggtcacca cgaacacgct actggcgacg gccgccccgc cctcggagat 58441 aatgccccgg agctgctcgc acagcgagct ttcgtgcgct ccgccgccga ggctcgaggc 58501 cgcgcacaca aacccggccc ggggacaggc caggacgaac ttgcgggtgc ggtcaaaaat 58561 aaggagcggg cacgcgtttt tgccgcccat caggctggcc cagttcccgg cctgaaacac 58621 acggtcgttg ccggccatgc cgtagtactt gctgatgctc aaccccaaca cgaccatggg FIGURE 9 (Continued)

58681 gcgcgccgcc atgacgggcc gcagcaggtt gcagctggcg aacatggacg tccacgcgcc 58741 cggatgcgcg tccacggcgt ccatcagcgc gcgggccccg gcctccaggc ccgccccgcc 58801 ctgcgcggac cacgcggccg cagcctgcac gctgggggga cggcgggacc ccgcgatgat 58861 ggccgtaagg gtgttgatga agtacgtcga gtgatcgcag taccgcagaa tctggtttgc 58921 catgtagtac atcgccagct cgctcacgtt gttgggggcc aggttaataa agtttatcgc 58981 gccgtagtcc agggaaaact ttttaatgaa cgcgatggtc tcgatgtcct cgcgcgacag 59041 gagccgggcg ggaagctggt tgcgttggag ggccgtccag aaccactgcg ggttcggctg 59101 gttggacccc gggggcttgc cgttggggaa gatggccgcg tggaactgct tcagcagaaa 59161 gcccagcggt ccgaggagga tgtccacgcg cttgtcgggc ttctggtagg cgctctggag 59221 gctggcgacc cgcgccttgg cggcctcgga cgcgttggcg ctcgcgcccg cgaacaacac 59281 gcggctcttg acgcgcagct ccttgggaaa ccccagggtc acgcgggcaa cgtcgccctc 59341 gaagctgctc tcggcggggg ccgtctggcc ggccgttagg ctgggggcgc agatagccgc 59401 cccctccgag agcgcgaccg tcagcgtttt ggccgacaga aacccgttgt taaacatgtc 59461 catcacgcgc cgccgcagca ccggttggaa ttgattgcga aagttgcgcc cctcgaccga 59521 ctgcccggcg aacacccgt ggcactggct cagggccagg tcctgataca cggcgaggtt 59581 ggatcgccgc ccgagaagct gaagcagggg gcatggcccg cacgcgtacg ggtccagcgt 59641 cagggacatg gcgtggttgg cctcgcccag accgtcgcga aacttgaagt tcctcccctc 59701 caccaggttg cgcatcagct gctccacctc gcggtccacg acctgcctga cgttgttcac 59761 caccgtatgc agggcctcgc ggttggtgat gatggtctcc agccgcccca tggccgtggg 59821 gaccgcctgg tccacgtact gcagggtctc gagttcggcc atgacgcgct cggtcgccgc 59881 gcggtacgtc tcctgcatga tggtccgggc ggtctcggat ccgtccgcgc gcttcagggc 59941 cgagaaggcg gcgtagtttc ccagcacgtc gcagtcgctg tacatgctgt tcatggtccc 60001 gaagacgccg atggctccgc gggcggcgct ggcgaacttg ggatggcgcg cccggaggcg 60061 catgagcgtc gtgtgtacgc aggcgtggcg cgtgtcgaag gtgcacaggt tgcagggcac 60121 gtcggtctgg ttggagtccg cgacgtatcg aaacacgtcc atctcctggc gcccgacgat 60181 cacgccgccg tcgcagcgct ccaggtaaaa cagcatcttg gccagcagcg ccggggaaaa 60241 cccacacagc atggccaggt gctcgccggc aaattcctgg gttccgccga cgagggcgc 60301 ggtgggccga ccctcgaacc cgggcaccac gtgtccctcg cggtccacct gtgggttggc FIGURE 9 (Continued)

60361 cgccacgtgg gtcccgggca cgaggaagaa gcggtaaaag gagggtttgc tgtggtcctt 60421 tgggtccgcc ggaccggcgt cgtccacctc ggtgagatgg agggccgagt tggtgctaaa 60481 taccatggcc cccacgagtc ccgcggcgcg cgccaggtac gccccgacgg cgttggcgcg 60541 ggccgcggcc gtgtcctggc cctcgcacag cggccatgcg gagatgtcgg tgggcggctc 60601 gtcgaagacg gccatcgaca cgatagactc gagggccagg gcggcgtctc cggccatgac 60661 ggaggccagg cgctgttcga acccgcccgc cgggcccttg ccgccgccgt cgcgcccacc 60721 ccgcggggtc ttaccctggc tggcttcgaa ggccgtgaac gtaatgtcgg cggggagggc 60781 ggcgccctcg tggttttcgt caaacgccag gtgggcggcc gcgcgggcca cggcgtccac 60841 gtttcggcat cgcagtgcca cggcggcggg tcccacgacc gcctcgaaca ggaggcggtt 60901 gagggggcgg ttaaaaaacg gaagcgggta ggtaaaattc tccccgatcg atcggtggtt 60961 ggcgttgaac ggctcggcga tgacccggct aaaatccggc atgaacagct gcaacggata 61021 cacgggtatg cggtgcacct ccgccccgcc tatggttacc ttgtccgagc ctcccaggtg 61081 cagaaaggtg ttgttgatgc acacggcctc cttgaagccc tcggtaacga ccagatacag 61141 gagggcgcgg tccgggtcca ggccgaggcg ctcacacagc gcctcccccg tcgtctcgtg 61201 tttgaggtcg ccgggccggg gggtgtagtc cgaaaagcca aaatggcggc gtgcccgctc 61261 gcagagtcgc gtcaggtttg gggcctgggt gttggggtcc aggtgccggc cgccgtgaaa 61321 gacgtacacg gacgagctgt agtgcgatgg cgtcagtttc agggacaccg cggtaccccc 61381 gagccccgtc gtgcgagaac ccacgaccac ggctacgttg gcctcaaagc cgctctccac 61441 ggtcaggccc acgaccaggg gcgccacggc gacgtcggca tcgccgctgc gcgccgacag 61501 taacgccaga agctcgatgc cttcggatgg acacgcgcga gcgtacacgt atcccagggg 61561 cccggggggg accttgatgg tggttgccgt cttgggcttt gtctccatgt cctcctggca 61621 atcggtccgc aaacggaggt aatcccggca cgacgacgga cgcccgacga ggtatgtctc 61681 ccgagcgtca aaatccgggg ggggcggcga cggtcaaggg gagggtggga gaccggggtt 61741 ggggaatgaa tccctaccct tcaccgacaa cccccgggta accacggggt gccgatgaac 61801 cccggcggct ggcaacgcgg ggtccctgcg agaggcacag atgcttacgg tcaggtgctc 61861 cgggccgggt gcgtctgata tgcggttggt atatgtacac tttacctggg ggcgtgccgg 61921 accgcaccag cccctcccac accccgcgcg tcatcagccg gtgggcgnnn nnnnnnnnnn 61981 nnnnnnnnnn nnnnnnnnnn nnnnnnnnnn nnnnnnnnnn nnnnnnnnnn nnnnnnnnnn FIGURE 9 (Continued)

62041 nnnnnnnnnn nnnnnnnnnn nnnnnnnnnt ttttataata gcggccacgc ccaccggcta 62101 cgtcacgctc ctgtcggccg ccggcggtcc ataagcccgg ccggccgggc cgacgcgaat 62161 aaaccgggcc gccggccggg gcgccgcgca gcagctcgcc gcccggatcc gccagacaaa 62221 caaggccctt gcacatgccg gccggggcga gcctgggggt ccggtaattt tgccatccca 62281 cccaagcggc ttttggggtt tttcctcttc cccctcccc acctcccccc tctttagggg 62341 ttcgggtggg aacaaccgcg atgttttccg gtggcggcgg cccgctgtcc cccggaggaa 62401 agtcggcggc cagggcggcg tccgggtttt ttgcgcccgc cggccctcgc ggagccggcc 62461 ggggaccccc gccttgtttg aggcaaaact tttacaaccc ctacctcgcc ccagtcggga 62521 cgcaacagaa gccgaccggg ccaacccagc gccatacgta ctatagcgaa tgcgatgaat 62581 ttcgattcat cgccccgcgg gtgctggacg aggatgcccc cccggagaag cgcgccgggg 62641 tgcacgacgg tcacctcaag cgcgcccccca aggtgtactg cggggggac gagcgcgacg 62701 tcctccgcgt cgggtcgggc ggcttctggc cgcggcgctc gcgcctgtgg ggcggcgtgg 62761 accacgcccc ggcggggttc gaccccaccg tcaccgtctt tcacgtgtat gacatcctgg 62821 agaacgtgga gcacgcgtac ggcatgcgcg cggcccagtt ccacgcgcgg tttatggacg 62881 ccatcacacc gacggggacc gtcatcacgc tcctgggcct gactccggaa ggccaccggg 62941 tggccgttca cgtttacggc acgcggcagt acttttacat gaacaaggag gaggttgaca 63001 ggcacctaca atgccgcgcc ccacgagatc tctgcgagcg catggccgcg gccctgcgcg 63061 agtccccggg cgcgtcgttc cgcggcatct ccgcggacca cttcgaggcg gaggtggtgg 63121 agcgcaccga cgtgtactac tacgagacgc gccccgctct gttttaccgc gtctacgtcc 63181 gaagcgggcg cgtgctgtcg tacctgtgcg acaacttctg cccggccatc aagaagtacg 63241 agggtggggt cgacgccacc acccggttca tcctggacaa ccccgggttc gtcaccttcg 63301 gctggtaccg tctcaaaccg ggccggaaca acacgctagc ccagccgcgg gccccgatgg 63361 ccttcgggac atccagcgat gtcgagttta actgtacggc ggacaacctg gccatcgagg 63421 ggggcatgag cgacctaccg gcatacaagc tcatgtgctt cgatatcgaa tgcaaggcgg 63481 gggggagga cgagctggcc tttccggtgg ccgggcaccc ggaggacctg gtcatccaga 63541 tatcctgtct gctctacgac ctgtccacca ccgccctgga gcacgtcctc ctgttttcgc 63601 tcggttcctg cgacctcccc gaatcccacc tgaacgagct ggcggccagg ggcctgccca 63661 cgcccgtggt tctggaattc gacagcgaat tcgagatgct gttggccttc atgacccttg FIGURE 9 (Continued)

63721 tgaaacagta cggccccgag ttcgtgaccg ggtacaacat catcaacttc gactggccct 63781 tcttgctggc caagctgacg gacatttaca aggtccccct ggacgggtac ggccgcatga 63841 acggccgggg cgtgtttcgc gtgtgggaca taggccagag ccacttccag aagcgcagca 63901 agataaaggt gaacggcatg gtgaacatcg acatgtacgg gattataacc gacaagatca 63961 agctctcgag ctacaagctc aacgccgtgg ccgaagccgt cctgaaggac aagaagaagg 64021 acctgagcta tcgcgacatc cccgcctact acgccgccgg gcccgcgcaa cgcggggtga 64081 tcggcgagta ctgcatacag gattccctgc tggtgggcca gctgtttttt aagtttttgc 64141 cccatctgga gctctcggcc gtcgcgcgct tggcgggtat taacatcacc cgcaccatct 64201 acgacggcca gcagatccgc gtctttacgt gcctgctgcg cctggccgac cagaagggct 64261 ttattctgcc ggacacccag gggcgattta ggggcgccgg gggggaggcg cccaagcgtc 64321 cggccgcagc ccgggaggac gaggagcggc cagaggagga gggggaggac gagaacgaac 64381 gcgaggaggg cgggggcgag cgggagccgg agggcgcgcg ggagaccgcc ggccggcacg 64441 tggggtacca gggggccagg gtccttgacc ccacttccgg gtttcacgtg aaccccgtgg 64501 tggtgttcga ctttgccagc ctgtacccca gcatcatcca ggcccacaac ctgtgcttca 64561 gcacgctctc cctgagggcc gacgcagtgg cgcacctgga ggcgggcaag gactacctgg 64621 agatcgagat gggggggcga cggctgttct tcgtcaaggc tcacgtgcga gagagcctcc 64681 tcagcatcct cctgcgggac tggctcgcca tgcgaaagca gatccgctcg cggattcccc 64741 agagcagccc cgaggaggcc gtgctcctgg acaagcagca ggccgccatc aaggtcgtgt 64801 gtaactcggt gtacgggttc acgggagtgc agcacggact cctgccgtgc ctgcatgttg 64861 ccgcgacggt gacgaccatc ggccgcgaga tgctgctcgc gacccgcgag tacgtccacg 64921 cgcgctgggc ggccttcgaa cagctcctgg ccgatttccc ggaggcggcc gacatgcgcg 64981 cccccgggcc ctattccatg cgcatcatct acggggacac ggactccata tttgtgctgt 65041 gccgcggcct cacggccgcc gggctgacgg ccatgggcga caagatggcg agccacatct 65101 cgcgcgcgct gtttctgccc cccatcaaac tcgagtgcga aaagacgttc accaagctgc 65161 tgctgatcgc caagaaaaag tacatcggcg tcatctacgg gggtaagatg ctcatcaagg 65221 gcgtggatct ggtgcgcaaa aacaactgcg cgtttatcaa ccgcacctcc agggccctgg 65281 tcgacctgct gttttacgac gataccgtat ccggagcggc cgccgcgtta gccgagcgcc 65341 ccgcagagga gtggctggcg cgacccctgc ccgagggact gcaggcgttc ggggccgtcc FIGURE 9 (Continued)

65401 tcgtagacgc ccatcggcgc atcaccgacc cggagaggga catccaggac tttgtcctca
65461 ccgccgaact gagcagacac ccgcgcgcgt acaccaacaa gcgcctggcc cacctgacgg
65521 tgtattacaa gctcatggcc cgccgcgcgc aggtcccgtc catcaaggac cggatcccgt
65581 acgtgatcgt ggcccagacc cgcgaggtag aggagacggt cgcgcggctg gccgccctcc
65641 gcgagctaga cgccgccgcc ccaggggacg agcccgcccc ccccgcggcc ctgccctccc
65701 cggccaagcg cccccgggag acgccgtcgc atgccgaccc cccgggaggc gcgtccaagc
65761 cccgcaagct gctggtgtcc gagctggccg aggatcccgc atacgccatt gcccacggcg
65821 tcgccctgaa cacggactat tacttctccc acctgttggg ggcggcgtgc gtgacattca
65881 aggccctgtt tgggaataac gccaagatca ccgagagtct gttaaaaagg tttattcccg
65941 aagtgtggca ccccccggac gacgtggccg cgcggctccg ggccgcaggg ttcggggcgg
66001 tgggtgccgg cgctacggcg gaggaaactc gtcgaatgtt gcatagagcc tttgatactc
66061 tagcatgagc cccccgtcga agctgatgtc cctcatttta caataaatgt ctgcggccga
66121 cacggtcgga atctccgcgt ccgtgggttt ctctgcgttg cgccggacca cgagcacaaa
66181 cgtgctctgc cacacgtggg cgacgaacct gtaccccggg cacgcggtga gcatccggtc
66241 tatgagccgg tagtgcaggt gggcggacgt gccgggaaag atgacgtaca gcatgtggcc
66301 cccgtaagtg gggtccgggt aaaacaacag ccgcgggtcg cacgccccgc ctccgcgcag
66361 gatcgtgtgg acgaaaaaaa gctcgggttg gccaagaatc ccggccaaga ggtcctggag
66421 gggggcgttg tggcggtcgg ccaacacgac caaggaggcc aggaaggcgc gatgctcgaa
66481 tatcgtgttg atctgctgca cgaaggccag gattagggcc tcgcggctgg tggcggcgaa
66541 ccgcccgtct cccgcgttgc acgcgggaca gcaacccccg atgcctaggt agtagcccat
66601 cccggagagg gtcaggcagt tgtcggccac ggtctggtcc agacagaagg gcagcgacac
66661 gggagtggtc ttcaccaggg gcaccgagag cgagcgcacg atggcgatct cctcggaggg
66721 cgtctgggcg agggcggcga aaaggccccg atagcgctgg cgctcgtgta aacacagctc
66781 ctgtttgcgg gcgtgaggcg gcaggctctt ccgggaggcc cgacgcacca cgcccagagt
66841 cccgccggcc gcagaggagc gcgaccgccg gcgctccttg ccgtgatagg gcccgggccg
66901 ggagccgcgg cgatgggggt cggtatcata cataggtaca cagggtgtgc tccagggaca
66961 ggagcgagat cgagtggcgt ctaagcagcg cgcccgcctc acggacaaat gtggcgagcg
67021 cggtgggctt tggtacaaat acctgatacg tcttgaaggt gtagatgagg gcacgcaacg FIGURE 9 (Continued)

67081 ctatgcagac acgcccctcg aactcgttcc cgcaggccag cttggccttg tggagcagca 67141 gctcgtcggg atgggtggcg gggggatggc cgaacagaac ccaggggtca acctccatct 67201 ccgtgatggc gcacatgggg tcacagaaca tgtgcttaaa gatggcctcg ggccccgcgg 67261 cccgcagcag gctcacaaac cggcccccgt ccccgggctg cgtctcgggg tccgcctcga 67321 gctggtcgac gacgggtacg atacagtcga agaggctcgt gttgttttcc gagtagcgga 67381 ccacggaggc ccggagtctg cgcagggcca gccagtaagc ccgcaccagt aacaggttac 67441 acagcaggca ttctccgccg gtgcgcccgc gcccccggcc gtgtttcagc acggtggcca 67501 tcagagggcc caggtcgagg tcgggctggg catcgggttc ggtaaactgc gcaaagcgcg 67561 gagccacgtc gcgcgtgcgt gccccgcgat gcgcttccca ggactggcgg accgtggcgc 67621 gacgggcctc cgcggcagcg cgcagctggg gccccgactc ccagacggcg gggtgccgg 67681 cgaggagcag caggaccaga tccgcgtacg cccacgtatc cggcgactcc tccggctcgc 67741 ggtccccggc gaccgtctcg aattccccgt tgcgagcggc ggcgcgcgta cagcagctgt 67801 ccccgccccc gcgccgaccc tccgtgcagt ccaggagacg ggcgcaatcc ttccagttca 67861 tcagtgcggt ggtaagcgac ggctgcgtgc cggataccgc cgccgacccc gccccctcct 67921 cgcccccgga ggccaaggtt ccgatgaggg cccgggtggc agactgcgcc aggaacgagt 67981 agttggagta ctgcaccttg gcggctcccg gggagggcga gggcttgggt tgcttctggg 68041 catgccgccc gggcaccccg ccgtcggtac ggaagcagca gtggagaaaa aagtgccggt 68101 ggatgtcgtt tatggtgagg gcaaagcgtg cgaaggagcc gaccagggtc gccttcttgg 68161 tgcgcagaaa gtggcggtcc atgacgtaca caaactcgaa cgcggccacg aagatgctag 68221 cggcgcagtg gggcgccccc aggcatttgg cacagagaaa cgcgtaatcg gccacccact 68281 gaggcgagag gcggtaggtt tgcttgtaca gctcgatggt gcggcagacc agacagggcc 68341 ggtccagcgc gaaggtgtcg atggccgccg cggaaaaggg cccggtgtcc aaaagcccct 68401 ccccacaggg atccgggggc gggttgcggg gtcctccgcg cccgcccgaa ccccctccgt 68461 cgcccgcccc cccgcgggcc cttgaggggg cggtgaccac gtcggcggcg acgtcctcgt 68521 cgagcgtacc gacgggcggc acacctatca cgtgactggc cgtcaggagc tcggcgcaga 68581 gagcctcgtt aagagccagg aggctgggat cgaaggccac atacgcgcgc tcgaacgccc 68641 ccgccttcca gctgctgccg ggggactctt cgcacaccgc gacgctcgcc aggaccccgg 68701 ggggcgaagt tgccatggct gggcgggagg ggcgcacgcg ccagcgaact ttacgggaca FIGURE 9 (Continued)

68761 caatccccga ctgcgcgctg cggtcccaga ccctggagag tctagacgcg cgctacgtct 68821 cgcgagacgg cgcgcatgac gcggccgtct ggttcgagga tatgaccccc gccgagctgg 68881 aggttgtctt cccgactacg gacgccaagc taaactacct gtcgcggacg cagcggctgg 68941 cctccctcct gacgtacgcc gggcctataa aagcgcccga cgacgccgcc gccccgcaga 69001 ccccggacac cgcgtgtgtg cacggcgagc tgctcgcccg caagcgggaa agattcgcgg 69061 cggtcattaa ccggttcctg gacctgcacc agattctgcg ggctgacgc gcgcgctgtt 69121 gggcgggacg gttcgcgaac cctttggtgg gtttacgcgg gcacgcacgc tcccatcgcg 69181 ggcgccatgg cgggactggg caagccctac accggccacc caggtgacgc cttcgagggt 69241 ctcgttcagc gaattcggct tatcgtccca tctacgttgc ggggcgggga cggggaggcg 69301 ggcccctact ctccctccag cctcccctcc aggtgcgcct ttcagtttca tggccatgac 69361 gggtccgacg agtcgtttcc catcgagtat gtactgcggc ttatgaacga ctgggccgag 69421 gtcccgtgca acccttacct gcgcatacag aacaccggcg tgtcggtgct gtttcagggg 69481 ttttttcatc gcccacacaa cgcccccggg ggcgcgatta cgccagagcg gaccaatgtg 69541 atcctggggt ccaccgagac gacggggttg tccctcggcg acctggacac catcaagggg 69601 cggctcggcc tggatgcccg gccgatgatg gccagcatgt ggatcagctg ctttgtgcgc 69661 atgccccgcg tgcagctcgc gtttcggttc atgggccccg aagatgccgg acggacgaga 69721 cggatcctgt gccgcgccgc cgagcaggct attacccgtc gccgccgaac ccggcggtcc 69781 cgggaggcgt acggggccga ggccgggctg ggggtggccg gaacgggttt ccgggccagg 69841 ggggacggtt ttggcccgct ccccttgtta acccaagggc cctcccgccc gtggcaccag 69901 gccctgcggg gtcttaagca cctacggatt ggcccccccg cgctcgtttt ggcggcggga 69961 ctcgtcctgg gggccgctat ttggtgggtg gttggtgctg gcgcgcgcct ataaaaaagg 70021 acgcaccgcc gccctaatcg ccagtgcgtt ccggacgcct tcgccccaca cagccctccc 70081 gaccgacacc cccatatcgc tccccgacct ccggtcccga tggccgtccc gcaatttcac 70141 cgccccagca ccgttaccac cgatagcgtc cgggcgcttg gcatgcgcgg gctcgtcttg 70201 gccaccaata actctcagtt tatcatggat aacaaccacc cacaccccca gggcacccaa 70261 ggggccgtgc gggagtttct ccgcggtcag gcggcggcac tgacggacct tggtctggcc 70321 cacgcaaaca acacgtttac cccgcagcct atgttcgcgg gcgacgcacc ggccgcctgg 70381 ttgcggcccg cgtttggcct gcggcgcacc tattcacctt ttgtcgttcg agaaccttcg FIGURE 9 (Continued)

70441 acgcccggga ccccgtgagg cccagggagt tccttctggg gtgttttaat caataaaaga 70501 ccacaccaac gcacgagcct tgcgtttaat gtcgtgttta ttcaagggag tgggataggg 70561 ttcgacggtt cgaaacttaa cacaccaaat aatcgagcgc gtctagccca gtaacatgcg 70621 cacgtgatgt aggctggtca gcacggcgtc gctgtgatga agcagcgccc ggcgggtccg 70681 ctgtaactgc tgttgtaggc ggtaacaggc gcggatcagc accgccaggg cgctacgacc 70741 ggtgcgttgc acgtagcgtc gcgacagaac tgcgtttgcc gatacgggcg gggggccgaa 70801 ttgtaagcgc gtcacctctt gggagtcatc ggcgtataac gcactgaatg gttcgttggt 70861 tatgggggag tgtggttccc cagggagtgg gtcgagcgcc tcggcctcgg aatccgagag 70921 gaacaacgag gtggcgtcgg agtcttcgtc gtcagagaca tacagggtct gaagcagcga 70981 cacgggcgtg gggtagcgt cgatgtgtag cgcgagggag gatgcccacg aagacacccc 71041 agacaaggag ctgcccgtgc gtggatttgt ggaagacgcg gaagccggga cggatgggcg 71101 gttttgcggt gcccggaacc gaaccgccgg atactccccg ggtgctacat gcccgttttg 71161 gggctggggt tggggctggg gcgcggacag gcggctgacg gtcaaatgcc cccgggggcg 71221 cgcagatgtg gcgggcgtgg ccaccggctg ccgtgtagtg gggcggcggg aaaccgggcc 71281 tccgggcgta acaccgccct ccagcgtcaa gtatgtgggg ggcgggcctg acgtcggggg 71341 cggggtgacg ggttggaccg cgggaggcgg gggagaggga cctgcgggag aggatgaggt 71401 cggctcggcc gggttgcggc ctaaaacagg ggccgtgggg tcggcggggt cccagggtga 71461 agggagggat tcccgcgatt cggacagcga cgcgacagcg gggcgcgtaa ggcgccgctg 71521 cggcccgcct acgggaaccc tggggggggt tggcgcggga cccgaggtta gcgggggggcg 71581 gcggttttcg cccccgggca aaaccgtgcc ggttgcgacc gggggcggaa cgggatcgat 71641 agggagagcg ggagaagcct ggccggcgga ctggggaccg agcgggaggg gcacaccaga 71701 caccaaagcg tggggcgctg gctctggggg tttgggaggg gccgggggc gcgcgaaatc 71761 ggtaaccggg gcgaccgtgt cggggagggc aggcggccgc caaccctggg tggtcgcgga 71821 agcctgggtg gcgcgcgcca gggagcgtgc ccggcggtgt cggcgcgcgc gcgacccgga 71881 cgaagaagcg gcagaagcgc gggaggaggc gggggggcgg ggggcggtgg catcgggggg 71941 cgccggggaa ctttgggggg acggcaagcg ccggacgtcg tcgcgggggc ccacgggcgc 72001 cggccgcgtg ctttcggccg ggacgcccgg tcgtgcttcg cgagccgtga ctgccggccc 72061 agggggccgc ggtgcacact gggatgtggg gacggactga tcggcggtgg gcgaaagggg FIGURE 9 (Continued)

72121 gtccggggca aggaggggcg cggggccgcc ggagtcgtca gacgcgagct cctccaggcc 72181 gtgaatccat gcccacatgc gagggggac gggctcgccg ggggtggcgt cggtgaatag 72241 cgtgggggcc aggcttccgg gccccaacga gccctccgtc ccaacaaggt ccgccgggcc 72301 gggggtcggg ttcgggaccg aggggctctg gtcgtcgggg gcgcgctggt acaccggatg 72361 ccccgggaat agctcccccg acaggaggga ggcgtcgaac ggccgccccga ggatagctcg 72421 tgcgaggaag gggtcctcgt cggtggcgct ggcggcgagg acgtcctcgc cgcccgccac 72481 aaacgggagc tcctcggtgg cctcgctgcc aacaaaccgc acgtcggggg ggccgggggg 72541 tccgggtttt cccacaacac cgcgaccggg gtcatggaga tgtccacgag caccagacac 72601 ggcgggcccc gggcgagggg ccgctcggcg atgagcgcgg acaggcgcgg gagctgtgcc 72661 gccagacacg cgttttcgat cgggttcagg tcggcgtgca ggaggcggac ggcccacgtc 72721 tcgatgtcgg acgacacggc atcgcgcaag gcggcgtccg gcccgcgagc gcgtgagtca 72781 aacagcgtga ggcacagctc cagctccgac tcgcgggaaa aggccgtggt gttgcggagc 72841 gccacgacga cgggcgcgcc caggagcact gccgccagca ccaggtccat ggccgtaacg 72901 cgcgccgcgg gggtgcggtg ggtggcggcg gccggcacgg cgacgtgctg gcccgtgggc 72961 cggtagaggg cgttgggggg agcgggggt gacgcctcgc gcccccccga ggggctcagc 73021 gtctgcccag attccagacg cgcggtcaga agggcgtcga aactgtcata ctctgtgtag 73081 tcgtccggaa acatgcaggt ccaaagagcg gccagcgcgg tgcttgggag acacatgcgc 73141 ccgaggacgc tcaccgccgc cagcgcctgg gcgggactca gctttcccag cgcggcgccg 73201 cgctcggttc ccagctcggg gaccgagcgc cagggcgcca gggggtcggt ttcggacaac 73261 ttgccgcggc gccagtctgc cagccgcgtg ccgaacatga ggcccccgggt cggagggcct 73321 ccggccgaaa acgctggcag cacgcggatg cgggcgtctg gatgcggggt caggcgctgc 73381 acgaatagca tggaatctgc tgcgttctga aacgcacggg ggagggtgag atgcatgtac 73441 tcgtgttggc ggaccagatc caggcgccaa aaggtgtaaa tgtgttccgg ggagctggcc 73501 accagcgcca ccagcacgtc gttctcgtta aaggaaacgc ggtgcctagt ggagctctgg 73561 ggtccgagcg gcggccccgg ggccgccgcg tcacccccc attccagctg ggcccagcga 73621 cacccaaact cgcgcgtgag agtggtcgcg acgagggcga cgtagagctc ggccgccgca 73681 tccatcgagg ccccccatct cgcctggcgg tggcgcacaa agcgtccgaa gagctgaaag 73741 ttggcggcct gggcgtcgct gagggccagc tgaagccggt tgatgacggt gaggacgtac FIGURE 9 (Continued)

73801 atggccgtga cggtcgaggc cgactccagg gtgtccgtcg gaagcggggg gcgaatgcat 73861 gccgcctcgg gacacatcag cagcgcgccg agcttgtcgg tcacggccgg gaagcagagc 73921 gcgtactgca gtggcgttcc atccgggacc aaaaagctgg gggcgaacgg ccgatccagc 73981 gtactggtgg cctcgcgcag caccaggggc cccgggcctc cgctcactcg caggtacgcc 74041 tcgccccggc ggcgcagcat ctgcgggtcg gcctcttggc cgggtggggc ggacgcccgg 74101 gcgcgggcgt ctagggcgcg aagatccacg agcaggggcg cgggcgcggc ggccgcgccc 74161 gcgcccgtct ggcctgtggc cttggcgtac gcgctatata agcccatgcg gcgttggatg 74221 agctcccgcg cgccccggaa ctcctccatc gcccatgggg ccaggtcccc ggccaccgcg 74281 tcgaattccg ccaacaggcc ccccagggta tcaaagttca tctcccaggc caccccttggc 74341 accacctcgt cccgcagccg ggcgctcagg tcggcgtgtt gggccacgcg ccccccgagc 74401 tcctccacgg ccccggcccg ctcggcgctc ttggcgccca ggacgccctg gtacttggcg 74461 ggaaggcgct cgtagtcccg ctgggctcgc agccccgaca cagtgttggt ggtgtcctgc 74521 agggcgcgaa gctgctcgca tgccgcgcga aatccctcgg gcgatttcca ggcccccccg 74581 cgaacgcggc cgaagcgacc ccatacctcg tcccactccg cctcggcctc ctcgagagac 74641 ctccgcaggg cctcgacgcg gcgacgggtg tcgaagagcg cctgcaggcg cgcgccctgt 74701 cgcgtcagga ggcccgggcc gtcgctgctg gccgcgctta gcgggtgcgt ctcaaaggta 74761 cgctgggcat gttccaacca ggcgaccgcc tgcacgtcga gctcgcgcgc cttctccgtc 74821 tggtccaaca gaatttcgac ctgatccgcg atctcctccg ccgagcgcgc ctggtccagc 74881 gtcttggcca cggtcgccgg gacggcgacc accttcagca gggtcttcag attggccaga 74941 ccctcggcct cgagctgggc ccggcgctcg cgcgcggcca gcacatcccg cagccccgcc 75001 gtgacccgct cggtggcttc ggcgcgctgc tgtttggcgc gcaccacggc gtccttggta 75061 tcggccaggt cctgtcgggt cacgaatgcg acgtagtcgg agtacgccgt gtccttcacg 75121 gggctctggt ccacgcgctc cagcgccgcc acgcacgcca ccagcgcgtc ctcgctcggg 75181 cagggcaggg tgacccctgc ccggacaagc tcggcggccg ccgccgggtc gttgcgcacc 75241 gcggatatct cctccgcggc ggcggccagg tccagcgcca cgcttccgat cgcgcgccgc 75301 gcgtcggccc ggagggcgtc caggcgatcg cggatatcca cgtactcggc gtagcccttt 75361 tgaaaaaacg gcacgtactg gcgcagggcc ggcacgcccc ccaagtcttc cgacaggtgt 75421 agtacggcct cgtggtagtc gataaacccg tcgttcgcct gggcccgctc cagcagcccc FIGURE 9 (Continued)

75481 cccgcgagcc gcagaagccg cgccaggggc tcggtgtcca cccgaaacat gtcggcgtac 75541 gtgtcggccg cggccccaaa ggccgcgctc cagtcgatgc ggtgaatggc tgcgagcggg 75601 gggagcatgg ggtggcgctg gttctcgggg gtgtatgggt taaacgcaag ggccgtctcc 75661 agggcaaggg tcaccgcctt ggcgttggtt cccagcgcct gctcggcccg ctttcggaag 75721 tcccgggggt tgtagccgtg cgtgcccgcc agcgcctgca ggcgacggag ctcgaccacg 75781 tcaaactcgg cactgctttc cacgcggtcc agcacggcct ccacgtcggc ggcccagcgc 75841 tcgtggctac tgcgggcgcg ctgggccgcc atcttctctc tgaggtcggc ggtggcggcc 75901 tcaagttcgt cggcgcggcg tcgcgtggcg ccgatgacct ttcccagctc ctgcagggcg 75961 cgcccgctgg gggagtggtc cccggccgtc ccttcggcgt gcaacaggcc cccgaacctg 76021 ccctcgtggc ccgcgaggct ttcccgcgcg ccggtggtcg cgcgcgtcgc ggcttggatc 76081 agggaggcat gctctccctt cggttggttg gcggcccggc gcacctggac gacaaggtcg 76141 gcggcagccg accctaaggt cgtgagctgg gcgatggccc cccgcgcgtc cagggccaac 76201 cgagtcgcct tgacgtatcc cgcggcgctg tcggccatgg ccgctaggaa ggccaggggg 76261 gaggccgggt cgctggcggc cgcgcccagg gccgtcaccg cgtcgaccag gacgcggtgc 76321 gcccgcacgg ccgcatccac cgtcgacgcg gggtctgccg tcgcgacggc ggcgctgccg 76381 gcgttgatgg cgttcgagac ggcgtgggct atgatcgggg cgtgatcggc gaagaactgc 76441 aagagaaacg gagtctcggg ggcgtcggcg aacaggttct tcagcaccac cacgaagctg 76501 ggatgcaagc cggacagagc cgtcgccgtg tccggagtcg ggtgctccag ggcatctcgg 76561 tactgcccca gcagccccca catgtccgcc cgcagcgccg ccgtaacctc agggggcgcc 76621 ccccgaacgg cctcggggag gtccgaccag cccgccggca gggaggcccg cagggtcgcc 76681 aggacggccg gacaggcctt tagccccaca aagtcaggga gggggcgcag gaccccctgg 76741 agtttgtgca agaacttctc ccgggcgtcg cgggccacct tcgcccgctc ccgcgctccc 76801 tcgagcattg cctccaggga gcgcgcgcgc tcccgcaaac ggacacgcgc atcgggggcg 76861 agctctgccg tcagcttggc ggcatccatg gcccgcgcct gccgcagcgc ttcctcggcc 76921 atgcgcgtgg cctctggcga cagcccgccg tcgtcggggt agggcgacgc gccgggcgca 76981 ggaacaaagg ccgcgtcgct gtccagctgc tggcccaggg ccgcatctag ggcgtcgaag 77041 cgccgcagct cggccagacc cgagctgcgg cgcgcctgct ggtcgttaat gtcgcggatg 77101 ctgcgcgcca gctcgtccag cggcttgcgt tctatcagcc cttggttggc ggcgtccgtc FIGURE 9 (Continued)

77161 aggacggaga gccaggccgc caggtcctcg ggggcgtcca gcgtctggcc ccgctgtatc 77221 agatcccgca acaggatggc cgtggggctg gtcgcgatcg ggggcggggc gggaatggcg 77281 gcgcgctgcg cgatgtcccg cgtgtgctgg tcgaagacag gcagggactc gagcagctgg 77341 accacgggca cgacggcggc cgaagccacg tgaaaccggc ggtcgttgtt gtcgctggcc 77401 tgtagagcct tggcgctgta tacggccccc cggtaaaagt actccttaac cgcccccctcg 77461 atcgcccgac gggcctgggt ccgcacctcc tccagccgaa cctgaacggc ctcggggccc 77521 aggggggtg ggcgcggagc cccctgcggg gccgccccgg ccggggcggg cattacgccg 77581 aggggcccgg cgtgctgtga gaccgcgtcg accccgcgag cgagggcgtc gagggcctcg 77641 cgcatctggc gatcctccgc ctccacccta atctcttcgc cacgggcaaa tttggccaga 77701 gcctggactc tatacagaag cggttctggg tgcgtcgggg tggcgggggc aaaaagggtg 77761 tccgggtggg cctgcgagcg ctccagaagc cactcgccga ggcgtgtata cagattggcc 77821 ggcggggccg cgcgaagctg cagctccagg tccgcgagtt ccccgtaaaa ggcgtccgtc 77881 tcccgaatga catccctagc cacaaggatc agcttcgcca gcgccaggcg accgatcaga 77941 gagttttcgt ccagcacgtg ctggacgagg ggcagatggg cggccacgtc ggccaggctc 78001 aggcgcgtgg aggccagaaa gtcccccacg gccgttttcc ggggcagcat gctcagggta 78061 aactccaaca gggcggcggc cgggccggcc accccggcct gggtgtgcgt ccgggccccg 78121 ttctcgatga gaaaggcgag gacgcgttca aagaaaaaaa taacacagag ctccagcagc 78181 cccggagaag ccggatacgg cgaccgtaag gcgctgatgg tgagccgcga acacgcggcg 78241 acctcgcggg ccagggcggc ggagcacgcg gtgaacttaa ccgccgtggc ggccacgttt 78301 gggtgggcct cgaacagctg ggcaaggtct gcgcccgggg gctcgggtga gcggcgagtc 78361 ttcagcgcct cgagggcctg cgaggacgcc ggaaccgtgg gcccgtcgtc ctcgcccgcc 78421 tcggcgaccg gcggcccggc cgggtcgggg ggtgccgagg cgaggacagg ctccggaacg 78481 gaggcgggga ccgcggcccc gacgggggtt ttgcctttgg gggtggattt cttcttggtt 78541 ttggcagggg gggccgagcg tttcgttttc tcccccgaag tcaggtcttc gacgctggaa 78601 ggcggagtcc aggtgggtcg gcggcgcttg ggatggccgg ccgagtagcg tgcccggtgc 78661 cgaccaaccg ggacgacgcc catctccagg acccgcatgt cgtcgtcatc ttcttcggcc 78721 gcctctgcgg cggggggctt gggggcggag ggaggcggtg gtgggatcgc ggagggtggg 78781 tcggcggagg ggggatccgt gggtggggta cccttcaggg ccaccgccca tacatcgtcg FIGURE 9 (Continued)

78841 ggcgcccgat tcgggcgctt ggcctctggt tttgccgacg gaccggccgt cccccgggat 78901 gtctcggagg ccctgtcgtc gcgacgggcc cgggtcggtg gcggcgactg ggcggctgtg 78961 ggcgggtgtg gccccgtgcc ccctaccccc tcccgggggc ccacgccgac gcagggctcc 79021 cccaggcccg cgatctcgcc ccgcaggggg tgcgtgatgg ccacgcgccg ttcgctgaac 79081 gcttcgtcct gcaggtaagt ctcgctggcc ccgtaaagat gcagagccgc ggccgtcaag 79141 tccgcaggag ccgcgggttc cgggcccgac ggcacgaaaa acaccatggc tcccgcccac 79201 cgtacgtccg ggcgatcgcg ggtgtaatac gtcaggtatg gatacatgtc ccccgcccgc 79261 actttggcga tgaacgcggg ggtgccctcc ggaaggccgt gcgggtcaaa aaggtatgcg 79321 gtgtcgccgt ccctgaacag ccccatccct agggggccaa tggttaggag cgtgtacgac 79381 agggggcgca gggcccacgg gccggcgaag aacgtgtgtg cggggcattg tgtctccagc 79441 aggcccgccg cgggctcccc gaagaagccc acctcgccgt atacgcgcga gaagacacag 79501 cgcagtccgc cgcgcgcccc tgggtactcg aggaagttgg ggagctcgac gatcgaacac 79561 atgcgcggcg gcccagggcc cgcggtcgcg cgcgtccact cgccccccctc gaccaaacaa 79621 ccctcgatgg cctccgcgga cagaacgtcg cgagggccca catcaaatat gaggctgaga 79681 aaggacagcg acgagcgcat gcacgatacc gacccccccg gctccaggtc gggcgcgaac 79741 tggttccgag caccggtgac cacgatgtcg cgatcccccc cgcgttccat cgtggagtgc 79801 ggtggggtgc ccgcgatcat atgtgcccta ctggccagag acccggcctg tttatggacc 79861 ggaccccegg ggttagtgtt gtttccgcca cccatgcccc cgtaccatgg ccccggttcc 79921 cctgattagg ctacgagtcg cggtgatcgc ttcccaaaaa ccgagctgcg tttgtctgtc 79981 ttgatcttcc cccccccccc cgcccgcccg cccgcccgcc cgcccgcaca ccataacacc 80041 gagaacaaca cacgggggtg ggcgtaacat aataaagctt tattggtaac tagttaacgg 80101 caagtccgtg ggtggcgcga cggtgtcctc cgggctcatc tcgtcgtcct cgacgggggt 80161 gttggaatga ggcgcccccct cgcggtccgc ctggcgtggg ccgtgcccat aggcctccgg 80221 cttctgtgcg tccatgggca taggcgcggg gagactgttt ccggcgtcgc ggacctccag 80281 gtccctggga gactccggtc cggctaacgg acgaaacgcg gaagcgcgaa acacgccgtc 80341 ggtgacccgc aggagctcgt tcatcagtaa ccaatccata ctcagcgtaa cggccagccc 80401 ctggcgagac agatccacgg agtccggaac cgcggtcgtc tggcccaggg ggccgaggct 80461 gtagtccccc caggccccta ggtcgcgacg gctcgtaagc acgacgcggt cggccgcggg FIGURE 9 (Continued)

80521 gctttgcggg ggggcgtcct cgggcgcatg cgccattacc tctcggatgg ccgcggcgcg 80581 ctggtcggcc gagctgacca agggcgccac gaccacggcg cgctccgtct gcaggccctt 80641 ccacgtgtcg tggagttcct ggacaaactc ggccacgggc tcgggtcccg cggccgcgcg 80701 cgcggcttga tagcaggccg agagacgccg ccagcgcgct agaaactgac ccatgaagca 80761 aaacccgggg acctggtctc ccgacagcag cttcgacgcc cgggtgtgaa tgccggacac 80821 aacggacaga aacccgtgaa tttcgcgccg gaccacggcc agcacgttgt cctcgtgcga 80881 cacctgggcc gccagctcgt cgcacacctc caggtgcgcc gtggtttcgg tgatgacgga 80941 acgcaggctc gcgagggacg cgaccagcgc gcgcttggcg tcgtgataca tgctgcagta 81001 ctgactcacc gcgtccccca tggcctcggg gggccagggc cccaggcggt cgggagtgtc 81061 cccgaccacc gcatacaggc ggcgcccgtc gctctcgaac cgacactcga aaaaggcgga 81121 gagcgtgcgc atgtgcagcc gcagcagcac gatggcgtcc tccagttggc gaatcagggg 81181 gtctgcgcgc tcggcgaggt cctgcagcac cccccgggcg gccagggcgt acatgctaat 81241 caacaggagg ctggtgccca cctcgggggg cgggggggc tgcagctgga ccaggggccg 81301 cagctgctcg acggcacccc tggagatcac gtacagctcc cggagcagct gctctatgtt 81361 gtcggccatc tgcatagtgg ggccgaggcc gccccgggcg gccggttcga ggagggtaat 81421 cagcgcgccc agtttggtgc gatggccctc gaccgtgggg agatagccca gcccaaagtc 81481 ccgggcccag gccaacacac gcagggcgaa ctcgaccggg cgtggaaggt aggccgcgct 81541 acacgtggcc cccaacgcgt ccccgaccac cagggccaga acgtagggga cgaagcccgg 81601 gtcggcgagg acgttggggt gaatgccctc gagggcgggg aagcggatct gggtcgccgc 81661 ggccaggtgg acagaggggg cgtggctggg ctgcccgacg gggagaagcg cggacagcgg 81721 cgtggccggg gtggtggggg tgatgtccca gtgggtctga ccatacacgt cgatccagat 81781 gagcgccgtc tcgcggagaa ggctgggttg accggaacta aagcggcgct cggccgtctc 81841 aaactccccc acgagcgccc gccgcaggct cgccagatgt tccgtcggca cggccggacc 81901 catgatacgc gccagtgtct ggctcagaac gcccccccgac aggccgaccg cctcgcagag 81961 ccgcccgtgc gtgtgctcgc tggcgccctg gacccgcctg aaagttttta cgtagttggc 82021 atagtacccg tattcccgcg ccagaccaaa cacgttcgac cccgcgaggg caatgcaccc 82081 aaagagctgc tggacttcgc cgagtccgtg gccggcgggc gtccgcgcgg ggacgcccgc 82141 cgccagaaac ccctccaggg ccgaaaggta gtgcgtgcag tgcgagggcg tgaacccagc FIGURE 9 (Continued)

82201 gtcgatcagg gtgttgatca ccacggaggg cgaattggta ttctggatca acgtccacgt 82261 ctgctgcagc agagccagca gccgctgctg ggcgccggcg gagggctgct ccccgagctg 82321 cagcaggctg gagacggcag gctggaagac tgccagtgcc gacgaactca ggaacggcac 82381 gtcgggatca aacacggcca cgtccgtccg cacgcgcgcc attagcgtcc ccgggggcgc 82441 acaggccgag cgcgggctga cgcggctgag ggccgtcgac acgcgcacct cctcgcggct 82501 gcgaaccatc ttgttggcct ccagtggcgg aatcattatg gccgggtcga tctcccgcac 82561 ggtgtgctga aactgcgcca acaggggcgg cgggaccaca gcccccccgct cgggggtcgt 82621 caggtactcg tccaccaggg ccaacgtaaa gagggcccgt gtgaggggag tgagggtcgc 82681 gtcgtctatg cgctggaggt gcgccgagaa cagcgtcacc cgattactca ccagggccaa 82741 gaaccggagg ccctcttgca cgaacggggc ggggaagagc aggctgtacg ccggggtggt 82801 aaggttcgcg ctgggctgcc ccaacgggac cggcgccatc ttgagtgacg tctccccaag 82861 ggcctcgatg gaggtccgcg ggctcatggc caagcagctc ttggtgacgg tttgccagcg 82921 gtctatccac tccacggcgc actggcggac gcggaccggc cccagggccg ccgcggtgcg 82981 caggccggcg gaatccagcg catgggacgt gtcggagccg gtgaccgcga ggatggtgtc 83041 cttgatgacc tccatctccc ggaaggcctg gtcgggggcc tcggggagag ccaccaccaa 83101 gcggtgtacg agcaacccgg ggaggttctc ggccaagagc gccgtctccg gaagcccgtg 83161 ggcccggtgg agcgcgcaca ggtgttccag cagcggccgc cagcatgccc gcgcgtctac 83221 cggggcaatg gccgttcccg acaacagaaa cgccgccatg gcggcgcgca gcttggccgt 83281 ggccagaaac gccgggtcgt ccgcccccgtt tgccgtctcg gccgtggggg ttggcggttg 83341 gcgaaggccg gctaggctcg ccaataggcg ctgcataggt ccgtccgagg gcggaccggc 83401 gggtgaggtc gtgacgacgg gggcctcgga cgggagaccg cggtctgcca tgacgcccgg 83461 ctcgcgtggg tgggggacag cgtagaccaa cgacgagatc gggcgggaat gactgtcgtg 83521 cgctgtaggg agcggcgaat tatcgatccc ccgcggccct ccaggaaccc cgcaggcgtt 83581 gcgagtaccc cgcgtcttcg cggggtgtta tacggccact taagtcccgg catcccgttc 83641 gcggacccag gcccggggga ttgtccggat gtgcgggcag cccggacggc gtgggttgcg 83701 gactttctgc ggggcggccc aaatggccct ttaaacgtgt gtatacggac gcgccgggcc 83761 agtcggccaa cacaacccac cggaggcggt agccgcgttt ggctgtgggg tgggtggttc 83821 cgccttgcgt gagtgtcctt tcgacccccc tcccccgggt tttgttaggt cgcgatctgc FIGURE 9 (Continued)

83881 agtcgcaatg aagaccaatc cgctacccgc aaccccttcc gtgtggggcg ggagtaccgt 83941 ggaactcccc cccaccacac gcgataccgc gggacagggc ctgcttcggc gcgtcctgcg 84001 ccccccgatc tctcgccgcg acggcccagt gctccccagg gggtcgggac cccggagggc 84061 ggccagcacg ctgtggttgc ttggcctgga cggcacagac gcgccccctg gggcgctgac 84121 ccccaacgac gataccgaac aggccctgga caagatcctg cggggcacca tgcgcggggg 84181 ggcggccctg atctgctccc cgcgccatca tctaacccgc caagtgatcc tgacggatct 84241 gtgccaaccc aacgcggatc gtgccgggac gctgcttctg gcgctgcggc accccgccga 84301 cctgcctcac ctggcccacc agcgcgcccc gccaggccgg cagaccgagc ggctgggcga 84361 ggcctggggc cagctgatgg aggcgaccgc cctggggtcg gggcgagccg agagcgggtg 84421 cacgcgcgcg ggcctcgtgt cgtttaactt cctggtggcg gcgtgtgccg cctcgtacga 84481 cgcgcgcgac gccgccgatg cggtacgggc ccacgtcacg gccaactacc gcgggacgcg 84541 ggtgggggcg cgcctggatc gtttttccga gtgtctgcgc gccatggttc acacgcacgt 84601 cttcccccac gaggtcatgc ggtttttcgg ggggctggtg tcgtgggtca cccaggacga 84661 gctagcgagc gtcaccgccg tgtgcgccgg gccacaggag gcggcgcaca ccggccaccc 84721 gggccggccc cgctcggccg tgatcctccc ggcgtgtgcg ttcgtggacc tggacgccga 84781 gctggggctg gggggcccgg gtgcggcgtt tctgtacctg gtattcactt accgccagcg 84841 ccgggaccag gagctgtgtt gtgtgtacgt gatcaagagc cagctccccc cgcgcgggtt 84901 ggagccggcc ctggagcggc tgtttgggcg cctccggatc accaacacga ttcacggcac 84961 cgaggacatg acgcccccgg ccccaaaccg aaaccccgac ttccccctcg cgggcctggc 85021 cgccaatccc caaaccccgc gttgctcggc tggccaggtc acgaaccccc agttcgccga 85081 caggctgtac cgctggcagc cggacctgcg ggggcgcccc accgcacgca cctgtacgta 85141 cgccgccttt gcagagctcg gcatgatgcc cgaggatagt ccccgctgcc tgcaccgcac 85201 cgagcgcttt ggggcggtca gcgtccccgt tgtcatcctg gaaggcgtgg tgtggcgccc 85261 cggcgagtgg cgggcatgcg cgtgagcgta gcaaacgccc cgcccacaca acgctccgcc 85321 cccaacccct tccccgctgt cactcgtggt tcgttgaccc ggacgtccgc caaataaagc 85381 cactgaaacc cgaaacgcga gtgttgtaac gtcctttggg cgggaggaag ccacaaaatg 85441 caaatgggat acatggaagg aacacacccc cgtgactcag gacatcggcg tgtccttttg 85501 ggtttcactg aaactggccc gcgccccacc cctgcgcgat gtggataaaa agccagcgcg FIGURE 9 (Continued)

85561 ggtggtttag ggtaccacag gtgggtgctt tggaaacttg tcggtcgccg tgctcctgtg 85621 agcttgcgtc cctccccggt ttcctttgcg ctcccgcctt ccggacctgc tcttgcctat 85681 cttctttggc tctcggtgcg attcgtcagg cagcggcctt gtcgaatctc gaccccacca 85741 ctcgccggac ccgccgacgt cccctctcga gcccaccgaa acccgccgcg tctgttgaaa 85801 tggccagccg cccagccgca tcctctcccg tcgaagcgcg ggccccggtt gggggacagg 85861 aggccggcgg ccccagcgca gccacccagg gggaggccgc cggggcccct ctcgcccacg 85921 gccaccacgt gtactgccag cgagtcaatg gcgtgatggt gctttccgac aagacgcccg 85981 ggtccgcgtc ctaccgcatc agcgatagca actttgtcca atgtggttcc aactgcacca 86041 tgatcatcga cggagacgtg gtgcgcgggc gcccccagga cccgggggcc gcggcatccc 86101 ccgctccctt cgttgcggtg acaaacatcg gagccggcag cgacggcggg accgccgtcg 86161 tggcattcgg gggaacccca cgtcgctcgg cggggacgtc taccggtacc cagacggccg 86221 acgtccccac cgaggccctt gggggccccc ctcctcctcc ccgcttcacc ctgggtggcg 86281 gctgttgttc ctgtcgcgac acacggcgcc gctctgcggt attcgggggg gagggggatc 86341 cagtcggccc cgcggagttc gtctcggacg accggtcgtc cgattccgac tcggatgact 86401 cggaggacac ggactcggag acgctgtcac acgcctcctc ggacgtgtcc ggcggggcca 86461 cgtacgacga cgcccttgac tccgattcgt catcggatga ctccctgcag atagatggcc 86521 ccgtgtgtcg cccgtggagc aatgacaccg cgcccctgga tgtttgcccc gggacccccg 86581 gcccgggcgc cgacgccggt ggtccctcag cggtagaccc acacgcgccg acgccagagg 86641 ccggcgctgg tcttgcggcc gatcccgccg tggcccggga cgacgcggag ggggctttcgg 86701 acccccggcc acgtctggga acgggcacgg cctaccccgt ccccctggaa ctcacgcccg 86761 agaacgcgga ggccgtggcg cgctttctgg gagatgccgt gaaccgcgaa cccgcgctca 86821 tgctggagta cttttgccgg tgcgcccgcg aggaaaccaa gcgtgtcccc cccaggacat 86881 tcggcagccc ccctcgcctc acggaggacg actttgggct tctcaactac gcgctcgtgg 86941 agatgcagcg cctgtgtctg gacgttcctc cggtcccgcc gaacgcatac atgccctatt 87001 atctcaggga gtatgtgacg cggctggtca acgggttcaa gccgctggtg agccggtccg 87061 ctcgccttta ccgcatcctg gggggttctgg tgcacctgcg gatccggacc cgggaggcct 87121 cctttgagga gtggctgcga tccaaggaag tggccctgga ttttggcctg acggaaaggc 87181 ttcgcgagca cgaagcccag ctggtgatcc tggcccaggc tctggaccat tacgactgtc FIGURE 9 (Continued)

87241 tgatccacag cacaccacac acgctggtcg agcgggggct gcaatcggcc ctgaagtatg 87301 aggagtttta cctaaagcgt tttggcgggc actacatgga gtccgtcttc cagatgtaca 87361 cccgcatcgc cggctttttg gcctgccggg ccacgcgcgg catgcgccac atcgccctgg 87421 ggcgagaggg gtcgtggtgg gaaatgttca agttcttttt ccaccgcctc tacgaccacc 87481 agatcgtacc gtcgaccccc gccatgctga acctggggac ccgcaactac tacacctcca 87541 gctgctacct ggtaaacccc caggccacca caaacaaggc gaccctgcgg gccatcacca 87601 gcaacgtcag tgccatcctc gcccgcaacg gggcatcgg gctatgcgtg caggcgttta 87661 acgactccgg ccccgggacc gccagcgtca tgcccgccct caaggtcctt gactcgctgg 87721 tggcggcgca caacaaagag agcgcgcgtc cgaccggcgc gtgcgtgtac ctggagccgt 87781 ggcacaccga cgtgcgggcc gtgctccgga tgaagggggt cctcgccggc gaagaggccc 87841 agcgctgcga caatatcttc agcgccctct ggatgccaga cctgtttttc aagcgcctga 87901 ttcgccacct ggacggcgag aagaacgtca catggaccct gttcgaccgg gacaccagca 87961 tgtcgctcgc cgactttcac ggggaggagt tcgagaagct ctaccagcac ctcgaggtca 88021 tggggttcgg cgagcagata cccatccagg agctggccta tggcattgtg cgcagcgcgg 88081 ccacgaccgg gagccccttc gtcatgttca aagacgcggt gaaccgccac tacatctacg 88141 acacccaggg ggcggccatc gccggctcca acctctgcac cgagatcgtc catccggcct 88201 ccaagcgatc cagtggggtc tgcaacctgg gaagcgtgaa tctggcccga tgcgtctcca 88261 ggcagacgtt tgactttggg cggctccgcg acgccgtgca ggcgtgcgtg ctgatggtga 88321 acatcatgat cgacagcacg ctacaaccca cgccccagtg cacccgcggc aacgacaacc 88381 tgcggtccat gggaatcggc atgcagggcc tgcacacggc ctgcctgaag ctggggctgg 88441 atctggagtc tgccgaattt caggacctga acaaacacat cgccgaggtg atgctgctgt 88501 cggcgatgaa gaccagcaac gcgctgtgcg ttcgcggggc ccgtcccttc aaccacttta 88561 agcgcagcat gtatcgcgcc ggccgctttc actgggagcg ctttccggac gcccggccgc 88621 ggtacgaggg cgagtgggag atgctacgcc agagcatgat gaaacacggc ctgcgcaaca 88681 gccagtttgt cgcgctgatg cccaccgccg cctcggcgca gatctcggac gtcagcgagg 88741 gctttgcccc cctgttcacc aacctgttca gcaaggtgac ccgggacggc gagacgctgc 88801 gccccaacac gctcctgcta aaggaactgg aacgcacgtt tagcgggaag cgcctcctgg 88861 aggtgatgga cagtctcgac gccaagcagt ggtccgtggc gcaggcgctc ccgtgcctgg FIGURE 9 (Continued)

88921 agcccaccca ccccctccgg cgattcaaga ccgcgtttga ctacgaccag aagttgttga 88981 tcgacctgtg tgcggaccgc gccccctacg tcgaccatag ccaatccatg accctgtatg 89041 tcacggagaa ggcggacggg accctcccag cctccaccct ggtccgcctt ctggtccacg 89101 catataagcg cggactaaaa acagggatgt actactgcaa ggttcgcaag gcgaccaaca 89161 gcggggtctt tggcggcgac gacaacattg tctgcacgag ctgcgcgctg tgaccgacaa 89221 accccctccg cgccaggccc gccgccactg tcgtcgccgt cccacgctct cccctgctgc 89281 catggattcc gcggccccag ccctctcccc cgctctgacg gcccttacgg gccagagcgc 89341 gacggcggac ctggcgatcc agattccaaa gtgccccgac cccgagaggt acttctacac 89401 ctcccagtgt cccgacatta accacctgcg ctccctcagc atccttaacc gctggctgga 89461 aaccgagctt gttttcgtgg gggacgagga ggacgtctcc aagctttccg agggcgagct 89521 cagcttttac cgcttcctct tcgctttcct gtcggccgcc gacgacctgg ttacggaaaa 89581 cctgggcggc ctctccggcc tgtttgagca gaaggacatt ctccactact acgtggagca 89641 ggaatgcatc gaagtcgtac actcgcgcgt gtacaacatc atccagctgg tgcttttcca 89701 caacaacgac caggcgcgcc gcgagtacgt ggccggcacc atcaaccacc cggccatccg 89761 cgccaaggtg gactggttgg aagcgcgggt gcgggaatgc gcctccgttc cggaaaagtt 89821 cattctcatg atcctcatcg agggcatctt ttttgccgcc tcgtttgccg ccatcgccta 89881 ccttcgcacc aacaaccttc tgcgggtcac ctgccagtca aacgacctca tcagccggga 89941 cgaggccgtg cacacgacgg cctcgtgtta catctacaac aactacctcg gcgggcacgc 90001 caagcccccg cccgaccgcg tgtacgggct gttccgccag gcggtcgaga tcgagatcgg 90061 atttatccga tcccaggcgc cgacggacag ccatatcctg agcccggcgg cgctggcggc 90121 catcgaaaac tacgtgcgat tcagcgcgga tcgcctgttg ggccttatcc acatgaagcc 90181 actgttttcc gccccacccc ccgacgccag ctttccgctg agcctcatgt ccaccgacaa 90241 acacaccaat tttttcgagt gtcgcagcac ctcctacgcc ggggcggtcg tcaacgatct 90301 gtgagtgtcg cggcgcgctt ctacccgtgt ttgcccataa taaacctctg aaccaaactt 90361 tgggtctcat tgtgattctt gtcagggacg cgggggtggg agaggataaa aggcggcgca 90421 aaaagcagta accaggtccg tccagattct gcgggcatag aataccataa ttttattggt 90481 gggtcgtttg ttcggggaca agcgcgctcg tctgacgttt gggctactcg tcccagaatt 90541 tggccaggac gtccttgtag aacgcgggtg ggggggcctg ggtccgcaac tgctccagaa FIGURE 9 (Continued)

90601 acctgtcggc gatatcaggg gccgtgatat gccgggtcac gatagatcgc gccaggtttt 90661 cgtcgcggat gtcctggtag ataggcaggc gtttcagaag agtccacggc ccccgctcct 90721 tggggccgat aagcgatatg acgtacttaa tgtagcggtg ttccaccagc tcggtgatgg 90781 tcatgggatc ggggagccag tccagggact ctggggcgtc gtggatgacg tggcgtcgcc 90841 ggttggccac ataactgcgg tgctcttcca gcagctgcgc gttcgggacc tggacgagct 90901 cgggcggggt gagtatctcc gaggaggacg acctggggcc ggggtggccc ccggtaacgt 90961 cccggggatc cagggggagg tcctcgtcgt cttcgtatcc gccggcgatc tgttgggtta 91021 gaatttcggt ccacgagacg cgcgtctcgg tgccgccggc ggccggcggc agagggggcc 91081 tggtttccgt ggagcgcgag ctggtgtgtt cccggcggat ggcccgccgg gtctgagagc 91141 gactcggggg ggtccagtga cattcgcgca gcacatcctc cacggaggcg taggtgttat 91201 tgggatggag gtcggtgtgg cagcggacaa agagggccag gaactggggg tagctcatct 91261 taaagtactt cagtatatcg cgacagttga tcgtgggaat gtagcaggcg ctaatatcca 91321 acacaatatc acagcccatc aacaggaggt cagtgtccgt ggtgtacacg tacgcgaccg 91381 tgttggtgtg atagaggttg gcgcaggcat cgtccgcctc caactgaccc gagttaatgt 91441 aggcgtaccc cagggcccgg agaacgcgaa tacagaacag atgcgccaga cgcagggccg 91501 gcttcgaggg cgcggcggac ggcagcgcgg ctccggaccc ggccgtcccc cgggtccccg 91561 aggccagaga ggtgccgcgt cggcgcatgt tggaaaaggc agagctgggt ctggagtcgg 91621 tgatggggga aggcggtgga gaggcgtcca cgtcactggc ctcctcgtcc gtccggcact 91681 gggccgtcgt gcgggccagg atggccttgg ctccaaacac aaccggctcc atacaattga 91741 ccccgcgatc ggtaacgaag atggggaaaa gggacttttg ggtaaacacc tttaataagc 91801 gacagaggca gtgtagcgta atggcctcgc ggtcgtaact ggggtatcgg cgctgatatt 91861 tgaccaccaa cgtgtacatg acgttccaca ggtccacggc aatgggggtg aagtacccgg 91921 ccggggcccc aaggccccgg cgcttgacca gatggtgtgt gtgggcaaac ttcatcatcc 91981 cgaacaaacc catgtcaggt cgattgtaac tgcggatcgg cctaactaag gcgtggttgg 92041 tgcgacggtc cgggacaccc gagcctgtct ctctgtgtat ggtgacccag acaacaacac 92101 cgacacaaga ggacaataat ccgttagggg acgctcttta taatttcgat ggcccaactc 92161 cacgcggatt ggtgcagcac cctgcatgcg ccggtgcggg ccaaccttcc ccccgctcat 92221 tgcctcttcc aaaagggtgt ggcctaacga gctgggggcg tatttaatca ggctagcgcg

FIGURE 9 (Continued)

92281 gcgggcctgc cgtagtttct ggctcggtga gcgacggtcc ggttgcttgg gtcccctggc 92341 tgccatcaaa accccaccct cgcagcggca tacgccccct ccgcgtcccg cacccgagac 92401 cccggcccgg ctgccctcac caccgaagcc cacctcgtca ctgtggggtg ttcccagccc 92461 gcgttgggat gacggattcc cctggcggtg tggccccccgc ctcccacgtg gaggacgcgt 92521 cggacgcgtc cctcgggcag ccggaggagg gggcgccctg ccaggtggtc ctgcagggcg 92581 ccgaacttaa tggaatccta caggcgtttg ccccgctgcg cacgagcctt ctggactcgc 92641 ttctggttat gggcgaccgg ggcatcctta tccataacac gatctttggg gagcaggtgt 92701 tcctgcccct ggaacactcg caattcagtc ggtatcgctg gcgcggaccc acggcggcgt 92761 tcctgtctct cgtggaccag aagcgctccc tcctgagcgt gtttcgcgcc aaccagtacc 92821 cggacctacg tcgggtggag ttggcgatca cgggccaggc cccgtttcgc acgctggttc 92881 agcgcatatg gacgacgacg tccgacggcg aggccgttga gctagccagc gagacgctga 92941 tgaagcgcga actgacgagc tttgtggtgc tggttcccca gggaaccccc gacgttcagt 93001 tgcgcctgac gaggccgcag ctcaccaagg tccttaacgc gaccggggcc gatagtgcca 93061 cgcccaccac gttcgagctc ggggttaacg gcaaaatttc cgtgttcacc acgagtacct 93121 gcgtcacatt tgctgcccgc gaggagggcg tgtcgtccag caccagcacc caggtccaga 93181 tcctgtccaa cgcgctcacc aaggcgggcc aggcggccgc caacgccaag acggtgtacg 93241 gggaaaatac ccatcgcacc ttctctgtgg tcgtcgacga ttgcagcatg cgggcggtgc 93301 tccggcgact gcaggtcggc gggggcaccc tcaagttctt cctcacgacc cccgtcccca 93361 gtctgtgcgt caccgccacc ggtcccaacg ctgtatcggc ggtatttctc ctgaaacccc 93421 agaagatttg cctggactgg ctgggtcata gccaggggtc tccttcagcc gggagctcgg 93481 cctcccgggc ctctgggagc gagccaacag acagcaagga ctccgcgtcg gacgcggtca 93541 gccacggcga tccggaagac ctcgatggcg ctgcccgggc gggagaggcg ggggcctcgc 93601 acgcctgtcc gatgccgtcg tcgaccacgc gggtcactcc cacgaccaag cgggggcgct 93661 cgggggggcga ggatgcgcgc gcggacacgg ccctaaagaa acctaagacg gggtcgccca 93721 ccgcaccccc gcccgcagat ccagtccccc tggacacgga ggacgactcc gatgcggcgg 93781 acgggacggc ggcccgtccc gccgctccag acgcccggag cggaagccgt tacgcgtgtt 93841 actttcgcga cctcccgacc ggagaagcaa gccccggcgc cttctccgcc ttccgggggg 93901 ggccccaaac cccgtatggt tttggattcc cctgacgggg cggggccttg gcggccgccc FIGURE 9 (Continued)

93961 aactctcgca ccatcccggg ttaatgtaaa taaacttggt attgcccaac actctcccgc 94021 gtgtcgcgtg tggttcatgt gtgtgcctgg cgtcccccac cctcgggttc gtgtatttcc 94081 tttccctgtc cttataaaag ccgtatgtgg ggcgctgacg gaaccacccc gcgtgccatc 94141 acggccaagg cgcgggatgc tccgcaacga cagccaccgg gccgcgtccc cggaggacgg 94201 ccagggacgg gtcgacgacg gacggccaca cctcgcgtgc gtgggggccc tggcgcgggg 94261 gttcatgcat atctggcttc aggccgccac gctgggtttt gcgggatcgg tcgttatgtc 94321 gcgcgggccg tacgcgaatg ccgcgtctgg ggcgttcgcc gtcgggtgcg ccgtgctggg 94381 ctttatgcgc gcaccccctc ccctcgcgcg gcccaccgcg cggatatacg cctggctcaa 94441 actggcggcc ggtggagcgg cccttgttct gtggagtctc ggggagcccg gcacgcagcc 94501 gggggccccg gccccgggcc cggccaccca gtgcctggcg ctgggcgccg cctatgcggc 94561 gctcctggtg ctcgccgatg acgtctatcc gctctttctc ctcgccccgg ggcccctgtt 94621 cgtcggcacc ctggggatgg tcgtcggcgg gctgacgatc ggaggcagcg cgcgctactg 94681 gtggatcggt gggcccgccg cggccgcctt ggccgcggcg gtgttggcgg gcccgggggc 94741 gaccaccgcc agggactgct tctccagggc gtgccccgac caccgccgcg tctgcgtcat 94801 cgtcgcaggc gagtctgttt cccgccgccc cccggaggac ccagagcgac ccggggaccc 94861 cgggccaccg tcccccccga caccccaacg atcccagggg ccgccggccg atgaggtcgc 94921 accggccggg gtagcgcggc ccgaaaacgt ctgggtgccc gtggtcacct ttctgggggc 94981 gggcgcgctc gccgtcaaga cggtgcgaga acatgcccgg ggaacgccgg gcccgggcct 95041 gccgctgtgg ccccaggtgt ttctcggagg ccatgtggcg gtggccctga cggagctgtg 95101 tcaggcgctt gcgccctggg accttacgga cccgctgctg tttgttcacg ccggactgca 95161 ggtcatcaac ctcgggttgg tgtttcggtt ttccgaggtt gtcgtgtatg cggcgctagg 95221 gggtgccgtg tggatttcgt tggcgcaggt gctggggctc cggcgtcgcc tgcgcaggaa 95281 ggaccccggg gacggggccc ggttggcggc gacgcttcgg ggcctcttct tctccgtgta 95341 cgcgctgggg tttggggtgg gggcgctgct gtgccctccg gggtcaacgg gcgggcggtc 95401 gggcgattga tatatttttc aataaaaggc attagtcccg aagaccgccg gtgtgtgatg 95461 atttcgccat aacacccaaa ccccggatgg ggcccgggta taaattccgg aaggggacac 95521 gggctaccct cactaccgag ggcgcttggt cgggaggccg catcgaacgc acaccccccat 95581 ccggtggtcc gtgtggaggt cgttttcagt gcccggtctc gctttgccgg gaacgctagc FIGURE 9 (Continued)

95641 cgatccctcg cgagggggag gcgtagggca tggccccggg gcgggtgggc cttgccgtgg 95701 tcctgtggag cctgttgtgg ctcggggcgg gggtgtccgg gggctcggaa actgcctcca 95761 ccgggcccac gatcaccgcg ggagcggtga cgaacgcgag cgaggccccc acatcggggt 95821 cccccgggtc agccgccagc ccggaagtca cccccacatc gaccccaaac cccaacaatg 95881 tcacacaaaa caaaaccacc cccaccgagc cggccagccc cccaacaacc cccaagccca 95941 cctccacgcc caaaagcccc cccacgtcca cccccgaccc caaacccaag aacaacacca 96001 cccccgccaa gtcgggccgc cccactaaac cccccgggcc cgtgtggtgc gaccgccgcg 96061 acccattggc ccggtacggc tcgcgggtgc agatccgatg ccggtttcgg aattccaccc 96121 gcatggagtt ccgcctccag atatggcgtt actccatggg tccgtccccc ccaatcgctc 96181 cggctcccga cctagaggag gtcctgacga acatcaccgc cccacccggg ggactcctgg 96241 tgtacgacag cgcccccaac ctgacggacc cccacgtgct ctgggcggag gggccggcc 96301 cgggtgccga ccctccgttg tattctgtca ccgggccgct gccgacccag cggctgatta 96361 tcggcgaggt gacgcccgcg acccagggaa tgtattactt ggcctggggc cggatggaca 96421 gcccgcacga gtacgggacg tgggtgcgcg tccgcatgtt ccgccccccg tctctgaccc 96481 tccagcccca cgcggtgatg gagggtcagc cgttcaaggc gacgtgcacg gccgacgcct 96541 actacccgcg taaccccgtg gagttggtct ggttcgagga cgaccgccag gtgtttaacc 96601 cgggccagat cgacacgcag acgcacgagc accccgacgg gttcaccacc gtctctaccg 96661 tgacctccga ggctgtcggc ggccaggtcc ccccgcggac cttcacctgc cagatgacgt 96721 ggcaccgcga ctccgtgaca ttctcgcgac gcaatgccac cgggctggcc ctggtgctgc 96781 cgcggccaac catcaccatg gaatttgggg tccggcatgt ggtctgcacg gccggctgcg 96841 tccccgaggg cgtgacgttt gcctggttcc tgggggacga cccctcaccg gcggctaagt 96901 cggccgttac ggcccaggag tcatgcgacc accccgggct ggctacggtc cggtccaccc 96961 tgcccatttc gtacgactac agcgagtaca tctgtcggtt gaccggatat ccggccggga 97021 ttcccgttct agaacaccac ggcagtcacc agcccccacc cagggacccc accgagcggc 97081 aggtgatcga ggcgatcgag tgggtgggga ttggaatcgg ggttctcgcg gcgggggtcc 97141 tggtcgtaac ggcgatcgtg tacgtcgtcc gcacatcaca gtcgcggcag cgtcatcggc 97201 ggtaacgcga gacccccccg ttaccttttt aatatctata tagtttggtc ccccctctat 97261 cccgcccacc gctgggcgct ataaagccgc caccctctct tccctcaggt catccttggt FIGURE 9 (Continued)

97321 cgatcccgaa cgacacacgg cgtggagcaa aacgcctccc cctgagccgc tttcctacca 97381 acacaccggc atgcctctgc gggcatcgga acacgcctac cggcccctgg gccccgggac 97441 accccccatg cgggctcggc tccccgccgc ggcctgggtt ggcgtcggga ccatcatcgg 97501 gggagttgtg atcattgccg cgttggtcct cgtgccctcg cgggcctcgt gggcactttc 97561 cccatgcgac agcggatggc acgagttcaa cctcgggtgc atatcctggg atccgacccc 97621 catggagcac gagcaggcgg tcggcggctg tagcgccccg gcgaccctga tcccccgcgc 97681 ggctgccaaa cagctggccg ccgtcgcacg cgtccagtcg gcaagatcct cgggctactg 97741 gtgggtgagc ggagacggca ttcgggcctg cctgcggctc gtcgacggcg tcggcggtat 97801 tgaccagttt tgcgaggagc ccgcccttcg catatgctac tatccccgca gtcccggggg 97861 ctttgttcag tttgtaactt cgacccgcaa cgcgctgggg ctgccgtgag gcgcgtgtac 97921 tgcggtctgt ctcgtctcct cttctcccct tccctccccc tccgcatccc aggatcacac 97981 cggccaacga gggttggggg gtccggcacg gacccaaaat aataaacaca caatcacgtg 98041 cgataaaaag aacacgcggt cccctgtggt gtttttggtt atttttatta aatctcgtcg 98101 acaaacaggg ggaaaggggc gtggtctagc gacggcagca cgggcggagg cgttcaccgg 98161 ctccggcgtc cttcgcgttt aagcttggtc aggagggcgc tcagggcggc gacgttggtc 98221 gggccgtcgt tggtcagggc gttggctcga tggcgggcga ggacgggcga ggggctcaac 98281 ggcgggggcg ggggcccggt gcggcccggg ggggaaaata gggcggatcc cccccagtcg 98341 tacaggggat tttccgcctc aatgtacggg gaggccggcg ctgcattcgc cgtgttcacg 98401 cagacgtttt cgtagacccg catccatggt atttcctcgt agacacgccc cccgtcctcg 98461 cgcaccgtct cgtatattga ctcgtcgtcc tcgtaggggg cgtgccgttc gcgggccgag 98521 gcggcgtggg tggctttgcg gcgggcgtcg tcgtcgtcgt cgtcggccgt cagatacgtg 98581 gcttccatct ggtcgggttc tccctccggg gcgggtcccc acacccgtgg ccgatcgagg 98641 ctccccagag acgcgcgccg gacgaggagg gggcacgtcg ccgccggcgg tcgcctgtcg 98701 ggtcccgcga cgttacgggc cgggaggcgc gggggcacct cccccatgtg cgtgtaatac 98761 gtggccggct gtgcggccgc agcgggggc tcggcgaccg ggtcgttcgc atccggaagc 98821 gggggccccg cgccgtccgc gcggcgcctc cggaacctcc gggtggacgc gggggtcgag 98881 tgtaggcgag gtcgggggag gggcgggggc tcgttgtcgc gccgcgcccg ctgaatcttt 98941 tcccgacagg tcccaccccc cgcgcgatgc ccccccgggc cgctggccat gtcgtccggg FIGURE 9 (Continued)

99001 ggaggccccg cggaccacgt cgtccggcga gacgccacga gccgcaggat ggactcgtag 99061 tggagcgacg gcgccccgct gcggagcaga tccgcggcca gggcggcccc gaaccaagcc 99121 ttgatgctca actccatccg ggcccagctg gggcggtca tcgtggggaa caggggggcg 99181 gtggtccgac agaaacgctc ctggctgtcc accgcggccc gcagatactc gttgttcagg 99241 ctgtcggtgg cccagacgcc gtacccggtg agggtcgcgt tgatgatata ctgggcgtgg 99301 tgatggacga tcgacagaac ctccaccgtg gatacgacgg tatccacggt cccgtacgta 99361 ccgccgctcc gcttgccggt ctgccacagg ttggctaggc gcgtcaggtg gcccaggacg 99421 tcgctgaccg ccgccctgag cgccatgcac tgcatggagc cggttgtgcc gctgggaccc 99481 cggtccagat ggcgcgcgaa cgtttccgcg ggcgcctccg ggctgccgcc gagcgggagg 99541 aaccggcgat tggagggact cagccggtga catacgtgct tgtctgtcgt ccacagcatc 99601 caggacgccc accggtacag cacggagacg taggccagga gctcgttgag ccgcagtgcg 99661 gtgtcggtgc tggggcggct tgggtccgcc gggcgcataa agaacatgta ctgctgaatc 99721 cgatggaggg cgtcgcgcag gccggccacg gtggcggcgt acttggccgc cacggccccg 99781 ctcttgaacg gggtgcgcgc cagcagcttt ggcgccaggg tgggccgcag cagcacgtga 99841 aggctggggt cgcagtcgcc cacggggtcc tcggggacgt ccaggccgct gggcaccacc 99901 gtctgcaggt acttccagta ctgcgtgagg atggcgcggc tcaactggcc gccgggcagc 99961 tccacctcgc ccagcgcctg ggtggcggcc gaagcgtagt gccggatgta ctcgtagtgc 100021 gggtcgctgg cgagcccgtc cacgatcaaa ctctcgggaa ccgtgttgtg ttgccgcgcg 100081 gccaaccgga cgctgcgatc ggtgcaggtc agaaacgccg gctgcgcgtc gtcggagcgc 100141 tgccgcaagg cgcccacggc cgcgctaagg agcccctccg gggtggggag cagacacccg 100201 ccgaagatgc gccgctcggg aacgcccgcg ttgtcgccgc ggatcaggtt ggcaggcgtc 100261 aggcaccgcg ccagccgcag ggagctcgcg ccgcgcgtcc ggcgctgcat ggtgacgccc 100321 gttcggtcgg gacccgccgg tcggagttat gccgcgtcca gggccatcgg ggcgcttttt 100381 atcgggagga gcttatgggc gtggcgggcc tcccagcccg gtcgcgcgcc tccccgacac 100441 gtgcgcccgc agggcggcgg ccccctcgtc tcccatcagc agtttcctaa actgggacat 100501 gatgtccacc acgcggaccc gcgggcccaa cacggacccg ccgcttacgg gggcgggggg 100561 gaagggctcc aggtccttga gaagaaaggc ggggtctgcc gtcccggaca cgggggcccg 100621 gggcgctgag gaggcggggc gcagatccac gtgctccgcg gccgcgcgga cgtccgccca FIGURE 9 (Continued)

100681 gaacttggcg gggtggtgc gcgcgtacag gggctgggtc gctcggagga cgcacgcgta 100741 gcgcaggggg gtgtacgtgc ccacctcggg ggccgtgaat cccccgtcaa acgcggccag 100801 tgtcacgcac gccaccacgg tgtcggcaaa gcccagcagc cgctgcagga cgagcccggc 100861 ggccagaatg gcgcgcgtgg ccgccgcgtc gtcccggcgc cggtgcgcgt ccccgcacgc 100921 ccgggcgtac tttaaggtca cggtcgccag ggccgtgtgc agcgcgtaca ccgcagcgcc 100981 cagcacggcg ttgagcccgc tgttggcgag cagccggcgc gctgcggtgt cgcccagcgc 101041 ctcgtgctcg gcccccacga ccgcggggct tcccaggggc agggcgcgaa acagctcctc 101101 ccgcgccacg tccgcaaagg cggggtggtg cacgtgcggg tgcaggcgcg cccccacgac 101161 caccgagagc cactggaccg tctgctccgc catcaccgcc agcacatcca gcacgcgccc 101221 caggaaggcg gcctcccgcg tcaaaacgca ccggacggcg tcgggattga agcgggcgag 101281 cagggccccg gtggccaggt acgtcatgcg gccggcatag cgggcggcca cgcgacagtc 101341 gcggtccagc agcgcgcgca ccccgggcca gtacagcagg gaccccagcg agctgcggaa 101401 caccgcggcg tcggggccgg attgggggga cactaacccc cccgcgctca gtaacggcac 101461 ggccgcggcc ccgacgggac gcaacgccgt gaggctcgcg aactgccgcc tcagctcggc 101521 cgccctgtcg tccaggtcag acccgcgcgc ctccgcgtga aggcgcgtcc cgcacaccca 101581 cccgttgatg gccagccgca cgacggcatc cgccaaaaag ctcatcgcct gggcggggct 101641 ggtttttgtt cgacgatccg tcaggtcaag aatcccatcg cccgtgatat accaggccaa 101701 cgcctcgccc tgctgcaggg tttggcggaa aaacaccgcg gggttgtcgg gggaggcgaa 101761 gtgcatgacc cccacgcgcg ataacccgaa cgcgctatcc ggacacgggt aaaacccggc 101821 cggatgcccc agggctaggg cggagcgcac ggactcgtcc cacacggcaa cctgaggggc 101881 cagtcgatcc aacgggaatg ccgcccggag ctccgggccc ggcacgcgtc cctccagaac 101941 ctccaccttg ggcggggaac gggccccgcc gccgtcctcc ggcccgacgg cttccgggta 102001 gtcgtcctcc tcgtactgca gctcctctag gaacagcggc gacggcgcca cccgcgaacc 102061 gccgacccgc cccaaaatag cccgcgcgtc gacgggaccc aggtatcccc cctgccgggc 102121 ctgcggagga ccgcggggaa cctcatcatc atcgtccagg cgaccgcgca ccgactggct 102181 acgggccgca tcgggcccgg ggcgctgccg ggacgctcgg cgatgggatg tgggcggggc 102241 ttccgacgcg cgccgtcgtc gggctcgcgg gccttcccgt cgacggcgca cgggcggctc 102301 gtcgcccgcc atctcctcca gagcctctag ctcgctgtcg tcatccccgc ggaacaccgc FIGURE 9 (Continued)

102361 acgcaggtac cccatgaacc ccacccccatc gcccgctggc tcgtccgcca cgggcgaggc
102421 gcgggggcgg gtggatgcgc gcctcctgcg ccccgcgggt tcgcgagccg acatggtggc
102481 gatagacgcg ggttatcgga tgtccgctac cccccaaaaa agaaaaagac cccacagcgc
102541 ggatggaggc cggggtaggt gccgccggac cccctcgcga tgggaatgga cgggagcgac
102601 ggggccggcg caaaaaaacg cagtatctcc cgcgaaggct acccgccgcc ccagcccccg
102661 gccaaatgcg gaaacggtcc cgcgctctcg cctttatacg cgggccgccc tgcgacacaa
102721 tcacccgtcc gtggtttcga atctacacga caggcccgca gacgcggcta acacacacgc
102781 cggcaaccca gaccccagtg ggttggttgc gcggtcccgt ctcctggcta gttctttccc
102841 ccaccaccaa ataatcagac gacaaccgca ggttttgtaa tgtatgtgct cgtgtttatt
102901 gtggatacga accggtgacg ggaggggaaa acccagacgg gggatgcggg tccggtcgcg
102961 ccccctaccc accgtactcg tcaattccaa gggcatcggt aaacatctgc tcaaactcga
103021 agtcggccat atccagagcg ccgtaggggg cggagtcgtg gggggtaaat cccggccccg
103081 gggaatcccc gtcccccaac atgtccagat cgaaatcgtc tagcgcgtcg gcatgcgcca
103141 tcgccacgtc ctcgccgtct aagtggagct cgtcccccag gctgacatcg gtcggggggg
103201 ccgtcgacag tctgcgcgtg tgtcccgcgg ggagaaagga caggcgcgga gccgccagcc
103261 ccgcctcttc gggggcgtcg tcgtccggga gatcgagcag gccctcgatg gtagacccgt
103321 aattgttttt cgtacgcgcg cggctgtacg cgtgttcccg catgaccgcc tcggagggcg
103381 aggtcgtgaa gctggaatac gagtccaact tcgcccgaat caacaccata aagtacccag
103441 aggcgcgggc ctgggtgcca tgcagggtgg gaggggtcgt caacggcgcc cctggctcct
103501 ccgtagccgc gctgcgcacc agcgggaggt taaggtgctc gcgaatgtgg tttagctccc
103561 gcagccggcg ggcctcgatt ggcactcccc ggacggtgag cgctccgttg acgaacatga
103621 agggctggaa cagacccgcc aactgacgcc agctctccag gtcgcaacag aggcagtcaa
103681 acaggtcggg ccgcatcatc tgctcggcgt acgcggccca taggatctcg cgggtcaaaa
103741 atagatacaa atgcaaaaac agaacacgcg ccagacgagc ggtctctcgg tagtacctgt
103801 ccgcgatcgt ggcgcgcagc atttctccca ggtcgcgatc gcgtccgcgc atgtgcgcct
103861 ggcggtgcag ctgccggacg ctggcgcgca ggtaccggta cagggccgag cagaagttgg
103921 ccaacacggt tcgatagctc tcctcccgcg cccgtagctc ggcgtggaag aaacgagaga
103981 gcgcttcgta gtagagcccg aggccgtcgc gggtggccgg aagcgtcggg aaggccacgt FIGURE 9 (Continued)

104041 cgccgtgggc gcgaatgtcg atttgggcgc gttcggggac gtacgcgtcc ccccattcca 104101 ccacatcgct gggcagcgtt gataggaatt tacactcccg gtacaggtcg gcgttggtcg 104161 gtagcgccga aaacagatcc tcgttccagg tatcgagcat ggtacatagc gcggggcccg 104221 cgctaaagcc caagtcgtcg aggagacggt taaagagggc ggcggggggg acgggcatgg 104281 gtggggaggg catgagctgg gcctggctca ggcgccccgt tgcgtacagc gggggggccg 104341 ccggggtgtt tttgggaccc ccggctgggc ggggggcgg tggcgaagcg ccgtccgcgt 104401 tcatgtcggc aaacagctcg tcgaccaaga ggtccattgg gtggggttga tacgggaaag 104461 acgatatcgg gcttttgatg cgatcgtccc cgcccgccca gagagtgtgg gacgcccgac 104521 ggcgcgggaa gagaaaaacc cccaaacgcg ttagaggacc ggacggacct tatgggggga 104581 agtgggcagc gggaaccccg tccgttcccg aggaatgaca gcccgtggtc gccaccacgc 104641 atttaagcaa cccgcacggg ccgccccgta cctcgtgact tccccccaca ttggctcctg 104701 tcacgtgaag gcgaaccgag ggcggctgtc caacccaccc cccgccaccc agtcccggtc 104761 cccgtcggat tgggaaacaa aggcacgcaa cgccaacacc gaatgaaccc ctgttggtgc 104821 tttattgtct gggtacggaa gttttcactc gacgggccgt ctggggcgag aagcggagcg 104881 ggctggggct cgaggtcgct cggtggggcg cgacgccgca gaacgccctc gagtcgccgt 104941 ggccgcgtcg acgtcctgca ccacgtctgg attcaccaac tcgttggcgc gctgaagcag 105001 gtttttgccc tcgcagaccg tcacgcggat ggtggtgatg ccaaggagtt cgttgaggtc 105061 ttcgtctgtg cgcggacgcg acatgtccca gagctggacc gccgccatcc gggcatgcat 105121 ggccgccagg cgcccgaccg cggcgcagaa gacgcgcttg ttaaagccgg ccacccgggg 105181 ggtccatggc gcgtcggggt ttgggggggc ggtgctaaag tgcagctttc tggccagccc 105241 ctgcgcgggt gtcttggatc gggttggcgc cgtcgacgcg ggggcgtctg ggagtgcggc 105301 ggattctggc tgggccgatt tcctgccgcg ggtggtctcc gccgccgggg ccgcgggggc 105361 cttagtcgcc acccgctggg ttcgggggc ccggggggcg gtggtgggtg tgcgtccggc 105421 ccctccggac ccagcgggtg gcggaggtgc ccgcgcaggc cccgggccgg acaaaaccgc 105481 cccggaaacg ggacgccgcg tccgggggac ctccgggtgt tcgtcgtctt cggatgacga 105541 gcccccgtag agggcataat ccgactcgtc gtactggacg aaacggacct cgcccctctg 105601 gcgcgagcgt gtctgtaggg cgccacggcg ggaggtgtca ggcggactat cgggactcgc 105661 catacctgaa gacggggtgt agtacagatc ctcgtactca tcgcgcggaa cctcccgcgg FIGURE 9 (Continued)

105721 acccgacttc acggagcggc gagaggtcat ggttccacga acacgctagg gtcggatgcg 105781 cggacaatta ggcctgggtt cggacggcgg gggtggtgca ggtgtggaga ggtcgagcga 105841 taggggcggc ccgggagaga agagagggtc cgcaaaaccc actggggatg cgtgagtggc 105901 cctctgtggg cggtggggga gagtcttata ggaagtgcat ataaccacaa cccatgggtc 105961 taaccaatcc ccaggggcca agaaacagac acgccccaaa cggtctcggt ttccgcgagg 106021 aaggggaagt cctgggacac cctccacccc cacccctcac cccacacagg gcgggttcag 106081 gcgtgcccgg cagccagtag cctctggcag atctgacaga cgtgtgcgat aatacacacg 106141 cccatcgagg ccatgcctac ataaaagggc accagggccc ccggggcaga catttggcca 106201 gtgttttggg tctcgcaccg cgcgcccccg atcccatcgc gcccgccctc ctcgccgggc 106261 ggctccccgt gcgggcccgc gtctcccgcc gctaaggcga cgagcaagac aaacaacagg 106321 cccgcccgac agacccttct gggggggccc atcgtcccta acaggaagat gagtcagtgg 106381 ggatccgggg cgatccttgt ccagccggac agcttgggtc gggggtacga tggcgactgg 106441 cacacggccg tcgctactcg cgggggcgga gtcgtgcaac tgaacctggt caacaggcgc 106501 gcggtggctt ttatgccgaa ggttagcggg gactccggat gggccgtcgg gcgcgtctct 106561 ctggacctgc gaatggctat gccggctgac ttttgcgcga ttattcacgc ccccgcgcta 106621 gccagccccg ggcaccacgt aatactgggt cttatcgact cggggtaccg cggaaccgtt 106681 atggccgtgg tcgtagcgcc taaaaggacg cgggaatttg cccccgggac cctgtgggtc 106741 gacgtgacgt tcctggacat cctggcgacc cccccggccc tcaccgagcc gatttccctg 106801 cggcagttcc cgcaactggc gcccccccct ccaaccgggg ccgggatacg cgaagatcct 106861 tggttggagg gggcgctcgg ggccccaagc gtgactacgg ccctaccggc gcgacgccga 106921 gggcggtccc tcgtctatgc cggcgagctg acgccggttc agacggaaca cggggacggc 106981 gtacgagaag ccatcgcctt ccttccaaaa cgcgaggagg atgccggttt cgacattgtc 107041 gtccgtcgcc cggtcaccgt cccggcaaac ggcaccacgg tcgtgcagcc atccctccgc 107101 atgctccacg cggacgccgg gcccgcggcc tgctatgtgt tggggcggtc gtcgctcaac 107161 gcccgcggcc tcctggtcgt tcctacgcgc tggctccccg ggcacgtatg tgcgtttgtt 107221 gtttacaacc ttacgggggt tcctgtgacc ctcgaggccg gcgccaaggt cgcccagctc 107281 ctggttgcgg gggcggacgc tcttccttgg atccccccgg acaactttca cgggaccaaa 107341 gcgcttcgaa actaccccag gggtgttccg gactcaaccg ccgaacccag gaacccgccg FIGURE 9 (Continued)

107401 ctcctggtgt ttacgaacga gtttgacgcg gaggcccccc cgagcgagcg cgggaccggg 107461 ggttttggct ctaccggtat ttagcccaca gctttgggtt cgttccgggc aataaaaaac 107521 gtttgtatcg catctttcct gtgtgtagtt gtttatgttg gatgcctgtg ggtctatcac 107581 acccgcccct ccatcccaca aacacaaaac acacgggttg gatgaaaaca cgcatttatt 107641 gacccaaaac acacggagct gctcgagatg ggccagggcg aggtgcggtt ggggaggctg 107701 taggtctggg aacggacacg cggggacacg attccggttt ggggtccggg agggcgtcgc 107761 cgtttcgggc ggcaggcgcc agcgtaacct ccgggggcgg cgtgtggggg tgccccaagg 107821 agggcgcctc ggtcacccca atcccccccg accgggttcc cccggcaacc ccgaaggcgg 107881 agaggccaag ggcccgttcg gcgatggcca catcctccat gaccacgtca ctctcggcca 107941 tgctccgaat agcctgggag acgagcacat ccgcggactt gtcagccgcc cccacggaca 108001 tgtacatctg caggatggtg gccatacacg tgtccgccag gcgccgcatc ttgtcctgat 108061 gggccgccac ggccccgtcg atcgtggggg cctcgagccc ggggtggtgg cgcgccagtc 108121 gttctaggtt caccatgcag gcgtggtacg tgcgggccaa ggcgcgggcc ttcacgaggc 108181 gtcgggtgtc gtccagggac cccagggcgt catcgagcgt gatgggggcg ggaagtagcg 108241 cgttaacgac cgccagggcc tcctgcagcc gcggctccgc ctccgagggc ggaacggccg 108301 cgcggatcat ctcatattgt tcctcggggc gcgctcccca gccacatata gccccgagaa 108361 gagaagccat cgcgggcggg tactggccct tgggcgcgcg gacgcaatgg ggcaggaaga 108421 cgggaaccgc ggggagaggc gggcggccgg gactcccgtg gaggtgaccg cgctttatgc 108481 gaccgacggg tgcgttatta cctcttcgat cgccctcctc acaaactctc tactgggggc 108541 cgagccggtt tatatattca gctacgacgc atacacgcac gatggccgtg ctgacgggcc 108601 cacggagcaa gacaggttcg aagagagtcg ggcgctctac caagcgtcgg gcgggctaaa 108661 tggcgactcc ttccgagtaa ccttttgttt attggggacg gaagtgggtg ggacccacca 108721 ggcccgcggg cgaacccgac ccatgttcgt ctgtcgcttc gagcgagcgg acgacgtcgc 108781 cgcgctacag gacgccctgg cgcacgggac cccgctacaa ccggaccaca tcgccgccac 108841 cctggacgcg gaggccacgt tcgcgctgca tgcgaacatg atcctggctc tcaccgtggc 108901 catcaacaac gccagccccc gcaccggacg cgacgccgcc gcggcgcagt atgatcaggg 108961 cgcgtcccta cgctcgctcg tggggcgcac gtccctggga caacgcggcc ttaccacgct 109021 atacgtccac cacgaggcgc gcgtgcttgc cgcgtaccgc agggcgtatt atggaagcgc

FIGURE 9 (Continued)

109081 gcagagtccc ttctggtttc ttagcaaatt cgggccggac gaaaaaagcc tggtgctcac 109141 cactcggtac tacctgcttc aggcccagcg tctgggggc gcgggggcca cgtacgacct 109201 gcaggccatc aaggacatct gcgccaccta cgcgattccc cacgcccccc gccccgacac 109261 cgtcagcgct gcgtccctga cctcgtttgc cgccatcacg cggttctgtt gcacgagcca 109321 gtacgcccgc ggggccgcgg cggccgggtt tccgctttac gtggagcgcc gtattgcggc 109381 cgacgtccgc gagaccagtg cgctggagaa gttcataacc cacgatcgca gttgcctgcg 109441 cgtgtccgac cgtgaattca ttacgtacat ctacctggcc cattttgagt gtttcagccc 109501 cccgcgccta gccacgcatc ttcgggccgt gacgacccac gaccccaacc ccgcggccag 109561 cacggagcag ccctcgcccc tgggcaggga ggccgtggaa caattttttt gtcacgtgcg 109621 cgcccaactg aatatcgggg agtacgtcaa acacaacgtg acccccggg agaccgtcct 109681 ggatggcgat acggccaagg cctacctgcg cgctcgcacg tacgcgcccg gggccctgac 109741 gcccgccccc gcgtattgcg gggccgtgga ctccgccacc aaaatgatgg ggcgtttggc 109801 ggacgccgaa aagctcctgg tcccccgcgg gtggcccgcg tttgcgcccg ccagtcccgg 109861 ggaggacacg gcgggcggca cgccgccccc acagacctgc ggaattgtca agcgcctcct 109921 gagactggcc gccacggaac agcagggcac cacaccccg gcgatcgcgg cgcttatccg 109981 taatgcggcg gtgcagactc ccctgcccgt ctaccggata tccatggtcc ccacgggaca 110041 ggcatttgcc gcgctggcct gggacgactg ggcccgcata acgcgggacg ctcgcctggc 110101 cgaagcggtc gtgtccgccg aagcggcggc gcaccccgac cacggcgcgc tgggcaggcg 110161 gctcacggat cgcatccgcg cccagggccc cgtgatgccc cctggcggcc tggatgccgg 110221 ggggcagatg tacgtgaatc gcaacgagat attcaacggc gcgctggcaa tcacaaacat 110281 catcctggat ctcgacatcg ccctgaagga gcccgtcccc tttcgccggc tccacgaggc 110341 cctgggccac tttaggcgcg gggctctggc tgcggttcag ctcctgtttc ccgcggcccg 110401 cgtggacccc gacgcatatc cctgttattt tttcaaaagc gcatgtcggc ccggcccggc 110461 gtccgtgggt tccggcagcg gactcggcaa cgacgacgac ggggactggt ttccctgcta 110521 cgacgacgcc ggtgatgagg agtgggcgga ggacccgggc gccatggaca catcccacga 110581 tcccccggac gacgaggttg cctactttga cctgtgccac gaagtcggcc ccacggcgga 110641 acctcgcgaa acggattcgc ccgtgtgttc ctgcaccgac aagatcggac tgcgggtgtg 110701 catgcccgtc cccgccccgt acgtcgtcca cggttctcta acgatgcggg gggtggcacg FIGURE 9 (Continued)

110761 ggtcatccag caggcggtgc tgttggaccg agattttgtg gaggccatcg ggagctacgt 110821 aaaaaacttc ctgttgatcg atacgggagt gtacgcccac ggccacagcc tgcgcttgcc 110881 gtattttgcc aaaatcgccc ccgacgggcc tgcgtgcgga aggctgctgc cagtgtttgt 110941 gatccccccc gcctgcaaag acgttccggc gtttgtcgcc gcgcacgccg acccgcggcg 111001 cttccatttt cacgcccccgc ccacctatct cgcttccccc cgggagatcc gtgtcctgca 111061 cagcctgggt ggggactatg tgagcttctt tgaaaggaag gcgtcccgca acgcgctgga 111121 acactttggg cgacgcgaga ccctgacgga ggtcctgggt cggtacaacg tacagccgga 111181 tgcgggaggg accgtcgagg ggttcgcatc ggaactgctg gggcggatag tcgcgtgcat 111241 cgaaacccac tttcccgaac acgccggcga atatcaggcc gtatccgtcc ggcgggccgt 111301 cagtaaggac gactgggtcc tcctacagct agtccccgtt cgcggtaccc tgcagcaaag 111361 cctgtcgtgt ctgcgcttta agcacggccg ggcgagtcgc gccacggcgc ggacattcgt 111421 cgcgctgagc gtcggggcca acaaccgcct gtgcgtgtcc ttgtgtcagc agtgctttgc 111481 cgccaaatgc gacagcaacc gcctgcacac gctgtttacc attgacgccg gtacgccatg 111541 ctcgccgtcc gttccctgca gcacctctca accgtcgtct tgataacggc gtacggcctc 111601 gtgctcgtgt ggtacaccgt cttcggtgcc agtccgctgc accgatgtat ttacgcggta 111661 cgcccccaccg gcaccaacaa cgacaccgcc ctcgtgtgga tgaaaatgaa ccagacccta 111721 ttgtttctgg gggccccgac gcaccccccc aacgggggct ggcgcaacca cgcccatatc 111781 tgctacgcca atcttatcgc gggtagggtc gtgcccttcc aggtcccacc cgacgccatg 111841 aatcgtcgga tcatgaacgt ccacgaggca gttaactgtc tggagaccct atggtacaca 111901 cgggtgcgtc tggtggtcgt agggtggttc ctgtatctgg cgttcgtcgc cctccaccaa 111961 cgccgatgta tgtttggtgt cgtgagtccc gcccacaaga tggtggcccc ggccacctac 112021 ctcttgaact acgcaggccg catcgtatcg agcgtgttcc tgcagtaccc ctacacgaaa 112081 attacccgcc tgctctgcga gctgtcggtc cagcggcaaa acctggttca gttgtttgag 112141 acggacccgg tcaccttctt gtaccaccgc cccgccatcg ggtcatcgt aggctgcgag 112201 ttgatgctac gctttgtggc cgtgggtctc atcgtcggca ccgctttcat atcccggggg 112261 gcatgtgcga tcacataccc cctgtttctg accatcacca cctggtgttt tgtctccacc 112321 atcggcctga cagagctgta ttgtattctg cggcggggcc cggcccccaa gaacgcagac 112381 aaggccgccg ccccggggcg atccaagggg ctgtctggcg tctgcgggcg ctgttgttcc FIGURE 9 (Continued)

112441 atcatcctct cgggcatcgc agtgcgattg tgttatatcg ccgtggtggc cggggtggtg 112501 ctcgtggcgc ttcactacga gcaggagatc cagaggcgcc tgtttgatgt atgacgtcac 112561 atccaggccg gcggaaaccg gaacggcata tgcaaattgg aaactgtcct gtcttggggc 112621 ccacccaccc gacgcgtcat atgcaaatga aaatcggtcc cccgaggcca cgtgtagcct 112681 ggatcccaac gacccccgccc atgggtccca attggccgtc ccgttaccaa gaccaaccca 112741 gccagcgtat ccacccccgc ccgggtcccc gcggaagcgg aacggtgtat gtgatatgct 112801 aattaaatac atgccacgta cttatggtgt ctgattggtc cttgtctgtg ccggaggtgg 112861 ggcggggccc ccgcccgggg ggcggaacga ggaggggttt gggagagccg gccccggcac 112921 cacgggtata aggacatcca ccacccggcc ggtggtggtg tgcagccgtg ttccaaccac 112981 ggtcacgctt ctgtgcctct ccccgattcg ggcccggtcg ctcgctaccg gtgcaccacc 113041 accagaggcc atatccgaca ccccagcccc gacggcagcc gacagcccgg tcatggcgac 113101 tgacattgat atgctaattg acctcggcct ggacctctcc gacagcgatc tggacgagga 113161 cccccccgag ccggcggaga gccgccgcga cgacctggca tcggacagca gcggggagtg 113221 ttcctcgtcg gacgaggaca tggaagaccc ccacggagag gacggaccgg agccgatact 113281 cgacgccgct cgcccggcgg tccgcccgtc tcgtccagaa gacccccggcg tacccagcac 113341 ccagacgcct cgtccgacgg agcggcaggg ccccaacgat cctcaaccag cgccccacag 113401 tgtgtggtcg cgcctcgggg cccggcgacc gtcttgctcc cccgagcagc acgggggcaa 113461 ggtggcccgc ctccaacccc caccgaccaa agcccagcct gcccgcggcg gacgccgtgg 113521 gcgtcgcagg ggtcggggtc gcggtggtcc cggggccgcc gatggtttgt cggacccccg 113581 ccggcgtgcc cccagaacca atcgcaaccc gggggacccc cgccccgggg cggggtggac 113641 ggacggcccc ggcgcccccc atggcgaggc gtggcgcgga agtgagcagc ccgacccacc 113701 cggaggcccg cggacacggg gcgtgcgcca agcacccccc ccgctaatga cgctggcgat 113761 tgcccccccg cccgcggacc cccgcgcccc ggccccggag cgaaaggcgc ccgccgccga 113821 caccatcgac gccaccacgc ggttggtcct gcgctccatc tccgagcgcg cggcggtcga 113881 ccgcatcagc gagagctttg gccgcagcgc acaggtcatg cacgacccct ttgggggggca 113941 gccgtttccc gccgcgaata gcccctgggc cccggtgttg gcgggccaag gagggcccctt 114001 tgacgccgag accagacggg tctcctggga aaccttggtc gcccacggcc cgagcctcta 114061 tcgcactttt gccggcaatc ctcgggccgc atcgaccgcc aaggccatgc gcgactgcgt FIGURE 9 (Continued)

114121 gctgcgccaa gaaaatttca tcgaggcgct ggcctccgcc gacgagacgc tggcgtggtg 114181 caagatgtgc atccaccaca acctgccgct gcgcccccag gaccccatta tcgggacggc 114241 cgcggctgtg ctggataacc tcgccacgcg cctgcggccc tttctccagt gctacctgaa 114301 ggcgcgaggc ctgtgcggcc tggacgaact gtgttcgcgg cggcgtctgg cggacattaa 114361 ggacattgca tccttcgtgt ttgtcattct ggccaggctc gccaaccgcg tcgagcgtgg 114421 cgtcgcggag atcgactacg cgacccttgg tgtcggggtc ggagagaaga tgcatttcta 114481 cctccccggg gcctgcatgg cgggcctgat cgaaatccta gacacgcacc gccaggagtg 114541 ttcgagtcgt gtctgcgagt tgacggccag tcacatcgtc gcccccccgt acgtgcacgg 114601 caaatatttt tattgcaact ccctgtttta ggtacaataa aaacaaaaca tttcaaacaa 114661 atcgccccac gtgttgtcct tctttgctca tggccggcgg ggcgtgggtc acggcagatg 114721 gcgggggtgg gcccggcgta cggcctgggt gggcggaggg aactaaccca acgtataaat 114781 ccgtccccgc tccaaggccg gtgtcatagt gcccttagga gcttcccgcc cgggcgcatc 114841 cccccttttg cactatgaca gcgacccccc tcaccaacct gttcttacgg gccccggaca 114901 taacccacgt tgcccccccct tactgcctca acgccacctg gcaggccgaa acggccatgc 114961 acaccagcaa aactgactcc gcttgcgtgg ccgtgtggag ttacctggtc cgcgcctcct 115021 gtgagaccag cggcacaatc cactgctttt tctttgtggt atacaaggac acccaccata 115081 cccctccgct gattaccgag ctccgcaact ttgcggacct ggttaaccac ccgccggtcc 115141 tacgcgaact ggaggataag cgcggggtgc ggctgcggtg tgcgcggccg tttagcgtcg 115201 ggacgattaa ggacgtctct gggtccggcg cgtcctcggc gggagagtac acgataaacg 115261 ggatcgtgta ccactgccac tgtcggtatc cgttctcaaa aacatgctgg atgggggcct 115321 ccgcggccct acagcacctg cgctccatca gctccagcgg catggccgcc cgcgcggcag 115381 agcatcgacg cgtcaagatt aaaattaagg cgtgatttcc aacccccccat gaatgtgtgt 115441 aacccccccc aaaaaaataa agagccgtaa cccaaccaaa ccaggcgtgg tgtgagtttg 115501 tggacccaaa gccctcagag acaacgcgac aggccagtat ggaccgtgag acttttattt 115561 attaactcac aggggcgctt accgccacag gaataccaga ataatgacca ccacaatcgc 115621 gaccacccca aatacagcat ggcgccccac cacgccacaa cagccctgtc gccggtatgg 115681 ggcatgatca gacgagccgc gagccgcgcg ttgggccctg tacagctcgc gcgaattgac 115741 cctaggaggc cgccacgcgc ccgagttttg cgttcgtcgc tggtcgtcgg gcaccaaagc FIGURE 9 (Continued)

115801 cccggacggc tgttcggtcg aacgaacggc cacgacagtg gcataggttg gggggtggtc 115861 cgacatagcc tcggcgtacg tcgggaggcc cgacaagagg tcccttgtga tgtcgggtgg 115921 ggccacaagc ctggtttccg gaagaaacag gggggttgcc aataacccgc cagggccaaa 115981 actccggccc tggcgcacgt cgttcggcgc ggcgccgggc gcgccgagcg gctcgctggg 116041 cggcttggcg tgagcggccc cgctccgacg cctcgccctc tccggaggag gttggtggaa 116101 ttggcacgga cgacaggggc ccagcagagt acggtggagg tgggtccgtg gggtgtcca 116161 gatcaataac gacaaacggc ccctcgttcc taccagacaa gctatcgtag gggggcgggg 116221 gatcaacaaa cgcgttcccc gcgctccata gacccgcgtc gggttgcgcc gcctccgaag 116281 ccatggatgc gccccaaagc cacgactccc gcgcgctagg tccttggggt aagggaaaag 116341 gccctactcc ccatccaagc cagccaagtt aacgggctac gccttcgggg atgggactgg 116401 caccccggcg gattttgttg ggctggcatg cgtcgcccaa ccgagggccg cgtccacggg 116461 acgcgccttt tataaccccg gggtcattc ccaacgatca catgcaatct aactggctcc 116521 cctctcctcc cctctcccct ctcccctctc ccctctcccc tctcccctct cccctcttag 116581 gttggggggt ggtccgacat agcctcggcg tacgtcggga ggcccgacaa gaggtccctt 116641 gtgatgtcgg gtggggccac aagcctggtt tccggaagaa acaggggggt tgccaagcgg 116701 cccggcccgc gctccccccc ccccggggcc gtgtccttgc tttccccccg tctccccccc 116761 cctcctcctc cttctcctcc tcctcgtttt tccaaacccc gcccacccgg cccggcccgg 116821 cccggccacc gccgcccacc cacccaccgc gggagaccca gccccggtcc cccgttcccc 116881 gggggccgtt atctccagcg ccccgtccgg cgcgccgccc cccgccgcta aaccccatcc 116941 cgcccccggg accccacata taagccccca gccacacgca agaacagaca cgcagaacgg 117001 ctgtgtttat ttaaataaac cgatgtcgga ataaacaaac acaaacaccc gcgacggggg 117061 gacggaggga ggggggtgac gggggacggg aacagacaca aaaaacaacc acaaaaaaac 117121 agccaccccc gacacccccc accccagtct cctcgccttt tcccacccac cccacgcccc 117181 cactgagccc ggtcgatcga cgagcacccc cgcccccgcc cctgccccgg cgacccccgg 117241 cccgcacgat cccgacaaca ataacaaccc caacggaaag cggcggggtg ttgggggagg 117301 cgaggaacaa ccgaggggaa cgggggatgg aaggacggga agtggaagtc ctgataccca 117361 tcctacaccc ccctgccttc caccctccgg ccccccgcga gtccacccgc cggccggcta 117421 ccgagaccga acacggcggc cgccgcagcc gccgcagccg ccgccgacac cgcagagccg FIGURE 9 (Continued)

117481 gcgcgcgcac acacaagcgg cagaggcaga aaggccccga gtcattgttt atgtggccgc 117541 gggccagcag acggcccgcg acaccccccc gcccgtgtgg gtatccggcc ccccgccccg 117601 cgccggtcca ttaagggcgc gcgtgcccgc gagatatcaa tccgttaagt gctctgcaga 117661 caggggcacc gcgcccggaa atccattagg ccgcagacga ggaaaataaa attacatcac 117721 ctacccacgt ggtgctgtgg cctgtttttg ctgcgtcatc tgagccttta taaaagcggg 117781 ggcgcggccg tgccgatcgc gggtggtgcg aaagactttc cgggcgcgtc cgggtgccgc 117841 ggctctccgg gcccccctgc agccggggcg gccaaggggc gtcggcgaca tcctcccccct 117901 aagcgccggc cggccgctgg tctgtttttt gttttccccg tttcgggggt ggggggggtt 117961 acggtttctg ttttttaaac ccgtctgggg tgtttttcgt tccgtcgccg ggatgtttcg 118021 ttcgttcggc ccctcacggg gcgaaggccg cgtacggccc gggacgaggg gcccccgacc 118081 gcggcggtcc gggccccgtc cgggcccgct cgccggcacg cgacgcgaaa aaggcccccc 118141 ggaggctttt ccgggttccc ggcccggggc ctgagataaa caatcggggt taccgccaac 118201 ggccggcccc cgtggcggcc cggcccgggg ccccggcgga cccaaggggc cccggcccgg 118261 ggccccacaa cggcccggcg catgcgctgt gttttttttt tcctcggtgt tctgccgggc 118321 tccgtcgcct ttcctgttct cgcttcttcc ccccccccttt cttcaccccc agtaccctcc 118381 tccctccctt cctccccccgt tatcccactc gtcgagggcg ccccggtgtc gttcaacaaa 118441 gacgccgcgt ttccaggtag gttagacacc tgcttctccc caatagaggg gggggggaccc 118501 aaacgacagg gggcgcccca gaggctaagg tcggccacgc cactcgcggg tgggctcgtg 118561 ttacagcaca ccagcccgtt cttttccccc cctcccaccc ttagtcagac tctgttactt 118621 acccgtccga ccaccaactg ccccccttatc taagggccgg ctggaagacc gccagggggt 118681 cggccggtgt cgctgtaacc ccccacgcca atgacccacg tactccaaga aggcatgtgt 118741 cccaccccgc ctgtgttttt gtgcctggct ctctatgctt gggtcttact gcctgggggg 118801 ggggatgcgg gggagggggg gtgtggaagg aaatgcacgg cgcgtgtgta cccccccccc 118861 aaagttgttc ctaaagcgag gatatggagg agtggcgggt gccgggggac gggggtgatc 118921 tctggcacgc ggggggggaa gggtcggggg agggggggat ggggtaccgg cccacctggc 118981 cgacgcgggt gcgcgtgcct ttgcacacca accccacgtc ccccggcggt ctctaagaag 119041 caccgccccc cctccttcat accaccgagc atgcctgggt gtgggttggt aaccaacacg 119101 cccatcccct cgtctcctgt gattctctgg ctgcaccgca ttcttgtttt ctaactatgt FIGURE 9 (Continued)

119161 tcctgtttct gtctcccccc cacccctccg ccccaccccc caacacccac gtctgtggtg 119221 tggccgaccc ccttttgggc gccccgtccc gccacccctc ccgtcctttg ttgccctata 119281 gtgtagttaa cccccccccc gccctttgtg gcggccagag gccaggtcag tccgggcggg 119341 caggcgctcg cggaaactta acacccacac ccagcccact gtggttctgg ctccatgcca 119401 gtggcaggat gctttcgggg atcggtggtc aggcagcccg ggccgcggct ctgtggttaa 119461 caccagagcc tgcccaacat ggcacccccca ctcccacgca cccccactcc cacgcacccc 119521 cactcccacg caccccccact cccacgcacc cccactccca cgcaccccca ctcccacgca 119581 cccccactcc cacgcacccc cactcccacg caccccccact cccacgcacc cccactccca 119641 cgcaccccca ctcccacgca cccccactcc cacgcacccc cactcccacg cacccccaag 119701 atccatccaa cacagacagg gaaaagatac aaaagtaaac ctttatttcc caatagacag 119761 caaaaatccc ctgagttttt tattagggcc aacactaaag acccgctggt gtgtggtgcc 119821 cgtgtctttc actttcccct ccccgacacg gattggctgg tgtagtgggc gcggccagag 119881 accacccagc acccgacccc cctccccaca aacacggggg gcgtccctta ttgttttccc 119941 tcgtccccggg tcgacgcccc ctgctccccg gaccacgggt gccgagaccg caggctgcgg 120001 aagtccaggg cgcccactag ggtgccctgg tcgaacagca tgttccccac gggggtcatc 120061 cagaggctgt tccactccga cgcgggggcc gtcgggtact cgggggggcat cacgtggtta 120121 cccgcggtct cggggagcag ggtgcggcgg ctccagccgg ggaccgcggc ccgcagccgg 120181 gtcgccatgt ttcccgtctg gtccaccagg accacgtacg ccccgatgtt ccccgtctcc 120241 atgtccagga tgggcaggca gtcccccgtg atagtcttgt tcacgtaagg cgacagggcg 120301 accacgctag agaccccccga gatgggcagg tagcgcgtga ggccgcccgc ggggacggcc 120361 ccggaagtct ccgcgtggcg cgtcttccgg gcacacttcc tcggcccccg cggcccagaa 120421 gcagcgcggg ggccgaggga ggtttcctct tgtctccctc ccagggcacc gacggccccg 120481 cccgaggagg cggaagcgga ggaggacgcg gccccggcgg cggaagaggc ggcccccgcg 120541 ggggtcgggg ccgaggagga agaggcagag gaggaagagg cggaggccgc cgaggacgtc 120601 agggggggtcc cgggcccacc ctggccgcgc ccccccggcc ctgagtcgga gggggggtgc 120661 gtcgccgccc tcttggcccc tgccggcgcg aggggggggac gcgtggactg gggggagggg 120721 ttttcctggc ccgacccgcg cctcttcctc ggacgcaccg ccgcctcctg ctcgacagag 120781 acggcggagg ggagcggggc ggcgccggag gggtgcggc cgcgggaggg cccgtgccca FIGURE 9 (Continued)

120841 ccctccacgc ccggcccccc cgagccgcgc gccaccgtcg cacgcgcccg gcacagactc 120901 tgttcttggt tcgcggcctg agccagggac gagtgcgact ggggcacacg gcgcgcgtcc 120961 gcggggcggg cggccggctc cgccccgggg gccggggcgc gggggccggg ccccggaggc 121021 ggcgctcgca cgcacggggc cacggccgcg cgggggcgcg cgggtcccga cgcggccgag 121081 gacgcggggg gcccggggcg gggggcggag cctggcatgg gcgccgcggg gggcctgtgg 121141 ggagaggccg ggggggagtc gctgatcact atggggtctc tgttgtttgc aagggggggcg 121201 ggtctgttga caaggggggcc cgtccggccc ctcggccgcc ccgcctccgc ttcaacaacc 121261 ccaaccccaa ccccaacccc cccggagggg ccagacgccc cccgcggcgc cgcggctcgc 121321 gactggcggg agccgccgcc gccgctgctg ttggtggtgg tgttggtgtt actgctgccg 121381 tgtggcccga tgggcgccga gggggcgct gtccgagccg cggccggctg gggggctgcg 121441 ttagacgccc cgcccgtcac gggggcgcg gcggtgcctc tgcgtggggg ggcgcggggc 121501 gtccggcggg gggcgggcgg gacgtagtct gctgcaagag acaacggggg gcgcgatcag 121561 gttacgcccc ctccccggcc cgccctttcc tcgcccgccc gcccattcct ccctcctcct 121621 cctcccccag ggtccttgcc gcccccgcc tcaccgtcgt ccaggtcgtc gtcatcctcg 121681 tccgtggtgg gctccgggtg ggtgggcgac agggccctca ccgtgtgccc ccccagggtc 121741 aggtaccgcg gggcgaaccg ctgattgccc gtccagataa agtccacggc cgtgcccgcc 121801 ctgacggcct cctcggcctc catgcgggtc tgggggtcgt tcacgatcgg gatggtgctg 121861 aacgacccgc tgggcgtcac gcccactatc aggtacacca gcttggcgtt gcacagcggg 121921 caggtgttgc gcaattgcat ccaggttttc atgcacggga tgcagaagcg gtgcatgcac 121981 gggaaggtgt cgcagcgcag gtggggcgcg atctcatccg tgcacacggc gcacacgtcg 122041 ccctcgtcgc tccccccgtc ctctcgaggg gggcgcccc cgcaactgcc ggggtcttcc 122101 tcgcgggggg ggctcccccc cgagaccgcc cccccatcca cgccctgcgg ccccagcagc 122161 cccgtctcga acagttccgt gtccgtgctg tccgcctcgg aggcggagtc gtcgtcatgg 122221 tggtcggcgt cccccgccc ccccacttcg gtctccgcct cagagtcgct gctgtccggc 122281 aggtctcggt cgcagggaaa cacccagaca tccggggcgg gctaagggga aaaaaggggg 122341 gcgggtaaga atgggggggg atttcccgcg tcaatcagcg cccacgagtt ccccctctcc 122401 cccccgcct cacaaagtcc tgccccctg ctggcctcgg aagaggggggg agaaaggggt 122461 ctgcaaccaa aggtggtctg ggtccgtcct ttggatcccg acccctcttc ttccctcttc FIGURE 9 (Continued)

122521 tcccgccctc cagacgcacc ggagtcgggg gtcccacggc gtcccccaaa tatggcgggc 122581 ggctcctccc caccccccta gatgcgtgtg agtaaggggg gcctgcgtat gagtcagtgg 122641 ggaccacgcc cccaacacgg cgaccccggt ccctgtgtgt ttgttgtggg ggcgtgtctc 122701 tgtgtatgag tcaggggtc ccacggcgac cccgggccct gcgtctgagt caaaggggcc 122761 atgtgtatgt gttgggggtc tgtatatata aagtcagggg gtcacatggc gacccccaac 122821 agggcgaccc cggtccctgt atatataggg tcaggggtt ccgcgccccc taacatggcg 122881 cccccggtcc ctgtatatat agtgtcacgg ggttccacgc cccctaacat ggcgccccaa 122941 catggcgccc ggctcccgtg tatgagtggg ggtcccccaa catgggggcc ggttccaggg 123001 taagggtcgg gggtccccca acatggcgcc ccccaatatg gcgccccaga catggcgccc 123061 ggcccctcac ctcgcgctgg gggcggccct caggccggcg ggtactcgct ccggggcggg 123121 gctccatggg ggtcgtatgc ggctggaggg tcgcggacgg agggtccctg ggggtcgcaa 123181 cgtaggcggg gcttctgtgg tgatgcggag agggggcggc ccgagtctgc ctggctgctg 123241 cgtctcgctc cgagtgccga ggtgcaaatg cgaccagacc gtcgggccag ggctaactta 123301 taccccacgc ctttcccctc cccaaagggg cggcagtgac gattccccca atggccgcgc 123361 gtcccagggg aggcaggccc accgcggggc ggccccgtcc ccggggacca acccggcgcc 123421 cccaaagaat atcattagca tgcacggccc ggcccccgat ttgggggacc aacccggtgt 123481 cccccaaaga accccattag catgcccctc ccgccgacgc aacaggggct tggcctgcgt 123541 cggtgccccg gggcttcccg ccttcccgaa gaaactcatt accatacccg gaaccccagg 123601 ggaccaatgc gggttcattg agcgacccgc gggccaatgc gcgaggggcc gtgtgttccg 123661 ccaaaaaagc aattagcata acccggaacc ccaggggagt ggttacgcgc ggcgcgggag 123721 gcggggaata ccggggttgc ccattaaggg ccgcgggaat tgccggaagc gggaagggcg 123781 gccggggccg cccattaatg agtttctaat taccataccg ggaagcggaa caaggcctct 123841 tgcaagtttt taattaccat accgggaagt gggcggcccg gcccattggg cggtaactcc 123901 cgcccaatgg gccgggcccc gaagactcgg cggacgctgg ttggccgggc cccgccgcgc 123961 tggcggccgc cgattggcca gtcccgcccc cgaggcgggc ccgccttggg ggcggaccgg 124021 ctcccagcgt atatatgcgc ggctcctgcc atcgtctctc cggagagcgg cttggtgcgg 124081 agctcccggg agctccgcgg aagacccagg cgcctcgggt gtaacgttag accgagttcg 124141 ccgggccggc tccgcgggcc agggcccggg cacgggcctc gggccccagg cacggcccga FIGURE 9 (Continued)

124201 tgaccgcctc ggcctccgcc acccggcgcc ggaaccgagc ccggtcggcc cgctcgcggg 124261 cccacgagcc gcggcgcgcc aggcgggcgg ccgaggccca gaccaccagg tggcgcaccc 124321 ggacgtgggg cgagaagcgc acccgcgcgg gggtcgcggg ggtcgcgggg gtcgcggggg 124381 tcgcgggggt cgcgggggtc gcgggggtcg cgggggtcgc gggggctcc ggcgccccct 124441 ccccgcccgc gcgtcgcagg cgcaggcgcg ccaggtgctc cgcggtgacg cgcaggcgga 124501 gggcgaggcg cggcggaagg cggaaggggc gcgagggggg gtgggagggg tcagccccgc 124561 cccccgggcc cacgccgggc ggtggggacc ggggccgggg ggcggcggcg gtgggccggg 124621 cctctggcgc cggctcgggc gggggctgt ccggccagtc gtcgtcatcg tcgtcgtcgg 124681 acgcggactc gggaacgtgg agccactggc gcagcagcag cgaacaagaa ggcgggggcc 124741 caccggcggg gggcggcggc ggggcggccg cgggcgcgct cctgaccgcg ggttccgagt 124801 tgggcgtgga ggttacctgg gactgtgcgg ttgggacggc gcccgtgggc ccgggcggcc 124861 gggggcggcg ggggccgcga tggcggcggc ggcgggccat ggagacagag agcgtgccgg 124921 ggtggtagag tttgacaggc aagcatgtgc gtgcagaggc gagtagtgct tgcctgtcta 124981 actcgctagt ctcggccgcg gggggcccgg gctgcccgcc gccgcgcttt aaagggccgc 125041 gcgcgacccc cggggggtgt gtttcggggg ggcccgtttt tggggtctgg ccgctcctcc 125101 cccgctcctc cccgtctgtg ggtggggctc ctcccccgct cctcccccgc tcctcccccg 125161 ctcctccccg tctgtgggtg gggctcctcc cccgctcccg cggcccccgcc ccccacgccc 125221 gccgcgcgcg cgcacgccgc ccggaccgcc gcccgccttt tttgcgcgcc gcccccgcgcg 125281 cgggggggccc gggctgccac aggtgtaaca acaccaacag aacaccaaca gcacggcgca 125341 ccggcgactc cggttcctca tccacacgtc acgtcatcca acacacctgc ccaacaacac 125401 aactcacagc gacaactcac cgcgcaacaa ctcctgttcc tcatccacac gtcaccgcgc 125461 accccccgct cctccagacg tcccccagcg caacacgccg ctcctgtcac acaccacagc 125521 cccagccctc cccagcccca gccctcccca gccccagccc tccccagccc cagccctccc 125581 cagccccagc cctccccagc cccagccctc cccagcccca gccctcccca gccccagccc 125641 tccccagccc cagccctccc cagccccagc cctccccagc cccagccctc cccagcccca 125701 gccctcccca gccgcgtccc gcgctccctc gggggggttc gggcatctct acctcagtgc 125761 cgccaatctc aggtcagaga tccaaaccct ccgggggcgc ccgcgcacca ccaccgcccc 125821 tcgccccctc ccgcccctcg ccccctcccg cccctcgccc cctcccgccc ctcgccccct FIGURE 9 (Continued)

125881 cccgcccctc gccccctccc gcccctcgcc ccctcccgcc cctcgccccc tcccgcccct 125941 cgccccctcc cgcccctcga ataaacaacg ctactgcaaa acttaatcag gtcgttgccg 126001 tttattgcgt cttcgggttt cacaagcgcc ccgccccgtc ccggcccgtt acagcacccc 126061 gtccccctcg aacgcgccgc cgtcgtcttc gtcccaggcg ccttcccagt ccacaacgtc 126121 ccgtcgcggg ggcgtggcca agcccgcctc cgcccccagc acctccacgg cccccgccgc 126181 cgccagcacg gtgccgctgc ggcccgtggc cgaggcccag cgaatcccgg gcggcgccgg 126241 cggcagggcc cccgggccgt cgtcgtcgcc gcgcagcacc agcggggggg cgtcgtcgtc 126301 gggctccagc agggcgcggg cgcaaaagtc cctccgcggc ccgcgccacc gggccgggcc 126361 ggcgcgcacc gcctcgcgcc ccagcgccac gtacacgggc cgcagcggcg cgcccaggcc 126421 ccagcgcgcg caggcgcggt gcgagtgggc ctcctcctcg cagaagtccg gcgcgccggg 126481 cgccatggcg tcggtggtcc ccgaggccgc cgcccggccg tccagcgccg gcagcacggc 126541 ccggcggtac tcgcgcgggg acatgggcac cggcgtgtcc gggccgaagc gcgtgcgcac 126601 gcggtagcgc acgttgccgc cgcggcacag gcgcagcggc ggcgcgtcgg ggtacaggcg 126661 cgcgtgcgcg gcctccacgc gcgcgaagac ccccgggccg aacacgcggc ccgaggccag 126721 caccgtgcgg cgcaggtcgc gcgccgccgg ccagcgcacg gcgcactgca cggcgggcag 126781 caggtcgcac gccaggtagg cgtgctgccg cgacaccgcg ggcccgtcgg cgggccagtc 126841 gcaggcgcgc acggtgttga ccacgatgag ccgccggtcg ccggcgctgg cgagcagccc 126901 cagaaactcc acggccccgg cgaaggccag gtcccgcgtg gacagcagca gcacgccctg 126961 cgcgcccagc gccgacacgt cgggggcgcc ggtccagttg cccgcccagg cggccgtgtc 127021 cggcccgcac agccggttgg ccagggccgc cagcaggcag gacagcccgc cgcgctcggc 127081 ggaccactcc ggcggccccc ccgaggcccc gccgccggcc aggtcctcgc ccggcagcgg 127141 cgagtacagc accaccacgc gcacgtcctc ggggtcgggg atctggcgca tccaggccgc 127201 catgcggcgc agcgggcccg aggcgcgcag gggggccaaag aggcggcccc cggcggcccc 127261 gtgggggtgg gggttctcgt cgtcgtcgcc gccgccgcac gcggcctggg cggcgggggc 127321 gggcccggcg caccgcgcgg cgatcgaggc cagggcccgc gggtcaaaca tgagggccgg 127381 tcgccagggg acggggaaca gcgggtggtc cgtgagctcg gccacggcgc gcggggagca 127441 gtaggcctcc agggcggcgg ccgcgggcgc cgccgtgtgg ctgggccccg ggggctgccg 127501 ccgccagccg cccagggggt cggggccctc ggcgggccgg cgcgacagcg ccacggggcg FIGURE 9 (Continued)

127561 cgggcgggcc tgcgccgcgg cggcccgggg cgccgcgggc tgggcggggg cgggctcggg
127621 ccccgggggc gtggaggggg gcgcgggcgc ggggaggggg gcgcgggcgt ccgagccggg
127681 ggcgtccgcg ccgctcttct tcgtcttcgg gggtcgcggg ccgccgcctc cgggcggccg
127741 ggccgggccg ggactcttgc gcttgcgccc ctcccgcggc gcggcggagg cggcggccgc
127801 gaccccccgaa gacgaagaag agcggcgcgg acccgccgcc agcagggggc gcaggctctg
127861 gttctcaaac agcaggtccg cggcggcggc ggccgcggag ctcggcaggc gcgggtcccg
127921 cggcagcgcg ggacccaggg ccccggcgac caggctcacg gcgcgcacgg cggccacggc
127981 ggcctcgctg ccgccggcca cgcgcaggtc cccgcgcagg cgcatgagca ccagcgcgtc
128041 gcgcacgaac cgcagctcgc gcagccacgc gcgcaggcgg ggcgcgtcgg cgtgcggcgg
128101 cggcggggaa gcggggcccg cgggtccctc cggccgcggg gggctggcgg gccgggcccc
128161 ggccagcccc gggacggccg ccaggtcgcc gtcgaagccc tcggccagcg cctccaggat
128221 cccgcggcag gcggccaggc actccacggc cacgcggccg gcctgggcgc ggcgcccggc
128281 gtcgtcgtcg gcgtcggcgt ggcgggcggc gtcggggtcg tcgccccccg cgggggaggc
128341 gggcgcggcg gacagccgcc ccagggcggc gaggatcccc gcggcgccgt acccggcggg
128401 caccgcgcgc tcgcccggtg cggcggcggc ggcgacgacg gcggcggcga ccccctcgtc
128461 atctgcgccg gcgccggggc tccccgcggc ccccgtcagc gccgcgttct cgcgcgccaa
128521 caggggcgcg taggcgcggc gcaggctggt cagcaggaag cccttctgcg cgcggtcgta
128581 tcggcggctc atggccacgg cggccgccgc gtgcgccagg ccccagccga agcggccggc
128641 cgccatggcg tagcccaggt ggggcacggc ccgcgccacg ctgccggtga tgaaggagct
128701 gctgttgcgc gcggcgcccg agatccggaa gcaggcctgg tccagcgcca cgtccccggg
128761 gaccacgcgc gggttctgga gccaccccat ggcctccgcg tccggggtgt acagcagccg
128821 cgtgatcagg gcgtactgct gcgcggcgtc gcccagctcg ggcgcccaca cggccgccgg
128881 ggcgcccgag gcctcgaacc ggcgtcgcgc ctcctccgcc tcgggcgccc cccagaggcc
128941 cgggcggctg tcgcccaggc cgccgtacag cacccgcccc gggggcgggg gcccggcgcc
129001 gggccacggc tccccgctga cgtacccgtc gcgatagcgc gcgtagaagg cgccggaggc
129061 cgcgtcggcg tccagctcga cccgccgggg ctgcccggcc gtgaagcggc ccgtggcgtc
129121 gcggccggcc accgccgcgc gggcccggcg gcgctcgatg cggcccgcgg aggccgcggg
129181 ggtcctcgcc gccgcccggg gcttgggcgc ggcctcggag aggggggtg gcccgggcgg FIGURE 9 (Continued)

129241 gggcggcgtc cgcccggggg cttccggcgc cgcgctcgac ggaccccgcc cgacggcccg 129301 cgcctcgcgt gcgtggtcgg ccgcgtcgtt gccgtcgtcg tcctcgtcct cgtcggacga 129361 cgaggacgaa gaggatgcgg acgacgagga cgaggacccg gagtccgacg aggtcgatga 129421 cgccgatggc cgccgccggc cgtgacgacg tctctgcggc ggctgggccg gcgggcgcgg 129481 cgacaggcgg tccgtggggt ccggatacgc gccgcgtagc ggggcctccc gtgcgcggcc 129541 ccgggccggg gcccggtcgc cggcggcgtc ggctgcgtcg tcgtactcgt ccccgtcatc 129601 gtcgtcggct cgaaaggcgg gggtccgggg cggcgaggcc gcggggtcgg gcgtcgggat 129661 cgtccggacg gcctcctcta ccatggaggc cagcagggcc agctgtcgcg gcgagacggc 129721 gtccccggcg tcctcgccgg cgtcggtgcc cgccgcgggg gccctcccgt cccgccgggc 129781 gtcgtcgagg tcgtgggggt ggtcggggtc gtggtcgggg tcgtccccgc cctcctccgt 129841 ctccgcgccc cacccgaggg ccccccgctc gtcgcggtct gggctcgggg tgggcggcgg 129901 cccgtcggtg gggcccgggg agccggggcg ctgcttgttc tccgacgcca tcgccgatgc 129961 ggggcgatcc tccggggata cgactgcgac ggcggacgta gcacggtagg tcacctacgg 130021 actctcgatg gggagggggc gagacccacg gaccccgacg accccccgccg tcgacgcgga 130081 actagcgcgg accggtcgat gcttgggtgg gaaaaaggac agggacggcc gatcccccctc 130141 ccgcgcttcg tccgcgtatc ggcgtcccgg cgcggcgagc gtctgacggt ctgtctctgg 130201 cggtcccgcg tcgggtcgtg gatccgtgtc ggcagccgcg ctccgtgtgg acgatcgggg 130261 cgtcctcggg ctcatatagt cccaggggcc ggcgggaagg aggagcagcg gaggccgccg 130321 gcccccccgcc cccacggcgg gcccgccccg aacggaattc cattatgcac gaccccgccc 130381 cgacgccggc acgccggggg cccgtggccg cggcccgttg gtcgaacccc cggccccgcc 130441 catccgcgcc atctgccatg ggcggggcgc tagggcgggt gggcccgcgc cccgccccgc 130501 atggcatctc attaccgccc gatccggcgg tttccgcttc cgttccgcat gctaacgagg 130561 aacgggcagg gggcggggcc cgggccccga cttcccggtt cggcggtaat gagatacgag 130621 ccccgcgcgc ccgttggccg tccccgggcc cccggtcccg cccgccggac gccgggacca 130681 acgggacggc gggcggccca agggccgccc gccttgccgc ccccccattg gccggcgggc 130741 gggaccgccc caagggggcg gggccgccgg gtaaaagaag tgagaacgcg aagcgttcgc 130801 acttcgtccc aatatatata tattattagg gcgaagtgcg agcactggcg ccgtgcccga 130861 ctccgcgccg gccccggggg cgggcccggg cggcgggggg cgggtctctc cggcgcacat FIGURE 9 (Continued)

130921 aaaggcccgg cgcgaccgac gcccgcagac ggcgccggcc acgaacgacg ggagctgctg 130981 cggagcacgc ggaccgggag cgggactcgc agagggccgt cggagcggac ggcgtcggca 131041 tcgcgacgcc ccggctcggg atcgggatcg catcggaaag ggacacgcgg aaagacccac 131101 ccacccccacc cacgaaacac aggggacgca ccccgggggc ctccgacgac agaaacccac 131161 cggtccgcct ttttgcacgg gtaagcacct tgggtgggcg gaggagggcg gaggaggggg 131221 gacgcggggg cggaggaggg gggacgcggg ggcggaggag gggggacgcg ggggcggagg 131281 agggggggacg cgggggcgga ggaggggggct cacccgcgtt cgtgccttcc cgcaggagga 131341 acgtcctcgt cgaggcgacc ggcggcgacc gttgcgtgga ccgcttcctg ctcgtcgggg 131401 cgaccggcgg cgaccgttgc gtggaccgct tcctgctcgt cggggcgacc ggcggcgacc 131461 gttgcgtgga ccgcttcctg ctcgtcgggg gggggggggg gaagccactg tggtcctccg 131521 ggacgttttc tggatggccg acatttcccc aggcgctttt gcgccttgtg taaaagcgcg 131581 gcgtcccgct ctccgatccc cgcccctggg cacgcgcaag cgcaagcgcc ctgcccgccc 131641 cctctcatcg gagtctgagg tcgaaaccga tacagccttg gagtctgagg tcgaatccga 131701 gacagcatcg gattcgaccg agtctgggga ccaggaggaa gcccccccgca tcggtggccg 131761 tagggccccc cggaggcttg gggggcggtt ttttctggac atgtcggcgg aatccaccac 131821 ggggacggaa acggatacgg cggtgtcgga cgaccccgac gacacgtccg actggtctta 131881 tgacgacatt cccccacgac ccaagcgggc ccgggtaaac ctgcggctca cgagctctcc 131941 cgatcggcgg gatggggtta tttttcctaa gatggggcgg gtccggtcta cccgggaaac 132001 gcagccccgg gccccaaccc cgtcggcccc aagcccaaat gcaatgctac ggcgctcggt 132061 gcgccaggcc cagaggcgga gcagcgcacg atggaccccc gacctgggct acatgcgcca 132121 gtgtatcaat cagctgtttc gggtcctgcg ggtcgcccgg gacccccacg gcagtgccaa 132181 ccgcctgcgc cacctgatac gcgactgtta cctgatggga tactgccgag cccgtctggc 132241 cccgcgcacg tggtgccgct tgctgcaggt gtccggcgga acctggggca tgcacctgcg 132301 caacaccata cgggaggtgg aggctcgatt cgacgccacc gcggaacccg tgtgcaaact 132361 tccttgtttg gaggccagac ggtacggccc ggagtgtgat cttagtaatc tcgagattca 132421 tctcagcgcg acaagcgatg atgaaatctc cgatgccacc gatctggagg ccgccggttc 132481 ggaccacacg ctcgcgtccc agtccgacac ggaggatgcc ccctcccccg ttacgctgga 132541 aaccccagaa ccccgcgggt ccctcgctgt gcgtctggag gatgagtttg gggagtttga FIGURE 9 (Continued)

132601 ctggaccccc caggagggct cccagccctg gctgtctgcg gtcgtggccg ataccagctc 132661 cgtggaacgc ccgggcccat ccgattctgg ggcgggtcgc gccgcagaag accgcaagtg 132721 tctggacggc tgccggaaaa tgcgcttctc caccgcctgc ccctatccgt gtagcgacac 132781 gtttctccgg ccgtgagtcc ggtcgccccg acccctttgt atgtcaccaa aataaaagac 132841 caaaatcaaa gcgtttgtcc cagcgtctta atggcgggaa gggcggagag aaacagacca 132901 cgcggacatg gggggtgttt ggggggtttat tggcaccggg ggctaaaggg tggtaaccgg 132961 atagcagatg tgaggaagtc ggggccgttc gccgcgaacg gcgatcagag ggtcagtttc 133021 ttgcggacca cggcccggcg atgtgggttg ctcgtctggg acctcgggca tgcccataca 133081 cgcacaacac ggacgccgca ccggatggga cgtcgtaagg gggcctgggg tagctgggtg 133141 gggtttgtgc agagcaatca gggaccgcag ccagcgcata caatcgcgct cccgtccgtt 133201 tgtcccgggc agtaccacgc cgtactggta ttcgtaccgg ctgagcaggg tctccagggg 133261 gtggttgggg gccgcgggga acggggtcca cgccacggtc cactcgggca aaaaccgagt 133321 cggcacggcc cacggttctc ccacccacgc gtctggggtc ttgatggcga taaatcttac 133381 cccgagccgg attttttggg cgtattcgag aaacggcaca cacagatccg ccgcgcctac 133441 cacccacaag tggtagatgc gaggggggct gggttggtct cggtgcagca gtcggaagca 133501 cgccacggcg tccacgacct cggtgctctc caaggggctg tcctccgcaa acaggcccgt 133561 ggtggtgttt gggggggcagc gacaggacct agtgcgcacg atcgggcggg tgggtttggg 133621 taagtccatc agcggctcgg ccaaccgtcg aaggttggcc ggacgaacga cgaccggggt 133681 acccaggggt tctgatgcca aaatgcggca ctgcctaagc aggaagctcc acagggccgg 133741 gcttgcgtcg acggaagtcc ggggcagggc gttgttctgg tcaaggaggg tcattacgtt 133801 gacgacaaca acgcccatgt tggtatatta caggcccgtg tccgatttgg ggcacttgca 133861 gatttgtaag gccacgcacg gcggggagac aggccgacgc gggggctgct ctaaaaattt 133921 aagggcccta cggtccacag acccgccttc ccgggggggg ggcccttgga gcgaccggca 133981 gcgtaggcgt ccgggggagg ggagggtgat ttacgggggg gtaggtcagg gggtgggtcg 134041 tcaaactgcc gctccttaaa accccggggc ccgtcgttcg gggtgctcgt tggttggcac 134101 tcacggtgcg gcgaatggcc tgtcgtaagt tttgtcgcgt ttacggggga cagggcagga 134161 ggaaggagga ggccgtcccg ccggagacaa agccgtcccg ggtgtttcct catggcccct 134221 tttataccccc agccgaggac gcgtgcctgg actccccgcc cccggagacc cccaaacctt

FIGURE 9 (Continued)

134281 cccacaccac accacccagc gaggccgagc gcctgtttca tctgcaggag atccttgccc 134341 agatgtacgg aaaccaggac taccccatag aggacgaccc cagcgcggat gccgcggacg 134401 atgtcgacga ggacgccccg gacgacgtgg cctatccgga ggaatacgca gaggagcttt 134461 ttctgcccgg ggacgcgacc ggtcccctta tcggggccaa cgaccacatc cctcccccgt 134521 gtggcgcatc tccccccggt atacgacgac gcagccggga tgagattggg gccacgggat 134581 ttaccgcgga agagctggac gccatggaca gggaggcggc tcgagccatc agccgcggcg 134641 gcaagccccc ctcgaccatg gccaagctgg tgactggcat gggctttacg atccacggag 134701 cgctcacccc aggatcggag gggtgtgtct ttgatagcag ccacccagat tacccccaac 134761 gggtaatcgt gaaggcgggg tggtacacga gcacgagcca cgaggcgcga ctgctgaggc 134821 gactggacca ccccgcgatc ctgcccctcc tggacctgca tgtcgtctcc ggggtcacgt 134881 gtctggtcct ccccaagtac caggccgacc tgtataccta tctgagtagg cgcctgaacc 134941 cgctgggacg cccgcagatc gcagcggtct cccggcagct cctaagcgcc gttgactaca 135001 ttcaccgcca gggcattatc caccgcgaca ttaagaccga aaatattttt attaacaccc 135061 ccgaggacat ttgcctgggg gactttggtg ccgcgtgctt cgtgcagggt tcccgatcaa 135121 gccccttccc ctacggaatc gccggaacca tcgacaccaa cgcccccgag gtcctggccg 135181 gggatccgta taccacgacc gtcgacattt ggagcgccgg tctggtgatc ttcgagactg 135241 ccgtccacaa cgcgtccttg ttctcggccc cccgcggccc caaaaggggc ccgtgtgaca 135301 gtcagatcac ccgcatcatc cgacaggccc aggtccacgt tgacgagttt tccccgcatc 135361 cagaatcgcg cctcacctcg cgctaccgct cccgcgcggc cgggaacaat cgcccgcctt 135421 acacccgacc ggcctggacc cgctactaca agatggacat agacgtcgaa tatctggttt 135481 gcaaagccct caccttcgac ggcgcgcttc gccccagcgc cgcagagctg ctttgtttgc 135541 cgctgtttca acagaaatga ccgcccccgg ggggcggtgc tgtttgcggg ttggcacaaa 135601 aagaccccga cccgcgtctg tggtgttttt ggcatcatgt cgccgggcgc catgcgtgcc 135661 gttgttccca ttatcccatt ccttttggtt cttgtcggtg tatcgggggt tcccaccaac 135721 gtctcctcca ccacccaacc ccaactccag accaccggtc gtccctcgca tgaagccccc 135781 aacatgaccc agaccggcac caccgactct cccaccgcca tcagccttac cacgcccgac 135841 cacacacccc ccatgccaag tatcggactg gaggaggagg aggaagagga ggagggggcc 135901 ggggatggcg aacatcttaa ggggggagat gggacccgtg acaccctacc ccagtccccg FIGURE 9 (Continued)

135961 ggtccagccg tcccgttggc cggggatgac gagaaggaca aacccaaccg tcccgtagtc 136021 ccacccccg gtcccaacaa ctccccgcg cgccccgaga ccagtcgacc gaagacaccc 136081 cccaccagta tcgggccgct ggcaactcga cccacgaccc aactcccctc aaaggggcga 136141 cccttggttc cgacgcctca acataccccg ctgttctcgt tcctcactgc ctcccccgcc 136201 ctggacaccc tcttcgtcgt cagcaccgtc atccacacct tatcgttttt gtgtattggt 136261 gcgatggcga cacacctgtg tggcggttgg tccagacgcg ggcgacgcac acaccctagc 136321 gtgcgttacg tgtgcctgcc gtccgaacgc gggtagggta tggggcgggg gatggggaga 136381 gcccacatgc ggaaagcaag aacaataaag gcggtggtat ctagttgata tgcatctctg 136441 ggtgtttttg gggtgtggcg gacgcggggc ggtcattgga cggggtgcag ttaaatacat 136501 gcccgggacc catgaagcat gcgcgacttc cgggcctcgg aacccacccg aaacggccaa 136561 cggacgtctg agccaggcct ggctatccgg agaaacagca cacgacttgg cgttctgtgt 136621 gtcgcgatgt ctctgcgcgc agtctggcat ctggggcttt tgggaagcct cgtgggggct 136681 gttcttgccg ccacccatcg gggacctgcg gccaacacaa cggacccctt aacgcacgcc 136741 ccagtgtccc ctcaccccag ccccctgggg ggctttgccg tccccctcgt agtcggtggg 136801 ctgtgcgccg tagtcctggg ggcggcgtgt ctgcttgagc tcctgcgtcg tacgtgccgc 136861 gggtgggggc gttaccatcc ctacatggac ccagttgtcg tataattccc cccccccctt 136921 ctccgcatgg gtgatgtcgg gtccaaactc ccgacaccac cagctggcat ggtataaatc 136981 accggtgcgc cccccaaacc atgtccggca gggggatggg ggggcgaatg cggagggcac 137041 ccaacaacac cgggctaacc aggaaatccg tggccccggc ccccaataaa gatcgcggta 137101 gcccggccgt gtgacactat cgtccatacc gaccacaccg acgaatcccc taagggggag 137161 gggccatttt acgaggagga ggggtataac aaagtctgtc tttaaaaagc aggggttagg 137221 gagttgttcg gtcataagct tcagcgcgaa cgaccaacta ccccgatcat cagttatcct 137281 taaggtctct tttgtgtggt gcgttccggt atgggggggg ctgccgccag gttgggggcc 137341 gtgattttgt ttgtcgtcat agtgggcctc catggggtcc gcggcaaata tgccttggcg 137401 gatgcctctc tcaagatggc cgaccccaat cgctttcgcg gcaaagacct tccggtcctg 137461 gaccagctga ccgaccctcc gggggtccgg cgcgtgtacc acatccaggc gggcctaccg 137521 gacccgttcc agccccccag cctcccgatc acggtttact acgccgtgtt ggagcgcgcc 137581 tgccgcagcg tgctcctaaa cgcaccgtcg gaggcccccc agattgtccg cggggcctcc FIGURE 9 (Continued)

137641 gaagacgtcc ggaaacaacc ctacaacctg accatcgctt ggtttcggat gggaggcaac 137701 tgtgctatcc ccatcacggt catggagtac accgaatgct cctacaacaa gtctctgggg 137761 gcctgtccca tccgaacgca gccccgctgg aactactatg acagcttcag cgccgtcagc 137821 gaggataacc tggggttcct gatgcacgcc cccgcgtttg agaccgccgg cacgtacctg 137881 cggctcgtga agataaacga ctggacggag attacacagt ttatcctgga gcaccgagcc 137941 aagggctcct gtaagtacgc cctcccgctg cgcatccccc cgtcagcctg cctgtccccc 138001 caggcctacc agcagggggt gacggtggac agcatcggga tgctgccccg cttcatcccc 138061 gagaaccagc gcaccgtcgc cgtatacagc ttgaagatcg ccgggtggca cgggcccaag 138121 gccccataca cgagcaccct gctgcccccg gagctgtccg agacccccaa cgccacgcag 138181 ccagaactcg ccccggaaga ccccgaggat tcggccctct tggaggaccc cgtggggacg 138241 gtggcgccgc aaatcccacc aaactggcac ataccgtcga tccaggacgc cgcgacgcct 138301 taccatcccc cggccacccc gaacaacatg ggcctgatcg ccggcgcggt gggcggcagt 138361 ctcctggcag ccctggtcat ttgcggaatt gtgtactgga tgcgccgccg cactcaaaaa 138421 gccccaaagc gcatacgcct cccccacatc cgggaagacg accagccgtc ctcgcaccag 138481 cccttgtttt actagatacc ccccttaat gggtgcgggg gggtcaggtc tgcggggttg 138541 ggatgggacc ttaactccat ataaagcgag tctggaaggg gggaaaggcg gacagtcgat 138601 aagtcggtag cgggggacgc gcacctgttc cgcctgtcgc acccacagct ttttttgcga 138661 accgtcccgt tccgggatgc cgtgccgccc gttgcagggc ctggtgctcg tgggcctctg 138721 ggtctgtgcc accagcctgg ttgtccgtgg ccccacggtc agtctggtat caaactcatt 138781 tgtggacgcc ggggccttgg ggcccgacgg cgtagtggag gaagacctgc ttattctcgg 138841 ggagcttcgc tttgtggggg accaggtccc ccacaccacc tactacgatg gggtcgtaga 138901 gctgtggcac taccccatgg gacacaaatg cccacgggtc gtgcatgtcg tcacggtgac 138961 cgcgtgccca cgtcgccccg ccgtggcttt cgccctgtgt cgcgcgaccg acaacactca 139021 cagccccgca tatcccaccc tggagctgaa tctggcccaa cagccgcttt tgcgggtccg 139081 gagggcgacg cgtgactatg ccggggtgta cgtgttacgc gtatgggtcg tggacgcacc 139141 aaacgccagc ctgtttgtcc tggggatggc catagccgcc gaagggactc tggcgtacaa 139201 cggctcggcc catggctcct gcgacccgaa actgcttccg tattcggccc cgcgtctggc 139261 cccggcgagc gtataccaac ccgcccctaa cccggcctcc accccctcga ccaccacctc FIGURE 9 (Continued)

139321 caccccctcg accaccacct ccaccccctc gaccaccacc tccaccccct cgaccaccac 139381 ctccaccccc tcgaccacca cctccacccc ctcgaccacc acctccaccc cctcgaccac 139441 catccccgct ccccaagcat cgaccacacc cttccccacg ggagacccaa aaccccaacc 139501 tcacggggtc aaccacgaac ccccatcgaa tgccacgcga gcgacccgcg actcgcgata 139561 cgcgctaacg gtgacccaga taatccagat agccatcccc gcgtccatta tagccctggt 139621 gtttctgggg agctgtattt gctttataca cagatgtcaa cgccgctacc gacgctcccg 139681 ccgcccgatt tacaaccccc agatacccac gggcatctca tgcgcggtga acgaagcggc 139741 catggcccgc ctcggagccg agctcaaatc gcatccgagc acccccccca aatcccggcg 139801 ccggtcgtca cgcacgccaa tgccctccct gacggccatc gccgaagagt cggagcccgc 139861 gggggcggct gggcttccga cgcccccccgt ggaccccacg acatccaccc caacgcctcc 139921 cctgttggta taggtccacg gccactggcc gggggcacca cataaccgac cgcagtcact 139981 gagttgggaa taaaccggta ttatttacct atatccgtgt atgtccattt ctttcccccc 140041 cccccccccc cggaaaccca aagaaggaag caaagaatgg atgggaggag ttcaggaagc 140101 cggggagagg gcccgcggcg catttaaggc gttgttgtgt tgactttggc tcttctggcg 140161 ggttggtgcg gtgctgtttg ttgggctccc attttacccg aagatcggct gctatccccg 140221 ggacatggat cgcggggcgg tggtggggtt tcttctcggt gtttgtgttg tatcgtgctt 140281 ggcgggaatg cccaaaacgt cctggagacg ggtgagtgtc ggcgaggacg tttcgttgct 140341 tccagctccg gggcctacgg ggcgcggccc gacccagaaa ctactatggg ccgtggaacc 140401 cctggatggg tgcggcccct tacacccgtc gtgggtctcg ctgatgcccc ccaagcaggt 140461 gcccgagacg gtcgtggatg cggcgtgcat gcgcgctccg gtcccgctgg cgatggcgta 140521 cgcccccccg gccccatctg cgaccggggg tctacgaacg gacttcgtgt ggcaggagcg 140581 cgcggccgtg gttaaccgga gtctggttat tcacggggtc cgagagacgg acagcggcct 140641 gtataccctg tccgtgggcg acataaagga cccggctcgc caagtggcct cggtggtcct 140701 ggtggtgcaa ccggccccag ttccgacccc acccccgacc ccagccgatt acgacgagga 140761 tgacaatgac gagggcgagg gcgaggacga aagtctagcc ggcactcccg ccagcgggac 140821 cccccggctc ccgcctcccc ccgccccccc gaggtcttgg cccagcgccc ccgaagtctc 140881 acacgtgcgt ggggtgaccg tgcgtatgga gactccggaa gctatcctgt tttcccccgg 140941 ggaggcgttt agcacgaacg tctccatcca tgccatcgcc cacgacgacc agacctacac FIGURE 9 (Continued)

141001 catggacgtc gtctggttga ggttcgacgt gccgacctcg tgtgccgaga tgcgaatata
141061 cgaatcgtgt ctgtatcacc cgcagctccc agagtgtctg tccccggccg acgctccgtg
141121 cgccgcgagt acgtggacgt ctcgcctggc cgtccgcagc tacgcggggt gttccagaac
141181 aaaccccccg ccgcgctgtt cggccgaggc tcacatggag cccttcccgg ggctggcgtg
141241 gcaggcggcc tccgtcaatc tggagttccg ggacgcgtcc ccacaacact ccggcctgta
141301 tctgtgcgtg gtgtacgtca acgaccatat tcacgcatgg ggccacatta ccatcagcac
141361 cgcggcgcag taccggaacg cggtggtgga acagcccctc ccacagcgcg gcgcggattt
141421 ggccgagccc acccacccgc acgtcggggc ccctccccac gcgcccccaa cccacggcgc
141481 cctgcggtta ggggcggtga tgggggccgc cctgctgctg tctgcgctgg ggttgtcggt
141541 gtgggcgtgt atgacctgtt ggcgcaggcg tgcctggcgg gcggttaaaa gcagggcctc
141601 gggtaagggg cccacgtaca ttcgcgtggc cgacagcgag ctgtacgcgg actggagctc
141661 ggacagcgag ggagaacgcg accaggtccc gtggctggcc cccccggaga gacccgactc
141721 tccctccacc aatggatccg gctttgagat cttatcacca acggctccgt ctgtataccc
141781 ccgtagcgat gggcatcaat ctcgccgcca gctcacaacc tttggatccg gaaggcccga
141841 tcgccgttac tcccaggcct ccgattcgtc cgtcttctgg taaggcgccc catcccgagg
141901 ccccacgtcg gtcgccgaac tgggcgaccg ccggcgaggt ggacgtcgga gacgagctaa
141961 tcgcgatttc cgacgaacgc ggaccccccc gacatgaccg cccgcccctc gccacgtcga
142021 ccgcgccctc gccacacccg cgacccccgg gctacacggc cgttgtctcc ccgatggccc
142081 tccaggctgt cgacgccccc tccctgtttg tcgcctggct ggccgctcgg tggctccggg
142141 gggcttccgg cctgggggcc gtcttgtgtg ggattgcgtg gtatgtgacg tcaattgccc
142201 gaggcgcata aagggccggt ggtccgccta gccgcagcaa attaaaaatc gtgagtcact
142261 gcgaccgcaa cttcccaccc ggagctttct tccggcctcg atgacgtccc ggctctccga
142321 tcccaactcc tcagcgcgat ccgacatgtc cgtgccgctt tatcccacgg cctcgccagt
142381 ttcggtcgaa gcctactact cggaaagcga agacgaggcg gccaacgact tcctcgtacg
142441 catgggccgc caacagtcgg tattaaggcg tcgacgcaga cgcacccgct gcgtcggcat
142501 ggtgatcgcc tgtctcctcg tggccgttct gtcgggcgga tttggggcgc tcctgatgtg
142561 gctgctccgc taaaagaccg catcgacacg cgcgtccttc ttgtcgtctc tcttcccccc
142621 atcaccccgc aatttgcacc cagcctttaa ctacattaaa ttgggttcga ttggcaatgt FIGURE 9 (Continued)

142681 tgtctcccgg ttgatttttg ggtgggtggg gagtgggtgg gtggggagtg ggtgggtggg 142741 gagtgggtgg gtggggagtg ggtgggtggg gagtgggtgg gtggggagtg ggtgggtggg 142801 gagtgggtgg gtggggagtg ggtgggtggg gagtgggtgg gtggggagtg ggtgggtggg 142861 gagtgggtgg gtggggagtg ggtgggtggg gagtgggtgg gtggggagtg ggtgggtggg 142921 gagtgggtgg gtggggagtg gcaaggaaga aacaagcccg accaccagac agaaaatgta 142981 accataccca aaccgactct gggggctgtt tgtggggtcg gaaccatagg atgaacaaac 143041 cacccccgtac ctcccgcacc cttgggtgcg ggtggctcat cggcatctgt ccggtatggg 143101 ttgttcccca cccactcgcg ttcggacgtc ttagaatcat ggcggtttct atgccgacat 143161 cggtttctcc cccgcaataa gacacgatgc gataaaatct gtttgtgaaa tttattaagg 143221 gtacaaattg ccctagcaca ggggtggggt tagggccggg tccccacacc caaacgcacc 143281 aaacagatgc aggcagtggg tcgagtacag ccccgcgtac gaacacgtcg atgcgtgtgt 143341 cagacagcac cagaaagcac aggccatcaa caggtcgtgc atgtgtcggt gggtttggac 143401 gcgggggggcc atggtgggtg ataaagttaa tggccgccgt ccgccagggc cacaggggcg 143461 acgtctcttg gttggcccgg agccactggg tgtggaccag ccgcgcgtgg cggcccaaca 143521 tggcccctgt agccgggggc gggggatcgc gcacgtttgc agcgcacatg cgagacacct 143581 cgaccacggt tcggaagaag gcccggtggt ccgcgggcaa catcaccagg tgcgcaagcg 143641 cccgggcgtc cagagggtag agccctgagt catccgaggt tggctcatcg cccgggtcat 143701 gccgcaagtg cgtgtgggtt gggcttccgg tgggcgggac gcgaaccgcg gtgtggagcc 143761 cgacgcgggc ccgagcgtac gctccatctt gtggggagaa ggggtctggg ctcgccaggg 143821 gggcatactt gcccgggcta tacagacccg cgagccgtac gtggttcgcg gggggtgcgt 143881 ggggtccggg gctcccgggg aggccggggc tcccggggtt gtcgtggatc cctggggtca 143941 cgcggtaccc tggggtctct gggagctcgc ggtactctgg gttccctagg ttctcggggt 144001 ggtcgcggaa cccggggctc ccggggaaca cgcggtgtcc tggggattgt tggcggtcgg 144061 acggcttcag atggcttcga gatcgtagtg tccgcaccga ctcgtagtag acccgaatct 144121 ccacattgcc ctgccgcttg atcattatca ccccgttgcg gggtccgga gatcatgcgc 144181 gggtgtcctc gaggtgcgtg aacacctctg gggtgcatgc cggcggacgg cacgcctttt 144241 aagtaaacat ctgggtcgcc cggcccaact ggggccgggg gttgggtctg gctcatctcg 144301 agagccacgg ggggaaccac cctccgccca gaaacttggg cgatggtcgt acccgggact FIGURE 9 (Continued)

144361 caacgggtta ccggattacg gggactgtcg gtcacggtcc cgccggttct tcgatgtgcc 144421 acacccaagg atgcgttggg ggcgattttg ggcagcagcc cgggagagcg cagcagagga 144481 cgctccgggt cgtgcacggc ggttctggcc gcctcccggt cctcacgccc ccttttattg 144541 atctcatcgc gtacgtcggc gtacgtcctg ggcccaaccc gcatgttgtc caggaaggtg 144601 tccgccattt ccagggccca cgacatgctc cccccccccc ccccgacgag caggaagcgg 144661 tccacgcaac ggtcgccgcc ggtcgccccg acgagcagga agcggtccac gcaacggtcg 144721 ccgccggtcg ccccgacgag caggaagcgg tccacgcaac ggtcgccgcc ggtcgcctcg 144781 acgaggacgt tcctcctgcg ggaaggcacg aacgcgggtg agccccctcc tccgcccccg 144841 cgtccccccct cctccgcccc cgcgtccccc ctcctccgcc cccgcgtccc ccctcctccg 144901 cccccgcgtc ccccctcctc cgccctcctc cgcccaccca aggtgcttac ccgtgcaaaa 144961 aggcggaccg gtgggtttct gtcgtcggag gcccccgggg tgcgtcccct gtgtttcgtg 145021 ggtggggtgg gtgggtcttt ccgcgtgtcc ctttccgatg cgatcccgat cccgagccgg 145081 ggcgtcgcga tgccgacgcc gtccgctccg acggccctct gcgagtcccg ctcccggtcc 145141 gcgtgctccg cagcagctcc cgtcgttcgt ggccggcgcc gtctgcgggc gtcggtcgcg 145201 ccgggccttt atgtgcgccg gagagacccg ccccccgccg cccgggcccg cccccggggc 145261 cggcgcggag tcgggcacgg cgccagtgct cgcacttcgc cctaataata tatatatatt 145321 gggacgaagt gcgaacgctt cgcgttctca cttcttttac ccggcggccc cgcccccttg 145381 gggcggtccc gcccgccggc caatgggggg gcggcaaggc gggcggccct tgggccgccc 145441 gccgtcccgt tggtcccggc gtccggcggg cgggaccggg ggcccgggga cggccaacgg 145501 gcgcgcgggg ctcgtatctc attaccgccg aaccgggaag tcggggcccg ggccccgccc 145561 cctgcccgtt cctcgttagc atgcggaacg gaagcggaaa ccgccggatc gggcggtaat 145621 gagatgccat gcggggcggg gcgcgggccc acccgcccta gcgccccgcc catggcagat 145681 ggcgcggatg ggcggggccg gggttcgac caacgggccg cggccacggg cccccggcgt 145741 gccggcgtcg gggcggggtc gtgcataatg gaattccgtt cggggcgggc ccgccgtggg 145801 ggcgggggc cggcggcctc cgctgctcct ccttcccgcc ggcccctggg actatatgag 145861 cccgaggacg ccccgatcgt ccacacggag cgcggctgcc gacacggatc cacgacccga 145921 cgcgggaccg ccagagacag accgtcagac gctcgccgcg ccgggacgcc gatacgcgga 145981 cgaagcgcgg gaggggatc ggccgtccct gtcctttttc ccacccaagc atcgaccggt FIGURE 9 (Continued)

146041 ccgcgctagt tccgcgtcga cggcgggggt cgtcggggtc cgtgggtctc gccccctccc 146101 catcgagagt ccgtaggtga cctaccgtgc tacgtccgcc gtcgcagtcg tatccccgga 146161 ggatcgcccc gcatcggcga tggcgtcgga gaacaagcag cgccccggct ccccgggccc 146221 caccgacggg ccgccgccca ccccgagccc agaccgcgac gagcgggggg ccctcgggtg 146281 gggcgcggag acggaggagg gcggggacga ccccgaccac gaccccgacc acccccacga 146341 cctcgacgac gccccggcggg acgggagggc ccccgcggcg ggcaccgacg ccggcgagga 146401 cgccggggac gccgtctcgc cgcgacagct ggccctgctg gcctccatgg tagaggaggc 146461 cgtccggacg atcccgacgc ccgaccccgc ggcctcgccg ccccggaccc ccgcctttcg 146521 agccgacgac gatgacgggg acgagtacga cgacgcagcc gacgccgccg gcgaccgggc 146581 cccggcccgg ggccgcgcac gggaggcccc gctacgcggc gcgtatccgg accccacgga 146641 ccgcctgtcg ccgcgcccgc cggcccagcc gccgcagaga cgtcgtcacg gccggcggcg 146701 gccatcggcg tcatcgacct cgtcggactc cgggtcctcg tcctcgtcgt ccgcatcctc 146761 ttcgtcctcg tcgtccgacg aggacgagga cgacgacggc aacgacgcgg ccgaccacgc 146821 acgcgaggcg cgggccgtcg ggcggggtcc gtcgagcgcg gcgccggaag cccccgggcg 146881 gacgccgccc ccgcccgggc cacccccccct ctccgaggcc gcgcccaagc cccgggcggc 146941 ggcgaggacc cccgcggcct ccgcgggccg catcgagcgc cgccgggccc gcgcggcggt 147001 ggccggccgc gacgccacgg gccgcttcac ggccgggcag ccccggcggg tcgagctgga 147061 cgcccgacgcg gcctccggcg ccttctacgc gcgctatcgc gacgggtacg tcagcgggga 147121 gccgtggccc ggcgccgggc ccccgccccc ggggcgggtg ctgtacggcg gcctgggcga 147181 cagccgcccg ggcctctggg gggcgcccga ggcggaggag gcgcgacgcc ggttcgaggc 147241 ctcgggcgcc ccggcggccg tgtgggcgcc cgagctgggc gacgccgcgc agcagtacgc 147301 cctgatcacg cggctgctgt acaccccgga cgcggaggcc atggggtggc tccagaaccc 147361 gcgcgtggtc cccggggacg tggcgctgga ccaggcctgc ttccggatct cgggcgccgc 147421 gcgcaacagc agctccttca tcaccggcag cgtggcgcgg gccgtgcccc acctgggcta 147481 cgccatggcg gccggccgct tcggctgggg cctggcgcac gcggcggccg ccgtggccat 147541 gagccgccga tacgaccgcg cgcagaaggg cttcctgctg accagcctgc gccgcgccta 147601 cgcgcccctg ttggcgcgcg agaacgcggc gctgacgggg gccgcgggga gccccggcgc 147661 cggcgcagat gacgaggggg tcgccgccgc cgtcgtcgcc gccgccgccg caccgggcga FIGURE 9 (Continued)

147721 gcgcgcggtg cccgccgggt acggcgccgc ggggatcctc gccgccctgg ggcggctgtc 147781 cgccgcgccc gcctcccccg cgggggggcga cgacccccgac gccgcccgcc acgccgacgc 147841 cgacgacgac gccgggcgcc gcgcccaggc cggccgcgtg gccgtggagt gcctggccgc 147901 ctgccgcggg atcctggagg cgctggccga gggcttcgac ggcgacctgg cggccgtccc 147961 ggggctggcc ggggcccggc ccgccagccc cccgcggccg gagggacccg cgggccccgc 148021 ttccccgccg ccgccgcacg ccgacgcgcc ccgcctgcgc gcgtggctgc gcgagctgcg 148081 gttcgtgcgc gacgcgctgg tgctcatgcg cctgcgcggg gacctgcgcg tggccggcgg 148141 cagcgaggcc gccgtggccg ccgtgcgcgc cgtgagcctg gtcgccgggg ccctgggtcc 148201 cgcgctgccg cgggacccgc gcctgccgag ctccgcggcc gccgccgccg cggacctgct 148261 gtttgagaac cagagcctgc gccccctgct ggcggcgggt ccgcgccgct cttcttcgtc 148321 ttcgggggtc gcggccgccg cctccgccgc gccgcgggag gggcgcaagc gcaagagtcc 148381 cggcccggcc cggccgcccg gaggcggcgg cccgcgaccc ccgaagacga agaagagcgg 148441 cgcggacgcc cccggctcgg acgcccgcgc ccccctcccc gcgcccgcgc ccccctccac 148501 gcccccgggg cccgagcccg cccccgccca gcccgcggcg ccccgggccg ccgcggcgca 148561 ggcccgcccg cgccccgtgg cgctgtcgcg ccggcccgcc gagggccccg accccctggg 148621 cggctggcgg cggcagcccc cggggcccag ccacacggcg gcgcccgcgg ccgccgccct 148681 ggaggcctac tgctccccgc gcgccgtggc cgagctcacg gaccacccgc tgttccccgt 148741 cccctggcga ccggccctca tgtttgaccc gcgggccctg gcctcgatcg ccgcgcggtg 148801 cgccgggccc gcccccgccg cccaggccgc gtgcggcggc ggcgacgacg acgagaaccc 148861 ccaccccccac ggggccgccg ggggccgcct ctttggcccc ctgcgcgcct cgggcccgct 148921 gcgccgcatg gcggcctgga tgcgccagat ccccgacccc gaggacgtgc gcgtggtggt 148981 gctgtactcg ccgctgccgg gcgaggacct ggccggcggc ggggcctcgg gggggccgcc 149041 ggagtggtcc gccgagcgcg gcgggctgtc ctgcctgctg gcggccctgg ccaaccggct 149101 gtgcgggccg gacacggccg cctgggcggg caactggacc ggcgcccccg acgtgtcggc 149161 gctgggcgcg cagggcgtgc tgctgctgtc cacgcgggac ctggccttcg ccggggccgt 149221 ggagtttctg ggctgctcg ccagcgccgg cgaccggcgg ctcatcgtgg tcaacaccgt 149281 gcgcgcctgc gactggcccg ccgacgggcc cgcggtgtcg cggcagcacg cctacctggc 149341 gtgcgacctg ctgcccgccg tgcagtgcgc cgtgcgctgg ccggcggcgc gcgacctgcg FIGURE 9 (Continued)

149401 ccgcacggtg ctggcctcgg gccgcgtgtt cggcccgggg gtcttcgcgc gcgtggaggc
149461 cgcgcacgcg cgcctgtacc ccgacgcgcc gccgctgcgc ctgtgccgcg gcggcaacgt
149521 gcgctaccgc gtgcgcacgc gcttcggccc ggacacgccg gtgcccatgt ccccgcgcga
149581 gtaccgccgg gccgtgctgc cggcgctgga cggccgggcg gcggcctcgg ggaccaccga
149641 cgccatggcg cccggcgcgc cggacttctg cgaggaggag gcccactcgc accgcgcctg
149701 cgcgcgctgg ggcctgggcg cgccgctgcg gcccgtgtac gtggcgctgg ggcgcgaggc
149761 ggtgcgcgcc ggcccggccc ggtggcgcgg gccgcggagg gacttttgcg cccgcgccct
149821 gctggagccc gacgacgacg cccccccgct ggtgctgcgc ggcgacgacg acggcccggg
149881 ggccctgccg ccggcgccgc ccgggattcg ctgggcctcg gccacgggcc gcagcggcac
149941 cgtgctggcg gcggcggggg ccgtggaggt gctgggggcg gaggcgggct tggccacgcc
150001 cccgcgacgg gacgttgtgg actgggaagg cgcctgggac gaagacgacg gcggcgcgtt
150061 cgagggggac ggggtgctgt aacgggccgg gacggggcgg ggcgcttgtg aaacccgaag
150121 acgcaataaa cggcaacgac ctgattaagt tttgcagtag cgttgtttat tcgaggggcg
150181 ggagggggcg aggggcggga gggggcgagg ggcgggaggg ggcgaggggc gggagggggc
150241 gaggggcggg agggggcgag gggcgggagg gggcgagggg cgggaggggg cgaggggcgg
150301 gagggggcga ggggcggtgg tggtgcgcgg gcgcccccgg agggtttgga tctctgacct
150361 gagattggcg gcactgaggt agagatgccc gaaccccccc gagggagcgc gggacgcggc
150421 tggggagggc tggggctggg gagggctggg gctggggagg gctggggctg gggagggctg
150481 gggctgggga gggctggggc tggggagggc tggggctggg gagggctggg gctggggagg
150541 gctggggctg gggagggctg gggctgggga gggctggggc tggggagggc tggggctggg
150601 gagggctggg gctgtggtgt gtgacaggag cggcgtgttg cgctgggggga cgtctggagg
150661 agcgggggggt gcgcggtgac gtgtggatga ggaacaggag ttgttgcgcg gtgagttgtc
150721 gctgtgagtt gtgttgttgg gcaggtgtgt tggatgacgt gacgtgtgga tgaggaaccg
150781 gagtcgccgg tgcgccgtgc tgttggtgtt ctgttggtgt tgttacacct gtggcagccc
150841 gggccccccg cgcgcggggc ggcgcgcaaa aaaggcgggc ggcggtccgg gcggcgtgcg
150901 cgcgcgcggc gggcgtgggg ggcggggccg cgggagcggg ggaggagccc cacccacaga
150961 cggggaggag cgggggagga gcgggggagg agcgggggag gagccccacc cacagacggg
151021 gaggagcggg ggaggagcgg ccagacccca aaaacgggcc cccccgaaac acaccccccg FIGURE 9 (Continued)

151081 ggggtcgcgc gcggcccttt aaagcgcggc ggcgggcagc ccgggccccc cgcgg

FIGURE 9 (Continued)

McKrae ICP4 amino acid sequence (SEQ ID NO: 2)

1 masenkqrpg spgptdgppp tpspdrderg algwgaetee ggddpdhdpd hphdlddarr 61 dgrapaagtd agedagdavs prqlallasm veeavrtipt pdpaassprt pafradddddg 121 deyddaadaa gdrapargra reaplrgayp dptdrlsprp paqppqrrrh grrrpsasst 181 ssdsgsssss sasssssssd ededddgnda adharearav grgpssaape apgrtppppg 241 ppplseaapk praaartpaa sagrierrra raavagrdat grftagqprr veldadaasg 301 afyaryrdgy vsgepwpgag ppppgrvlyg glgdsrpglw gapeaeearr rfeasgapaa 361 vwapelgdaa qqyalitrll ytpdaeamgw lqnprvvpgd valdqacfri sgaarnsssf 421 itgsvaravp hlgyamaagr fgwglahaaa avamsrrydr aqkgflltsl rrayapllar 481 enaaltgaag spgagaddeg vaaavvaaaa apgeravpag ygaagilaal grlsaapasp 541 aggddpdaar hadadddagr raqagrvave claacrgile alaegfdgdl aavpglagar 601 paspprpegp agpasppppph adaprlrawl relrfvrdal vlmrlrgdlr vaggseaava 661 avravslvag algpalprdp rlpssaaaaa adllfenqsl rpllaagprr sssssgvaaa 721 asaapregrk rkspgparpp ggggprppkt kksgadapgs daraplpapa ppstppgpep 781 apaqpaapra aaaqarprpv alsrrpaegp dplggwrrqp pgpshtaapa aaaleaycsp 841 ravaeltdhp lfpvpwrpal mfdpralasi aarcagpapa aqaacgggdd denphphgaa 901 ggrlfgplra sgplrrmaaw mrqipdpedv rvvvlysplp gedlagggas ggppewsaer 961 gglscllaal anrlcgpdta awagnwtgap dvsalgaqgv lllstrdlaf agaveflgll 1021 asagdrrliv vntvracdwp adgpavsrqh aylacdllpa vqcavrwpaa rdlrrtvlas 1081 grvfgpgvfa rveaaharly pdapplrlcr ggnvryrvrt rfgpdtpvpm spreyrravl 1141 paldgraaas gttdamapga pdfceeeahs hracarwglg aplrpvyval greavragpa 1201 rwrgprrdfc arallepddd applvlrgdd dgpgalppap pgirwasatg rsgtvlaaag 1261 avevlgaeag latpprrdvv dwegawdedd ggafegdgvl

FIGURE 10

HSV McKrae strain amino acid sequence of ICP22 (SEQ ID NO: 3)

```
  1 madispgafa pcvkarrpal rspplgtrkr krparplsse sevetdtale sevesetasd
 61 stesgdqeea priggrrapr rlggrffldm saesttgtet dtavsddpdd tsdwsyddip
121 prpkrarvnl ritsspdrrd gvifpkmgrv rstretqpra ptpsapspna mlrrsvrqaq
181 rrssarwtpd lgymrqcinq lfrvlrvard phgsanrlrh lirdcylmgy crarlaprtw
241 crllqvsggt wgmhlrntir evearfdata epvcklpcle arrygpecdl snleihlsat
301 sddeisdatd leaagsdhtl asqsdtedap spvtletpep rgslavrled efgefdwtpq
361 egsqpwlsav vadtssverp gpsdsgagra aedrkcldgc rkmrfstacp ypcsdtflrp
```

FIGURE 11

HSV McKrae strain amino acid sequence of ICP47 (SEQ ID NO: 4)

1 mswalemadt fldnmrvgpr tyadvrdein krgredreaa rtavhdperp llrspgllpk 61 iapnaslgva hrrtggtvtd sprnpvtr

FIGURE 12

HSV McKrae strain nucleotide sequence of ICP4 (SEQ ID NO: 5)

126001 tttattgcgt cttcgggttt cacaagcgcc ccgccccgtc ccggcccgtt acagcacccc
126061 gtccccctcg aacgcgccgc cgtcgtcttc gtcccaggcg ccttcccagt ccacaacgtc
126121 ccgtcgcggg ggcgtggcca agcccgcctc cgcccccagc acctccacgg cccccgccgc
126181 cgccagcacg gtgccgctgc ggcccgtggc cgaggcccag cgaatcccgg gcggcgccgg
126241 cggcagggcc cccgggccgt cgtcgtcgcc gcgcagcacc agcggggggg cgtcgtcgtc
126301 gggctccagc agggcgcggg cgcaaaagtc cctccgcggc ccgcgccacc gggccgggcc
126361 ggcgcgcacc gcctcgcgcc ccagcgccac gtacacgggc cgcagcggcg cgcccaggcc
126421 ccagcgcgcg caggcgcggt gcgagtgggc ctcctcctcg cagaagtccg gcgcgccggg
126481 cgccatggcg tcggtggtcc ccgaggccgc cgcccggccg tccagcgccg gcagcacggc
126541 ccggcggtac tcgcgcgggg acatgggcac cggcgtgtcc gggccgaagc gcgtgcgcac
126601 gcggtagcgc acgttgccgc cgcggcacag gcgcagcggc ggcgcgtcgg ggtacaggcg
126661 cgcgtgcgcg gcctccacgc gcgcgaagac ccccgggccg aacacgcggc ccgaggccag
126721 caccgtgcgg cgcaggtcgc gcgccgccgg ccagcgcacg gcgcactgca cggcgggcag
126781 caggtcgcac gccaggtagg cgtgctgccg cgacaccgcg ggcccgtcgg cgggccagtc
126841 gcaggcgcgc acggtgttga ccacgatgag ccgccggtcg ccggcgctgg cgagcagccc
126901 cagaaactcc acggccccgg cgaaggccag gtcccgcgtg gacagcagca gcacgccctg
126961 cgcgcccagc gccgacacgt cgggggcgcc ggtccagttg cccgcccagg cggccgtgtc
127021 cggcccgcac agccggttgg ccagggccgc cagcaggcag gacagcccgc cgcgctcggc
127081 ggaccactcc ggcggccccc ccgaggcccc gccgccggcc aggtcctcgc ccggcagcgg
127141 cgagtacagc accaccacgc gcacgtcctc ggggtcgggg atctggcgca tccaggccgc
127201 catgcggcgc agcgggcccg aggcgcgcag ggggccaaag aggcggcccc cggcggcccc
127261 gtgggggtgg gggttctcgt cgtcgtcgcc gccgccgcac gcggcctggg cggcgggggc
127321 gggcccggcg caccgcgcgg cgatcgaggc cagggcccgc gggtcaaaca tgagggccgg
127381 tcgccagggg acggggaaca gcgggtggtc cgtgagctcg gccacggcgc gcggggagca
127441 gtaggcctcc agggcggcgg ccgcgggcgc cgccgtgtgg ctgggccccg ggggctgccg
127501 ccgccagccg cccagggggt cggggccctc ggcgggccgg cgcgacagcg ccacggggcg
127561 cgggcgggcc tgcgccgcgg cggcccgggg cgccgcgggc tgggcggggg cgggctcggg

FIGURE 13

127621 ccccgggggc gtggaggggg gcgcgggcgc ggggaggggg gcgcgggcgt ccgagccggg 127681 ggcgtccgcg ccgctcttct tcgtcttcgg gggtcgcggg ccgccgcctc cgggcggccg 127741 ggccgggccg ggactcttgc gcttgcgccc ctcccgcggc gcggcggagg cggcggccgc 127801 gaccccccgaa gacgaagaag agcggcgcgg acccgccgcc agcagggggc gcaggctctg 127861 gttctcaaac agcaggtccg cggcggcggc ggccgcggag ctcggcaggc gcgggtcccg 127921 cggcagcgcg ggacccaggg ccccggcgac caggctcacg gcgcgcacgg cggccacggc 127981 ggcctcgctg ccgccggcca cgcgcaggtc cccgcgcagg cgcatgagca ccagcgcgtc 128041 gcgcacgaac cgcagctcgc gcagccacgc gcgcaggcgg ggcgcgtcgg cgtgcggcgg 128101 cggcggggaa gcggggcccg cgggtccctc cggccgcggg gggctggcgg gccgggcccc 128161 ggccagcccc gggacggccg ccaggtcgcc gtcgaagccc tcggccagcg cctccaggat 128221 cccgcggcag gcggccaggc actccacggc cacgcggccg gcctgggcgc ggcgcccggc 128281 gtcgtcgtcg gcgtcggcgt ggcgggcggc gtcggggtcg tcgccccccg cgggggaggc 128341 gggcgcggcg gacagccgcc ccagggcggc gaggatcccc gcggcgccgt acccggcggg 128401 caccgcgcgc tcgcccggtg cggcggcggc ggcgacgacg gcggcggcga ccccctcgtc 128461 atctgcgccg gcgccggggc tccccgcggc ccccgtcagc gccgcgttct cgcgcgccaa 128521 caggggcgcg taggcgcggc gcaggctggt cagcaggaag cccttctgcg cgcggtcgta 128581 tcggcggctc atggccacgg cggccgccgc gtgcgccagg ccccagccga agcggccggc 128641 cgccatggcg tagcccaggt ggggcacggc ccgcgccacg ctgccggtga tgaaggagct 128701 gctgttgcgc gcggcgcccg agatccggaa gcaggcctgg tccagcgcca cgtccccggg 128761 gaccacgcgc gggttctgga gccaccccat ggcctccgcg tccggggtgt acagcagccg 128821 cgtgatcagg gcgtactgct gcgcggcgtc gcccagctcg ggcgcccaca cggccgccgg 128881 ggcgcccgag gcctcgaacc ggcgtcgcgc ctcctccgcc tcgggcgccc cccagaggcc 128941 cgggcggctg tcgcccaggc cgccgtacag cacccgcccc gggggcgggg gcccggcgcc 129001 gggccacggc tccccgctga cgtacccgtc gcgatagcgc gcgtagaagg cgccggaggc 129061 cgcgtcggcg tccagctcga cccgccgggg ctgcccggcc gtgaagcggc ccgtggcgtc 129121 gcggccggcc accgccgcgc gggcccggcg gcgctcgatg cggcccgcgg aggccgcggg 129181 ggtcctcgcc gccgcccggg gcttgggcgc ggcctcggag aggggggtg gcccgggcgg 129241 gggcggcgtc cgcccggggg cttccggcgc cgcgctcgac ggacccccgcc cgacggcccg FIGURE 13 (Continued)

129301 cgcctcgcgt gcgtggtcgg ccgcgtcgtt gccgtcgtcg tcctcgtcct cgtcggacga 129361 cgaggacgaa gaggatgcgg acgacgagga cgaggacccg gagtccgacg aggtcgatga 129421 cgccgatggc cgccgccggc cgtgacgacg tctctgcggc ggctgggccg gcgggcgcgg 129481 cgacaggcgg tccgtggggt ccggatacgc gccgcgtagc ggggcctccc gtgcgcggcc 129541 ccgggccggg gcccggtcgc cggcggcgtc ggctgcgtcg tcgtactcgt ccccgtcatc 129601 gtcgtcggct cgaaaggcgg gggtccgggg cggcgaggcc gcggggtcgg gcgtcgggat 129661 cgtccggacg gcctcctcta ccatggaggc cagcagggcc agctgtcgcg gcgagacggc 129721 gtccccggcg tcctcgccgg cgtcggtgcc cgccgcgggg gccctcccgt cccgccgggc 129781 gtcgtcgagg tcgtgggggt ggtcggggtc gtggtcgggg tcgtccccgc cctcctccgt 129841 ctccgcgccc cacccgaggg ccccccgctc gtcgcggtct gggctcgggg tgggcggcgg 129901 cccgtcggtg gggcccgggg agccggggcg ctgcttgttc tccgacgcca tcgccgatgc 129961 ggggcgatcc tccggggata cgactgcgac ggcggacgta gcacggtagg tcacctacgg FIGURE 13 (Continued)

HSV McKrae strain nucleotide sequence of ICP22 (SEQ ID NO: 6)

132481 ggtcctccgg gacgttttct ggatggccga catttcccca ggcgcttttg tgccttgtgt 132541 aaaagcgcgg cgtcccgctc tccgatcccc gcccctgggc acgcgcaagc gcaagcgccc 132601 tgcccgcccc ctctcatcgg agtctgaggt cgaatccgag acagccttgg agtctgaggt 132661 cgaatccgag acagcatcgg attcgaccga gtctggggac caggaggaag ccccccgcat 132721 cggtggccgt agggcccccc ggaggcttgg ggggcggttt tttctggaca tgtcggcgga 132781 atccaccacg ggacggaaa cggatgcgtc ggtgtcggac gaccccgacg acacgtccga 132841 ctggtcttgt gacgacattc cccacgacc caagcgggcc cgggtaaacc tgcggctcac 132901 tagctctccc gatcggcggg atggggttat ttttcctaag atggggcggg tccggtctac 132961 ccgggaaacg cagccccggg cccccacccc gtcggcccca agcccaaatg caatgctccg 133021 gcgctcggtg cgccaggccc agaggcggag cagcgcacga tggaccccg acctgggcta 133081 catgcgccag tgtatcaatc agctgtttcg ggtcctgcgg gtcgcccggg acccccacgg 133141 cagtgccaac cgcctgcgcc acctgatacg cgactgttac ctgatgggat actgccgagc 133201 ccgtctggcc ccgcgcacgt ggtgccgctt gctgcaggtg tccggcggaa cctggggcat 133261 gcacctgcgc aacaccatac gggaggtgga ggctcgattc gacgccaccg cagaacccgt 133321 gtgcaagctt ccttgtttgg aggccagacg gtacggcccg gagtgtgatc ttagtaatct 133381 cgagattcat ctcagcgcga caagcgatga tgaaatctcc gatgccaccg atctggaggc 133441 cgccggttcg gaccacacgc tcgcgtccca gtccgacacg gaggatgccc cctcccccgt 133501 tacgctggaa accccagaac cccgcgggtc cctcgctgtg cgtctggagg atgagtttgg 133561 ggagtttgac tggacccccc aggagggctc ccagccctgg ctgtctgcgg tcgtggccga 133621 taccagctcc gtggaacgcc cgggcccatc cgattctggg gcgggtcgcg cagcagaaga 133681 ccgcaagtgt ctggacggct gccggaaaat gcgcttctcc accgcctgcc cctatccgtg 133741 cagcgacacg tttctccggc cgtgagtccg gtcgccccga ccccttgta tgtccccaaa

FIGURE 14

HSV McKrae strain nucleotide sequence of ICP47 (SEQ ID NO: 7)

```
145081 tccgcccaga gactcgggtg atggtcgtac ccgggactca acgggttacc ggattacggg
145141 gactgtcggt cacggtcccg ccggttcttc gatgtgccac acccaaggat gcgttggggg
145201 cgatttcggg cagcagcccg ggagagcgca gcaggggacg ctccgggtcg tgcacggcgg
145261 ttctggccgc ctcccggtcc tcacgccccc ttttattgat ctcatcgcgt acgtcggcgt
145321 acgtcctggg cccaacccgc atgttgtcca ggaaggtgtc cgccatttcc agggcccacg
145381 acatgctttt ccccccgacg agcaggaagc ggtccacgca acggtcgccg ccggtcgcct
```

FIGURE 15

Human cytomegalovirus enhancer nucleotide sequence (SEQ ID NO: 8)

gaagatctttggttatatagcataaatcaatattggctattggccattgcatacgttgtatccatatcataatatgt
acatttatattggctcatgtccaacattaccgccatgttgacattgattattgactagttattaatagtaatcaatt
acggggtcattagttcatagcccatatatggagttccgcgttacataacttacggtaaatggcccgcctggctgacc
gcccaacgacccccgcccattgacgtcaataatgacgtatgttcccatagtaacgccaatagggactttccattgac
gtcaatgggtggagtatttacggtaaactgcccacttggcagtacatcaagtgtatcatatgccaagtacgcccccct
attgacgtcaatgacggtaaatggcccgcctggcattatgcccagtacatgaccttatgggactttcctacttggca
gtacatctacgtattagtcatcgctattaccatggtgatgcggttttggcagtacatcaat

FIGURE 16

Calcitonin gene-related peptide promoter (SEQ ID NO: 9)

aatgggtttg ggtgtgtgta aatgagtgtg
accggaagcg agtgtgagct tgatctaggc agggaccaca cagcactgtc acacctgcct
gctctttagt agaggactga agtgcggggg tggggtacg gggccggaat agaatgtctc
tgggacatct tggcaaacag cagccggaag caaagggca gctgtgcaaa cggctcaggc
aggtgatgga tggcagggta ggaaggggga ggtccagagg tctggatgga ggcttccgca
tctgtacctt gcaactcacc cctcaggccc agcaggtcat cggccccctc ctcacacatg
taatgacgta gaagagtacc ccgggacagt ccggggagat ggagattcgg aaagtatcca
tggagctctt acagaatccc ctgtgcggac caggaaactc ttgtagatcc ctgcctatct
gaggcccagg cgctgggctg tttctcacaa tattccttca agatgagatt gtggtcccca
tttcaaagat gagtacactg agcctctgtg aagttacttg cccatgatca cacaaccagg
aattgggcca actgtaattg aactcctgtc taacaaagtt cttgctccca gctccgtctc
ttgtttccca cgagccctgg ccctctgtgg gtaataccag ctactggagt cagatttctt
gggcccagaa cccaccctta ggggcattaa cctttaaaat ctcacttggg caggggtctg
ggatcagagt tggaagagtc cctacaatcc tggacccttt ccgccaaatc gtgaaaccag
gggtggagtg gggcgagggt tcaaaaccag gccggactga gaggtgaaat tcaccatgac
gtcaaactgc cctcaaattc ccgctcactt taagggcgtt acttgttggt gcccccacca
tcccccacca tttccatcaa tgacctcaat gcaaatacaa gtgggacggt cctgctgacg
cctccaggtt ctggaagcat gagggtgacg caacccaggg gcaaaggacc cctccgccca
ttggttgctg tgcactggcg gaactttccc gacccacagc ggcgggaata agagcagtcg
ctggcgctgg gaggcatcag agacactgcc cagcccaagt gtcgccgccg cttccacagg
gctctggctg gacgccgccg ccgccgctgc

FIGURE 17

Bovine growth hormone polyadenylation signal nucleotide sequence (SEQ ID NO: 10)

```
ggatcccgactgtgccttctagttgccagccatctgttgtttgcccctcccccgtgccttccttgaccctggaaggt
gccactcccactgtcctttcctaataaaatgaggaaattgcatcgcattgtctgagtaggtgtcattctattctggg
gggtggggtggggcaggacagcaaggggaggattgggaagacaatagcaggcatgctggggaagatcttc
```

FIGURE 18

HIGH-TRANSDUCING HSV VECTORS

CROSS REFERENCE TO RELATED APPLICATIONS

The present application is the National Stage of International Application No. PCT/US17/124092, filed Mar. 24, 2017, which claims priority to U.S. Provisional Application No. 62/313,391, filed Mar. 25, 2016, the entire contents of which are herein incorporated by reference.

SEQUENCE LISTING

In accordance with 37 CFR 1.52(e)(5), the present specification makes reference to a Sequence Listing (submitted electronically as a .txt file named "2017-05-18 SL 2012073-0008_ST25". The .txt file was generated on May 18, 2017, and is 225,280 bytes in size. The entire contents of the Sequence Listing are herein incorporated by reference.

BACKGROUND

Systemic delivery of certain therapeutic agents can be problematic for agents with poor pharmacokinetics and/or a risk of off target adverse effects. Local injection at particular target sites may require highly invasive techniques or be infeasible. Delivery of agents by viral vectors allows the ability to specifically target cell populations to provide local production and/or delivery of agents.

SUMMARY OF THE INVENTION

The present disclosure provides compositions and methods for viral vector delivery of agents to target cells.

In some embodiments, the disclosure provides variants of herpes simplex virus (HSV) McKrae strain whose genome contains an alteration such that the variant fails to express a functional protein characterized by an amino acid sequence of SEQ ID NO: 16.

In some embodiments, the disclosure provides variants of herpes simplex virus McKrae strain having a truncated genome of total size less than about 150,000 base pairs and including a deletion of one or more residues within an element corresponding to residues 126049 to 130014 of SEQ ID NO: 1.

In some embodiments, the disclosure provides vectors comprising a variant herpes simplex virus (HSV) McKrae strain genome which genome contains an alteration such that the variant fails to express a functional protein characterized by an amino acid sequence of SEQ ID NO: 2. In some embodiments, the vector comprises a neuron specific promoter. In some embodiments, the promoter is a calcitonin gene-related peptide (CGRP) promoter.

In some embodiments, the vector comprises a human cytomegalovirus (HCMV) enhancer. In some embodiments, the vector comprises a bovine growth hormone (BGH) polyadenylation signal. In some embodiments, the vectors comprise a nucleic acid that encodes a therapeutic polypeptide.

In some embodiments, the disclosure provides cells transduced with a HSV McKrae strain viral vector as described herein.

In some embodiments, the disclosure provides pharmaceutical compositions comprising an HSV McKrae strain viral vector as described herein and a pharmaceutically acceptable carrier.

In some embodiments, the disclosure provides methods of propagating a vector comprising a variant herpes simplex virus (HSV) McKrae strain genome which genome contains an alteration such that the variant fails to express a functional protein characterized by an amino acid sequence of SEQ ID NO: 16, the method comprising steps of: (i) infecting cultured ICP4 complementing cells containing DNA encoding HSV protein ICP4 with the vector, and (ii) isolating supernatant from the culture of step (i).

In some embodiments, the method comprises a step of purifying vector in the supernatant by chromatography. In some embodiments, the method comprises a step of concentrating the purified vector. In some embodiments, purified vector is concentrated by tangential flow filtration.

In some embodiments, the disclosure provides methods of preparing a vector comprising a variant herpes simplex virus (HSV) McKrae strain genome which genome contains an alteration such that the variant fails to express a functional protein characterized by an amino acid sequence of SEQ ID NO: 16, and wherein the vector expresses a marker element, the method comprising incubating cells transfected with:

(a) a first nucleic acid molecule:

(i) comprising a portion of HSV McKrae strain genome but does not encode a functional protein characterized by an amino acid sequence of SEQ ID NO: 16; and (ii) comprising a first homology region (HR1) and a second homology region (HR2), and (b) a second nucleic acid molecule comprising a sequence that encodes a marker element, wherein the sequence is flanked by a first homology region (HR1') and a second homology region (HR2'), wherein HR1 is homologous to HRP and HR2 is homologous to HR2' such that the sequence that encodes the marker element in the second nucleic acid molecule integrates into the first nucleic acid molecule via homologous recombination.

In some embodiments, the cells are ICP4 complementing cells. In some embodiments, the cells complement ICP4 and at least one other viral gene. In some embodiments, the cells complement ICP4 and at least one immediate early gene. In some embodiments, the cells are ICP4, ICP27, and UL55 complementing cells. In some embodiments, the cells are ICP4, ICP22, and ICP47 complementing cells.

In some embodiments, the marker element is a polypeptide. In some embodiments, the polypeptide is detectable by fluorescence. In some embodiments, the marker element is a green fluorescent peptide. In some embodiments, the method comprises a step of purifying viral plaques that express the marker element.

In some embodiments, the disclosure provides methods of preparing a vector comprising a variant herpes simplex virus (HSV) McKrae strain genome which genome contains an alteration such that the variant fails to express a functional protein characterized by an amino acid sequence of SEQ ID NO: 16, and wherein the vector expresses an agent of interest, the method comprising incubating cells transfected with:

a) a first nucleic acid molecule:

(i) comprising a portion of HSV McKrae strain genome but does not encode a functional protein characterized by an amino acid sequence of SEQ ID NO: 16; and (ii) comprising a sequence that encodes a marker element, wherein the sequence that encodes the marker element is flanked by a first homology region (HR1) and a second homology region (HR2), and (b) a second nucleic acid molecule comprising a sequence that encodes an agent of interest, wherein the sequence encoding the agent of interest is flanked by a first homology region (HR1') and a second homology region (HR2'), wherein HR1 is homologous to HR1' and HR2 is homologous to HR2' such the sequence encoding the agent of interest is integrated into the first nucleic acid molecule via homologous recombination.

In some embodiments, the cells are ICP4 complementing cells. In some embodiments, the cells complement ICP4 and at least one other viral gene. In some embodiments, the cells complement ICP4 and at least one immediate early gene. In some embodiments, the cells are ICP4, ICP27, and UL55 complementing cells. In some embodiments, the cells are ICP4, ICP22, and ICP47 complementing cells.

In some embodiments the method comprises a step of purifying viral plaques that do not express the marker element.

In some embodiments, the disclosure provides methods of expressing a polypeptide in dorsal root ganglion (DRG) of a subject comprising administering to the subject an HSV McKrae strain vector as described herein. In some embodiments, the vector is administered in vivo. In some embodiments, the vector is administered by contact with skin. In some embodiments, the vector is administered by intradermal injection.

In some embodiments, the disclosure provides methods of measuring transduction efficiency in dorsal root ganglion (DRG) of an HSV McKrae strain viral vector comprising (a) contacting the skin of an animal with an HSV McKrae strain viral vector (b) removing DRG tissue from the animal, and (c) assaying the number of HSV genomes transduced in the DRG. In some embodiments, the number of genomes is measured by an amplification technique. In some embodiments, the number of genomes is measured by quantitative polymerase chain reaction (PCR).

In some embodiments, the disclosure provides methods of measuring transduction efficiency in dorsal root ganglion (DRG) of an HSV McKrae strain viral vector that contains an expression cassette comprising a polypeptide payload, the method comprising steps of: (a) contacting the skin of an animal with an HSV McKrae strain viral vector, (b) removing DRG tissue from the animal, and (c) assaying the amount of a polypeptide encoded by a nucleic acid of the expression cassette. In some embodiments, the amount of polypeptide is measured by an immunoassay. In some embodiments, the amount of polypeptide is measured by an enzyme linked immunosorbent assay (ELISA).

BRIEF DESCRIPTION OF THE DRAWINGS

The drawings are for illustration purposes only, not for limitation.

FIG. 9 depicts an exemplary HSV McKrae strain nucleotide sequence (SEQ ID NO: 1) which is identified as accession number JQ730035.1

FIG. 10 depicts an exemplary HSV McKrae strain ICP4 amino acid sequence (SEQ ID NO: 2).

FIG. 11 depicts an exemplary HSV McKrae strain ICP22 amino acid sequence (SEQ ID NO: 3).

FIG. 12 depicts an exemplary HSV McKrae strain ICP47 amino acid sequence (SEQ ID NO: 4).

FIG. 13 depicts an exemplary HSV McKrae strain nucleotide sequence of ICP4 (SEQ ID NO: 5).

FIG. 14 depicts an exemplary HSV McKrae strain nucleotide sequence of ICP22 (SEQ ID NO: 6).

FIG. 15 depicts an exemplary HSV McKrae strain nucleotide sequence ICP47 (SEQ ID NO: 7).

FIG. 16 depicts an exemplary human cytomegalovirus enhancer nucleotide sequence (SEQ ID NO: 8).

FIG. 17 depicts an exemplary calcitonin gene-related peptide nucleotide sequence (SEQ ID NO: 9).

FIG. 18 depicts an exemplary bovine growth hormone polyadenylation signal (SEQ ID NO: 10).

DEFINITIONS

Figure 1:
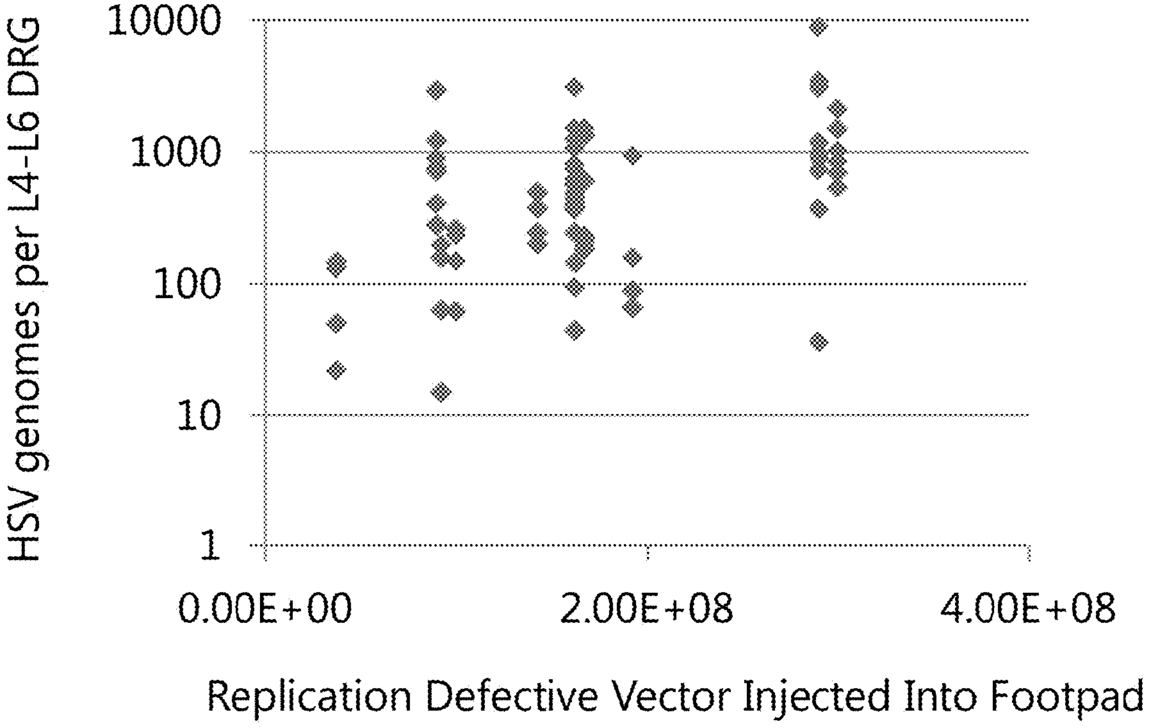
FIG. 1 depicts an exemplary graph that shows the number of HSV genomes per L4-L6 dorsal root ganglia (DRG) detected in a qPCR assay as a result of different doses of replication-defective viral vector injected into the footpad.

In this application, unless otherwise clear from context, (i) the term “a” may be understood to mean “at least one”; (ii) the term “or” may be understood to mean “and/or”; (iii) the terms “comprising” and “including” may be understood to encompass itemized components or steps whether presented by themselves or together with one or more additional components or steps; and (iv) the terms “about” and “approximately” may be understood to permit standard variation as would be understood by those of ordinary skill in the art; and (v) where ranges are provided, endpoints are included.

Administration: As used herein, the term “administration” refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal transdermal, vaginal and vitreal. In some embodiments, administration may involve intermittent dosing. In some embodiments, administration may involve continuous dosing (e.g., perfusion) for at least a selected period of time.

Agent: As used herein, the term "agent" refers to a compound or entity of any chemical class including, for example, polypeptides, nucleic acids, saccharides, lipids, small molecules, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc.

Amelioration: As used herein, the term "amelioration" refers to the prevention, reduction or palliation of a state, or improvement of the state of a subject. Amelioration includes, but does not require complete recovery or complete prevention of a disease, disorder or condition.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Characteristic sequence: As used herein, the term "characteristic sequence" refers to a sequence that is found in all members of a family of polypeptides or nucleic acids, and therefore can be used by those of ordinary skill in the art to define members of the family.

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Composition: As used herein, the term "composition" or a "pharmaceutical composition" refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present disclosure, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 999/0, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Marker element: As used herein, the term "marker element" refers to a detectable or selectable agent. In some embodiments, a "marker element" is a detectable or selectable nucleic acid sequence. In some embodiments a "marker element" is an expression product (e.g., RNA or protein) whose presence or absence is detectable and/or selectable in cells. In some embodiments, an expression product is or comprises an enzyme. In some embodiments, an expression product is a fluorophore.

Nucleic acid: As used herein, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present disclosure. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: As used herein, the terms "prevent" or "prevention", when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Subject: As used herein, the term "subject" refers to a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Treatment: As used herein, the term "treatment" (also "treat" or "treating") refers to any administration of a substance that partially or completely alleviates, ameliorates, relieves, inhibits, delays onset of, reduces severity of, and/or reduces incidence of one or more symptoms, features, and/or causes of a particular disease, disorder, and/or condition (e.g., neuropathy). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated to a viral genome or portion thereof. Certain vectors are capable of autonomous replication in a host cell into which they are introduced (e.g., bacterial vectors having a bacterial origin of replication, episomal mammalian vectors, herpes simplex virus (HSV) vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION

Various aspects of the invention are described in detail in the following sections. The use of sections is not meant to limit the invention. Each section can apply to any aspect of the invention. In this application, the use of "or" means "and/or" unless stated otherwise or clear from context to be disjunctive.

The present disclosure provides, among other things, compositions comprising HSV vectors and methods for use and production of same. In particular, the present disclosure relates to McKrae strain vectors for the delivery of payloads to neuronal cells.

Viral Vectors and HSV

Viral vectors can be used to facilitate the transfer of nucleic acids into cells. Known viral vectors include those derived from retroviruses, adenoviruses, adeno-associated virus (AAV), vaccinia virus, and baculovirus. Vectors derived from herpes simplex viruses (HSV), such as herpes simplex virus 1 (HSV-1) and herpes simplex virus-2 (HSV- 2) are particularly useful for delivery of agents to specifically targeted tissues. Considerations for choosing a particular vector and delivery system include, for example, characteristics of target cells, desired longevity of expression, virulence and invasiveness of the vector, and, size of the genetic material to be transferred.

HSV-1 vectors can typically accommodate up to 25 kb of foreign DNA sequences. HSV-1 has an approximate 152-kb double-stranded linear DNA genome that can be maintained episomally in the nucleus of cells. The HSV-1 virion is enveloped and approximately 110 nm in diameter. Viral infection is initiated in epithelial cells of the skin or mucosal membranes by binding of the viral envelope glycoproteins to heparin sulfate moieties on the plasma membrane. HSV is particularly well suited for the delivery of genes to the nervous system and possesses a natural tropism for sensory neurons. The virus can establish a latent state in which viral genomes persist for the life of the host as an intranuclear episomal element. The life-long persistence of latent genomes in human trigeminal ganglia without the development of sensory loss or histologic damage to the ganglia exemplifies the effectiveness of the latency mechanisms. Wild-type HSV virus may be reactivated from latency under the influence of a variety of stresses. However, recombinant viral vectors that are rendered replication defective retain the ability to establish a persistent quiescent state in neurons yet are unable to replicate (or reactivate) in the nervous system.

Vectors based upon HSV-1 may have one or more HSV genes necessary for replication rendered nonfunctional (e.g., by deletion or disruption). HSV genes necessary for replication include, for example, immediate early genes such as ICP4 and ICP 27. In some embodiments, the disclosure provides replication defective HSV vectors with one or more of ICP0, ICP4, ICP22, ICP27, and ICP47 deleted or disrupted. In some embodiments, the disclosure provides HSV vectors with a nonfunctional ICP4 gene. In some embodiments, the disclosure provides HSV vectors with nonfunctional ICP4, ICP22, and ICP47 genes. In some embodiments, the disclosure provides an HSV vector with ICP4 deleted and ICP22 and ICP47 disrupted. In some embodiments, the disclosure provides an HSV vector with ICP4 deleted and expression of ICP22 and ICP47 disrupted or delayed. In some embodiments, the disclosure provides an HSV vector with ICP4 deleted ICP0, ICP22, ICP27, and/or ICP47 not expressed as immediate early genes.

HSV-1 vectors that have deleted HSV genes can be produced in cell lines that express the deficient protein in trans. In some embodiments, HSV-1 vectors are produced in a mammalian cell line. In some embodiments, HSV-1 vectors are produced in a mammalian cell line of Vero lineage. In some embodiments, the cell line expresses ICP4. In some embodiments, the cell line expresses one or more of ICP0, ICP4, ICP22, ICP27, and ICP47. In some embodiments, the cell line expresses ICP4 and at least one additional immediate early gene. In some embodiments, the cell line expresses ICP4, ICP22, and ICP 47. In some embodiments, the cell line expresses ICP4, ICP22, and UL55. In some embodiments, the cell line expresses ICP4, ICP27 and UL55. In some embodiments, the cell line comprises a nucleic acid molecule having a simian virus 40 polyadenylation signal (SV40 pA). In some embodiments, viral vectors are produced in Vero 6-5C cells. In some embodiments, viral vectors are produced in Vero D cells.

McKrae Strain

At least 17 strains of HSV-1 have been isolated, including but not limited to, McKrae, strain 17, strain F, H129, HF10, MacIntyre, Strain HF, ATCC 2011 and KOS (for review, see Watson et al., Virology (2012)). A McKrae strain was isolated from a patient with herpes simplex keratitis and subsequently passaged in tissue culture. A partial genome sequence of McKrae is shown in FIG. 9 (SEQ ID NO: 1) (accession number JQ730035).

Inter-strain differences in HSV-1 peripheral replication and virulence are observed after injection into animals. McKrae undergoes spontaneous or induced reactivation at a higher frequency than other known strains and is among the most virulent HSV-1 strains. McKrae is also more neuroinvasive than other known strains, such as strain 17, KOS, F, and H129. In one study, KOS or McKrae was injected into the cornea and genital tract of mice to compare pathogenesis (Wang et al. (2013) Virus Res. 173(2):436-440. Each was found to replicate to a similar extent in the corneal epithelium and trigeminal ganglia; however, McKrae titers were over 100 fold higher in brainstem. Upon intravaginal injection, McKrae and KOS replicated to a similar extent except for a transient spike in McKrae titer at four days. McKrae, but not KOS, elicited significant inflammation of external genitalia along with weight loss in the animals. KOS was not detected in neural tissue and McKrae was rarely detected.

In some embodiments, the disclosure provides HSV viral vectors with deletion of genes that render HSV replication defective, but do not reduce HSV neuroinvasiveness. Thus, the HSV vectors are able to traverse the peripheral nervous system to reach neurons in the dorsal root ganglion upon administration to the skin.

HSVgenes influence viral characteristics and phenotype. There are at least 9 genes and several non-coding sequences unique to McKrae strain. In addition to those associated with pathogenesis and latency reactivations, such as RL1, RS1, and RL2, three UL genes (UL36, UL49A, UL56) and three US genes (US7, US10, and US11) are unique for McKrae strain. In addition to gene variations, non-coding sequences such as LAT, 'a' sequence, and miRNAs contain variations unique to McKrae.

One or more of following gene and non-coding sequences can be considered characteristic of McKrae strain. In McKrae, RL1 (ICP34.5) has an extended P-A-T repeat between residues 159 and 160 that results in 8 iterations, while other strains contain only 3-5 iterations. The P-A-T repeat is thought to influence cellular localization of the ICP34.5 protein. (Mao & Rosenthal, J. Biol. Chem. 277(13):11423-31 (2012). ICP34.5 is thought to be a neurovirulence factor involved in viral replication and anti-host response.

McKrae strain also contains an extended repeat element of six iterations of the internal tandem repeat STPSTTT (SEQ ID NO: 11) located within the coding sequence of US07 (gI). Additionally in McKrae, UL 36 contains a premature stop codon introduced due to a G nucleotide deletion in a mononucleotide string encoding amino acid residue 2453 (nt 72,535) and UL 56 (180 aa) contains a single base pair insertion at nucleotide 115,992 (amino acid 97). McKrae strain also contains an extended ORF in US10 resulting from a single bp insertion at nucleotide 143,416 and the frameshift causes a stop codon loss in McKrae and a unique C-terminal protein sequence. McKrae has amino acid differences at UL49A at residues 28 and 51 compared to other strains. McKrae has histidine and threonine at residues 28 and 51, respectively, whereas strain 17 has arginine and threonine and other strains (e.g., KOS) have histidine and alanine. Also, McKrae strain contains reduced tandem repeats found at the UL-RL junction (49 bp in McKrae as opposed to 181 bp in strain 17 and KOS) and approximately 330 nucleotides missing immediately following the UL-RL junction repeat. McKrae also contains unique variation within the 'a' sequence direct repeat 2 (DR2) array. Instead of a series of unbroken tandem repeats, the McKrae DR2 repeats are interrupted twice by identical guanine-rich sequences.

Major variation within the LAT intron between strains is due to differences in a repeat element (GCACCCC-CACTCCCAC) (SEQ ID NO: 12) that varies in iteration number beginning at nucleotide 119,482 in McKrae strain, with McKrae containing 13 repeats while strains F, H129 and 17 contain 9 repeats and KOS contains 15 repeats. Also, tandem repeat variation between strains is found beginning in McKrae at base 125,520. McKrae repeat elements include twelve iterations of CCCCAGCCCTCCCCAG (SEQ ID NO: 13) and eight iterations of CCCCTCGCCCCCTCCCG (SEQ ID NO: 14). The first repeat unit is unique from other strains in that it contains a G-A transition, and strain McKrae contains three iterations more than any other strain. The McKrae strain second repeat element is collapsed, missing 188 nucleotides relative to all other strains, and separated from the upstream repeat by a 100% conserved sequence of 105 bp containing miR-H5.

McKrae further contains a unique coding sequence for ICP4 that is not found in other known strains. (Watson et al., Virology (2012)). ICP4 is an immediate early transcriptional regulator and has been implicated in reactivation. Whereas other strains contain an alanine rich region (AASAP-DAADALAAA) (SEQ ID NO: 15) between residues 707 and 720, in McKrae the alanine rich region is replaced by a serine rich sequence (GPRRSSSSSGVAA) (SEQ ID NO: 16). The serine rich block of substitutions present in McKrae is adjacent to the nuclear localization signal (NLS) (amino acid 728-734). A change in conformation of this region may alter the NLS and in turn affect localization of not only ICP4, but also other viral proteins (e.g. ICP0, ICP8) that are affected by ICP4 localization (Knipe and Smith, 1986). Thus, this region may influence viral phenotype in part by altering the localization of proteins to the nucleus.

Replication Defective McKrae Vector

McKrae Backbone

Viral genes are expressed in a tightly regulated, ordered cascade, which begins with the production of the immediate-early (1E) genes. The resulting IE proteins, which include infected cell proteins ICP0, ICP4, ICP22, ICP27, and ICP47, are responsible for regulating viral gene expression during subsequent phases of the replication cycle. Replication-defective variant viruses are defective for one or more functions that are essential for viral genome replication or synthesis and assembly of viral particles. Such viruses can be propagated in complementing cell lines expressing the missing gene product(s); however, in normal (i.e., non-complementing) cells, the viruses express viral gene products but do not replicate to form progeny virions.

Replication-defective viruses can be created through various methods known in the art for modifying genes. In some embodiments, one or more nucleotides are rendered different relative to the wild-type sequence. In some embodiments, one or more nucleotides are deleted. In some embodiments, the deletion of one or more nucleotides creates a premature stop codon. In some embodiments, the deletion of one or more nucleotides creates a gene encoding a truncated polypeptide. In some embodiments, the deletion of one or more nucleotides creates a gene encoding a nonfunctional polypeptide. In some embodiments, the deletion of one or more nucleotides renders a gene nonfunctional by disruption. In some embodiments, a gene is disrupted by deletion of its promoter.

In some embodiments, one or more genes are deleted to render a virus replication defective. In some embodiments, the gene encoding ICP0 is fully or partially deleted. In some embodiments, the gene encoding ICP4 is fully or partially deleted. In some embodiments, the gene encoding IC22 is fully or partially deleted. In some embodiments, the gene encoding ICP27 is fully or partially deleted. In some embodiments, the gene encoding ICP47 is fully or partially deleted. In some embodiments, the gene encoding ICP 4 is fully or partially deleted, without disrupting expression of any additional immediate early genes. In some embodiments, the gene encoding ICP4 is fully or partially deleted, and one or more other immediate early (1E) genes are disrupted. In some embodiments, the gene encoding ICP4 is deleted and ICP22 and ICP47 are disrupted.

HSV-1 IE promoters contain one or more copies of an IE-specific regulatory sequence of consensus TAATGARAT (SEQ ID NO: 19) (where R is a purine). These motifs are normally located within a few hundred base pairs of the proximal IE promoter sequences, but in conjunction with their flanking sequences they are discrete functional entities which can confer IE-specific regulation to other proximal promoter elements of different temporal class. In some embodiments, replication-defective viruses are created by deleting nucleotides in an IE-specific regulatory sequence. In some embodiments, an IE-specific regulatory sequence contains an internal deletion. In some embodiments, an IE-specific regulatory sequence contains a terminal deletion. In some embodiments, an IE-specific regulatory sequence is completely deleted.

A schematic of an exemplary replication defective McKrae strain viral vector is depicted below. The schematic shows complete deletions of both copies of the viral ICP4 gene, and a human cytomegalovirus (HCMV) immediate early promoter driven expression cassette inserted within both copies of the deleted ICP4 loci. The expression cassette contains a payload of interest for expression in target cells.

Figure 19:
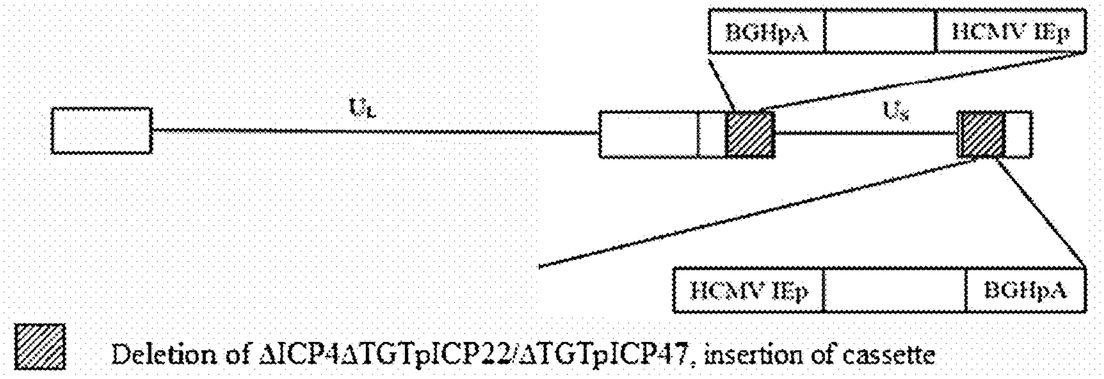
FIG. 19 depicts the extent of the ICP4 deletion resulting in the removal of the upstream promoter sequences of two additional immediate early viral genes: ICP22 and ICP47.

The extent of the ICP4 deletion results in the removal of the upstream promoter sequences of two additional immediate early viral genes: ICP22 and ICP4? (FIG. 19).

Payload

Viral vectors in accordance with the present disclosure contain a nucleic acid molecule comprising the payload of the vector. In some embodiments, a payload comprises a nucleic acid molecule that encodes a protein. In some embodiments, a payload comprises a nucleic acid molecule that comprises a sequence complementary to a nucleic acid sequence that encodes a protein. In some embodiments, a payload encodes a nucleic acid molecule that is regulatory. In some embodiments, a payload encodes a small interfering RNA (siRNA) polynucleotide. In some embodiments, a payload encodes a micro RNA (miRNA) polynucleotide.

In some embodiments, the payload is a nucleic acid molecule that encodes a protein that is exogenous to the target tissue or subject to which the vector is administered. In some embodiments, the payload is a nucleic acid molecule that encodes a protein that is endogenous to the target tissue or subject to which the vector is administered. In some embodiments, a nucleic acid molecule is codon optimized.

Regulatory Elements

The inclusion of non-native regulatory sequences, gene control sequences, promoters, non-coding sequences, introns, or coding sequences in a nucleic acid of the present disclosure is contemplated herein. The inclusion of nucleic acid tags or signaling sequences, or nucleic acids encoding protein tags or protein signaling sequences, is further contemplated herein. Typically, the coding region is operably linked with one or more regulatory nucleic acid components.

A promoter included in a nucleic acid of the present disclosure can be a tissue- or cell type-specific promoter, a promoter specific to multiple tissues or cell types, an organ-specific promoter, a promoter specific to multiple organs, a systemic or ubiquitous promoter, or a nearly systemic or ubiquitous promoter. Promoters having stochastic expression, inducible expression, conditional expression, or otherwise discontinuous, inconstant, or unpredictable expression are also included within the scope of the present disclosure. A promoter of the present disclosure may include any of the above characteristics or other promoter characteristics known in the art.

Examples of known promoters include, but are not limited to, the cytomegalovirus (CMV) promoter CMV/human beta 3 globin promoter GFAP promoter, chicken beta actin (CBA) promoter the p-glucuronidase (GUSB) promoter and ubiquitin promoters such as those isolated from human ubiquitin A, human ubiquitin B, and human ubiquitin C.

In some embodiments, a promoter is a neuron specific promoter in that it is a promoter having specific expression in neurons, preferential expression in neurons, or that typically drives expression of an associated coding sequence in neurons or a subset of neurons but not in one or more other tissues or cell types. Examples of such promoters include calcitonin gene-related peptide (CGRP), synapsin I (SYN), calcium/calmodulin-dependent protein kinase II, tubulin alpha I, neuron-specific enolase, microtubule-associated protein 1B (MAP1B), and platelet-derived growth factor beta chain promoters, as well as derivatives thereof. In some embodiments, the promoter is a calcitonin gene-related peptide (CGRP) promoter or derivative thereof.

Other regulatory elements may additionally be operatively linked to the payload, such as an enhancer and a polyadenylation site. In some embodiments, an enhancer comprises a human cytomegalovirus (HCMV) sequence. In some embodiments, a polyadenylation site comprises a bovine growth hormone (BGH) polyadenylation signal.

In some embodiments, a promoter is a chimeric of one or more promoters or regulatory elements found in nature. In some embodiments, the viral vectors comprise a payload whose expression is driven by a CGRP promoter with an HCMV enhancer sequence.

Preparation of Vectors

The present disclosure relates particularly to McKrae strain viral vectors that are replication defective. In some embodiments, viral vectors are generated by deletion or disruption of one or more immediate early genes. Viral genes may be deleted or disrupted using methods of recombinant technology known in the art. In some embodiments a viral vector of the present disclosure may be rendered replication defective as a result of a homologous recombination event. In some embodiments, replication defective viral vectors are generated by deletion of an ICP4 gene. In some embodiments, replication defective viral vectors are generated by deletion of an ICP4 gene and deletion of a promoter for one or more other immediate early genes (e.g., ICP22 and/or ICP47).

In some embodiments, viral vectors of the present disclosure are generated by deletion of loci encoding one or more ICPs (e.g., ICP4) through homologous recombination. In some embodiments, generation of a viral vector of the present disclosure includes a step of homologous recombination of a first plasmid with a second plasmid. In some embodiments, the first plasmid contains nucleic acid sequences homologous to regions of an HSV genome that are adjacent to a nucleic acid region of an HSV genome that is intended to be replaced. In some embodiments, the second plasmid contains an HSV genome, or fragment thereof. In some embodiments, the first plasmid contains nucleic acid sequence encoding a gene of interest between the homologous nucleic acid sequences. In some embodiments, the gene of interest may be or include a marker protein that is detectable by fluorescence, chemiluminescence, or other property, which can be used to select for vectors resulting from successful homologous recombination.

In some embodiments, a viral vector of the present disclosure is generated by homologous recombination of a first plasmid containing a nucleic acid sequence homologous to regions upstream of the ICP4 promoter including the viral origin contained within the short inverted repeat regions of HSV, with a second plasmid containing an HSV McKrae strain genome.

In some embodiments, a vector is made by first replacing both copies of the ICP4 loci by homologous recombination using plasmid SASB3 and screening for green fluorescent protein (GFP)-expressing plaques. In some embodiments, a plasmid is constructed by cloning the Sph I to Afl III (Sal I linkered) fragment (1928 bp) of the HSV-1 KOS strain genome (nucleotides 124485-126413) into Sph I/Sal I digested pSP72 followed by insertion of the 695 bp Bgl II to BamH I fragment (nucleotides 131931 to 132626) containing regions upstream of the ICP4 promoter including the viral origin contained within the short inverted repeat regions into the Bgl II to BamH I sites of the vector plasmid. In some embodiments, a plasmid is constructed by cloning a HCMV-eGFP fragment in the BamHI site of a plasmid as described above. In some embodiments, a plasmid as described above is then recombined into a specific locus of a wild-type McKrae virus. In some embodiments, the resulting vector is isolated using a stable cell line that expresses one or more genes deleted or disrupted in the HSV genome that are required for replication.

In some embodiments, a vector is made by first replacing both copies of the ICP4 loci by homologous recombination using plasmid SDAXB and screening for green fluorescent protein (GFP)-expressing plaques. In some embodiments, a plasmid is constructed by cloning the Sph I to Afl III fragment (1928 bp) of the HSV-1 KOS strain genome (nucleotides 124346 to 126273 of accession KT899744) into Sph I/Afl III digested pSP72 to make SDA followed by changing the Afl III site to a BamHI site (SDAB). A BamHI to Bgl II DNA PCR fragment containing regions upstream of the ICP4 promoter including the viral origin (nucleotides 144933 to 145534 of accession JQ730035) contained within the short inverted repeat regions was cloned into the BamHI site of SDAB to make SDAXB. In some embodiments, a plasmid is constructed by cloning a HCMV-eGFP fragment in the BamHI site of a plasmid as described above. In some embodiments, a plasmid as described above is then recombined into a specific locus of a wild-type McKrae virus. In some embodiments, the resulting vector is isolated using a stable cell line that expresses one or more genes deleted or disrupted in the HSV genome that are required for replication.

Characterization of Vectors

Viral vectors in accordance with the present disclosure can be characterized by genomic sequencing in order to determine if the expected vector was successfully created. Any method of sequencing known in the art is acceptable for this purpose. Methods of sequencing include, for example, nanopore sequencing, single molecule real time sequencing (SMRT), DNA nanoball (DNB) sequencing, pyrosequencing and using DNA arrays.

The expression of a payload from a viral vector can be detected by any method known in the art for detecting proteins or nucleic acids. Methods of detecting protein expression include immunohistochemistry, flow cytometry, Western blotting, enzyme-linked immunosorbent assay (ELISA), immune-electron microscopy, individual protein immunoprecipitation (IP), protein complex immunoprecipitation (Co-IP), chromatin immunoprecipitation (ChIP), RNA immunoprecipitation (RIP), immunoelectrophoresis, spectrophotometry, and bicinchoninic acid assay (BCA). Methods of detecting nucleic acid expression include Southern blotting, Northern blotting, polymerase chain reaction (PCR), quantitative PCR, and RT-PCR.

In some embodiments, the present disclosure provides methods for testing the ability of viral vectors to transduce neurons. In some embodiments, the neurons are peripheral neurons. In some embodiments, the neurons are sensory neurons. In some embodiments, the neurons comprise dorsal root ganglia (DRG).

In some embodiments, a viral vector preparation may be injected into the one or more dermatomes corresponding to a section of DRG for example, the left and right L4, L5, and L6 DRG. DRG are removed are removed and DNA is isolated from the DRG and analyzed for vector genome copies using a qPCR assay that targets a sequence within HSV-1. In some embodiments, a qPCR assay targets a sequence within the HSV-1 glycoprotein (UL-22) gene.

Applications/Uses

Viral vectors in accordance with the present disclosure are useful for a wide variety of therapeutic applications. In some embodiments, vectors as described herein are useful to deliver one or more payloads to one or more target cells. In some embodiments, target cells reside in tissues that are poorly vascularized and difficult to reach by systemic circulation. In some embodiments, target cells are cells susceptible to infection by HSV. In some embodiments, target cells are particularly susceptible to infection by a McKrae strain of HSV. In some embodiments, target cells are or include one or more of neuronal cells. In some embodiments, target cells are dorsal root ganglion (DRG) cells.

Gene Therapy

Viral vectors in accordance with the present disclosure are useful in any context in which gene therapy is contemplated. For example, viral vectors comprising a heterologous nucleic acid segment operably linked to a promoter are useful for any disease or clinical condition associated with reduction or absence of the protein encoded by the heterologous nucleic acid segment, or any disease or clinical condition that can be effectively treated by expression of the encoded protein within the subject. Viral vectors that contain an expression cassette for synthesis of an RNAi agent (e.g., one or more siRNAs or shRNAs) are useful in treating any disease or clinical condition associated with overexpression of a transcript or its encoded protein in a subject, or any disease or clinical condition that may be treated by causing reduction of a transcript or its encoded protein in a subject. Viral vectors that comprise an expression cassette for synthesis of one or more RNAs that self-hybridize or hybridize with each other to form an RNAi agent targeted to a transcript encoding a cytokine may be used to regulate immune system responses (e.g., responses responsible for organ transplant rejection, allergy, autoimmune diseases, inflammation, etc.). Viral vectors that provide a template for synthesis of one or more RNAs that self-hybridize or hybridize with each other to form an RNAi agent targeted to a transcript of an infectious agent or targeted to a cellular transcript whose encoded product is necessary for or contributes to any aspect of the infectious process may be used in the treatment of infectious diseases.

Administration

Compositions comprising viral vectors as described herein may be formulated for delivery by any available route including, but not limited to parenteral (e.g., intravenous), intradermal, subcutaneous, oral (e.g., inhalation), transdermal (topical), transmucosal, rectal, and vaginal. Preferred routes of delivery include intradermal. In some embodiments, pharmaceutical compositions include a viral vector in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. In some embodiments, viral vectors are formulated in glycerol. In some embodiments, viral vectors are formulated in approximately 10% glycerol in phosphate buffered saline.

It is advantageous to formulate compositions in dosage unit form for ease of administration and uniformity of dosage. Dosage unit form as used herein refers to physically discrete units suited as unitary dosages for the subject to be treated; each unit containing a predetermined quantity of a viral vector calculated to produce the desired therapeutic effect in association with a pharmaceutical carrier.

The pharmaceutical composition can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a viral vector can include a single treatment or, in many cases, can include a series of treatments.

Compositions

In some embodiments, the active agents, i.e., a viral vector of the disclosure and/or other agents to be administered together with a viral vector of the disclosure, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. In some embodiments the composition is targeted to particular cell types or to cells that are infected by a virus.

Combination Therapy

According to the present disclosure, provided compositions may be administered in combination with one or more other active agents and/or therapeutic modalities, such as known therapeutic agents and/or independently active biologically active agents. In some embodiments, provided compositions include one or more such other active agents; in some embodiments, such other active agents are provided as part of distinct compositions. In some embodiments, combination therapy involves simultaneous administration of one or more doses or units of two or more different active agents and/or therapeutic modalities; in some embodiments, combination therapy involves simultaneous exposure to two or more different active agents and/or therapeutic modalities, for example through overlapping dosing regimens.

In some embodiments, provided compositions include or are administered in combination with one or more other active agents useful for the treatment of the relevant disease, disorder and/or condition.

EXAMPLES

Example 1: Assay for Assessment of Transduction of DRG

This Example shows an exemplary method for assaying transduction of viral vectors in dorsal root ganglion (DRG) tissue.

Subsequent to intradermal administration of a viral vector, L4, L5, and L6 DRG are removed and vortexed, with inversion, for 40 seconds in a pre-chilled Lysing Matrix A tube (MP Biomedicals) with 350 μL of a 0.5% Reagent DX (Qiagen) in Buffer RLT Plus/DTT solution.

DNA and RNA are isolated from the sample homogenate using the AliPrep DNA/RNA Mini Kit (Qiagen). The RNA isolation portion includes an on-column DNase treatment step. The DNA is eluted in 2×100 μL, of UltraPure Distilled Water (Invitrogen) after a 10-15 minute room temperature incubation per elution. The RNA is eluted in 2×30 μL of RNase-free water* after a 3 minute room temperature incubation per elution. The DNA is concentrated by open incubation at 37° C. overnight.

Ten (10) μL of concentrated DNA is analyzed in a 50-4, reaction for HSV vector genomes by a qPCR assay that targets a region in the UL22 (glycoprotein H) gene.

For mRNA expression analyses, 8 μL of RNA first undergoes reverse transcription using the SuperScript™ III First-Strand Synthesis SuperMix for qRT-PCR (Invitrogen) followed by RNase treatment. The RNase-treated cDNA can then be analyzed by any of a number of qPCR assays that target either a particular transgene (e.g., payload transcript), the stable 2 kb LAT intron, or the 5' LAT exon.

Example 2: Comparison of Nerve Transduction Capabilities of Different HSV Strains This example demonstrates that a McKrae strain vector transduces neurons more effectively than a KOS strain vector.

Two different wild-type strains of HSV-1 (McKrae and KOS) were prepared and injected into the dorsum and plantar surface of the right and left hind feet of three Sprague-Dawley (SD) rats each, at 100 μL per injection. All animals were euthanized five days after vector injection. During the terminal procedures, the left and right L4, L5, and L6 dorsal root ganglia (DRG) were removed, frozen at −70° C., and shipped on dry ice.

DNA was isolated from the left L4-L6 DRG of all animals in the study using a QIAamp DNA Mini Kit (Qiagen). The sample DNA was analyzed for vector genome copies using a qPCR assay that targets a sequence within the HSV-1 glycoprotein H (UL-22) gene on a Rotor-Gene Q Real-Time PCR Cycler (Qiagen). As shown in Table 1, McKrae strain appears to transduce the neurons significantly better than the KOS strain. The mean genome copy number detected in the DRG of the KOS group was 73, while that of the McKrae group was 21,347.

TABLE 1

| Strain | Name | Ct | Calc Conc (Copies) | Mean Ct | Mean Ct SD | Mean Calc Conc | Total DF | Total Sample Genomes |
|---|---|---|---|---|---|---|---|---|
| KOS | 5a1R A1G1 L-DRG | 35.27 | 7.00E±00 | 35.31 | 0.06 | 7.00E±00 | 20 | 1.40E±02 |
| | 5a1R A1G1 L DRG | 35.36 | 6.00E±00 | | | | | |
| KOS | 5a1R A2G1 L-DRG | 36.10 | 4.00E±00 | 36.05 | 0.07 | 4.00E±00 | 20 | 8.00E±01 |
| | 5a1R A2G1 L DRG | 36.01 | 4.00E±00 | | | | | |
| KOS | 5a1R A3G1 L-DRG | 37.15 | 2.00E±00 | 37.15 | | 2.00E±00 | 34.97 | <LOQ |
| | 5a1R A3G1 L-DRG | | | | | | | |
| McK | 5a1R A4G2 L-DRG | 37.31 | 2.00E±00 | 36.43 | 1.25 | 3.00E±00 | 40.65 | <LOQ |
| | 5a1R A4G2 L-DRG | 35.54 | 6.00E±00 | | | | | |
| McK | 5a1R A5G2 L-DRG | 26.73 | 1.95E±03 | 26.74 | 0.01 | 1.94E±03 | 32.89 | 6.38E±04 |
| | 5a1R A5G2 L-DRG | 26.74 | 1.93E±03 | | | | | |
| McK | 5a1R A6G2 L-DRG | 35.23 | 7.00E±00 | 34.79 | 0.61 | 9.00E±00 | 28.57 | 2.57E±02 |
| | 5a1R A6G2 L-DRG | 34.36 | 1.20E±01 | | | | | |

| Name | Ct | Calc Conc (Copies) | Mean Ct | Mean Ct SD | Mean Calc Conc | Spk (Cop) | % Recovery |
|---|---|---|---|---|---|---|---|
| 5aS2 A2G1 L-DRG | 36.93 | 2 | 37.22 | 0.42 | 2 | <LOQ | |
| 5aS2 A2G1 L-DRG | 37.52 | 2 | | | | | |
| 5aS2 A2G1 L-DRG spk-25 | 32.67 | 38 | 32.79 | 0.18 | 35 | 25 | 140% |
| 5aS2 A2G1 L-DRG spk-25 | 32.92 | 32 | | | | | |

Example 3: Preparation of Vectors

This example describes methods of preparing and formulating exemplary vectors for gene therapy.

Genetic Structure of Vector

A vector is made by first replacing both copies of the ICP4 loci by homologous recombination using a plasmid and screening for marker element expressing plaques. A plasmid is constructed by cloning a fragment of a HSV-1 genome comprising regions upstream of the ICP4 promoter including the viral origin contained within the short inverted repeat regions. The plasmid is further modified by cloning a marker element, for example HCMV-eGFP, fragment into the plasmid. This plasmid is then recombined into the ICP4 locus of a wild-type HSV virus. The resulting vector is isolated using a stable ICP4 expressing Vero cell line, such as '6-5C'. Vero 6-5C cells are complementing cells that express ICP4.

In order to replace the marker element (e.g., GFP) with a gene of interest (GOI) in the vector described above, a plasmid is constructed by cloning HCMV-GOI-pA into the plasmid. Plaques which do not express the marker element are isolated and tested by ELISA for GOI expression.

Production of Crude Vector

ICP4 complementing Vero cells are cultured in tissue culture flasks using complete media (DMEM supplemented with FBS, HEPES, and Pen Strep) and expanded into 6-12xT175 flasks at a seeding density of 3-4×$10^4$ cells/cm2. The culture flasks are incubated at 37° C./7.5% $CO_2$ for 3-4 days.

When cells are 1-2 days over confluent, they are infected at a multiplicity of infection (MOI) of ~0.1 with a virus stock of known concentration. The infection is initiated by removing the culture supernatant from each flask and infecting with a total of 2.5 mL of complete media containing the appropriate amount of a virus stock. The virus is adsorbed on the cell monolayers by incubating the cultures for 1.5-2 hours, shaking and rotating the flasks every 15-20 minutes. After the adsorption step, an additional 10 mL of complete medium is added to each flask and the cultures are incubated again at 37° C./7.5% $CO_2$.

Approximately 48 hours after initiating the infection, the flasks are viewed by microscope to confirm cells show signs of cytopathogenic effect and detachment from the flask surface. At that point the cells and supernatant are harvested, pooled together, and centrifuged at ~1500×g for ~10 min. The supernatant is removed from the cell pellet and held separately for later processing.

The cell pellet is resuspended in 4-5 mL of complete media, homogenized, and then frozen at −80° C. After the cell suspension has been frozen for >20 minutes, it is thawed and centrifuged at ~1500×g for ~10 min. This second cell pellet supernatant is removed and combined with the first collected supernatant.

The pooled supernatant is aliquoted into centrifuge tubes. The virus is then centrifuged at ~40,000×g for ~30 minutes at 2-8° C. in order to pellet the virus. After the centrifugation step is completed, the supernatant from the tubes is removed and discarded. The following day the virus pellets are homogenized by pipetting and pooled together. The resuspended virus stock is then aliquoted into cryovials typically at volumes of ~120 μL per vial. Complete medium (200-300 lit) is added to the virus pellets in order to cover them with liquid and are stored at 2-8° C. overnight to loosen the virus particles. The vials are labeled and frozen at −80° C. Later, a frozen vial is thawed in order to perform a virus plaque titration assay to determine the concentration of the prepared virus stock prior to using in any in vivo or in vitro studies.

Manufacture of Clarified Vector

Cell Thaw and Expansion

Vero cells (e.g., Vero 6-5, VeroD cells) from a working cell bank are thawed at 37° C. and transferred to a conical tube and pooled. VeroD cells are complementing cells that express or ICP4, ICP27, and L155. The cells are vialed at approximately 1.0×$10^7$ viable cells/mL/tube. The cells are gradually diluted with complete medium and a sample is removed to obtain viable cell counts. The cells are plated in tissue culture flasks at a density of 3.0-5.0×$10^4$ cells/cm2.

The cells are incubated at 37° C., 7.5% $CO_2$ and examined periodically by phase microscopy. The cells are passaged while subconfluent. The complete medium is removed, rinsed with PBS, and the cells are dissociated. The flasks are incubated until the cells detach, then they are re-suspended in complete medium, pooled, counted and seeded into new flasks at a density between 1.0-4.0×$10^4$ cells/cm2. The cells are expanded and allowed to extend to 1-2 days post-confluence prior to infection.

Infection with Vector

When the cells reach the desired confluence, a model flask is subcultured and the cells are counted to estimate the number of cells per cell factory. A master virus bank vector inoculum is prepared by thawing the appropriate volume required to obtain a multiplicity of infection (MOI) of 0.1 and diluting the stock with complete medium up to the target volume desired for the infection. The cell factories are infected by an initial adsorption period followed by incubation for the first day of infection in complete medium. After approximately 24 hours, the culture medium is removed and replaced with an equal volume of serum-free medium. The cell factories are placed in the incubator and the temperature is reduced to 33° C./with 7.5% $CO_2$. The cultures are monitored daily and the percent cytopathic effect estimated by visual inspection.

Crude Viral Harvest and Clarification

The infection is stopped by placing the cell factories in a biosafety cabinet and pooling the supernatant and cell debris into a sterile bag. This bulk unclarified harvest is sampled for adventitious agents. After sampling, the sodium chloride level of the harvest is increased and then it is mixed. The harvest is then aliquoted into centrifuge tubes and the cell debris removed by centrifugation. The supernatant is pooled into a sterile bag. After pre-treatment of a clarification filter capsule with sterile water, the virus-containing supernatant is then pumped through the filter capsule into another sterile bag, followed by sterile water to recover remaining virus in the capsule. The bag is mixed and the filtrate was stored overnight at 4° C.

Afterwards, the filtrate is warmed and adjusted to −2 mM $MgCl_2$ by addition of 2 volumes of 3 mM $MgCl_2$ in sterile water. The diluted filtrate is mixed and treated with an endonuclease.

Cation Exchange Column Chromatography

A BPG 400 column is packed with SP high performance resin, sanitized with 0.5N NaOH and equilibrated with wash buffer (PBS pH 7.0) and strip buffer (1M NaCl-PBS pH 7.0) before loading endonuclease treated virus.

The process bag containing the endonuclease-treated filtrate is connected to the inlet using a tubing welder and the virus is loaded onto the column. The flow through is collected in a sterile bag. The virus capture step is followed by washing with PBS until the UV absorbance returns to baseline. The pump is stopped and a process hag containing 0.45 M NaCl-PBS (pH 7.0) is connected to the inlet. The outlet tubing is transferred to a sterile container in a biosafety cabinet. The buffer is pumped into the column and when the UV absorbance begins to increase sharply, the column outlet is transferred to a new sterile container to collect the eluted virus. The collection is stopped after the UV absorbance returns to near baseline. This is the purified viral elute fraction. A process bag containing strip buffer is connected to the inlet and the end of the outlet tubing is transferred into a sterile bottle to collect the strip fraction. The buffer is pumped through the column until UV absorbance reaches a peak and returns to near baseline. The collected elute is stored at 4° C. overnight.

Tangential Flow Filtration

The tangential-flow filtration system, using a 0.1 micrometer pore size hollow fiber filter cartridge is prepared by assembling the tubing and cartridge and sterilizing the system by autoclaving. The system is flushed with sterile PBS (pH 7.0) and the virus eluate fraction is added to the system reservoir and equilibrated by recirculation. After equilibration, the permeate collection pump is turned on and filtrate is collected. The system is run until the loaded volume is reduced to approximately 500 ml. The retentate in the reservoir is diluted with DPBS (pH 7.0) with continuous constant volume diafiltration, and the product in the retentate is recovered when the permeate conductivity is within 10% of the diafiltering buffer (DPBS pH 7.0).

Formulation, Final Filtration and Packaging

The recovered retentate is adjusted to 10% final volume with sterile glycerol and mixed well prior to filtering through a 0.45 μm disc filter unit. The product is dispensed into labeled cryovials for storage at <−65° C.

Example 4: Analysis of Transduction of McKrae Strain in DRG after Paw Injection This example demonstrates that administration of a McKrae strain-based vector results in transduction of dorsal root ganglia (DRG) in vivo.

A replication-defective HSV-1 vector as described above was injected into the footpad of rats. As shown in FIG. 1, a replication-defective HSV-1 vector can transduce the DRG neurons in a dose-dependent manner (five days after injection). The ordinate shows a portion of the total number of genomes detectable under assay conditions and indicates that the number of genomes increases relative to dose of vector injected.

Figure 2:
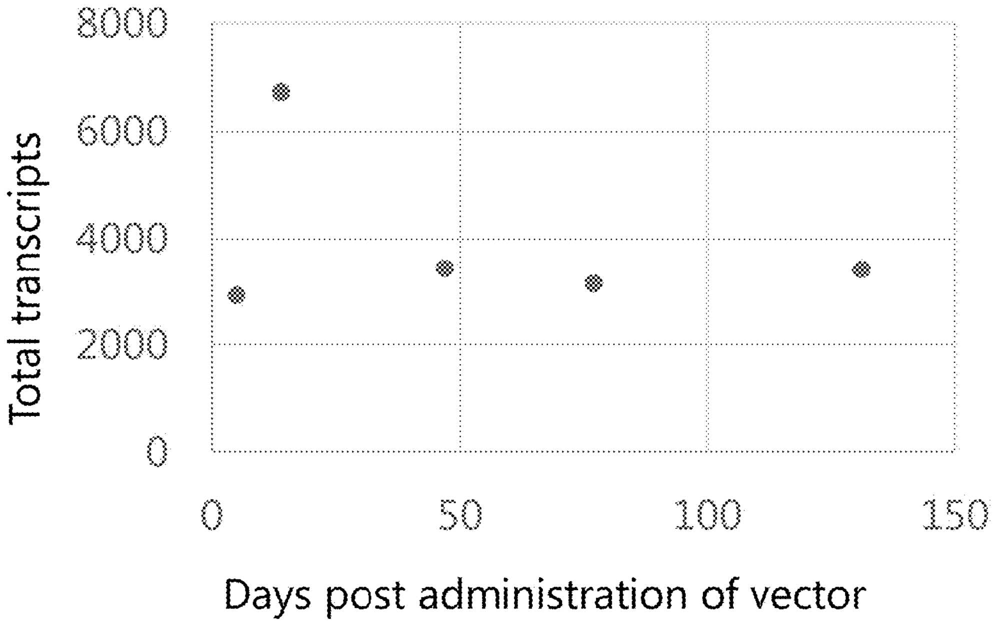
FIG. 2 depicts an exemplary graph that shows the total number of transcripts of payload in L4-L6 DRG at 5, 14, 47, 77, and 131 days post administration with HSV viral vectors having a HCMV promoter.
Figure 3:
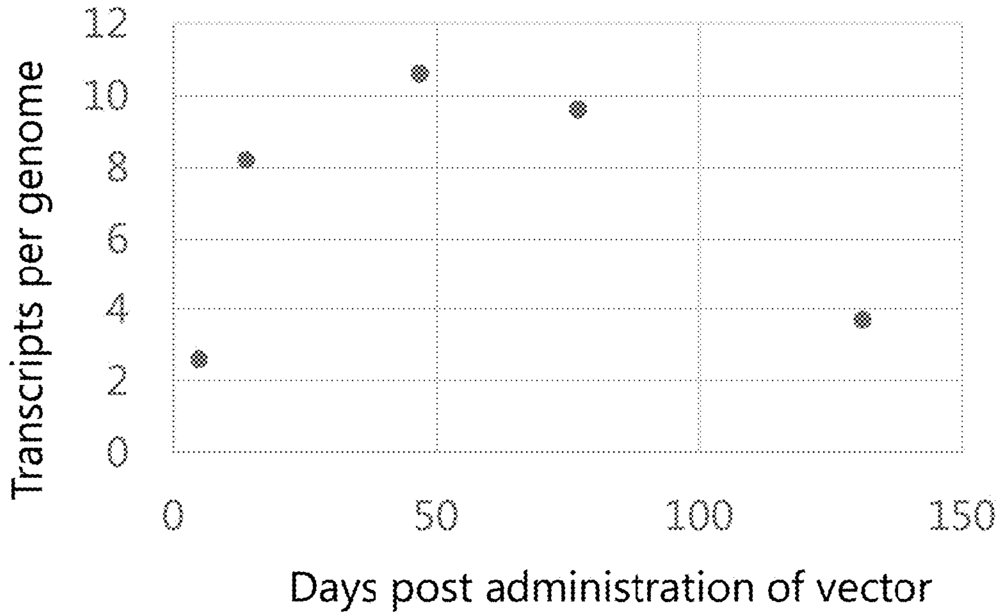
FIG. 3 depicts an exemplary graph that shows the number of transcripts of payload per genome in L4-L6 DRG at 5, 14, 47, 77, and 131 days post administration with HSV viral vectors having a HCMV promoter.

FIG. 2 shows the total number of transcripts of a payload in DRG at 5, 14, 47, 77, and 131 days after injection into the footpad of a rodent. FIG. 3 shows the data from the same experiment as number of transcripts of payload per genome. Expression of the payload was driven by the HCMV promoter.

Example 5: Analysis of Transduction and Expression of Payload with Different Promoters This example demonstrates increased gene expression can be obtained in DRG using a neuron specific promoter.

Figure 4:
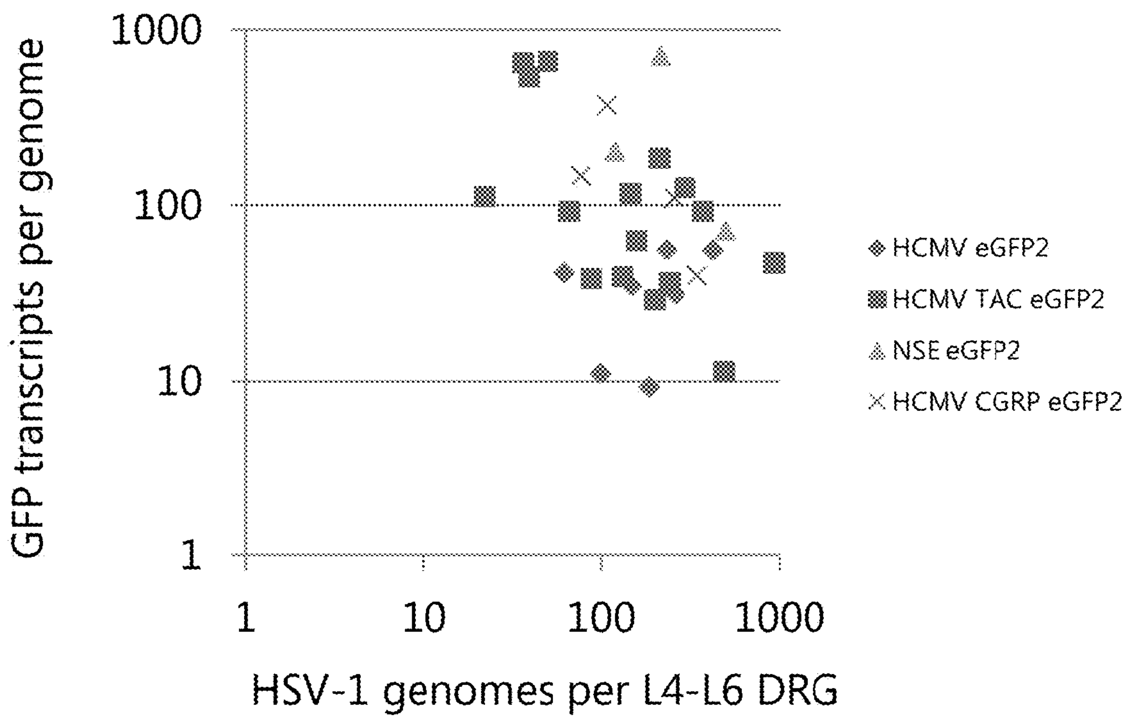
FIG. 4 depicts an exemplary graph that shows the number of GFP transcripts per genome and the number of HSV-1 genomes per L4-L6 DRG as a result of administering viral vectors with different promoters.

Four different promoters (HCMV, HCMV TAC, NSE and HCMV CGRP) were tested for efficacy in delivering HSV-1 vectors to DRG. The vector comprising a NSE promoter did not have a CMV enhancer, just a neuron-specific promoter. As shown in FIG. 4, a vector with an HCMV promoter averaged 29 transcripts per genome in DRG, while HCMV TAC, NSE and HCMV CGRP promoters averaged 176, 327 and 166 transcripts per genome, respectively.

Figure 5:
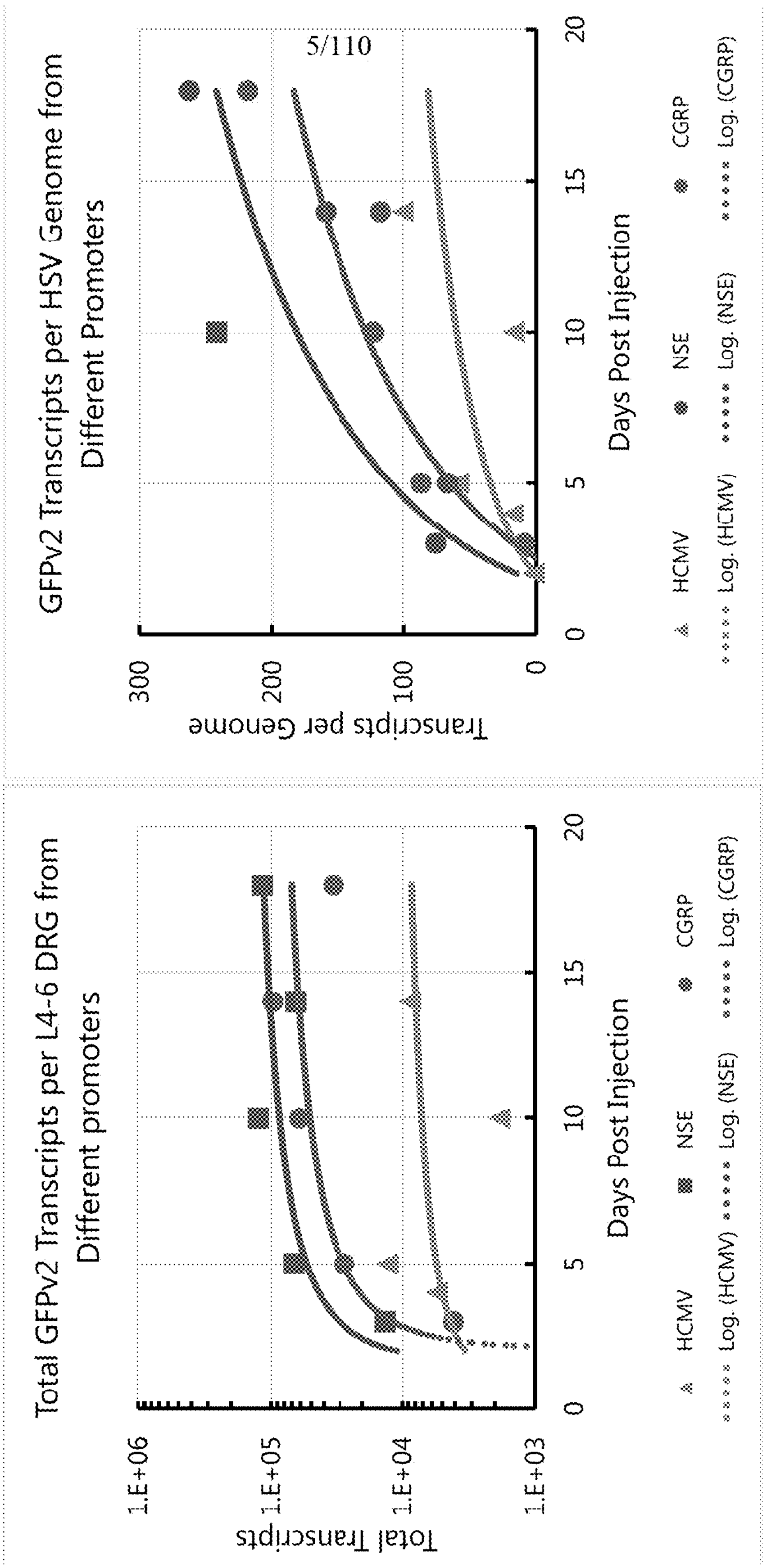
FIG. 5 depicts an exemplary graph that shows the total number of GFP transcripts and total transcripts per genome in L4-L6 DRG over 18 days after administration of HSV viral vectors with tissue specific promoters.

McKrae viral vectors comprising Green Fluorescent Protein (GFP) operatively linked to HCMV, NSE, or CGRP promoters were injected into the footpad of rats and GFP transcripts were measured in L4-L6 DRG over time. As shown in FIG. 5, tissue specific promoters improved transcription in DRG neurons between 5 and 18 days after footpad inoculation.

Figure 6:
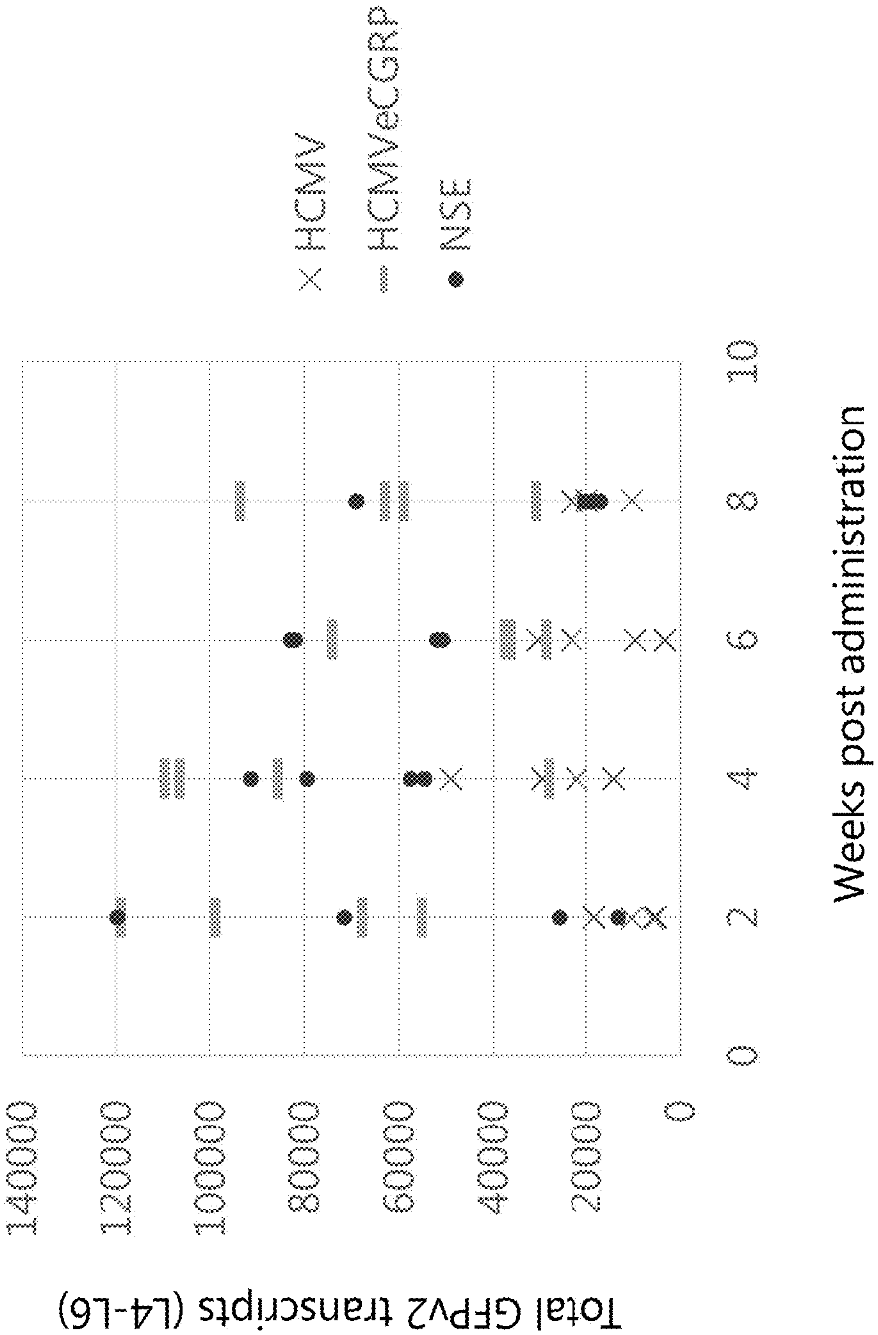
FIG. 6 depicts an exemplary graph that shows the number of total GFP transcripts in L4-L6 DRG over 8 weeks after administration of HSV viral vectors with tissue specific promoters.
Figure 7:
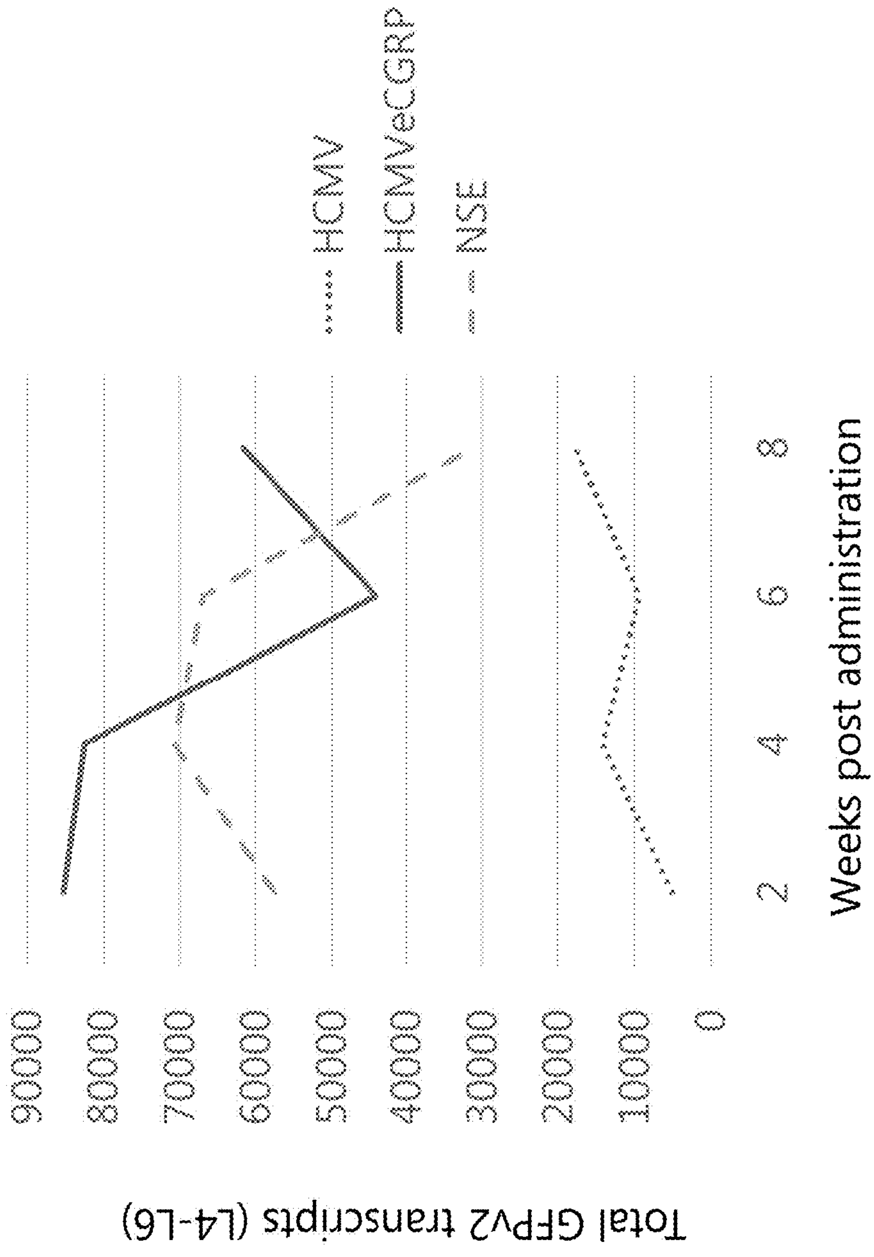
FIG. 7 depicts an exemplary graph that shows the total number of GFP transcripts in L4-L6 DRG over 8 weeks after administration of HSV viral vectors with tissue specific promoters.

Additionally, when three different promoters (HCMV, HCMVeCGRP and NSE) were compared over time (2-8 weeks), vectors containing either a NSE or HCMVeCGRP promoter resulted in more total transcripts in DRG than a vector containing a HCMV promoter (see FIGS. 6 and 7).

Figure 8:
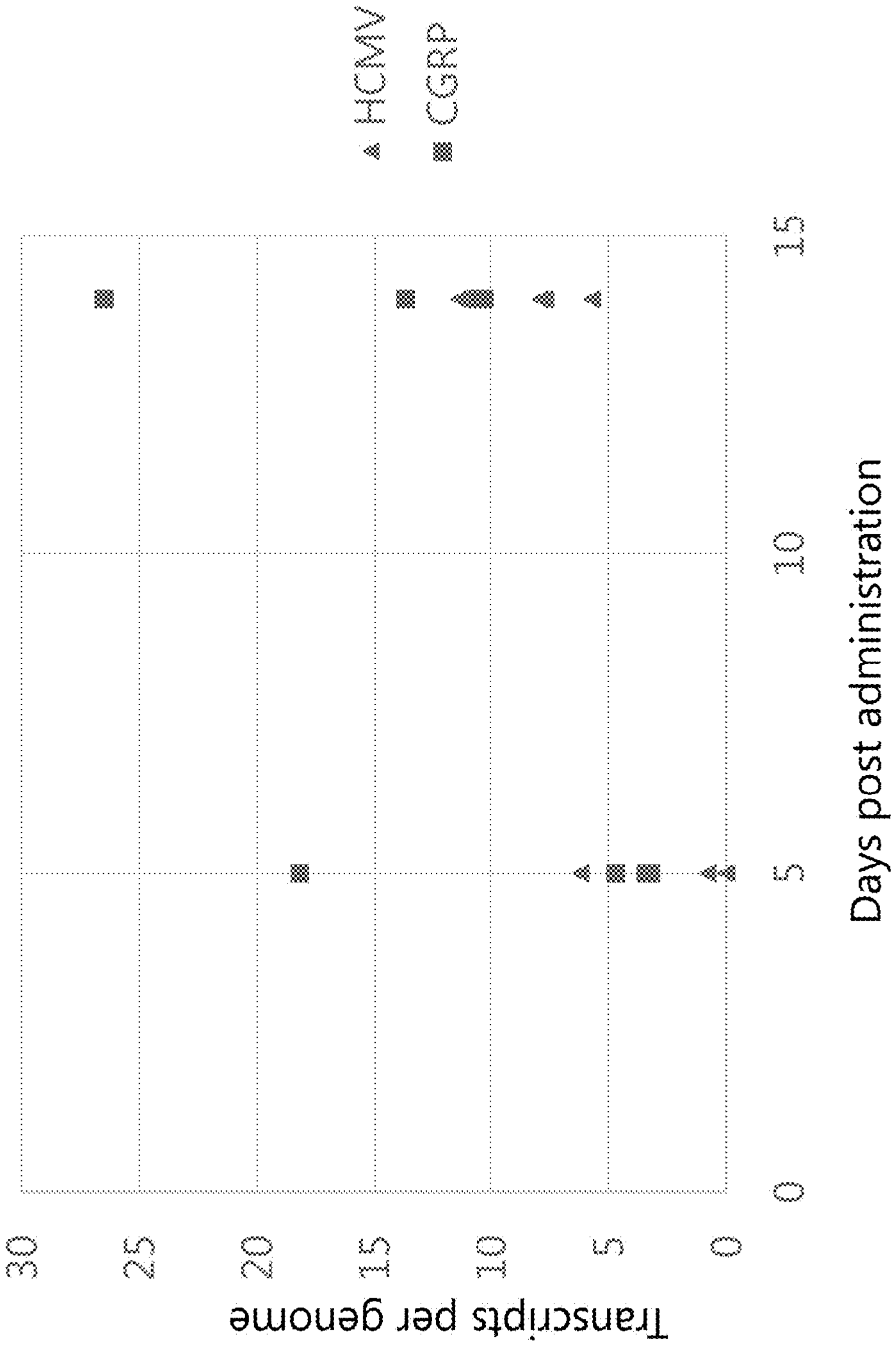
FIG. 8 depicts an exemplary graph that shows the total number of transcripts of payload per genome in L4-L6 DRG after administration with HSV viral vectors having a human cytomegalovirus (HCMV) promoter compared to HSV viral vectors having a chimeric calcitonin gene-related peptide (CGRP) promoter with an HCMV enhancer.

Transcripts of payload were measured in DRG of rats receiving an injection of a McKrae viral vector comprising a polypeptide payload operatively coupled to a CGRP chimeric promoter or an HCMV promoter. As measured at 5 and 14 days post-injection, the CGRP promoter, comprising an HCMV enhancer upstream of the promoter, showed higher transcript numbers of the polypeptide payload per genome than the HCMV promoter (FIG. 8).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A gene therapy vector comprising a replication-defective variant of herpes simplex virus (HSV) McKrae strain whose genome contains an alteration such that the variant fails to express a functional ICP4 protein comprising SEQ ID NO: 16, wherein the gene therapy vector is capable of expressing a payload in neurons for at least 18 days.

2. The gene therapy vector of claim 1, wherein the gene therapy vector comprises a neuron specific promoter.

3. The gene therapy vector of claim 2, wherein the neuron specific promoter is a calcitonin gene-related peptide (CGRP) promoter.

4. The gene therapy vector of claim 1, wherein the gene therapy vector comprises a human cytomegalovirus (HCMV) enhancer.

5. The gene therapy vector of claim 1, wherein the gene therapy vector comprises a bovine growth hormone (BGH) polyadenylation signal.

6. The gene therapy vector of claim 1, further comprising a nucleic acid that encodes a therapeutic polypeptide.

7. A cell transduced with a gene therapy vector according to claim 1.

8. A pharmaceutical composition comprising a gene therapy vector according to claim 1 and a pharmaceutically acceptable carrier.

9. The gene therapy vector of claim 1, wherein the functional ICP4 protein has an amino acid sequence of SEQ ID NO: 2.

10. The gene therapy vector of claim 1, wherein the gene therapy vector is capable of expressing a payload in neurons for at least 50 days.

11. The gene therapy vector of claim 1, wherein the gene therapy vector is capable of expressing a payload in neurons for at least 100 days.

12. The gene therapy vector of claim 1, wherein the gene therapy vector is capable of producing in neurons a mean genome copy number of greater than 5,000 transcripts.

13. The gene therapy vector of claim 1, wherein the gene therapy vector is capable of producing in neurons a mean genome copy number of greater than 10,000 transcripts.

14. The gene therapy vector of claim 1, wherein the gene therapy vector is capable of producing in neurons a mean genome copy number of greater than 15,000 transcripts.

* * * * *

```
SEQUENCE LISTING

<160> NUMBER OF SEQ ID NOS: 19

<210> SEQ ID NO 1
<211> LENGTH: 151135
<212> TYPE: DNA
<213> ORGANISM: human herpesvirus 1 strain McKrae
<220> FEATURE:
<221> NAME/KEY: misc_feature
<222> LOCATION: (61968)..(62069)
<223> OTHER INFORMATION: n is a, c, g, or t

<400> SEQUENCE: 1

gcagcccggg ccccccgcgc gcggggcggc gcgcaaaaaa ggcgggcggc ggtccgggcg     60

gcgtgcgcgc gcgcggcggg cgtgggggc ggggccgcgg gagcggggga ggagccccac    120

ccacagacgg ggaggagcgg gggaggagcg ggggaggagc gggggaggag ccccacccac    180

agacggggag gagcggggga ggagcggcca gaccccaaaa acgggccccc ccgaaacaca    240

ccccccgggg gtcgcgcgcg gcccttttaaa gcgcggcggc gggcagcccg ggccccccgc    300

ggccgagact agcgagttag acaggcaagc actactcgcc tctgcacgca catgcttgcc    360

tgtcaaactc taccaccccg gcacgctctc tgtctccatg gcccgccgcc gccgccatcg    420

cggcccccgc cgcccccggc cgcccgggcc cacgggcgcc gtcccaaccg cacagtccca    480
```

-continued

```
ggtaacctcc acgcccaact cggaacccgc ggtcaggagc gcgcccgcgg ccgccccgcc    540
gccgcccccc gccggtgggc ccccgccttc ttgttcgctg ctgctgcgcc agtggctcca    600
cgttcccgag tccgcgtccg acgacgacga tgacgacgac tggccggaca gcccccccgcc   660
cgagccggcg ccagaggccc ggcccaccgc cgccgccccc cggccccggt ccccaccgcc    720
cggcgtgggc ccggggggcg gggctgaccc ctcccacccc ccctcgcgcc ccttccgcct    780
tccgccgcgc ctcgccctcc gcctgcgcgt caccgcggag cacctggcgc gcctgcgcct    840
gcgacgcgcg ggcggggagg gggcgccgga gcccccccgcg acccccgcga cccccgcgac   900
ccccgcgacc cccgcgaccc ccgcgacccc cgcgaccccc gcgacccccg cgcgggtgcg    960
cttctcgccc cacgtccggg tgcgccacct ggtggtctgg gcctcggccg cccgcctggc   1020
gcgccgcggc tcgtgggccc gcgagcgggc cgaccgggct cggttccggc gccgggtggc   1080
ggaggccgag gcggtcatcg ggccgtgcct ggggcccgag gcccgtgccc gggccctggc   1140
ccgcggagcc ggcccggcga actcggtcta acgttacacc cgaggcgcct gggtcttccg   1200
cggagctccc gggagctccg caccaagccg ctctccggag agacgatggc aggagccgcg   1260
catatatacg ctgggagccg gtccgccccc aaggcgggcc cgcctcgggg gcgggactgg   1320
ccaatcggcg gccgccagcg cggcggggcc cggccaacca gcgtccgccg agtcttcggg   1380
gcccggccca ttgggcggga gttaccgccc aatgggccgg gccgcccact tcccggtatg   1440
gtaattaaaa acttgcaaga ggccttgttc cgcttcccgg tatggtaatt agaaactcat   1500
taatgggcgg ccccggccgc ccttcccgct tccggcaatt cccgcggccc ttaatgggca   1560
accccggtat tccccgcctc ccgcgccgcg cgtaaccact cccctggggt tccgggttat   1620
gctaattgct tttttggcgg aacacacggc ccctcgcgca ttggcccgcg ggtcgctcaa   1680
tgaacccgca ttggtcccct ggggttccgg gtatggtaat gagtttcttc gggaaggcgg   1740
gaagccccgg ggcaccgacg caggccaagc ccctgttgcg tcggcgggag gggcatgcta   1800
atggggttct ttgggggaca ccgggttggt cccccaaatc gggggccggg ccgtgcatgc   1860
taatgatatt ctttgggggc gccgggttgg tccccgggga cggggccgcc ccgcggtggg   1920
cctgcctccc ctgggacgcg cggccattgg gggaatcgtc actgccgccc ctttggggag   1980
gggaaaggcg tggggtataa gttagccctg gcccgacggt ctggtcgcat ttgcacctcg   2040
gcactcggag cgagacgcag cagccaggca gactcgggcc gcccccctctc cgcatcacca  2100
cagaagcccc gcctacgttg cgacccccag ggaccctccg tccgcgaccc tccagccgca   2160
tacgaccccc atggagcccc gccccggagc gagtacccgc cggcctgagg gccgccccca   2220
gcgcgaggtg aggggccggg cgccatgtct ggggcgccat attgggggc gccatgttgg    2280
gggacccccg acccttaccc tggaaccggc ccccatgttg ggggaccccc actcatacac   2340
gggagccggg cgccatgttg ggcgccatg ttagggggcg tggaaccccg tgacactata    2400
tatacaggga ccgggggcgc catgttaggg ggcgcggaac cccctgaccc tatatataca   2460
gggaccgggg tcgccctgtt gggggtcgcc atgtgacccc ctgactttat atatacagac   2520
ccccaacaca tacacatggc ccctttgact cagacgcagg gcccggggtc gccgtgggac   2580
cccctgactc atacacagag acacgccccc acaacaaaca cacagggacc ggggtcgccg   2640
tgttgggggc gtggtcccca ctgactcata cgcaggcccc ccttactcac acgcatctag   2700
gggggtgggg aggagccgcc cgccatattt gggggacgcc gtgggacccc cgactccggt   2760
gcgtctggag ggcgggagaa gagggaagaa gaggggtcgg gatccaaagg acggacccag   2820
accacctttg gttgcagacc cctttctccc ccctcttccg aggccagcag gggggcagga   2880
```

-continued

```
ctttgtgagg cggggggga gagggggaac tcgtgggcgc tgattgacgc gggaaatccc   2940
cccccattct tacccgcccc cctttttcc ccttagcccg ccccggatgt ctgggtgttt   3000
ccctgcgacc gagacctgcc ggacagcagc gactctgagg cggagaccga agtgggggg   3060
cggggggacg ccgaccacca tgacgacgac tccgcctccg aggcggacag cacggacacg   3120
gaactgttcg agacggggct gctggggccg cagggcgtgg atggggggc ggtctcgggg   3180
gggagccccc cccgcgagga agaccccggc agttgcgggg gcgcccccc tcgagaggac   3240
ggggggagcg acgagggcga cgtgtgcgcc gtgtgcacgg atgagatcgc gccccacctg   3300
cgctgcgaca ccttcccgtg catgcaccgc ttctgcatcc cgtgcatgaa aacctggatg   3360
caattgcgca acacctgccc gctgtgcaac gccaagctgg tgtacctgat agtgggcgtg   3420
acgcccagcg ggtcgttcag caccatcccg atcgtgaacg acccccagac ccgcatggag   3480
gccgaggagg ccgtcagggc gggcacggcc gtggacttta tctggacggg caatcagcgg   3540
ttcgccccgc ggtacctgac cctgggggg cacacggtga gggccctgtc gcccacccac   3600
ccggagccca ccacggacga ggatgacgac gacctggacg acggtgaggc gggggcggc   3660
aaggaccctg ggggaggagg aggagggagg aatgggcggg cgggcgagga aagggcgggc   3720
cggggagggg gcgtaacctg atcgcgcccc ccgttgtctc ttgcagcaga ctacgtcccg   3780
cccgcccccc gccggacgcc ccgcgccccc ccacgcagag gcaccgccgc gccccccgtg   3840
acgggcgggg cgtctaacgc agcccccag ccggccgcgg ctcggacagc gcccccctcg   3900
gcgcccatcg ggccacacgg cagcagtaac accaacacca ccaccaacag cagcggcggc   3960
ggcggctccc gccagtcgcg agccgcggcg ccgcgggggg cgtctggccc ctccgggggg   4020
gttggggttg gggttggggt tgttgaagcg gaggcggggc ggccgagggg ccggacgggc   4080
ccccttgtca acagacccgc cccccttgca aacaacagag accccatagt gatcagcgac   4140
tccccccgg cctctcccca caggccccc gcggcgccca tgccaggctc cgcccccgc   4200
cccgggcccc ccgcgtcctc ggccgcgtcg ggacccgcgc gcccccgcgc ggccgtggcc   4260
ccgtgcgtgc gagcgccgcc tccggggccc ggcccccgcg ccccggcccc cggggcggag   4320
ccggccgccc gccccgcgga cgcgcgccgt gtgccccagt cgcactcgtc cctggctcag   4380
gccgcgaacc aagaacagag tctgtgccgg gcgcgtgcga cggtggcgcg cggctcgggg   4440
gggccgggcg tggagggtgg gcacgggccc tcccgcggcc gcaccccctc cggcgccgcc   4500
ccgctcccct ccgccgtctc tgtcgagcag gaggcggcgg tgcgtccgag gaagaggcgc   4560
gggtcgggcc aggaaaaccc ctcccccag tccacgcgtc ccccctcgc gccggcaggg   4620
gccaagaggg cggcgacgca cccccctcc gactcagggc cgggggggcg cggccagggt   4680
gggcccggga cccccctgac gtcctcggcg gcctccgcct cttcctcctc tgcctcttcc   4740
tcctcggccc cgacccccgc gggggccgcc tcttccgccg ccggggccgc gtcctcctcc   4800
gcttccgcct cctcgggcgg ggccgtcggt gccctgggag ggagacaaga ggaaacctcc   4860
ctcggcccc gcgctgcttc tgggccgcgg gggccgagga agtgtgcccg gaagacgcgc   4920
cacgcggaga cttccggggc cgtccccgcg ggcggcctca cgcgctacct gcccatctcg   4980
ggggtctcta gcgtggtcgc cctgtcgcct tacgtgaaca agactatcac gggggactgc   5040
ctgcccatcc tggacatgga gacggggaac atcggggcgt acgtggtcct ggtggaccag   5100
acgggaaaca tggcgacccg gctgcgggcc gcggtccccg gctggagccg ccgcaccctg   5160
ctccccgaga ccgcgggtaa ccacgtgatg cccccgagt acccgacggc cccgcgtcg   5220
```

-continued

```
gagtggaaca gcctctggat gaccccccgtg gggaacatgc tgttcgacca gggcacccta   5280
gtgggcgccc tggacttccg cagcctgcgg tctcggcacc cgtggtccgg ggagcagggg   5340
gcgtcgaccc gggacgaggg aaaacaataa gggacgcccc ccgtgtttgt ggggaggggg   5400
gtcgggtgct gggtggtctc tggccgcgcc cactacacca gccaatccgt gtcggggagg   5460
ggaaagtgaa agacacgggc accacacacc agcgggtctt tagtgttggc cctaataaaa   5520
aactcagggg atttttgctg tctattggga aataaaggtt tacttttgta tcttttccct   5580
gtctgtgttg gatggatctt gggggtgcgt gggagtgggg gtgcgtggga gtgggggtgc   5640
gtgggagtgg gggtgcgtgg gagtgggggt gcgtgggagt gggggtgcgt gggagtgggg   5700
gtgcgtggga gtgggggtgc gtgggagtgg gggtgcgtgg gagtgggggt gcgtgggagt   5760
gggggtgcgt gggagtgggg gtgcgtggga gtgggggtgc gtgggagtgg gggtgccatg   5820
ttgggcaggc tctggtgtta accacagagc cgcggcccgg gctgcctgac caccgatccc   5880
cgaaagcatc ctgccactgg catggagcca gaaccacagt gggctgggtg tgggtgttaa   5940
gtttccgcga gcgcctgccc gcccggactg acctggcctc tggccgccac aaagggcggg   6000
ggggggggtta actacactat agggcaacaa aggacgggag gggtggcggg acggggcgcc   6060
caaaaggggg tcggccacac cacagacgtg ggtgttgggg ggtggggcgg aggggtgggg   6120
gggagacaga aacaggaaca tagttagaaa acaagaatgc ggtgcagcca gagaatcaca   6180
ggagacgagg ggatgggcgt gttggttacc aacccacacc caggcatgct cggtggtatg   6240
aaggaggggg ggcggtgctt cttagagacc gccgggggac gtggggttgg tgtgcaaagg   6300
cacgcgcacc cgcgtcggcc aggtgggccg gtaccccatc ccccccctccc ccgacccttc   6360
cccccccgcg tgccagagat cacccccgtc ccccggcacc cgccactcct ccatatcctc   6420
gctttaggaa caactttggg ggggggggtac acacgcgccg tgcatttcct tccacacccc   6480
ccctccccccg catcccccccc cccaggcagt aagacccaag catagagagc caggcacaaa   6540
aacacaggcg gggtgggaca catgccttct tggagtacgt gggtcattgg cgtggggggt   6600
tacagcgaca ccggccgacc ccctggcggt cttccagccg gcccttagat aagggggcag   6660
ttggtggtcg gacgggtaag taacagagtc tgactaaggg tgggaggggg ggaaaagaac   6720
gggctggtgt gctgtaacac gagcccaccc gcgagtggcg tggccgacct tagcctctgg   6780
ggcgccccct gtcgtttggg tcccccccccc tctattgggg agaagcaggt gtctaaccta   6840
cctggaaacg cggcgtcttt gttgaacgac accggggcgc cctcgacgag tgggataacg   6900
ggggaggaag ggagggagga gggtactggg ggtgaagaag ggggggggga agaagcgaga   6960
acaggaaagg cgacggagcc cggcagaaca ccgaggaaaa aaaaaacaca gcgcatgcgc   7020
cgggccgttg tggggccccg ggccggggcc ccttgggtcc gccggggccc cgggccgggc   7080
cgccacgggg gccggccgtt ggcggtaacc ccgattgttt atctcaggcc ccgggccggg   7140
aacccggaaa agcctccggg gggccttttt cgcgtcgcgt gccggcgagc gggcccggac   7200
ggggcccgga ccgccgcggt cgggggcccc tcgtcccggg ccgtacgcgg ccttcgcccc   7260
gtgaggggcc gaacgaacga aacatcccgg cgacggaacg aaaaacaccc cagacgggtt   7320
taaaaaacag aaaccgtaac ccccccccacc cccgaaacgg ggaaaacaaa aaacagacca   7380
gcggccggcc ggcgcttagg gggaggatgt cgccgacgcc ccttggccgc cccggctgca   7440
ggggggcccg gagagccgcg gcacccggac gcgcccggaa agtctttcgc accacccgcg   7500
atcggcacgg ccgcgccccc gcttttataa aggctcagat gacgcagcaa aaacaggcca   7560
cagcaccacg tgggtaggtg atgtaatttt attttcctcg tctgcggcct aatggatttc   7620
```

```
cgggcgcggt gcccctgtct gcagagcact taacggattg atatctcgcg ggcacgcgcg   7680
cccttaatgg accggcgcgg ggcggggggc cggataccca cacgggcggg ggggtgtcgc   7740
gggccgtctg ctggcccgcg gccacataaa caatgactcg ggcctttct gcctctgccg    7800
cttgtgtgtg cgcgcgccgg ctctgcggtg tcggcggcgg ctgcggcggc tgcggcggcc   7860
gccgtgttcg gtctcggtag ccggccggcg ggtggactcg cggggggccg gagggtggaa   7920
ggcagggggg tgtaggatgg gtatcaggac ttccacttcc cgtccttcca tcccccgttc   7980
ccctcggttg ttcctcgcct cccccaacac cccgccgctt tccgttgggg ttgttattgt   8040
tgtcgggatc gtgcgggccg ggggtcgccg gggcaggggc gggggcgggg gtgctcgtcg   8100
atcgaccggg ctcagtgggg gcgtggggtg ggtgggaaaa ggcgaggaga ctggggtggg   8160
gggtgtcggg ggtggctgtt tttttgtggt tgttttttgt gtctgttccc gtcccccgtc   8220
accccctcc ctccgtcccc ccgtcgcggg tgtttgtgtt tgtttattcc gacatcggtt    8280
tatttaaata aacacagccg ttctgcgtgt ctgttcttgc gtgtggctgg gggcttatat   8340
gtggggtccc gggggcggga tggggtttag cggcgggggg cggcgcgccg gacggggcgc   8400
tggagataac ggcccccggg gaacggggga ccggggctgg gtctcccgcg gtgggtgggt   8460
gggcggcggt ggccgggccg ggccgggccg ggtgggcggg gtttggaaaa acgaggagga   8520
ggagaaggag gaggaggggg ggggagacgg ggggaaagca aggacacggc cccgggggg    8580
ggggagcgcg ggccgggccg cttggcaacc cccctgtttc ttccggaaac caggcttgtg   8640
gccccacccg acatcacaag ggacctcttg tcgggcctcc cgacgtacgc cgaggctatg   8700
tcggaccacc ccccaaccta agaggggaga ggggagaggg gagaggggag aggggagagg   8760
ggagagggga ggagaggggg tatataaacc aacgaaaagc gcgggaacgg ggatacgggg   8820
cttgtgtggc acgacgtcgt ggttgtgtta ctgggcaaac acttggggac tgtaggtttc   8880
tgtggtgccg accctaggcg ctatggggat tttgggttgg gttgggctta ttgccgttgg   8940
ggttttgtgt gtgcgggggg gcttgccttc aaccgaatat gttattcgga gtcgggtggc   9000
tcgagaggtg ggggatatat taaaggtgcc ttgtgtgccg ctcccgtctg acgatcttga   9060
ttggcgctac gagacccct cggctataaa ctatgctttg atagacggta tatttttgcg    9120
ttatcactgt cccggattgg acacggtctt gtgggatagg cacgcccaga gggcgtattg   9180
ggttaacccc tttttgtttg gggcgggttt tttggaggac ttgagtcatc ccgcgtttcc   9240
tgccgacacc caggaaacag aaacgcgctt ggccctttat aaagagatac gccaggcgct   9300
ggacagtcgc aagcaggccg ccagccacac acctgtgaag gctgggtgtg tgaactttga   9360
ctattcgcgc acccgccgct gtgtagggcg ccaggatttg ggacttacca acagaacgtc   9420
tggacggacc ccggttctgc cgtcggacga tgaagcgggc ctgcagccga agcccctcac   9480
cacgccgtcg cccatcatcg ccacgtcgga ccccaccccg cgacgggacg ccgccacaaa   9540
aagcagacgc cgacgacccc attcccggcg catctaatga tgcctcgacg gaaaaccgtc   9600
cgggtttggg gggcgaaccg gccgcctgtc gctcgtcagg gccggcgggc gctcctcgcc   9660
gccctagagg ctgtcccgct ggtgtgacgt tttcctcgtc cgcgcccccc gaccctccca   9720
tggatttaac aaacgggggg gtgtcgcctg cggcgacctc ggcgcctctg gactggacca   9780
cgtttcggcg tgtgtttctg atcgacgacg cgtggcggcc cctgttggag cctgagctgg   9840
cgaacccctt aaccgcccac ctcctggccg aatataatcg tcggtgccag accgaagagg   9900
tgctgccgcc gcgggaggat gtgttttcgt ggactcgtta ttgcaccccc gacgaggtgc   9960
```

-continued

```
gcgtggttat catcggccag gacccatatc accaccccgg ccaggcgcac ggacttgcgt  10020
ttagcgtgcg cgcgaacgtg ccgcctcccc cgagtcttcg gaatgtcttg gcggccgtca  10080
agaactgtta tcccgaggca cggatgagcg gccacggttg cctggaaaag tgggcgcggg  10140
acggcgtcct gttactaaac acgaccctga ccgtcaagcg cggggcggcg gcgtcccact  10200
ctagaatcgg ttgggaccgc ttcgtgggcg gagttatccg ccggttggct gcgcgccgcc  10260
ccggcctggt gtttatgctc tggggcgcac atgcccagaa tgccatcagg ccggaccctc  10320
gggtccattg cgtcctcaag ttttcgcacc cgtcgcccct ctccaaggtt ccgttcggaa  10380
catgccagca tttcctcgtg gcgaatcgat atctcgagac ccggtcgatt tcacccatcg  10440
actggtcggt ttgaaaggca tcgacgtccg gggttttcgt ctgtgggggc ttttgggtat  10500
ttccgatgaa taaagacggt taatggttaa acctctggtc tcatacgggt cggtgatgtc  10560
gggcgtcggg ggagagggag ttccctctgc gcttgcgatt ctagcctcgt ggggctggac  10620
gttcgacacg ccaaaccacg agtcagggat atcgccagat acgactcccg cagattccat  10680
tcggggggcc gctgtggcct cacctgacca acctttacac gggggcccgg aacgggaggc  10740
cacagcgccg tctttctccc caacgcgcgc ggatgacggc ccgccctgta ccgacgggcc  10800
ctacgtgacg tttgataccc tgtttatggt gtcgtcgatc gacgaattag ggcgtcgcca  10860
gctcacggac accatccgca aggacctgcg gttgtcgctg gccaagttta gcattgcgtg  10920
caccaagacc tcctcgtttt cgggaaacgc cccgcgccac cacagacgcg gggcgttcca  10980
gcgcggcacg cgggcgccgc gcagcaacaa aagccttcag atgtttgtgt tgtgcaaacg  11040
cgcccacgcc gctcgagtgc gagagcagct tcgggtcgtt attcagtccc gcaagccgcg  11100
caagtattac acgcgatctt cggacgggcg gctctgcccc gccgtccccg tgttcgtcca  11160
cgagttcgtc tcgtccgagc caatgcgcct ccaccgagat aacgtcatgc tggcctcggg  11220
ggccgagtaa ccgccccccc cccgcgccac cctcactgcc cgtcgcgcgt gtttgatgtt  11280
aataaataac acataaattt ggctggttgt ttgttgtctt taatggaccg cccgcagggg  11340
gggtggcatt tcagtgtcgg gtgacgagcg cgatccggcc gggatcctag gaccccaaaa  11400
gtttgtctgc gtattccagg gcggggctca gttgaatctc ccgcagcacc tctaccagca  11460
ggtccgcggt gggctggaga aactcggccg tcccggggca ggcggtcgtc gggagtggag  11520
gcgcggcgcc caccccgtgt gccgcgcctg gcgtctcctc tgggggcgac ccgtaaatgg  11580
ttgcagtgat gtaaatggtg tccgcggtcc agaccacggt caaaatgccg gccgtggtgc  11640
tccgggcgct ttcgccgcgc gaggagctga cccaggagtc gaacggatac gcgtacatat  11700
gggcgtccca cccgcgttcg agcttctggt cgctgtcccg gcctataaag cggtaggcac  11760
aaaattcggc gcgacagtcg ataatcacca acagcccaat gggggtgtgc tggataacaa  11820
cgcctccgcg cggcaggcgg tcctggcgct cccggccccg taccataatc gcgcgggtgc  11880
cgtactcaaa aacatgcacc acctgcgcgg cgtcgggcag tgcgctggtc agcgaggccc  11940
tggcgtggca taggctatac gcgatggtcg tctgtggatt ggacatctcg cggtgggtag  12000
tgagtccccc gggccgggtt cggtagaact gtaaggggac ggcgggttaa tagacaatga  12060
ccacgttcgg atcgcgcaga gccgatagta tgtgctcact aatgacgtca tcgcgctcgt  12120
ggcgctcccg gagcggattt aagttcatgc gaaggaattc ggaggaggtg gtgcgggaca  12180
tggccacgta cgcgctgttg aggcgcaggt tgccgggcgt aaagcagatg gcgaccttgt  12240
ccaggctaag gccctgggag cgcgtgatgg tcatggcaag cttggagctg atgccgtagt  12300
cggcgtttat ggccatggcc agctccgtag agtcaatgga ctcgacaaac tcgctgatgt  12360
```

-continued

```
tggtgttgac gacggacatg aagccgtgtt ggtcccgcaa gaccacgtaa ggcagggggg  12420
cctcttccag taactcggcc acgttggccg tcgcgtgccg cctccgcagc tcgtccgcaa  12480
aggcaaacac ccgtgcgtac gtgtatccca tgagcgtata attgtccgtc tgcagggcga  12540
cggacatcag ccccccgcgc ggcgagccgg tcagcatctc gcagccccgg aagataacgt  12600
tgtccacgta cgtgctaaag ggggcgcctt caaatgcctc cccgaagagc tcttggagga  12660
ttcggaatct cccgaggaag gcccgcttca gcagcgcaaa ctgggtgtga acggcggcgg  12720
tggtctccgg ttccccgggg gtgtagtggc agtaaaacac gtcgagctgt tgttcgtcca  12780
gccccgcgaa aataacgtcg aggtcgtcgt cgggaaaatc gtccgggccc ccgtcccgcg  12840
gccccagttg cttaaaatca aacgcacgct cgccgggggc gcctgcgtcg gctattaccg  12900
acgcctgcgt cggcgccccc gaagatttgg ggcgcagaga cagaatctcc gccgttagtt  12960
ctcccatgcg ggcgtaggcg agggtcctct gggtcgcatc caggcccggg cgctgcagaa  13020
agttgtaaaa ggagataagc ccgctaaata tgagccgcga caggaacctg taggcaaact  13080
ccaccgaagt ctccccctga gtctttacaa agctgtcgtc acgcaacact gcctcgaagg  13140
cccggaacgt cccactaaac ccaaaaacca gttttcgcag gcgcgcggtc accgcgatct  13200
ggctgttgag gacgtaagtg acgtcgttgc gggccacgac cagctgctgt ttgctgtgca  13260
cctcgcagcg catgtgcccc gcgtcctggt cctggctctg cgagtagttg gtgatgcggc  13320
tggcgttggc cgtgagccac ttttcaatag tcaggccggg ctggtgtgtc agccgtcggt  13380
attcgtcaaa ctccttgacc gacacgaacg taagcacggg gagggtgaac acgacgaact  13440
ccccctcacg ggtcaccttc aggtaggcgt ggagcttggc catgtacgcg ctcacctctt  13500
tgtgggagga gaacagccgc gtccagccgg ggaggttggc ggggttggtg atgtagcttt  13560
ccgggacgac gaagcgatcc acgaactgca tgtgctcctc ggtgatgggc aggccgtact  13620
ccagcacctt catgaggtta ccgaactcgt gctcgacgca ccgtttgttg ttaataaaaa  13680
tggcccagct atacgagagg cgggcgtact cgcgcagcgt gcggttgcag atgaggtacg  13740
tgagcacgtt ctcgctctgg cggacggaac accgcagttt ctggtgctcg aaggtcgact  13800
ccagggacgc cgtctgcgtc ggcgagccca cacacaccaa cacgggccgc aggcgggccg  13860
catactgggg ggtgtggtac agggcgttaa tcatccacca gcaatacacc acggccgtga  13920
ggaggtgacg cccaaggagc ccggcctcgt ctatgacgat cacgttgctg cgggtaaagg  13980
ccggcagcgc cccgtgggtg gccggggcca accgcgtcag ggcgccctcg gccaacccca  14040
gggtccgttc cagggcggcc agggcgcgaa actcgttccg cgactcctcg cccccggagg  14100
cggccagggc gcgcttcgtg aggtccaaaa tcacctccca gtagtacgtc agatctcgtc  14160
gctgcaggtc ctccagcgag gcggggttgc tggtcagggt gtacgggtac tgtcccagtt  14220
gggcctggac gtgattcccg cgaaacccaa attcatgaaa gatggtgttg atgggtcggc  14280
tgagaaaggc gcccgagagt ttggcgtaca tgttttgggc cgcaatgcgc gtggcgcccg  14340
tcaccacaca gtccaagacc tcgttgattg tctgcacgca cgtgctcttt ccggagccag  14400
cgttgccggt gataagatac accgcgaacg gaaactccct gaggggcagg cctgcggggg  14460
actctaaggc cgccacgtcc cggaaccact gcagacgggg cacttgcgct ccgtcgagct  14520
gttgttgcga gagctctcgg atgcgcttaa ggattggctg caccccgtgc atagacgtaa  14580
aatttaaaaa ggcctcggcc ctccctggaa cggctggtcg gtccccgggt tgctgaaggt  14640
gcggcgggcc gggtctctgt ccgtctagct ggcgctcccc gccggccgcc gccatgaccg  14700
```

-continued

```
caccacgctc gcgggccccc actacgcgtg cgcgggggga cacggaagcg ctgtgctccc  14760
ccgaggacgg ctgggtaaag gttcacccca cccccggtac gatgctgttc cgtgagattc  14820
tccacgggca gctggggtat accgagggcc agggggtgta caacgtcgtc cggtccagcg  14880
aggcgaccac ccggcagctg caggcggcga tctttcacgc gctcctcaac gccaccactt  14940
accgggacct cgaggcggac tggctcggcc acgtggcggc ccgcggtctg cagccccaac  15000
ggctggttcg ccggtacagg aacgcccggg aggcggatat cgccggggtg gccgagcggg  15060
tgttcgacac gtggcggaac acgcttagga cgacgctgct ggactttgcc cacgggttgg  15120
tcgcctgctt tgcgccgggc ggcccgagcg gcccgtcaag cttccccaaa tatatcgact  15180
ggctgacgtg cctggggctg gtccccatat tacgcaagcg acaagaaggg ggtgtgacgc  15240
agggtctgag ggcgtttctc aagcagcacc cgctgacccg ccagctggcc acggtcgcgg  15300
aggccgcgga gcgcgccggc cccgggtttt ttgagctggc gctggccttc gactccacgc  15360
gcgtggcgga ctacgaccgc gtgtatatct actacaacca ccgccggggc gactggctcg  15420
tgcgagaccc catcagcggg cagcgcggag aatgtctggt gctgtggcct cccttgtgga  15480
ccggggaccg tctggtcttc gattcgcccg tccagcggct gtttcccgag atcgtcgcgt  15540
gtcactccct ccgggaacac gcgcacgtct gccggctgcg caataccgcg tccgtcaagg  15600
tgctgctggg gcgcaagagc gacagcgagc gcggggtggc cggcgccgcg cgggtcgtta  15660
acaaggtgtt gggggaggac gacgagacca aggccgggtc ggccgcctca cgcctcgtgc  15720
ggcttatcat caacatgaag ggcatgcgcc acgtaggcga cattaacgac accgtgcgtg  15780
cctacctcga cgaggccggg gggcacctga tagacgcccc ggccgtcgac ggtaccctcc  15840
ctggattcgg caagggcgga aacagccgcg ggtctgcggg ccaggaccag ggggggcggg  15900
cgccgcagct tcgccaggcc ttccgcacgg ccgtggttaa caacatcaac ggcgtgttgg  15960
agggctatat aaataacctg tttggaacca tcgagcgcct gcgcgagacc aacgcgggcc  16020
tggcgaccca attgcaggag cgcgaccgcg agctccggcg cgcaacagcg ggggccctgg  16080
agcgccagca gcgcgcggcc gacctggcgg ccgagtccgt gaccggtgga tgcggcagcc  16140
gccctgcggg ggcggacctg ctccgggccg actatgacat tatcgacgtc agcaagtcca  16200
tggacgacga catgtacgtc gccaacagct ttcagcaccc gtacatccct tcgtacgccc  16260
aggacctgga gcgcctgtcg cgcctctggg agcacgagct ggtgcgctgt tttaaaattc  16320
tgtgtcaccg caacaaccag ggccaagaga cgtcgatctc gtactccagc ggggcgatcg  16380
ccgcattcgt cgccccctac tttgaggcag tgcttcgggc cccccgggta ggcgcgccca  16440
tcacgggctc cgatgtcatc ctgggggagg aggagttatg ggatgcggtg tttaagaaaa  16500
cctgcctgca aacgtacctg acagacatcg cggccctgtt cgtcgcggac gtccagcacg  16560
cagcgctgcc cccgcccccc tccccggtcg gcgccgattt ccggcccggc gcgtccccgc  16620
ggggccggtc cagatcgcgg tcgcccggaa gaactgcgcg aggcgcaccg gaccagggcg  16680
ggggcatcgg gcaccgggat ggccgccgcg acggccgacg atgaggggtc ggccgtcacc  16740
atcctcaagc aggccatcgc cggggaccgc agcctggtcg aggcggccga ggcgattagc  16800
cagcagacgc tgctccgcct ggcctgcgag gtgcgccagg tcggcgaccg ccagccgcgg  16860
tttaccgcca ccagcatcgc gcgcgtcgac gtcgcgcctg ggtgccggtt gcggttcgtt  16920
ctggacggga gtcccgagga cgcctatgtg acgtcggagg attactttaa gcgctgctgc  16980
ggccagtcca gttatcgcgg cttcgcggtg gcggtcctga cggccaacga ggaccacgtg  17040
cacagcctgg ccgtgccccc cctcgttctg ctgcaccggt tctccctgtt caaccccagg  17100
```

-continued gacctcctgg actttgagct tgcctgtctg ctgatgtacc tggagaactg cccccgaagc 17160
cacgccaccc cgtcgacctt tgccaaggtt ctggcgtggc tcggggtcgc gggtcgccgc 17220
acgtccccat tcgaacgcgt tcgctgcctt ttcatccgca gttgccactg ggtcctaaac 17280
acactcatgt tcatggtgca cgtaaaaccg ttcgacgacg agttcgtcct gccccactgg 17340
tacatggccc ggtacctgct ggccaacaac ccgccccccg ttctctcggc cctgttctgt 17400
gccaccccga cgagctcctc attccggctg ccggggccgc ccccccgctc cgactgcgtg 17460
gcctataacc ccgccgggat catggggagc tgctgggcgt cggaggaggt gcgcgcgcct 17520
ctggtctatt ggtggctttc ggagacccca aaacgacaga cgtcgtcgct gttttatcag 17580
ttttgttgaa ttttagtaaa taaacccggt tttgtttcta tggcctcctg acggatgcgc 17640
gtgtccttac tccgttttgg tgggtgggtg gctgtgtatg gcgtcccatc tgtgcgggga 17700
gggggcaagt cggcacgtat tcggacagac tcaagcacac acgggggagc gctcttggct 17760
cagggcaatg tttttattgg tcaaactcag gcaaacagaa acaacatctt gtcgtcaaag 17820
ggatacacaa acttcccccc ctcgccccat actcccgcca gcaccccggt aaacaccaac 17880
tcaatctcgc gcaggatttc gcgcaggtga tgagcgcagt ccacgggggg gagcacaagg 17940
ggccgcgggt atagatcgac ggggacgccg accgactccc cgcctccggg acagacacgc 18000
acgacgcgcc gccagtagtg ctctgcgtcc aacaaggcgc cgccgcggaa ggcagtgggg 18060
ggcaaggggt cgctggcctc aaagggggac acccgaacgc tccagtactc cgcgtccaac 18120
cgtttattaa acgcgtccac gataaggcgg tcgcaggcgt cctccataag gccccgggcc 18180
gtgagcgcgt cctcctccgg cacgcctgcc gttgtcaggc ccaggacccg tcgcagcgtg 18240
tcgcgtacga ccccggccgc cgtggtgtac gcgggcccgc ggagaggaaa tcccccaaga 18300
tggtcagtgt tgtcgcggga gttccagaac cacactcccg cttggctcca ggcgacggcg 18360
tgggtgtaga cgccctcgag cgccaggcac agtgggtgcc gcagccggag gccgttggcc 18420
ataagcacgg ctcccacggc cgtctcgatg gcccgccggg cgtcctcgat caccccggaa 18480
gccgcatccg cgtcttgggg gtccacgtta aagacacccc agaacgcacc cccatcgccc 18540
ccgcagaccg cgaacttaac cgagctggcc gtctcctcaa tctgcaggca gacggcggcc 18600
atcaccccgc ccaggagctg ccgcagcgca gggcaggcgt cgcacgtgtc cgggaccagg 18660
cgctccaaga cggccccggc ccagggctct gagggagcgg ccaccaccag cgcgtccagt 18720
cttgctaggc ccgtccggcc gtggggttcc gccagcccgc tccccccgag gtcggccagg 18780
gccgccagga gctgggcgcg aagtccgggg aagcaaaacc gcgccgtcca gacgggcccg 18840
acggccgcgg gcgggtctaa cagttggatg attttagtgg cgggatgcca ccgcgccacc 18900
gcctcccgca ccgcgggcag gaggcatccg gctgccgccg aggccacgcc gggccaggct 18960
cgcgggggga ggacgaccct ggcccccacc gcgggccagg cccccaggag cgcggcgtaa 19020
gcggccgcgg ccccgcgcac caggtcccgt gccgactcgg ccgtggccgg cacggtgaac 19080
gtgggccaac ccggaaaccc caggacggca aagtacggga cgggtccccc ccggacctca 19140
aactcgggcc ccagaaaggc aaagacgggg gccagggccc cgggggcggc gtggaccgtg 19200
gtatgccact gccggaaaag ggcgacgagc gccggcgcgg agaacttctc gccggcgctt 19260
acaaagtagt cgtaatcgcg gggcagcagc acccgtgccg tgactcgttg cgggtgcccg 19320
cgtggccgca ggcccacctc gcacacctcg accaggtccc cgaacgctcc ctccttcttg 19380
atcggcggaa acgcaagagt ctggtattcg cgcgcaaata gcgcggttcc ggtggtgatg 19440

-continued

```
ttaacggtca gcgaagcggc ggacgcgcac tggggggtgt cgcgaatggc cgccaggcgc  19500
gcccacgcca gccgcgcgtc gggatgctcg gcaacgcgcg ccgccagggc catagggtcg  19560
atgtcaatgt tggcctccgc gaccaggaga gcggcgcgag gggcggcggg cgggccccac  19620
gacgctctct caactttcac caccagtccc gtgcgtgggt ccgagccgat acgcagcggg  19680
gcgaacaggg ccaccggccc ggtctggcgc tccagggccg ccaggacgca cgcgtacagc  19740
gcccgccaca gagtcgggtt ctccaggggc tccagcgggg aggcggccgg cgtcgtcgcg  19800
gcgcgggcgg ccgccacgac ggcctggacg gagacgtccg cggagccgta gaaatcccgc  19860
agctccgtcg cggtgacgga gacctccgca aagcgcgcgc gaccctcccc tgcggcgttg  19920
cgacatacaa aatacaccag ggcgtggaag tactcgcgag cgcggggggg cagccatacc  19980
gcgtaaaggg taatggcgct gacgctctcc tccacccaca cgatatctgc ggtgtccatc  20040
gcacggcccc taaggatcac gggcggtctg tgggtcccat gctgccgtgc ctggccgggc  20100
ccggtgggtc gcggaaaccg gtgacggggg ggggcggttt ttggggttgg ggtgggggtg  20160
ggaaacggcc cgggtccggg ggccaacttg gcccctcggt gcgttccggc aacagcgccg  20220
ccggtccgcg gacgaccacg taccgaacga gtgcggtccc gagacttata gggtgctaaa  20280
gttcaccgcc ccctgcatca tggccaggc ctcggtgggg agctccgaca gcgccgcctc  20340
caggatgatg tcagcgttgg ggttggcgct ggatgagtgc gtgcgcaaac agcgccccca  20400
cgcgggcacg cgtagcttga agcgcgcgcc cgcaaactcc cgcttgtggg ccataagcag  20460
ggcgtacagc tgcctgtggg tccggcaggc gctgtggtcg atgtggtggg cgtccaacaa  20520
ccccacgatt gtctgtttgg tgaggttttt aacgcgcccc gccccgggaa acgtctgcgt  20580
gcttttggcc atctgcacgc caaacagttc gccccagatt atcttgaaca gcgccaccgc  20640
gtggtccgtc tcgctaacgg acccgcgcgg gggacagccg cttagggcgt cggcgacgcg  20700
cttgacggct tcctccgaga gcagaagtcc gtcggttacg ttacagtggc ccagttcgaa  20760
caccagctgc atgtagcggt cgtagtgggg ggtcagtagg tccagcacgt catcggggcc  20820
gaaggtcctc ccagatcccc cggccgccga gtcccaatgc aggcgcgcgg ccatggtgct  20880
gcacaggcac aacagctccc agacgggggt tacgttcagg gtgggggca gggccacgag  20940
ctccagctct ccggtgacgt tgatcgtggg gatgacgccc gtggcgtagt ggtcatagat  21000
ccgccgaaat atggcgctgc tgcgggtggc catgggaacg cggagacagg cctccagcaa  21060
cgccaggtaa ataaaccgcg tgcgtcccat caggctgttg aggttgcgca tgagcgcgac  21120
aatttccgcc ggcgcgacat cggaccggag gtatttttcg acgaaaagac ccacctcctc  21180
cgtctcggcg gcctgggccg gcagcgacgc ctcgggatcc cggcaccgca gctcccgtag  21240
atcgcgctgg gccctgaggg cgtcgaaatg tacgccccgc aaaaacagac agaagtcctt  21300
tggggtcagg gtatcgtcgt gtccccagaa gcgcacgcgt atgcagttta gggtcagcag  21360
catgtgaagg atgttaaggc tgtccgagag acacgccagc gtgcatctct caaagtagtg  21420
tttgtaacgg aatttgttgt agatgcgcga cccccgcccc agcgacgtgt cgcatgccga  21480
cgcgtcacag cgccccttga accggcgaca cagcaggttt gtgacctggg agaactgcgc  21540
gggccactgg ccgcaggaac tgaccacgtg gttcaggagc atgggcgtaa agacgggctc  21600
cgagcgcgcc ccggagccgt ccatgtaaat cagtagctcc cccttgcgga gggtgcgcac  21660
ccgtcccagg gactggtaca cggacaccat gtccggtccg tagttcatgg gtttcacgta  21720
ggcgaacatg ccatcaaagt gcaggggatc gaagctgagg cccacggtta cgaccgtcgt  21780
gtatataacc acgcggtatt ggccccacgt ggtcacgtcc ccgagggggg tgagcgagtg  21840
```

aagcaacagc acgcggtccg taaactgacg gcagaaccgg gccacgatct ccgcgaagga 21900
gaccgtcgat gaaaaaatgc agatgttatc gcccccgcca aggcgcgctt ccagctcccc 21960
aaagaacgtg gccccccggg cgtccggaga ggcgtccgga gacgggccgc ttggcggccc 22020
gggcgggcgc agggcagcct gcaggagctc ggtccccaga cgcgggagaa acaggcaccg 22080
gcgcgccgaa aacccgggca tggcgtactc gccgaccacc acatgcacgt ttttttcgcc 22140
ccggagaccg cacaggaagt ccaccaactg cgcgttggcg gttgcgtcca tggcgatgat 22200
ccgaggacag gtgcgcagca ggcgtagcat taacgcatcc acgcggccca gttgctgcat 22260
cgttggcgaa tagagctggc ccagcgtcga cataacctcg tccagaacga ggacgtcgta 22320
gttgttcaga aggttggggc ccacgcgatg aaggctttcc acctggacga taagtcggtg 22380
gaaggggcgg tcgttcataa tgtaattggt ggatgagaag taggtgacaa agtcgaccag 22440
gcctgactca gcgaaccgcg tcgccagggt ctgggtaaaa ctccgacgac aggagacgac 22500
gagcacactc gtgtccggag agtggatcgc ttcccgcagc cagcggatca gcgcggtagt 22560
ttttcccgac cccattggcg cgcggaccac agtcacgcac ctggccgtcg ggcgctcgc 22620
gttggggaag gtgacgggtc cgtgctgctg ccgctcgatc gttgttttcg ggtgaacccg 22680
gggcacccat tcggccaaat cccccccgta caacatccgc gctagcgata cgctcgacgt 22740
gtactgttcg cactcgtcgt ccccaatggg acgcccggcc cccagaggat cccccgactc 22800
cgcgcccccc acgaaaggca tgaccggggc gcggacggcg tggtgggtct ggtgtgtgca 22860
ggtggcgacg tttgtggtct ctgcggtctg cgtcacgggg cttctcgtcc tggcctctgt 22920
gttccgggca cggtttccct gcttttatgc cacggcgagc tcttatgccg gggtgaactc 22980
cacggccgag gtgcgcgggg gtgtagccgt gcccctcagg ttggacacgc agagccttgt 23040
gggcacttat gtaatcacgg ccgtgttgtt gttggccgcg gccgtgtatg ccgtggtcgg 23100
cgccgtgacc tcccgctacg accgcgccct ggacgcgggc cgccgtctgg ctgcggcccg 23160
catggccatg ccgcacgcca cgctgatcgc cggaaacgtc tgctcttggt tgctgcagat 23220
caccgtcctg ttgctggccc atcgcatcag ccagctggcc cacctggttt acgtcctgca 23280
ctttgcgtgt ctggtgtatt ttgcggccca tttttgcacc agggggggtcc tgagcgggac 23340
gtatctgcgt caggtgcacg gcctgatgga gccggccccg actcatcatc gcgtcgtcgg 23400
cccggctcga gccgtgctga caaacgcctt gctgttgggc gtcttcctgt gcacggccga 23460
cgccgcggta tccctgaata ccatcgccgc gttcaacttt aatttttcgg ccccgggcat 23520
gctcatatgc ctgaccgtgc tgttcgccct tctcgtcgta tcgctgttgt tggtggtcga 23580
gggggtgttg tgtcactacg tgcgcgtgtt ggtgggcccc cacctggggg ccgtggccgc 23640
cacgggcatc gtcggcctgg cctgcgagca ctattacacc aacggctact acgttgtgga 23700
gacgcagtgg ccgggggccc agacgggagt ccgcgtcgcc ctcgccctgg tcgccgcctt 23760
tgccctcggc atggccgtgc tccgctgcac ccgcgcctat ctgtatcaca ggcggcacca 23820
caccaaattt tttatgcgca tgcgcgacac gcgacaccgc gcacattccg ccctcaggcg 23880
cgtacgcagt tccatgcgcg gatcgcgaga cggccgccac aggcccgcac ccggcagccc 23940
gcccgggatt cccgaatatg cggaagaccc ctacgcgatc tcatacggcg gccagctcga 24000
ccggtacgga gattccgacg gggagccgat ttacgacgag gtggctgacg accaaaccga 24060
cgtattgtac gccaagatac aacacccgcg gcacctgccc gacgacgagc ccatctatga 24120
caccgttggg gggtacgacc ccgagcccgc cgaggacccc gtgtacagca ccgtccgccg 24180

-continued ttggtagctg tttggttccg ttttaataaa ccgtttgtgt ttaacccgac cgtggtgtat 24240
gtctggtgtg tggcgtccga tcccgttact atcaccgttt cccccccccc cccctcaacc 24300
ccggcgattg tgggtttttt aaaaacgaca cgcgtgcgac cgtatacaga acattgtttt 24360
ggtttttatt cgctatcgga catggggggt ggaaactggg tggcggggca ggcgcctccg 24420
ggggtccgcc ggtgagtgtg gcgcgagggg gggtccgacg aacgcaggcg ctgtctcccc 24480
ggggcccgcg taaccacgcg catatccggg ggcacgtaga aattaccttc ctcttcggac 24540
tcgatatcca cgacatcaaa gtcgtgggcg gtcagcgaga cgacctcccc gtcgtcggtg 24600
atgaggacgt tgtttcggca gcagcagggc cgggcccggg agaacgagag gcccatagct 24660
cggcgagcgt gtcgtcgaac gccaggcggc tgcttcgctg gatggcctta tagatctccg 24720
gatcgatgcg gacgggggta atgatcaggg cgatcggaac ggcctggttc gggagaatgg 24780
acgccttgct gggtcctgcg gccccgagag ccccggcgcc gtcctccagg cggaacgtta 24840
cgccctcctc cgcgctggtg cggtgcctgc cgataaacgt caccagatgc gggtgggggg 24900
ggcagtcggg gaagtggctg tcgagcacgt agccctgcac caagatctgc ttaaagttcg 24960
ggtgacgggg gttcgcgaag acgggctcgc ggcggaccag atccccggag ctccaggaca 25020
cgggggagat ggtgtggcgt ccgaggtcgg gggcgccaaa cagaagcacc tccgagacaa 25080
cgccgctatt taactccacc aaggcccgat ccgcggcgga gcaccgcctt ttttcgcccg 25140
aggcgtgggc ctctgaccag gcctggtctt gcgtgacgag agcctcctcc gggccgggga 25200
cgcgcccggg cgcgaagtat cgcacgctgg gcttcgggat cgaccggata aatgcccgga 25260
acgcctccgg ggaccggtgt gtcatcaagt cctcgtacgc ggaggccgtg gggtcgctgg 25320
ggtccatggg gtcgaaagcg tacttggccc ggcatttgac ctcgtaaaag gccagggggg 25380
tcttggggac tggggccagg tagccgtgaa tgtcccgagg acagacgaga atatccaggg 25440
acgccccgac catccccgtg tgaccgtcca tgaggacccc acacgtatgc acgttctctt 25500
cggtgaggtc gctgggttcg tggaagataa agcgccgcgt gtcggcgccg gcctcgccgc 25560
cgtcgtccgc gcggcccacg cagtagcgaa acagcaggct tcgggccgtc ggctcgttca 25620
cccgcccgaa catcaccgcc gaagactgta catccggccg caggctggcg ttgtgcttca 25680
gccactgggg cgagaaacac ggaccctggg ggccccagcg gagggtggat gcggtcgtga 25740
ggccccgccg gagcagggcc catagctggc agtcggcctg gttttgcgtg gccgcctcgt 25800
aaaaccccat gaggggccgg ggcgccacgg cgtccgcggc ggccgggggc ccgcggcgcg 25860
tcaggcgcca taggtgccgg ccgagtccgc ggtccaccat acccgcctcc tcgaggacca 25920
cggccaggga acacagataa tccaggcggg cccagagggg accgatggcc agaggggcgc 25980
ggacgccgcg cagcaacccg cgcaggtggc gctcgaacgt ctcggctagt atatgggagg 26040
gcagcgcgtt ggggatcacc gacgccgacc acatagagtc aaggtccggg gagtcgggat 26100
cggcgtccgg gtcgcgggcg tgggtgcccc caggagatag cggaatgtct ggggtcggag 26160
gccctgaggc gtcagaaagt gccggcgacg cggcccgggg cttttcgtct gcggtgtcgg 26220
tggcgtgctg atcacgtggg gggttaacgg gcgaatggga gctcgggtcc acagctgacg 26280
tcgtctgggg tgggggggc aggggacgga aggtggttgt cagcggaaga ctgttagggc 26340
gggggcgctt ggggggctg tcggggccac gaggggtgtc ctcggccagg gcccagggac 26400
gcttagtcac ggtgcgtccc ggcggacatg ctgggcctac cgtggactcc atttccgaga 26460
cgacgtgggg gagcggtggt tgagcgcgcc gccgggtgaa cgctgattct cacgacagcg 26520
cgtgccgcgc gcacgggttg gtgtgacaca ggcgggacac cagcaccagg agaggcttaa 26580

-continued

```
gctcgggagg cagcgccacc gacgacagta tcgccttgtg tgtgtgctgg taatttatac  26640
accgatccgt aaacgcgcgc cgaatcttgg gattgcggag gtggcgccgg atgccctctg  26700
gtacgtcata cgccaggccg tgggtgttgg tctcggccga gttgacaaac agggctgggt  26760
gcagcacgca gcgataggcg agcagggcca gggcgaagtc cggcgacagc tggttgttga  26820
aatactggta accgggaaac cggtcacgg gtacgcccag gctcggggcg acgtacacgc  26880
taaccaccaa ctccagcagc gtctggccaa gggcgtacag gtcaaccgct aacccgacgt  26940
cgtgcttcag gcggtggttg gtaaattcgg cccgttcgtt gttaaggtat ttcaccaaca  27000
gctccggggg ctggttatac ccgtgaccca ccagggtgtg aaagttggct gtggttaggg  27060
cggtgggcat gccaaacatc cggggggact tgaggtccgg ctcctggagg caaaactgcc  27120
cccgggcgat cgtggagttg gagttgaggg tgacgaggct aaagtcggcg aggacggccc  27180
gccggagcga gacggcgtcc gaccgcagca tgacgaggat gttggcgcac ttgatatcca  27240
ggtggctgat cccgcaggtg gtgtttaaaa acacaacggc gcgggccagc tccgtgaagc  27300
actggtggag ggccgtcgag accgaggggt ttgttgtgcg cagggacgcc agttggccga  27360
tatacttacc gaggtccatg tcgtacgcgg ggaacactat ctgtcgttgt tgcagcgaga  27420
acccgagggg cgcgatgaag ccgcggatgt tgtgggtgcg gccggcgcgt agagcgcact  27480
ccccgaccaa cagggtcgcg atgagctcaa cggcaaacca ctccttttcc tttatggtct  27540
taacggcaag cttatgttcg cgaatcagtt ggacgtcgcc gtatccccca gacccccga  27600
agcttcgggc cccggggatc tcgagggtcg tgtagtgtag ggcggggttg atggcgaaca  27660
cggggctgca tagcttgcgg atgcgcgtga gggtaaggat gtgcgagggg gacgaggggg  27720
gtgcggttaa cgccgcctgg gatctgcgca ggggcgggcg gttcagtttg gccgccgtac  27780
cgggcgtctc gggggacgcg cggcgatgag acgagcggct cattcgccat cgggatagtc  27840
ccgcgcgaag ccgctcgcgg aggccggatc ggtggcggga cccgtgggag gagcgggagc  27900
cggcggcgtc ctggagagag gggccgctgg ggcgcccgga ggccccgtgt gggttggagt  27960
gtatgtagga tgcgagccaa tccttgaagg accgttggcg tgcaccttgg gggctgaggt  28020
tagctgccac atgaccagca ggtcgctgtc tgcgggactc atccatcctt cggccaggtc  28080
gccgtctccc cacagagaag cgttggtcgc tgcttcctcg agttgctcct cctggtccgc  28140
aagacgatcg tccacggcgt ccaggcgctc accaagcgcc ggatcgaggt accgtcggtg  28200
tgcggttaga aagtcacgac gcgccgcttg ctcctccacg cgaattttaa cacaggtcgc  28260
gcgctgtcgc atcatctcta agcgcgcgcg ggactttagc cgcgcctcca attccaagtg  28320
ggccgccttt gcagccataa aggcgccaac aaaccgagga tcttgggtgc tgacgccctc  28380
ccggtgcagc tgcagggtct ggtccttgta aatctcggct cggaggtgcg tctcggccag  28440
gcgtcggcgc agggccgcgt gggcggcatc tcggtccatt ccgccaccct gcgggcgacc  28500
cggggggtgc tctgatagtc tcgcgtgccc aaggcccgtg atcggggtac ttcgccgccg  28560
cgacccgcca cccggtgtgc gcgatgtttg gtcagcagct ggcgtccgac gtccagcagt  28620
acctggagcg cctcgagaaa cagaggcaac ttaaggtggg cgcggacgag gcgtcggcgg  28680
gcctcacaat gggcggcgat gccctacgag tgccctttt agatttcgcg accgcgaccc  28740
ccaagcgcca ccagaccgtg gtcccgggcg tcgggacgct ccacgactgc tgcgagcact  28800
cgccgctctt ctcggccgtg gcgcggcggc tgctgtttaa tagcctggtg ccggcgcaac  28860
taaaggggcg tgatttcggg ggcgaccaca cggccaagct ggaattcctg gcccccgagt  28920
```

-continued tggtacgggc ggtggcgcga ctgcggttta aggagtgcgc gccggcggac gtggtgcctc 28980
agcgtaacgc ctactatagc gttctgaaca cgtttcaggc cctccaccgc tccgaagcct 29040
ttcgccagct ggtgcacttt gtgcgggact ttgcccagct gcttaaaacc tccttccggg 29100
cctccagcct cacggagacc acgggccccc ccaaaaaacg ggccaaggtg gacgtggcca 29160
cccacggccg gacgtacggc acgctggagc tgttccaaaa aatgatcctt atgcacgcca 29220
cctactttct ggccgccgtg ctcctcgggg accacgcgga gcaggtcaac acgttcctgc 29280
gtctcgtgtt tgagatcccc ctgtttagcg acgcggccgt gcgccacttc cgccagcgcg 29340
ccaccgtgtt tctcgtcccc cggcgccacg gcaagacctg gtttctagtg cccctcatcg 29400
cgctgtcact ggcctccttt cgggggatca agatcggcta cacggcgcac atccgcaagg 29460
cgaccgagcc ggtgtttgag gagatcgacg cctgcctgcg ggctggttc ggttcggccc 29520
gagtggacca cgttaaaggg gaaaccatct ccttctcgtt tccggacggg tcgcgcagta 29580
ccatcgtgtt tgcctccagc cacaacacaa acgtaagtcc tcttttcttt cgcatggctc 29640
tcccaagggg ccccgggtcg acccgaccca cacccaccca cccacccaca tacacacaca 29700
accagacgcg ggaggaaagt ctgccccgtg ggcactgatt tttattcggg atcgcttgag 29760
gaggcccggg caacggcccg ggcaacggtg gggcaactcg tagcaaatag gcgactgatg 29820
tacgaagaga agacacacag gcgccacccg gcgctggtcg gggggatgtt gtccgcgccg 29880
caccgtcccc cgacgacctc ttgcagacgg tccgtgatgc aaggacggcg gggggcctgc 29940
agcagggtga ccgtatccac gggatggcca aagagaagcg gacacaggct agcatccccc 30000
tggaccgcca gggtacactg ggccatcttg gcccacagac acggggcgac gcagggacag 30060
gactccgtta cgacggagga gagccacagt gcgttggcgg aatcgatgtg gggcggcggg 30120
gcgcaggact cgcagccccc cgggtggttg gtgatcctgg ccaggagcca tcccagatgg 30180
cgggccctgc ttcccggtgg acagagcgac cccaggtcgc tgtccatggc ccagcagtag 30240
atctggccgc tggggaggtg ccaccaggcc cccgggccca aggcgcagca cgcgcccggc 30300
tccgggggg tcttcgcggg gaccagatac gcgccatcca gctcgccgac cactggctcc 30360
tccgcgagct gttcggtggt tgggtcgggg gtttcctccg ggggggtggc cgcccgtatg 30420
cgggcgaacg tgagggtgca caggagcggg gtcagggggt gcgtcacgct ccggaggtgg 30480
acgatcgcgc agtagcggcg ctcgcggtta aagaaaaaga gggcaaagaa ggtgttcggg 30540
ggcaaccgca gcgccttggg gcgcgtcaga tacagaaaaa tctcgcagaa gagggcgcgc 30600
ccggggtctg ggttaggaag ggccacctga cacagaggct cggtgaggac cgttagacac 30660
cgaaagatct tgagccgctc gtccgcccga acgacgcgcc acacaaagac ggagttgaca 30720
atgcgcgcga tagagtcgac gtccgtcccc aggtcgtcga ctctgtcgcg cgtgccgcga 30780
gctccggccc gggaatccgg ccggggcaag gtccccgggg gaccaggcgg cgccaggggc 30840
cgccggggtc ccagctgcgc catgccgggg gcgggggggag ggcaaacccc agaggcgggg 30900
gccaacggcg cggggaggag tgggtgggcg aggtggccgg gggaaggcgc ccgctagcga 30960
gaacggccgt tcccggacga caccttgcga caaaacctaa ggacagcggc ccgcgcgacg 31020
gggtccgaga ggctaaggta ggccgcgatg ttaatggtga acgcaaagcc gccgggaaag 31080
acaactatgc cacagaggcg gcgattaaac cccaggcaga ggtaggcgta gctttccccg 31140
ggcaggtatt gctcgcagac cctgcgtggg gctgtggagg ggacggcctc catgaagcga 31200
catttactct gctcgcgttt actgacgtca ccatccatcg ccacggcgat tggacgattg 31260
ttaagccgca gcgtgtctcc gcttgtgctg tagtagtcaa aaacgtaatg gccgtcggag 31320

-continued

```
tcggcaaagc gggccgggag gtcgtcgccg agcgggacga cccgccgccc ccgaccgccc  31380
cgtcccccca ggtgtgccag gacggccagg gcatacgcgg tgtgaaaaaa ggagtcgggg  31440
gcggtcccct cgacggcgca catcaggttc tcgaggagaa tggggaagcg cctggtcacc  31500
tcccccaacc acgcgcgttg gtcggggcca aagtcatagc gcaggcgctg tgagattcgc  31560
gggccgccct gaagcgcggc ccggatggcc tggcccaggg cccggaggca cgccagatgt  31620
atgcgcgcgg taaaggcgac ctcggcggcg atgtcaaagg gcggcaggac ggggcgcggg  31680
tggcgcaggg gcacctcgag cgcgggaaag cgtagcagca gctccgcctg cccagcggga  31740
gacagctggt gggggcgcac gacgcgttct gcggcgcagg cctcggtcag ggccgtggcc  31800
agcgccgagg acagcagcgg agggcgggcg cgtcgcccgc cccacgccac ggagttctcg  31860
taggagacga cgacgaagcg ctgcttggtt ccgtagtggt ggcgcaggac cacggagata  31920
gaacgacggc tccacagcca gtccggccgg tcgccgccgg ccagggcttc ccatccgcga  31980
tccaaccact cgaccagcga ccgcggcttt gcggtaccag gggtcagggt tagaacgtcg  32040
ttcaggatgt cctcgccccc gggcccgtgg ggcacggggg ccacaaagcg gcccccgcct  32100
gggggctcca gacccgccaa caccgcatct gcgtcagccg cccccatggc gcccccgctg  32160
acggcctggt gaaccagggc gccctggcgg agccccgatg caacgccaca ggccgcacgc  32220
ccggtccgag cgcggaccgg gtggcggcgg gtgacgtcct gcactgcccg ctgaaccaac  32280
gcgaggatct cctcgttctc ctgcgcgatg gacacgtcct gggccgcggt cgtgtcgccg  32340
ccgggggccg tcagctgctc ctccggggag atgggggggt cggacgcccc gacgatgggc  32400
gggtctgcgg gcgcccccgc gtggggccgg gccaagggct gcggacgcgg ggacgcgctt  32460
tcccccagac ccatggacag gtgggccgca gcctccttcg cggccggcgg ggcggcggcg  32520
ccaagcagag cgacgtagcg gcacaaatgc cgacagacgc gcatgatgcg cgtgctgtcg  32580
gccgcgtagc gcgtgttggg ggggacgagc tcgtcgtaac taaacagaat cacgcgggca  32640
cagctcgccc ccgagcccca cgcaaggcgc agcgccgcca cggcgtacgg gtcatagacg  32700
ccctgcgcgt tacacaccac gggcagggag acgaacaacc ccccggcgct ggacgcacgc  32760
ggaaggaggc cagggtgtgc cggcacgacg ggggccagaa gctcccccac cgcatccgcg  32820
ggcacgtagg cggcaaacgc cgtgcaccac ggggtacagt cgccggtggc atgagcccga  32880
gtctggattt cgacctggaa gtttgcggcc gtcccgagtc cggggtggcc gcgcatcagg  32940
gcggccagag ggattcccgc ggccgccagg cactcgctgg atatgatgac gtgaaccaaa  33000
gacgagggcc gacccgggcc gtggccgaga tcgtactgga cctcgttggc caagtgcgcg  33060
ttcatggttc gggggtgggt gtgggtgtgt aggcgatgcg ggtcccccga gtccgcggga  33120
agggcgtggg tttggcgcgc gtatgcgtat tcgccaacgg aggcgtgcgt gcttatgcgc  33180
ggcgcgtttc ttctgtctct agggaatccg aggccaggac tttaacctgc tctttgtcga  33240
cgaggccaac tttattcgcc cggatgcggt ccagacgatt atgggctttc tcaaccaggc  33300
caactgcaag attatcttcg tgtcgtccac caacaccggg aaggccagta cgagcttttt  33360
gtacaacctc cgcggggccg cagacgagct tctcaacgtg gtgacctata tatgcgatga  33420
tcacatgccg agggtggtga cgcacacaaa cgccacggcc tgttcttgtt atatcctcaa  33480
caagcccgtt ttcatcacga tggacggggc ggttcgccgg accgccgatt tgtttctggc  33540
cgattccttc atgcaggaga tcatcggggg ccaggccagg gagaccggcg acgaccggcc  33600
cgttctgacc aagtctgcgg gggagcggtt tctgttgtac cgcccctcga ccaccaccaa  33660
```

-continued

```
cagcggcctc atggcccccg atttgtacgt gtacgtggat cccgcgttca cggccaacac  33720
ccgagcctcc gggaccggcg tcgctgtcgt cgggcggtac cgcgacgatt atatcatctt  33780
cgccctggag cactttttc tccgcgcgct cacgggctcg gcccccgccg acatcgcccg  33840
ctgcgtcgtc cacagtctga cgcaggtcct ggccctgcat cccggggcgt ttcgcggcgt  33900
ccgggtggcg gtcgagggaa atagcagcca ggactcggcc gtcgccatcg ccacgcacgt  33960
gcacacagag atgcaccgcc tactggcctc ggagggggcc gacgcgggct cgggccccga  34020
gcttctcttc taccactgcg agcctcccgg gagcgcggtg ctgtacccct ttttcctgct  34080
caacaaacag aagacgcccg cctttgaaca ctttattaaa aagtttaact ccgggggcgt  34140
catggcctcc caggagatcg tttccgcgac ggtgcgcctg cagaccgacc cggtcgagta  34200
tctgctcgag cagctaaata acctcaccga aaccgtctcc cccaacactg acgtccgtac  34260
gtattccgga aaacggaacg gcgcctcgga tgaccttatg gtcgccgtca ttatggccat  34320
ctacctcgcg gcccaggccg gacctccgca cacattcgct cctatcacac gcgtcttgtg  34380
agcgcccaat aaacacaccc aggtatgcta cgcacgacca cggtgtcgtc tgttaagggg  34440
ggggggaagg gggtgttggc gggaagcgtg ggaacacggg ggattctctc acgaccggca  34500
ccagtaccac ccccctgtga acacagaaac cccaacccaa atcccataaa catacgacac  34560
acaggcatat tttggaattt cttaggtttt tatttattta ggtatgctgg ggtttctccc  34620
tggatgccca cccccacccc cccgtgggtc tagccgggcc ttagggatag cgtataacgg  34680
gggccatgtc tccggaccgc acaacggccg cgccgtcaaa ggtgcacacc cgaaccacgg  34740
gagccagggc caaggtgtct cctagttggc ccgcgtgggt cagccaggcg acgagcgcct  34800
cgtaaagcgg cagccttcgc tctccatcct gcatcagggc cggggcttcg gggtgaatga  34860
gctgggcggc ctcccgcgtg acactctgca tctgcaggag agcgttcacg tacccgtcct  34920
gggcacttag cgcaaagagc cgggggatta gcgtaaggat gatggtggtt ccctccgtga  34980
tcgagtaaac catgttaagg accagcgatc gcagctcggc gtttacggga ccgagttgtt  35040
ggacgtccgc cagcagcgag aggcgactcc cgttgtagta cagcacgttg aggtctggca  35100
gccctccggg gtttctgggg ctggggttca ggtcccggat gcccctggcc acgagccgcg  35160
ccacgatttc gcgcgccagg ggcgatggaa gcggaacggg aaaccgcaac gtgaggtcca  35220
gcgaatccag gcgcacgtcc gtcgcttggc cctcgaacac gggcgggacg aggctgatgg  35280
ggtccccgtt acagagatct acgggggagg tgttgcgaag gttaacggtg ccggcgtggg  35340
tgaggcccac gtccaggggg caggcgacga ttcgcgtggg aagcacccgg gtgatgaccg  35400
cggggaagcg ccttcggtac gccagcaaca accccaacgt gtcgggactg acgcctccgg  35460
agacgaagga ttcgtgcgcc acgtcggcca gcgtcagttg ccggcggatg gtcggcagga  35520
ataccacccg cccttcgcag cgctgcagcg ccgccgcatc ggggcgcgag atgcccgagg  35580
gtatcgcgat gtcagtttca aagccgtccg ccagcatggc gccgatccac gcggcaggga  35640
gtgcagtggt gggtcgggtg gcgggaggag cgcggtgggg gtcagcggcg tagcagagac  35700
gggcgaccaa cctcgcatag gacggggggt gggtcttagg gggttgggag gcgacaggga  35760
ccccagagca tgcgcgggga ggtctgtcgg gcccagacgc accgagagcg aatccgtccg  35820
cggagtcccg gcttgggttt tatggggccc ggccctcgga atcgcggctt gtcggcgggg  35880
acaaaggggg cggggctagg ggcttgcgga aacagaagac gcgtgggata aaagaatcgc  35940
actaccccaa ggaagggcgg ggcggtttat tacagagcca gtcccttgag cggggatgcg  36000
tcatagacga gatactgcgc gaagtgggtc tcccgcgcgt gggcttcccc gttgcgggcg  36060
```

ctgcggagga gggcggggtc gctggcgcag gtgagcgggt aggcctcctg aaacaggcca 36120
cacgggtcct ccacgagttc gcggcacccc ggggggcgct taaactgtac gtcgctggcg 36180
gcggtggccg tggacaccgc cgaacccgtc tccacgatca ggcgctccag gcagcgatgt 36240
ttggcggcga tgtcggccga cgtaaagaac ttaaagcagg ggctgagcac cggcgaggcc 36300
ccgttgaggt ggtaggcccc gttatagagc aggtccccgt acgaaaatcg ctgcgacgcc 36360
cacgggttgg ccgtggccgc gaaggcccgg gacgggtcgc tctggccgtg gtcgtacatg 36420
agggcggtga catccccctc cttgtccccc gcgtaaacgc ccccggcggc gcgtccccgg 36480
gggttgcagg gccggcggaa gtagttgacg tcggtcgaca cgggggtggc gataaactca 36540
cacacggcgt cctggccgtg gtccatccct gcgcgccgcg gcacctgggc gcacccgaac 36600
acggggacgg gctgggccgg ccccaggcgg tttcccgcca cgaccgcgtt ccgcaggtac 36660
acggctgccg cgttgtccag gagaggggga gccccgcggc ccaggtaaaa gttttgggga 36720
aggttgccca tgtcggtgac ggggttgcgg acggttgccg tggccacgac ggcggtgtag 36780
cccacgccca ggtccacgtt cccgcgcggc tgggtgagcg tgaagtttac ccccccgcca 36840
gtttcgtgcc gggccacctg gagctggccc aggaagtacg cctccgacgc gcgctccgag 36900
aacagcacgt tctcagtcac aaagcggtcc tgtcggacga cggtgaaccc aaacccggga 36960
tggaggcccg tcttgagctg atgatgcaag gccacgggac tgatcttgaa gtaccccgcc 37020
atgagcgcgt aggtcagcgc gttctccccg gccgcgctct cgcggacgtg ctgcacgacg 37080
ggctgtcgga tcgacgaaaa gtagttggcc cccagagccg gggggaccag ggggacctgc 37140
cgcgacaggt cgcgcagggc cggggggaaa ttgggcgcgt tcgccacgtg gtcggccccg 37200
gcgaacagcg cgtggacggg gagggggtaa aaatagtcgc cattttggat ggtatggtcc 37260
agatgctggg gggccatcag caggattccg gcgtgcaacg ccccgtcgaa tatgcgcatg 37320
ttggtggtgg acgcggtgtt ggcgcccgcg tcgggcgccg ccgagcagag cagcgccgtt 37380
gtgcgttcgg ccatgttgtg ggccagcacc tgcagcgtga gcatggcggg cccgtccact 37440
accacgcgcc cgttgtgaaa catggcgttg accgtgttgg ccaccagatt ggccgggtgc 37500
agggggtgcg cggggtccgt cacggggtcg ctggggcact cctcgccggg ggcgatctcc 37560
gggaccacca tgttctgcag ggtggcgtat acgcggtcga agcgaacccc cgcggtgcag 37620
cagcggcccc gcgagaaggc gggcaccatc acgtagtagt aaatcttgtg gtgcacggtc 37680
cagtccgccc cccggtgcgg ccggtcatcc gcggcgtccg cggctcgggc ctgggtgttg 37740
tgcagcagct ggccgtcgtt gcggttgaag tccgcggtcg ccacgttaca tgccgccgcg 37800
tacacggggt cgtggccccc cgcgctaacc cggcagtcgc gatggcggtc cagggccgcg 37860
cgccgcatca gggcgtcaca gtcccacacg aggggtggca gcagcgccgg gtctcgcatt 37920
aggtgattca gctcggcttg cgcctgcccg cccagctccg ggccggtcag ggtaaagtca 37980
tcaaccagct gggccagggc ctcgacgtgc gccaccaggt cccggtacac ggccatgcac 38040
tcctcgggaa ggtctccccc gaggtaggtc acgacgtacg agaccagcga gtagtcgttc 38100
acgaacgccg cgcaccgcgt gttgttccag tagctggtga tgcactggac cacgagccgg 38160
gccagggcgc agaagacgtg ctcgctgccg tgtatggcgg cctgcagcag gtaaaacacc 38220
gccgggtagt tgcggtcgtc gaacgccccg cgaacggcgg cgatggtggc gggggccatg 38280
gcgtggcgtc ccaccccag ctccaggccc cgggcgtccc ggaacgccgc cggacatagc 38340
gccaggggca agttgccgtt caccacgcgc caggtggcct ggatctcccc cgggccggcc 38400

-continued

```
gggggaacgt cccccccggg cagctccacg tcggccaccc ccacaaagaa gtcgaacgcg  38460
gggtgcagct caagagccag gttggcgttg tcgggctgca taaactgctc cggggtcatc  38520
tggccttccg cgacccatcg gacccgcccg tgggccaggc gctgccccca ggcgttcaaa  38580
aacagctgct gcatgtctgc ggcggggccg gccggggccg ccacgtacgc cccgtacgga  38640
ttggcggctt cgacggggtc gcggttaagg cccccgaccg ccgcgtcaac gttcatcagc  38700
gaagggtggc acacggtccc gatcgcgtgt tccagagaca ggcgcagcac ctggcggtcc  38760
ttcccccaaa aaaacagctg gcggggcggg aaggcgcggg gatccgggtg gccgggggcg  38820
gggactaggt ccccggcgtg cgcggcaaac cgttccatga ccggattgaa caggcccagg  38880
ggcaggacga acgtcaggtc catggcgccc accaggggt agggaacgtt ggtggcggcg  38940
tagatgcgct tctccagggc ctccagaaag accagcttct cgccgatgga caccagatcc  39000
gcgcgcacgc gcgtcgtctg gggggcgctc tcgagctcgt ccagcgtctg ccggttcagg  39060
tcgagctgct cctcctgcat ctccagcagg tggcggccca cgtcgtccag acttcgcacg  39120
gccttgccca tcacgagcgc cgtgaccagg ttggccccgt tcaggaccat ctcgccgtac  39180
gtcaccggca cgtcggcttc ggtgtcctcc gctttcagga aggactgcag gaggcgctgt  39240
ttgatcgggg cggtggtgac gagcaccccg tcgaccggcc gcccgcgcgt gtcggcatgc  39300
gtcagacggg gcacggccac ggagggctgc gtggccgtgg tgaggtccac gagccaggcc  39360
tcgacggcct cccggcggtg gcccgccttg cccaggaaaa agctcgtctc gcagaagctt  39420
cgctttagct cggcgaccag ggtcgcccgg gccaccctgg tggccaggcg gccgttgtcc  39480
aggtatcgtt gcatcggcaa caacaaagcc aggggcggcg ccttttccag cagcacgtgc  39540
agcatctggt cggccgtgcc gcgctcaaac gccccgagga cggcctggac gttgcgagcg  39600
agctgttgga tggcgcgcaa ctggcgatgc gcgccgatac ccgtcccgtc cagggcctcc  39660
cccgtgagca gggcgatggc ctcggtggcc aggctgaagg cggcgttcag ggcccggcgg  39720
tcgataatct tggtcatgta attgtgtgtg ggttgctcga tggggtgcgg gccgtcgcgg  39780
gcaatcagcg gctggtggac ctcgaactgt acgcgcccct cgttcatgta ggccagctcc  39840
ggaaacttgg tacacacgca cgccaccgac aacccgagct ccagaaagcg cacgagcgac  39900
agggtgttgc aatacgaccc cagcagggcg tcgaactcga cgtcgtacag gctgtttgca  39960
tcggagcgca cgcgggaaaa aaaatcgaac aggcgtcgat gcgacgccac ctcgatcgtg  40020
ctaaggaggg acccggtcgg caccatggcc gcggcatacc ggtatcccgg agggtcgcgg  40080
ttgggagctg ccatggggtc gcgtggagat cggctggatc tagcgatatt tgcccgggga  40140
ggctaagatc caccccaacg cccggccacc cgtgtacgtg cccgacggcc caaggtccac  40200
cgaaagacac gacgggcccg gacccaaaaa ggcgggggat gctgtgtgag gggccgggtg  40260
tcggtcgggg gggaaaggca ccgggagaag gctgcggcct cgttccagga gaacccagtg  40320
tccccaacag acccggggac gtgggatccc aggccttata taccccccc gccccacccc  40380
cgttagaacg cgacgggtgc attcaagatg gccctggtcc aaaagcgtgc caggaagaaa  40440
ttggcagagg cggcaaagct gtccgccgcc gccacccaca tcgaggcccc ggccgcgcag  40500
gctatcccca gggcccgtgt gcgcagggga tcggtgggcg gcagcatttg gttggtggcg  40560
ataaagtgga aaagcccgtc cggactgaag gtctcgtggg cggcggcgaa caaggcacac  40620
agggccgtgc ctcccaaaaa cacggacatc ccccaaaaca ctggcgccga caacggcaga  40680
cgatccctct tgatgttaac gtacaggagg agcgcccgca ccgcccacgt aacgtagtag  40740
ccgacgatgg cggccaggat acaggccggc gccaccaccc ttccggtcag cccgtaatac  40800
```

atgcccgctg ccaccatctc caacggcttc aggaccaaaa acgaccaaag gaacagaatc 40860
acgcgctttg aaaagaccgg ctgggtatgg ggcggaagac gcgagtatgc cgaactgaca 40920
aaaaaatcag aggtgccgta cgaggacaat gaaaactgtt cctccagcgg cagttctccc 40980
tcctcccccc cgaaggcggc ctcgtcgacc agatctcgat ccaccagagg aaggtcatcc 41040
cgcatggtca tggggtgtgc ggtggaggtg gggagaccga aaccgcaaag ggtcgcttac 41100
gtcagcagga tcccgagatc aaagacaccc gggttcttgc acaaacacca cccgggttgc 41160
atccgcggag gcgagtgttt tgataaggcc gttccgcgcc ttgatataac ctttgatgtt 41220
gaccacaaaa cccggaattt acgcctacgc cccaatgccc acgcaagatg aggtaggtaa 41280 ccccccgtg ggtgtgacgt tgcgtttagt tcattggagg ccaaggggaa aaatggggtg 41340
gggaggaaac ggaaaaccca gtaggccgtg tcgggaacac gcccggggtt gtcctcaaaa 41400
ggcagggtcc atactacgga agccgtcgtt gtattcgaga cctgcctgtg cgacgcacgt 41460
cggggttgcc tgtgtccggt tcggccccca ccgcgtgcgg cacgcacgag gacgagtccg 41520
cgtgctttat tggcgttcca agcgttgccc tccagtttct gttgtcggtg ttcccccata 41580
cccacgccca catccaccgt aggggcctc tgggccgtgt tacgtcgccg cccgcgatgg 41640
agcttagcta cgccaccacc atgcactacc gggacgttgt gttttacgtc acaacggacc 41700
gaaaccgggc ctactttgtg tgcgggggt gtgtttattc cgtggggcgg ccgtgtgcct 41760
cgcagcccgg ggagattgcc aagtttggtc tggtcgttcg agggacaggc ccagacgacc 41820
gcgtggtcgc caactatgta cgaagcgagc tccgacaacg cggcctgcag gacgtgcgtc 41880
ccattgggga ggacgaggtg tttctggaca gcgtgtgtct tctaaacccg aacgtgagct 41940
ccgagctgga tgtgattaac acgaacgacg tggaagtgct ggacgaatgt ctggccgagt 42000
actgcacctc gctgcgaacc agcccgggtg tgctaatatc cgggctgcgc gtgcgggcgc 42060
aggacagaat catcgagttg tttgaacacc caacgatagt caacgtttcc tcgcactttg 42120
tgtatacccc gtccccatac gtgttcgccc tggcccaggc gcacctcccc cggctcccga 42180
gctcgctgga ggccctggtg agcggcctgt ttgacggcat ccccgcccca cgccagccac 42240
ttgacgccca caacccgcgc acggatgtgg ttatcacggg ccgccgcgcc ccacgaccca 42300
tcgccgggtc gggggcgggg tcggggggcg cgggcgccaa gcgggccacc gtcagcgagt 42360
tcgtgcaagt caaacacatt gaccgcgtgg gccccgctgg cgtttcgccg gcgcctccgc 42420
caaacaacac cgactcgagt tccctggtgc ccggggccca ggattccgcc ccgcccggcc 42480
ccacgctaag ggagctgtgg tgggtgtttt atgccgcaga ccgggcgctg gaggagcccc 42540
gcgccgactc tggcctcacc cgcgaggagg tacgtgccgt acgtgggttc cgggagcagg 42600
cgtggaaact gtttggctcc gcgggggccc cgcgggcgtt tatcggggcc gcgttgggcc 42660
tgagccccct ccaaaagctg gccgtttact actatatcat ccaccgagag aggcgcctgt 42720 ccccttccc cgcgctagtc cggctcgtag gccggtacac acagcgccac ggcctgtacg 42780
tccctcggcc cgacgaccca gtcttggccg atgccatcaa cgggctggtt cgcgacgcgc 42840
tggcggccgg aaccacagcc gagcagctcc tcatgttcga ccttctcccc ccaaaggacg 42900
tgccggtggg aagcgacgtg caggccgaca gcaccgctct gctgcgcttt atagaatcgc 42960
aacgtctcgc cgtccccggg ggggtgatct cccccgagca cgtcgcgtac cttggtgcgt 43020
tcctgagcgt gctgtacgct ggccgcgggc gcatgtccgc agccacgcac accgcgcggc 43080
tgacaggggt gacctccctg gtgctagcgg tgggtgacgt ggaccgtctt tccgcgtttg 43140

-continued

```
accgcggagc ggcgggcgcg gccagccgca cgcgggccgc cgggtacctg gatgtgcttc  43200
ttaccgttcg tctcgctcgc tcccaacacg gacagtctgt gtaaaagacc ccaataaacg  43260
tatgtcgcta ctacaccctt gtgtgtcaat ggacgcctct ccgggggggg gaagggaaag  43320
caaagagggg ctgggggagc ggcaccaccg gggcctgaac aaacaaacca cagacacggt  43380
tacagtttat tcggtcgggc ggagaaacgg ccgaagccac gcccacttta ttcgcgtctc  43440
caaaaaaacg ggacacttgt ccggagaacc tttaggatgc cagccagggc ggcggtaatc  43500
ataaccacgc ccagcgcaga ggcggccaga aacccgggcg caattgcggc cacgggctgc  43560
gtgtcaaagg ctagcaaatg aatgacggtt ccgtttggaa atagcaacaa ggccgtggac  43620
ggcacgtcgc tcgaaaacac gcttggggcg ccctccgtcg gcccggcggc gatttgctgc  43680
tgtgtgttgt ccgtatccac cagcaacaca gacatgacct ccccggccgg ggtgtagcgc  43740
ataaacacgg cccccacgag ccccaggtcg cgctggtttt gggtgcgcac cagccgcttg  43800
gactcgatat cccgggtgga gccttcgcat gtcgcggtga ggtaggttag gaacagtggg  43860
cgtcggacgt cgacgccggt gagcttgtag ccgatccccc ggggcagagg ggagtgggtg  43920
acgacgtagc tggcgctgtg ggtgatgggt accaggatcc gtggctcgac gttggcagac  43980
tgccccccgc accgatgtga ggcctcaggg acgaaggcgc ggatcagggc gttgtagtgt  44040
gcccaacgcg tcagggtcga ggcgaggccg tgggtctgct gggccaggac ttcgaccggg  44100
gtctcggatc gggtggcttg agccagcgcg tccaggataa acacgctctc gtctagatca  44160
aagcgcaggg aggccgcgca tggcgaaaag tggtccggaa gccaaaagag ggtttctgg  44220
tggtcggccc gggccagcgc ggtccggagg tcggcgttgg tcgctgcggc gacgtcggac  44280
gtacacaggg ccgaggctat cagaaggctc cggcgggcgc gttcccgctg caccgccgag  44340
gggacgccag ccaagaacgg ctgccggagg acagccgagg cgtaaaatag cgcccggtgg  44400
acgaccgggg tggtcagcac gcggccccct agaaactcgg catacagggc gtcgatgaga  44460
tgggctgcgc tgggcgccac tgcgtcgtac gccgaggggc tatccagcac gaaggccagc  44520
tgatagccca gcgcgtgtaa tgccaagctc tgttcgcgct ccagaatctc ggccaccagg  44580
tgctggagcc gagcctctag ctgcaggcgg gccgtgggat ccaagactga cacattaaaa  44640
aacacagaat ccgcggcaca gcccgcggcc ccgcgggcgg ccaacccggc aagcgcgcgc  44700
gagtgggcca aaaagcctag caggtcggag aggcagaccg cgccgtttgc gtgggcggcg  44760
ttcacgaaag caaaacccga cgtcgcgagc agccccgtta ggcgccagaa gagagggggg  44820
cgcgggccct gctcggcgcc cgcgtccccc gagaaaaact ccgcgtatgc ccgcgacagg  44880
aactgggcgt agttcgtgcc ctcctccggg tagccgccca cgcggcggag ggcgtccagc  44940
gcggagccgt tgtcggcccg cgtcagggac cctaggacaa agacccgata ccgggggccg  45000
cccggggcc cgggaagagc ccccgggggg ttttcgtccg cggggtcccc gacccgatct  45060
agcgtctggc ccgcggggac caccatcact tccaccggag ggctgtcgtg catggatatc  45120
acgagcccca tgaattcccg cccgtagcgc gcgcgcacca gcgcggcatc gcacccgagc  45180
accagctccc ccgtcgtcca gatgcccacg ggccacgtcg aggccgacgg ggagaaatac  45240
acgtacctac ctggggatct caacaggccc cgggtggcca accaggtcgt ggacgcgttg  45300
tgcaggtgcg tgatgtccag ctccgtcgtc gggtgccgcc gggccccaac cggcggtcgg  45360
gggggcggtg tatcacgcgg cccgctcggg tggctcgccg tcgccacgtt gtctccccgc  45420
gggaacgtca gggcctcggg gtcagggacg gccgaaaacg ttacccaggc ccgggaacgc  45480
agcaacacgg aggcggctgg attgtgcaag agacccttaa ggggggcgac cgaggggga  45540
```

-continued

```
ggctgggcgg tcggctcgac cgtggtgggg gcgggcaggc tcgcgttcgg gggccggccg  45600
agcaggtagg tcttcgggat gtaaagcagc tggccggggt cccgcggaaa ctcggccgtg  45660
gtgaccaata caaaacaaaa gcgctcctcg taccagcgaa gaaggggcag agatgccgta  45720
gtcaggttta gttcgtccgg cggcgccaga aatccgcgcg gtggtttttg ggggtcgggg  45780
gtgtttggca gccacagacg cccggtgttc gtgtcgcgcc agtacatgcg gtccatgccc  45840
aggccatcca aaaaccatgg gtctgtctgc tcagtccagt cgtggacctg accccacgca  45900
acgcccaaaa taataacccc cacgaaccat aaaccattcc ccatggggga ccccgtccct  45960
aacccacggg gcccgtggct atggcagggc ttgccgcccc gacgttggct gcgagccctg  46020
ggccttcacc cgaacttggg gggtggggtg gggaaaagga agaaacgcgg gcgtattggc  46080
cccaatgggg tctcggtggg gtatcgacag agtgccagcc ctgggaccga accccgcgtt  46140
tatgaacaaa cgacccaaca cccgtgcgtt ttattctgtc tttttattgc cgtcatagcg  46200
cgggttactt ccggtattgt ctccttccgt gtttcagtta gcctccccca tctcccgggc  46260
aaacgtgcgc gccaggtcgc agatcgtcgg tatggagccg ggggtggtga cgtgggtctg  46320
gaccatcccg gaggtaagtt gcagcagggc gtcccggcag ccggcgggcg attggtcgta  46380
atccaggata aagacgtgca tgggacggag gcgtttggcc aagacgtcca aggcccaggc  46440
aaacacgtta tacaggtcgc cgttgggggc cagcaactcg ggggcccgaa acagggtaaa  46500
taacgtgtcc ccgatatggg gttgtgggcc cgcgttgctc tggggctcgg caccctgggg  46560
cggcacggcc gtccccgaaa gctgtcccca atcctcccgc cacgacccgc cgccctgcag  46620
ataccgcacc gtattggcaa gcagctcgta aacgcggcga atcgcggcca acatagccag  46680
gtcaagccgc tcgccggggc gctggcgttt ggccaggcgg tcgatgtgtc tgtcctccgg  46740
aagggccccc aacacgatgt ttgtgccggg caaggtcggc gggatgaggg ccacgaacgc  46800
cagcacggcc tggggggtca tgctgcccat aaggtatcgc gcggccgggt aacacaggag  46860
ggcggcgatg ggatggcggt cgaagatgag ggtgagggcc gggggcgggg catgtgagct  46920
cccagcctcc cccccgatat gaggagccag aacggcgtcg gtcacggcat aaggcatgcc  46980
cattgttatc tgggcgcttg tcattaccac cgccgcgtcc ccggccgata tctcaccctg  47040
gtcgaggcgg tgttgtgtgg tgtagatgtt cgcgattgtc tcggaagccc ccaacacccg  47100
ccagtaagtc atcggctcgg gtacgtagac gatatcgtcg cgcgaaccca gggccaccag  47160
cagttgcgtg gtggtggttt tccccatccc gtggggaccg tctatataaa cccgcagtag  47220
cgtgggcatt ttctgctcca ggcggacttc cgtggctttt tgctgccggc gagggcgcaa  47280
cgccgtacgt cggttgttat ggccgcgaga acgcgcagcc tggtcgaacg cagacgcgtg  47340
ttgatggcag gggtacgaag ccatacgcgc ttctacaagg cgctggccga agaggtgcgg  47400
gagtttcacg ccaccaagat ctgcggcacg ctgttgacgc tgttaagcgg gtcgctgcag  47460
ggtcgctcgg tattcgaggc cacacgcgtc accttaatat gcgaagtgga cctgggaccg  47520
cgccgccccg actgcatctg cgtgttcgaa ttcgccaatg acaagacgct gggcggggtt  47580
tgtgtcatca tagaactaaa gacatgcaaa tatatttctt ccggggacac cgccagcaaa  47640
cgcgagcaac gggccacggg gatgaagcag ctgcgccact ccctgaagct cctgcagtcc  47700
ctcgcgcctc cgggtgacaa gatagtgtac ctgtgccccg tcctggtgtt tgtcgcccaa  47760
cggacgctcc gcgtcagccg cgtgacccgg ctcgtcccgc agaaggtctc cggtaatatc  47820
accgcagtcg tgcggatgct ccagagcctg tccacgtata cggtccccat tgagcctagg  47880
```

-continued

```
acccagcgag cccgtcgccg ccgcggcggc gccgcccggg ggtctgcgag cagaccgaaa  47940
aggtcacact ctggggcgcg cgacccgccc gagtcagcgg cccgccagtt accacccgcc  48000
gaccaaaccc ccgcctccac ggagggcggg ggggtgctta agaggatcgc ggcgctcttc  48060
tgcgtgcccg tggccaccaa gaccaaaccc cgagccgcct ccgaatgaga gtgtttcgtt  48120
ccttcccccct cccccgcgt cagacaaacc ctaaccaccg cttaagcggc ccccgcgagg  48180
tccgaagact catttggatc cggcgggagc cacccgacaa cagcccccgg gttttcccac  48240
gccagacgcc ggtccgctgt gccatcgcgc cccctcatcc caccccccat cttgtcccca  48300
aataaaacaa ggtctggtag ttaggacaac gaccgcagtt ctcgtgtgtt attttcgctc  48360
tccgcctctc gcagatggac ccgtactgcc catttgacgc tctggacgtc tgggaacaca  48420
ggcgcttcat agtcgccgat tcccgaaact tcatcacccc cgagttcccc cgggactttt  48480
ggatgtcgcc cgtctttaac ctcccccggg agacggcggc ggagcaggtg gtcgtcctac  48540
aggcccagcg cacagcggct gccgctgccc tggagaacgc cgccatgcag gcggccgagc  48600
tccccgtcga tatcgagcgc cggttacgcc cgatcgaacg gaacgtgcac gagatcgcag  48660
gcgccctgga ggcgctggag acggcggcgg ccgccgccga agaggcggat gccgcgcgcg  48720
gggatgagcc ggcgggtggg ggcgacgggg gggcgccccc gggtctggcc gtcgcggaga  48780
tggaggtcca gatcgtgcgc aacgacccgc cgctacgata cgacaccaac ctccccgtgg  48840
atctgctaca catggtgtac gcgggccgcg gggcgaccgg ctcgtcgggg gtggtgttcg  48900
ggacctggta ccgcactatc caggaccgca ccatcacgga ctttcccctg accacccgca  48960
gtgccgactt tcgggacggc cggatgtcca agaccttcat gacggcgctg gtcctgtccc  49020
tgcagtcgtg cggccggctg tatgtgggcc agcgccacta ttccgccttc gagtgcgccg  49080
tgttgtgtct ctacctgctg taccgaaaca cgcacggggc cgccgacgat agcgaccgcg  49140
ctccggtcac gttcggggat ctgctgggcc ggctgccccg ctacctggcg tgcctggccg  49200
cggtgatcgg gaccgagggc ggccggccac agtaccgcta ccgcgacgac aagctcccca  49260
agacgcagtt cgcggccggc gggggccgct acgaacacgg agcgctggcg tcgcacatcg  49320
tgatcgccac gctgatgcac cacggggtgc tcccggcggc cccgggggac gtcccccggg  49380
acgcgagtac ccacgttaac cccgacggcg tggcgcacca cgacgacata aaccgcgccg  49440
ccgccgcgtt cctcagccgg ggccacaacc tattcctgtg ggaggaccag actctgctgc  49500
gggcaaccgc gaacaccata acggccctgg gcgttatcca gcggctcctc gcgaacggca  49560
acgtgtacgc ggaccgcctc aacaaccgcc tgcagctggg catgctgatc cccggagccg  49620
tcccttcgga ggccatcgcc cgtggggcct ccgggtccga ctcgggggcc atcaagagcg  49680
gagacaacaa tctggaggcg ctatgtgcca attacgtgct tccgctgtac cgggccgacc  49740
cggcggtcga gctgacccag ctgtttcccg gcctggccgc cctgtgtctt gacgcccagg  49800
cggggcggcc ggtcgggtcg acgcggcggg tggtggatat gtcatcgggg gcccgccagg  49860
cggcgctggt gcgcctcacc gccctggaac tcatcaaccg cacccgcaca aaccccaccc  49920
ccgtggggga ggttatccac gcccacgacg ccctggcgat ccaatacgaa caggggcttg  49980
gcctgctggc gcagcaggca cgcattggct tgggctccaa caccaagcgt ttctccgcgt  50040
tcaacgttag cagcgactac gacatgttgt actttttatg tctggggttc attccacagt  50100
acctgtcggc ggtttagtgg gtggtgggcg aggggggagg gggcattagg gagaaagaac  50160
aagagcctcc gttgggtttt ctttgtgcct gtactcaaaa ggtcataccc cgtaaacggc  50220
gggctccagt cccggcccgg tggttggcgt gaacgcaacg gcgggagctg ggttagcgtt  50280
```

-continued

```
tagtttagca ttcgctctcg cctttccgcc cgccccccga ccgttgcgcc tttttttttcg  50340
tccaccaaag tctctgtggg tgcgcgcatg gcagccgatg ccccgggaga ccggatggag  50400
gagcccctgc ccgacagggc cgtgcccatt tacgtggctg ggtttttggc cctgtatgac  50460
agcggggact cgggcgagtt ggcattggat ccggatacgg tgcgggcggc cctgcctccg  50520
gataacccac tcccgattaa cgtggaccac cgcgctggct gcgaggtggg gcgggtgctg  50580
gccgtggtcg acgacccccg cgggccgttt tttgtggggc tgatcgcctg cgtgcagctg  50640
gagcgcgtcc tcgagacggc cgccagcgct gcgattttcg agcgccgcgg gccgccgctc  50700
tcccgggagg agcgcctgtt gtacctgatc accaactacc tgccctcggt ctccctggcc  50760
acaaaacgcc tgggggggcga ggcgcacccc gatcgcacgc tgttcgcgca cgtcgcgctg  50820
tgcgcgatcg ggcggcgcct cggcactatc gtcacctacg acaccggtct cgacgccgcc  50880
atcgcgccct ttcgccacct gtcgccggcg tctcgcgagg gggcgcggcg actggccgcc  50940
gaggccgaga tcgcgctgtc cgggcgcacc tgggcgcccg gcgtggaggc gctgacccac  51000
acgctgcttt ccaccgccgt taacaacatg atgctgcggg accgctggag cctggtggcc  51060
gagcggcggc ggcaggccgg gatcgccgga cacacctacc tccaggcgag cgaaaaattc  51120
aaaatgtggg gggcggagcc tgtttccgcg ccggcgcgcg ggtataagaa cggggccccg  51180
gagtccacgg acataccgcc cggctcgatc gctgccgcgc cgcagggtga ccggtgccca  51240
atcgtccgtc agcgcggggt cgccttgtcc ccggtactgc cccccatgaa ccccgttccg  51300
acatcgggca ccccggcccc cgcgccgccc ggcgacggga gctacctgtg gatcccggcc  51360
tcccattaca accagctcgt cgccggccat gccgcgcccc aaccccagcc gcattccgcg  51420
tttggtttcc cggctgcggc gggggccgtg gcctatgggc ctcacggcgc gggtctttcc  51480
cagcattacc ctccccacgt cgcccatcag tatcccgggg tgctgttctc gggacccagc  51540
ccactcgagg cgcagatagc cgcgttggtg ggggccatag ccgcggaccg ccaggcgggc  51600
ggtcagccgg ccgcgggaga ccctggggtc cgggggtcgg gaaagcgtcg ccggtacgag  51660
gcggggccgt cggagtccta ctgcgaccag gacgaaccgg acgcggacta cccgtactac  51720
cccggggagg ctcgaggcgg gccgcgcggg gtcgactctc ggcgcgcggc ccgccagtct  51780
cccgggacca acgagaccat cacggcgctg atgggggcgg tgacgtcttt gcagcaggaa  51840
ctggcgcaca tgcgggctag gaccagcgcc ccctatggga tgtacacgcc ggtggcgcac  51900
tatcgccctc aggtgggggga gccggaacca acaacgaccc acccggccct ttgtcccccg  51960
gaggccgtgt atcgcccccc accacacagc gccccctacg gtcctcccca gggtccggcg  52020
tcccatgccc ccactccccc gtatgcccca gctgcctgcc cgccaggccc gccaccgccc  52080
ccatgtcctt ccacccagac gcgcgcccct ctaccgacgg agcccgcgtt cccccccgcc  52140
gccaccggat cccaaccgga ggcatccaac gcggaggccg gggcccttgt caacgccagc  52200
agcgcagcac acgtggacgt tgacacggcc cgcgccgccg atttgttcgt ctctcagatg  52260
atgggggccc gctgattcgc cccggtcttt ggtaccatgg gatgtcttac tgtatatctt  52320
tttaaataaa ccaggtaata ccaaagaaga cccattggtg tatgttcttt ttttattggg  52380
aggcgcgggt aggcgggtag ctttacaatg caaaagcctt cgacgtggag gaaggcgtgg  52440
gggggaatcg gcactgacca agggggtccg ttttgtcacg ggaaaggaaa gaggaaacag  52500
gccgcggaca cccgggggag tttatgtgtt ccccttttctt tcttcccaca cacacaaaag  52560
gcgtaccaaa caaacaaacc aaaagatgca catgcggttt aacacccgtg gtttttattt  52620
```

-continued

```
acaacaaacc ccccgtcaca ggtcgtcctc gtcggcgtca ccgtctttgt tgggaacttg  52680
ggtgtagttg gtgttgcggc gcttgcgcat gaccatgtcg gtgaccttgg cgctgagcag  52740
cgcgctcgtg cccttcttct tggccttgtg ttccgtgcgc tccatggcag acaccagggc  52800
catgtaccgt atcatctccc gggcctcggc tagcttggcc tcgtcaaagt cgccgccctc  52860
ctcgccctcc ccggacgcgt ccgggttggt ggggttcttg agctccttgg tggttagcgg  52920
gtacagggcc ttcatggggt tgctctgcag ccgcatgacg tagcgaaagg cgaagaaggc  52980
cgccgccagg ccggccagga ccaacagacc cacggccagc gccccaaagg ggttggacat  53040
gaaggaggac acgcccgaca cggccgatac cacgccgccc acgatgccca tcaccacctt  53100
gccgaccgcg cgccccaggt cgcccatccc ctcgaagaac gcgcccaggc ccgcaaacat  53160
ggcggcgttg gcgtcggcgt ggatgaccgt gtcgatgtcg gcgaagcgca ggtcgtgcag  53220
ctggttgcgg cgctggacct ccgtgtagtc cagcaggccg ctgtccttga tctcgtggcg  53280
ggtgtacacc tccaggggga caaactcgtg atcctccagc atggtgatgt tgaggtcgat  53340
gaaggtgctg acggtggtga tgtcggcgcg gctcagctgg tgggagtacg cgtactcctc  53400
gaagtacacg tagcccccac cgaaggtgaa gtagcgccgg tgtcccacgg tacacggctc  53460
gatcgcatcg cgcgtcagcc gcagctcgtt gttctccccc agctgcccct cgaccaacgg  53520
gccctggtct tcgtaccgaa agctgaccag gggggcggctg tagcaggccc cgggccgcga  53580
gctgatgcgc atcgagtttt ggacgatcac gttgtccgcg gcgaccggca cgcacgtgga  53640
gacggccatc acgtcgccga gcatccgcgc gctcacccgc cggcccacgg tggccgaggc  53700
gatggcgttg gggttcagct tgcgggcctc gttccacagg gtcagctcgt gattctgcag  53760
ctcgcaccac gcgatggcaa cgcggcccaa catatcgttg acatggcgct gtatgtggtt  53820
gtacgtaaac tgcagcctgg cgaactcgat ggaggaggtg gtcttgatgc gctccacgga  53880
cgcgttggcg ctggccccgg gcggcggggg cgtggggttt gggggcttgc ggctctgctc  53940
tcggaggtgt tcccgcacgt acagctccgc gagcgtgttg ctgagaaggg gctggtacgc  54000
gatcagaaag cccccattgg ccaggtagta ctgcggctgg cccaccttga tgtgcgtcgc  54060
gttgtacctg cgggcgaaga tgcggtccat ggcgtcgcgg gcgtccttgc cgatgcagtc  54120
ccccaggtcc acgcgcgaga gcgggtactc ggtcaggttg gtggtgaagg tggtggatat  54180
ggcgtcggag gagaatcgga aggagccgcc gtactcggag cgcagcatct cgtccacctc  54240
ctgccacttg gtcatggtgc agaccgacgg gcgctttggc acccagtccc aggccacggt  54300
gaacttgggg gtcgtgagca ggttccgggt ggtcggcgcc gtggcccggg ccttggtggt  54360
gaggtcgcgc gcgtagaagc cgtcgacctg cttgaagcgg tcggcggcgt agctggtgtg  54420
ttcggtgtgc gacccctccc ggtagccgta aaacggggac atgtacacaa agtcgccagt  54480
cgccagcaca aactcgtcgt acgggtacac cgagcgcgcg tccacctcct cgacgatgca  54540
gtttaccgtc gtcccgtacc ggtggaacgc ctccacccgc gaggggttgt acttgaggtc  54600
ggtggtgtgc cagccccggc tcgtgcgggt cgcggcgttg gccggtttca gctccatgtc  54660
ggtctcgtgg tcgtcccggt gaaacgcggt ggtctccagg ttgttgcgca cgtacttggc  54720
cgtggaccga cagacccccct tggcgttgat cttgtcgatc acctcctcga aggggacggg  54780
ggcgcggtcc tcaaagatcc ccataaactg ggagtagcgg tggccgaacc acacctgcga  54840
aacggtgacg tctttgtagt acatggtggc cttgaacttg tacggggcga tgttctcctt  54900
gaagaccacc gcgatgccct ccgtgtagtt ctgaccctcg ggccgggtcg ggcagcggcg  54960
cggctgctcg aactgcacca ccgtggcgcc cgtggggggt gggcacacgt aaaagtttgc  55020
```

-continued

```
atcggtgttc tccgccttga tgtcccgcag gtgctcgcgc agggtggcgt ggcccgcggc  55080
gacggtcgcg ttgtcgccgg cggggcgcgg cggctttggg ggtttcggtt ttttgttctt  55140
cttcggtttc gggtcccccg ttgggggggc gccaggggcg ggcggcgccg gagtggcagg  55200
gcccccgttc gccgcctggg tcgcggccgc gaccccaggc gtgccggggg aactcggagc  55260
cgccgacacc accaggaccc ccagcgtcaa ccccaagagc gcccatacga cgaaccaccg  55320
gcgcccccgc gcgggggcgc cctggcgcat ggcgggacta cgggggcccg tcgtgccccc  55380
cgtcaggtag cctgggggcg aggtgctgga ggaccgagta gaggatcgag aaaacgtctc  55440
ggtcgtagac cacgaccgac cgggggccga tacagccgtc gggggcgctc tcgacgatgg  55500
ccaccagcgg acagtcggag tcgtacgtga gatatacgcc gggcgggtaa cggtaacgac  55560
cttcggaggt cgggcggctg cagtccgggc ggcgcaactc gagctccccg caccggtaga  55620
ccgaggcaaa gagtgtggtg gcgataatca gctcgcgaat atatcgccag gcggcgcgct  55680
gagtgggcgt tattccggaa atgccgtcaa aacagtaaaa cctctgaaat tcgctgacgg  55740
cccaatcagc acccgagccc cccgccccca tgatgaaccg ggcgagctcc tccttcaggt  55800
gcggcaggag ccccacgttc tcgacgctgt aatacagcgc ggtgttgggg ggctgggcga  55860
agctgtgggt ggagtgatca aagaggggcc cgttgacgag ctcgaagaag cgatgggtga  55920
tgctggggag cagggccggg tccacctggt gtcgcaggag agacgctcgc atgaaccggt  55980
gcgcgtcgaa cacgcccggc gccgagcggt tgtcgatgac cgtgcccgcg cccgccgtca  56040
gggcgcagaa gcgcgcgcgc gccgcaaagc cgttggcgac cgcggcgaac gtcgcgggca  56100
gcacctcgcc gtggacgctg acccgcagca tcttctcgag ctccccgcgc tgctcgcgga  56160
cgcagcgccc caggctggcc aacgaccgct tcgtcaggcg gtccgcgtac agccgccgtc  56220
gctcccgcac gtccgcggcc gcttgcgtgg cgatgtcccc ccacgtctcg ggcccctgcc  56280
ccccgggccc gcggcgacgg tcttcgtcct cgcccccgcc cccgggagct cccaaccccc  56340
gtgccccttc ctctacggcg acacggtccc cgtcgtcgtc ggggcccgcg ccgcccttgg  56400
gcgcgtccgc cgcgcccccc gcccccatgc gcgccagcac gcgacgcagc gcctcctcgt  56460
cgcactgttc ggggctgacg aggcgccgca agagcggcgt cgtcaggtgg tggtcgtagc  56520
acgcgcggat gagcgcctcg atctgatcgt cgggtgacgt ggcctgaccg ccgattatta  56580
gggcgtccac catatccagc gccgccaggt ggctcccgaa cgcgcgatcg aaatgctccg  56640
cccgccgccc gaacagcgcc agttccacgg ccaccgcggc ggtctcctgc tgcaactcgc  56700
gccgcgccag cgcggtcagg ttgctggcaa acgcgtccat ggtggtctgg ccggcgcggt  56760
cgccggacgc gagccagaat cgcaattcgc tgatggcgta caggccgggc gtggtggcct  56820
gaaacacgtc gtgcgcctcc agcagggcgt cggcctcctt gcggaccgag tcattctcgg  56880
gcgacgggtg gggctgcccg tcgccccccg cggtccgggc cagcgcatgg tccaacacgg  56940
agagcgcccg cgcgcggtcg gcgtccgaca gcccggcggc gtggggcagg taccgccgca  57000
gctcgttggc gtccagccgc acctgcgcct gctgggtgac gtggttacag atacggtccg  57060
ccaggcggcg ggcgatcgtc gccccctggt tcgccgtcac acacagttcc tcgaaacaga  57120
ccgcgcaggg gtgggacggg tcgctaagct ccggggggac gataaggccc gaccccaccg  57180
cccccaccat aaactcccga acgcgctcca gcgcggcggt ggcgccgcgc gagggggtga  57240
tgaggtggca gtagtttagc tgctttagaa agttctcgac gtcgtgcagg aaacacagct  57300
ccatatggac ggtcccgcca tacgtatcca gcctgacccg ttggtgatac ggacagggtc  57360
```

-continued

```
gggccaggcc catggtctcg gtgaaaaacg ccgcgacgtc tcccgcggtc gcgaacgtct  57420
ccaggctgcc caggagccgc tcgccctcgc gccacgcgta ctctagcagc aactccaggg  57480
tgaccgacag cggggtgaga aaggccccgg cctgggcctc caggcccggc ctcagacgac  57540
gccgcagcgc ccgcacctga agcgcgttca gcttcagttg gggg agcttc ccccgtccga  57600
tgtgggggtc gcaccgccgg agcagctcta tctgaaacac ataggtctgc acctgcccga  57660
gcagggctaa caacttttga cggccacgg tgggctcgga caccggggcg gccatctcgc  57720
ggcgccgatc tgtaccgcgg ccggagtatg cggtggaccg aggcggtccg tacgctaccc  57780
ggcgtctggc tgagccccgg ggtccccctc ttcggggcgg cctcccgcgg gcccgccgac  57840
cggcaagccg ggagtcggcg gcgcgtgcgt ttctgctcta ttcccagaca ccgcggagag  57900
gaatcacggc ccgcccagag atatagacac ggaacacaaa caagcacgga tgtcgtagca  57960
ataatttatt ttacacacat tccccgcccc gccctaggtt cccccacccc caacccctca  58020
cagcatatcc aacgtcaggt ctccctttttt gtcggggggc ccctccccaa acgggtcatc  58080
cccgtggaac gcccgtttgc ggccggcaaa tgccggtccc ggggcccccg ggccgccgaa  58140
cggcgtcgcg ttgtcgtcct cgcagccaaa atccccaaag ttaaacacct ccccggcgtt  58200
gccgagttgg ctgactaggg cctcggcctc gtgcgccacc tccagggccg cgtccgtcga  58260
ccactcgccg ttgccgcgct ccagggcacg cgcggtcagc tccatcatct cctcgcttag  58320
gtactcgtcc tccaggagcg ccagccagtc ctcgatctgc agctgctggg tgcggggccc  58380
caggcttttc acggtcacca cgaacacgct actggcgacg gccgccccgc cctcggagat  58440
aatgccccgg agctgctcgc acagcgagct ttcgtgcgct ccgccgccga ggctcgaggc  58500
cgcgcacaca aacccggccc ggggacaggc caggacgaac ttgcgggtgc ggtcaaaaat  58560
aaggagcggg cacgcgtttt tgccgcccat caggctggcc cagttcccgg cctgaaacac  58620
acggtcgttg ccggccatgc cgtagtactt gctgatgctc aaccccaaca cgaccatggg  58680
gcgcgccgcc atgacgggcc gcagcaggtt gcagctggcg aacatggacg tccacgcgcc  58740
cggatgcgcg tccacggcgt ccatcagcgc gcgggccccg gcctccaggc ccgccccgcc  58800
ctgcgcggac cacgcggccg cagcctgcac gctgggggga cggcgggacc ccgcgatgat  58860
ggccgtaagg gtgttgatga agtacgtcga gtgatcgcag taccgcagaa tctggtttgc  58920
catgtagtac atcgccagct cgctcacgtt gttgggggcc aggttaataa agtttatcgc  58980
gccgtagtcc agggaaaact ttttaatgaa cgcgatggtc tcgatgtcct cgcgcgacag  59040
gagccgggcg ggaagctggt tgcgttggag ggccgtccag aaccactgcg ggttcggctg  59100
gttggacccc gggggcttgc cgttggggaa gatggccgcg tggaactgct tcagcagaaa  59160
gcccagcggt ccgaggagga tgtccacgcg cttgtcgggc ttctggtagg cgctctggag  59220
gctggcgacc cgcgccttgg cggcctcgga cgcgttggcg ctcgcgcccg cgaacaacac  59280
gcggctcttg acgcgcagct ccttgggaaa ccccagggtc acgcgggcaa cgtcgccctc  59340
gaagctgctc tcggcggggg ccgtctggcc ggccgttagg ctgggggcgc agatagccgc  59400
cccctccgag agcgcgaccg tcagcgtttt ggccgacaga aacccgttgt taaacatgtc  59460
catcacgcgc cgccgcagca ccggttggaa ttgattgcga aagttgcgcc cctcgaccga  59520
ctgcccggcg aacaccccgt ggcactggct cagggccagg tcctgataca cggcgaggtt  59580
ggatcgccgc ccgagaagct gaagcagggg gcatggcccg cacgcgtacg ggtccagcgt  59640
cagggacatg gcgtggttgg cctcgcccag accgtcgcga aacttgaagt tcctcccctc  59700
caccaggttg cgcatcagct gctccacctc gcggtccacg acctgcctga cgttgttcac  59760
```

caccgtatgc agggcctcgc ggttggtgat gatggtctcc agccgcccca tggccgtggg 59820
gaccgcctgg tccacgtact gcagggtctc gagttcggcc atgacgcgct cggtcgccgc 59880
gcggtacgtc tcctgcatga tggtccgggc ggtctcggat ccgtccgcgc gcttcagggc 59940
cgagaaggcg gcgtagtttc ccagcacgtc gcagtcgctg tacatgctgt tcatggtccc 60000
gaagacgccg atggctccgc gggcggcgct ggcgaacttg ggatggcgcg cccggaggcg 60060
catgagcgtc gtgtgtacgc aggcgtggcg cgtgtcgaag gtgcacaggt tgcagggcac 60120
gtcggtctgg ttggagtccg cgacgtatcg aaacacgtcc atctcctggc gcccgacgat 60180
cacgccgccg tcgcagcgct ccaggtaaaa cagcatcttg gccagcagcg ccggggaaaa 60240
cccacacagc atggccaggt gctcgccggc aaattcctgg gttccgccga cgaggggcgc 60300
ggtgggccga ccctcgaacc cgggcaccac gtgtccctcg cggtccacct gtgggttggc 60360
cgccacgtgg gtcccgggca cgaggaagaa gcggtaaaag gagggtttgc tgtggtcctt 60420
tgggtccgcc ggaccggcgt cgtccacctc ggtgagatgg agggccgagt tggtgctaaa 60480
taccatggcc cccacgagtc ccgcggcgcg cgccaggtac gccccgacgg cgttggcgcg 60540
ggccgcggcc gtgtcctggc cctcgcacag cggccatgcg gagatgtcgg tgggcggctc 60600
gtcgaagacg gccatcgaca cgatagactc gagggccagg gcggcgtctc cggccatgac 60660
ggaggccagg cgctgttcga acccgcccgc cgggcccttg ccgccgccgt cgcgcccacc 60720
ccgcggggtc ttaccctggc tggcttcgaa ggccgtgaac gtaatgtcgg cggggagggc 60780
ggcgccctcg tggttttcgt caaacgccag gtgggcggcc gcgcgggcca cggcgtccac 60840
gtttcggcat cgcagtgcca cggcggcggg tcccacgacc gcctcgaaca ggaggcggtt 60900
gagggggcgg ttaaaaaacg gaagcgggta ggtaaaattc tccccgatcg atcggtggtt 60960
ggcgttgaac ggctcggcga tgacccggct aaaatccggc atgaacagct gcaacggata 61020
cacgggtatg cggtgcacct ccgccccgcc tatggttacc ttgtccgagc ctcccaggtg 61080
cagaaaggtg ttgttgatgc acacggcctc cttgaagccc tcggtaacga ccagatacag 61140
gagggcgcgg tccgggtcca ggccgaggcg ctcacacagc gcctccccccg tcgtctcgtg 61200
tttgaggtcg ccgggccggg gggtgtagtc cgaaaagcca aaatggcggc gtgcccgctc 61260
gcagagtcgc gtcaggtttg gggcctgggt gttggggtcc aggtgccggc cgccgtgaaa 61320
gacgtacacg gacgagctgt agtgcgatgg cgtcagtttc agggacaccg cggtaccccc 61380
gagccccgtc gtgcgagaac ccacgaccac ggctacgttg gcctcaaagc cgctctccac 61440
ggtcaggccc acgaccaggg gcgccacggc gacgtcggca tcgccgctgc gcgccgacag 61500
taacgccaga agctcgatgc cttcggatgg acacgcgcga gcgtacacgt atcccagggg 61560
cccggggggg accttgatgg tggttgccgt cttgggcttt gtctccatgt cctcctggca 61620
atcggtccgc aaacggaggt aatcccggca cgacgacgga cgcccgacga ggtatgtctc 61680
ccgagcgtca aaatccgggg ggggcggcga cggtcaaggg gagggtggga gaccggggtt 61740
ggggaatgaa tccctaccct tcaccgacaa cccccgggta accacggggt gccgatgaac 61800
cccggcggct ggcaacgcgg ggtccctgcg agaggcacag atgcttacgg tcaggtgctc 61860
cgggccgggt gcgtctgata tgcggttggt atatgtacac tttacctggg ggcgtgccgg 61920
accgcaccag cccctcccac accccgcgcg tcatcagccg gtgggcgnnn nnnnnnnnnn 61980
nnnnnnnnnn nnnnnnnnnn nnnnnnnnnn nnnnnnnnnn nnnnnnnnnn nnnnnnnnnn 62040
nnnnnnnnnn nnnnnnnnnn nnnnnnnnnt ttttataata gcggccacgc ccaccggcta 62100

-continued

```
cgtcacgctc ctgtcggccg ccggcggtcc ataagcccgg ccggccgggc cgacgcgaat  62160
aaaccgggcc gccggccggg gcgccgcgca gcagctcgcc gcccggatcc gccagacaaa  62220
caaggccctt gcacatgccg gcccgggcga gcctgggggt ccggtaattt tgccatccca  62280
cccaagcggc ttttggggtt tttcctcttc cccctcccc acctcccccc tctttagggg  62340
ttcgggtggg aacaaccgcg atgttttccg gtggcggcgg cccgctgtcc cccggaggaa  62400
agtcggcggc cagggcggcg tccgggtttt ttgcgcccgc cggccctcgc ggagccggcc  62460
ggggaccccc gccttgtttg aggcaaaact tttacaaccc ctacctcgcc ccagtcggga  62520
cgcaacagaa gccgaccggg ccaacccagc gccatacgta ctatagcgaa tgcgatgaat  62580
ttcgattcat cgccccgcgg gtgctggacg aggatgcccc cccggagaag cgcgccgggg  62640
tgcacgacgg tcacctcaag cgcgccccca aggtgtactg cggggggggac gagcgcgacg  62700
tcctccgcgt cgggtcgggc ggcttctggc cgcggcgctc gcgcctgtgg ggcggcgtgg  62760
accacgcccc ggcggggttc gaccccaccg tcaccgtctt tcacgtgtat gacatcctgg  62820
agaacgtgga gcacgcgtac ggcatgcgcg cggcccagtt ccacgcgcgg tttatggacg  62880
ccatcacacc gacggggacc gtcatcacgc tcctgggcct gactccggaa ggccaccggg  62940
tggccgttca cgtttacggc acgcggcagt acttttacat gaacaaggag gaggttgaca  63000
ggcacctaca atgccgcgcc ccacgagatc tctgcgagcg catggccgcg gccctgcgcg  63060
agtccccggg cgcgtcgttc cgcggcatct ccgcggacca cttcgaggcg gaggtggtgg  63120
agcgcaccga cgtgtactac tacgagacgc gccccgctct gttttaccgc gtctacgtcc  63180
gaagcgggcg cgtgctgtcg tacctgtgcg acaacttctg cccggccatc aagaagtacg  63240
agggtggggt cgacgccacc acccggttca tcctggacaa ccccgggttc gtcaccttcg  63300
gctggtaccg tctcaaaccg ggccggaaca acacgctagc ccagccgcgg gccccgatgg  63360
ccttcgggac atccagcgat gtcgagttta actgtacggc ggacaacctg gccatcgagg  63420
ggggcatgag cgacctaccg gcatacaagc tcatgtgctt cgatatcgaa tgcaaggcgg  63480
ggggggagga cgagctggcc tttccggtgg ccgggcaccc ggaggacctg gtcatccaga  63540
tatcctgtct gctctacgac ctgtccacca ccgccctgga gcacgtcctc ctgttttcgc  63600
tcggttcctg cgacctcccc gaatccccacc tgaacgagct ggcggccagg ggcctgccca  63660
cgcccgtggt tctggaattc gacagcgaat tcgagatgct gttggccttc atgacccttg  63720
tgaaacagta cggccccgag ttcgtgaccg ggtacaacat catcaacttc gactggccct  63780
tcttgctggc caagctgacg gacatttaca aggtcccccct ggacgggtac ggccgcatga  63840
acggccgggg cgtgtttcgc gtgtgggaca taggccagag ccacttccag aagcgcagca  63900
agataaaggt gaacggcatg gtgaacatcg acatgtacgg gattataacc gacaagatca  63960
agctctcgag ctacaagctc aacgccgtgg ccgaagccgt cctgaaggac aagaagaagg  64020
acctgagcta tcgcgacatc cccgcctact acgccgccgg gcccgcgcaa cgcggggtga  64080
tcggcgagta ctgcatacag gattccctgc tggtgggcca gctgtttttt aagtttttgc  64140
cccatctgga gctctcggcc gtcgcgcgct tggcgggtat taacatcacc cgcaccatct  64200
acgacggcca gcagatccgc gtctttacgt gcctgctgcg cctggccgac cagaagggct  64260
ttattctgcc ggacacccag gggcgattta ggggcgccgg gggggaggcg cccaagcgtc  64320
cggccgcagc ccgggaggac gaggagcggc cagaggagga gggggaggac gagaacgaac  64380
gcgaggaggg cgggggcgag cgggagccgg agggcgcgcg ggagaccgcc ggccggcacg  64440
tggggtacca gggggccagg gtccttgacc ccacttccgg gtttcacgtg aaccccgtgg  64500
```

```
tggtgttcga ctttgccagc ctgtacccca gcatcatcca ggcccacaac ctgtgcttca  64560
gcacgctctc cctgagggcc gacgcagtgg cgcacctgga ggcgggcaag gactacctgg  64620
agatcgagat gggggggcga cggctgttct tcgtcaaggc tcacgtgcga gagagcctcc  64680
tcagcatcct cctgcgggac tggctcgcca tgcgaaagca gatccgctcg cggattcccc  64740
agagcagccc cgaggaggcc gtgctcctgg acaagcagca ggccgccatc aaggtcgtgt  64800
gtaactcggt gtacgggttc acgggagtgc agcacggact cctgccgtgc ctgcatgttg  64860
ccgcgacggt gacgaccatc ggccgcgaga tgctgctcgc gacccgcgag tacgtccacg  64920
cgcgctgggc ggccttcgaa cagctcctgg ccgatttccc ggaggcggcc gacatgcgcg  64980
cccccgggcc ctattccatg cgcatcatct acggggacac ggactccata tttgtgctgt  65040
gccgcggcct cacggccgcc gggctgacgg ccatgggcga caagatggcg agccacatct  65100
cgcgcgcgct gtttctgccc cccatcaaac tcgagtgcga aaagacgttc accaagctgc  65160
tgctgatcgc caagaaaaag tacatcggcg tcatctacgg gggtaagatg ctcatcaagg  65220
gcgtggatct ggtgcgcaaa aacaactgcg cgtttatcaa ccgcacctcc agggccctgg  65280
tcgacctgct gttttacgac gataccgtat ccggagcggc cgccgcgtta gccgagcgcc  65340
ccgcagagga gtggctggcg cgacccctgc ccgagggact gcaggcgttc ggggccgtcc  65400
tcgtagacgc ccatcggcgc atcaccgacc cggagaggga catccaggac tttgtcctca  65460
ccgccgaact gagcagacac ccgcgcgcgt acaccaacaa gcgcctggcc cacctgacgg  65520
tgtattacaa gctcatggcc cgccgcgcgc aggtcccgtc catcaaggac cggatcccgt  65580
acgtgatcgt ggcccagacc cgcgaggtag aggagacggt cgcgcggctg gccgccctcc  65640
gcgagctaga cgccgccgcc ccaggggacg agcccgcccc ccccgcggcc ctgccctccc  65700
cggccaagcg cccccgggag acgccgtcgc atgccgaccc cccgggaggc gcgtccaagc  65760
cccgcaagct gctggtgtcc gagctggccg aggatcccgc atacgccatt gcccacggcg  65820
tcgccctgaa cacggactat tacttctccc acctgttggg ggcggcgtgc gtgacattca  65880
aggccctgtt tgggaataac gccaagatca ccgagagtct gttaaaaagg tttattcccg  65940
aagtgtggca ccccccggac gacgtggccg cgcggctccg ggccgcaggg ttcggggcgg  66000
tgggtgccgg cgctacggcg gaggaaactc gtcgaatgtt gcatagagcc tttgatactc  66060
tagcatgagc cccccgtcga agctgatgtc cctcatttta caataaatgt ctgcggccga  66120
cacggtcgga atctccgcgt ccgtgggttt ctctgcgttg cgccggacca cgagcacaaa  66180
cgtgctctgc cacacgtggg cgacgaacct gtaccccggg cacgcggtga gcatccggtc  66240
tatgagccgg tagtgcaggt gggcggacgt gccgggaaag atgacgtaca gcatgtggcc  66300
cccgtaagtg gggtccgggt aaaacaacag ccgcgggtcg cacgccccgc ctccgcgcag  66360
gatcgtgtgg acgaaaaaaa gctcgggttg gccaagaatc ccggccaaga ggtcctggag  66420
gggggcgttg tggcggtcgg ccaacacgac caaggaggcc aggaaggcgc gatgctcgaa  66480
tatcgtgttg atctgctgca cgaaggccag gattagggcc tcgcggctgg tggcggcgaa  66540
ccgcccgtct cccgcgttgc acgcgggaca gcaacccccg atgcctaggt agtagcccat  66600
cccggagagg gtcaggcagt tgtcggccac ggtctggtcc agacagaagg gcagcgacac  66660
gggagtggtc ttcaccaggg gcaccgagag cgagcgcacg atggcgatct cctcggaggg  66720
cgtctgggcg agggcggcga aaaggccccg atagcgctgg cgctcgtgta aacacagctc  66780
ctgtttgcgg gcgtgaggcg gcaggctctt ccgggaggcc cgacgcacca cgcccagagt  66840
```

-continued

```
cccgccggcc gcagaggagc gcgaccgccg gcgctccttg ccgtgatagg gcccgggccg  66900
ggagccgcgg cgatgggggt cggtatcata cataggtaca cagggtgtgc tccagggaca  66960
ggagcgagat cgagtggcgt ctaagcagcg cgcccgcctc acggacaaat gtggcgagcg  67020
cggtgggctt tggtacaaat acctgatacg tcttgaaggt gtagatgagg gcacgcaacg  67080
ctatgcagac acgcccctcg aactcgttcc cgcaggccag cttggccttg tggagcagca  67140
gctcgtcggg atgggtggcg gggggatggc cgaacagaac ccaggggtca acctccatct  67200
ccgtgatggc gcacatgggg tcacagaaca tgtgcttaaa gatggcctcg ggccccgcgg  67260
cccgcagcag gctcacaaac cggcccccgt ccccgggctg cgtctcgggg tccgcctcga  67320
gctggtcgac gacgggtacg atacagtcga agaggctcgt gttgttttcc gagtagcgga  67380
ccacggaggc ccggagtctg cgcagggcca gccagtaagc ccgcaccagt aacaggttac  67440
acagcaggca ttctccgccg gtgcgcccgc gcccccggcc gtgtttcagc acggtggcca  67500
tcagagggcc caggtcgagg tcgggctggg catcgggttc ggtaaactgc gcaaagcgcg  67560
gagccacgtc gcgcgtgcgt gccccgcgat gcgcttccca ggactggcgg accgtggcgc  67620
gacgggcctc cgcggcagcg cgcagctggg gccccgactc ccagacggcg ggggtgccgg  67680
cgaggagcag caggaccaga tccgcgtacg cccacgtatc cggcgactcc tccggctcgc  67740
ggtccccggc gaccgtctcg aattccccgt tgcgagcggc ggcgcgcgta cagcagctgt  67800
ccccgccccc gcgccgaccc tccgtgcagt ccaggagacg ggcgcaatcc ttccagttca  67860
tcagtgcggt ggtaagcgac ggctgcgtgc cggataccgc cgccgacccc gccccctcct  67920
cgcccccgga ggccaaggtt ccgatgaggg cccgggtggc agactgcgcc aggaacgagt  67980
agttggagta ctgcaccttg gcggctcccg gggagggcga gggcttgggt tgcttctggg  68040
catgccgccc gggcaccccg ccgtcggtac ggaagcagca gtggagaaaa aagtgccggt  68100
ggatgtcgtt tatggtgagg gcaaagcgtg cgaaggagcc gaccagggtc gccttcttgg  68160
tgcgcagaaa gtggcggtcc atgacgtaca caaactcgaa cgcggccacg aagatgctag  68220
cggcgcagtg gggcgccccc aggcatttgg cacagagaaa cgcgtaatcg gccacccact  68280
gaggcgagag gcggtaggtt tgcttgtaca gctcgatggt gcggcagacc agacagggcc  68340
ggtccagcgc gaaggtgtcg atggccgccg cggaaaaggg cccggtgtcc aaaagcccct  68400
ccccacaggg atccgggggc gggttgcggg gtcctccgcg cccgcccgaa ccccctccgt  68460
cgcccgcccc cccgcgggcc cttgaggggg cggtgaccac gtcggcggcg acgtcctcgt  68520
cgagcgtacc gacgggcggc acacctatca cgtgactggc cgtcaggagc tcggcgcaga  68580
gagcctcgtt aagagccagg aggctgggat cgaaggccac atacgcgcgc tcgaacgccc  68640
ccgccttcca gctgctgccg ggggactctt cgcacaccgc gacgctcgcc aggaccccgg  68700
ggggcgaagt tgccatggct gggcgggagg ggcgcacgcg ccagcgaact ttacgggaca  68760
caatccccga ctgcgcgctg cggtcccaga ccctggagag tctagacgcg cgctacgtct  68820
cgcgagacgg cgcgcatgac gcggccgtct ggttcgagga tatgaccccc gccgagctgg  68880
aggttgtctt cccgactacg gacgccaagc taaactacct gtcgcggacg cagcggctgg  68940
cctccctcct gacgtacgcc gggcctataa aagcgcccga cgacgccgcc gccccgcaga  69000
ccccggacac cgcgtgtgtg cacggcgagc tgctcgcccg caagcgggaa agattcgcgg  69060
cggtcattaa ccggttcctg gacctgcacc agattctgcg gggctgacgc gcgcgctgtt  69120
gggcgggacg gttcgcgaac cctttggtgg gtttacgcgg gcacgcacgc tcccatcgcg  69180
ggcgccatgg cgggactggg caagccctac accggccacc caggtgacgc cttcgagggt  69240
```

```
ctcgttcagc gaattcggct tatcgtccca tctacgttgc ggggcgggga cggggaggcg  69300
ggcccctact ctccctccag cctcccctcc aggtgcgcct ttcagtttca tggccatgac  69360
gggtccgacg agtcgtttcc catcgagtat gtactgcggc ttatgaacga ctgggccgag  69420
gtcccgtgca acccttacct gcgcatacag aacaccggcg tgtcggtgct gtttcagggg  69480
ttttttcatc gcccacacaa cgcccccggg ggcgcgatta cgccagagcg gaccaatgtg  69540
atcctggggt ccaccgagac gacggggttg tccctcggcg acctggacac catcaagggg  69600
cggctcggcc tggatgcccg gccgatgatg gccagcatgt ggatcagctg ctttgtgcgc  69660
atgccccgcg tgcagctcgc gtttcggttc atgggccccg aagatgccgg acggacgaga  69720
cggatcctgt gccgcgccgc cgagcaggct attacccgtc gccgccgaac ccggcggtcc  69780
cgggaggcgt acggggccga ggccgggctg gggggtggccg gaacgggttt ccgggccagg  69840
ggggacggtt ttggcccgct ccccttgtta acccaagggc cctcccgccc gtggcaccag  69900
gccctgcggg gtcttaagca cctacggatt ggcccccccg cgctcgtttt ggcggcggga  69960
ctcgtcctgg gggccgctat ttggtgggtg gttggtgctg gcgcgcgcct ataaaaaagg  70020
acgcaccgcc gccctaatcg ccagtgcgtt ccggacgcct tcgccccaca cagccctccc  70080
gaccgacacc cccatatcgc tccccgacct ccggtcccga tggccgtccc gcaatttcac  70140
cgccccagca ccgttaccac cgatagcgtc cgggcgcttg gcatgcgcgg gctcgtcttg  70200
gccaccaata actctcagtt tatcatggat aacaaccacc cacaccccca gggcacccaa  70260
ggggccgtgc gggagtttct ccgcggtcag gcggcggcac tgacggacct tggtctggcc  70320
cacgcaaaca acacgtttac cccgcagcct atgttcgcgg gcgacgcacc ggccgcctgg  70380
ttgcggcccg cgtttggcct gcggcgcacc tattcacctt ttgtcgttcg agaaccttcg  70440
acgcccggga ccccgtgagg cccagggagt tccttctggg gtgttttaat caataaaaga  70500
ccacaccaac gcacgagcct tgcgtttaat gtcgtgttta ttcaagggag tgggataggg  70560
ttcgacggtt cgaaacttaa cacaccaaat aatcgagcgc gtctagccca gtaacatgcg  70620
cacgtgatgt aggctggtca gcacggcgtc gctgtgatga agcagcgccc ggcgggtccg  70680
ctgtaactgc tgttgtaggc ggtaacaggc gcggatcagc accgccaggg cgctacgacc  70740
ggtgcgttgc acgtagcgtc gcgacagaac tgcgtttgcc gatacgggcg gggggccgaa  70800
ttgtaagcgc gtcacctctt gggagtcatc ggcgtataac gcactgaatg gttcgttggt  70860
tatgggggag tgtggttccc cagggagtgg gtcgagcgcc tcggcctcgg aatccgagag  70920
gaacaacgag gtggcgtcgg agtcttcgtc gtcagagaca tacagggtct gaagcagcga  70980
cacgggcgtg ggggtagcgt cgatgtgtag cgcgagggag gatgcccacg aagacacccc  71040
agacaaggag ctgcccgtgc gtggatttgt ggaagacgcg gaagccggga cggatgggcg  71100
gttttgcggt gcccggaacc gaaccgccgg atactccccg ggtgctacat gcccgttttg  71160
gggctggggt tggggctggg gcgcggacag gcggctgacg gtcaaatgcc cccgggggcg  71220
cgcagatgtg gcgggcgtgg ccaccggctg ccgtgtagtg gggcggcggg aaaccgggcc  71280
tccgggcgta acaccgccct ccagcgtcaa gtatgtgggg ggcgggcctg acgtcggggg  71340
cggggtgacg ggttggaccg cgggaggcgg gggagaggga cctgcgggag aggatgaggt  71400
cggctcggcc gggttgcggc ctaaaacagg ggccgtgggg tcggcggggt cccagggtga  71460
agggagggat tcccgcgatt cggacagcga cgcgacagcg gggcgcgtaa ggcgccgctg  71520
cggcccgcct acgggaaccc tgggggggt tggcgcggga cccgaggtta gcgggggcg  71580
```

-continued gcggttttcg cccccgggca aaaccgtgcc ggttgcgacc gggggcggaa cgggatcgat 71640
agggagagcg ggagaagcct ggccggcgga ctggggaccg agcgggaggg gcacaccaga 71700
caccaaagcg tggggcgctg gctctggggg tttgggaggg gccgggggc gcgcgaaatc 71760
ggtaaccggg gcgaccgtgt cggggagggc aggcggccgc caaccctggg tggtcgcgga 71820
agcctgggtg gcgcgcgcca gggagcgtgc ccggcggtgt cggcgcgcgc gcgacccgga 71880
cgaagaagcg gcagaagcgc gggaggaggc gggggggcgg ggggcggtgg catcgggggg 71940
cgccggggaa ctttgggggg acggcaagcg ccggacgtcg tcgcgggggc ccacgggcgc 72000
cggccgcgtg ctttcggccg ggacgcccgg tcgtgcttcg cgagccgtga ctgccggccc 72060
agggggccgc ggtgcacact gggatgtggg gacggactga tcggcggtgg gcgaaagggg 72120
gtccggggca aggaggggcg cggggccgcc ggagtcgtca gacgcgagct cctccaggcc 72180
gtgaatccat gcccacatgc gagggggac gggctcgccg ggggtggcgt cggtgaatag 72240
cgtgggggcc aggcttccgg gccccaacga gccctccgtc ccaacaaggt ccgccgggcc 72300
gggggtcggg ttcgggaccg aggggctctg gtcgtcgggg gcgcgctggt acaccggatg 72360
ccccgggaat agctcccccg acaggaggga ggcgtcgaac ggccgcccga ggatagctcg 72420
tgcgaggaag gggtcctcgt cggtggcgct ggcggcgagg acgtcctcgc cgcccgccac 72480
aaacgggagc tcctcggtgg cctcgctgcc aacaaaccgc acgtcggggg ggccgggggg 72540
tccgggtttt cccacaacac cgcgaccggg gtcatggaga tgtccacgag caccagacac 72600
ggcgggcccc gggcgagggg ccgctcggcg atgagcgcgg acaggcgcgg gagctgtgcc 72660
gccagacacg cgttttcgat cggttcagg tcggcgtgca ggaggcggac ggcccacgtc 72720
tcgatgtcgg acgacacggc atcgcgcaag gcggcgtccg gcccgcgagc gcgtgagtca 72780
aacagcgtga ggcacagctc cagctccgac tcgcgggaaa aggccgtggt gttgcggagc 72840
gccacgacga cgggcgcgcc caggagcact gccgccagca ccaggtccat ggccgtaacg 72900
cgcgccgcgg gggtgcggtg ggtggcggcg gccggcacgg cgacgtgctg gcccgtgggc 72960
cggtagaggg cgttgggggg agcgggggt gacgcctcgc gcccccccga ggggctcagc 73020
gtctgcccag attccagacg cgcggtcaga agggcgtcga aactgtcata ctctgtgtag 73080
tcgtccggaa acatgcaggt ccaaagagcg gccagcgcgg tgcttgggag acacatgcgc 73140
ccgaggacgc tcaccgccgc cagcgcctgg gcgggactca gctttcccag cgcggcgccg 73200
cgctcggttc ccagctcggg gaccgagcgc cagggcgcca gggggtcggt ttcggacaac 73260
ttgccgcggc gccagtctgc cagccgcgtg ccgaacatga ggccccgggt cggagggcct 73320
ccggccgaaa acgctggcag cacgcggatg cgggcgtctg gatgcggggt caggcgctgc 73380
acgaatagca tggaatctgc tgcgttctga aacgcacggg ggagggtgag atgcatgtac 73440
tcgtgttggc ggaccagatc caggcgccaa aaggtgtaaa tgtgttccgg ggagctggcc 73500
accagcgcca ccagcacgtc gttctcgtta aaggaaacgc ggtgcctagt ggagctctgg 73560
ggtccgagcg gcggccccgg ggccgccgcg tcaccccccc attccagctg ggcccagcga 73620
cacccaaact cgcgcgtgag agtggtcgcg acgagggcga cgtagagctc ggccgccgca 73680
tccatcgagg ccccccatct cgcctggcgg tggcgcacaa agcgtccgaa gagctgaaag 73740
ttggcggcct gggcgtcgct gagggccagc tgaagccggt tgatgacggt gaggacgtac 73800
atggccgtga cggtcgaggc cgactccagg gtgtccgtcg gaagcggggg gcgaatgcat 73860
gccgcctcgg gacacatcag cagcgcgccg agcttgtcgg tcacggccgg gaagcagagc 73920
gcgtactgca gtggcgttcc atccgggacc aaaaagctgg gggcgaacgg ccgatccagc 73980

-continued gtactggtgg cctcgcgcag caccaggggc cccgggcctc cgctcactcg caggtacgcc 74040
tcgccccggc ggcgcagcat ctgcgggtcg gcctcttggc cgggtggggc ggacgcccgg 74100
gcgcgggcgt ctagggcgcg aagatccacg agcaggggcg cgggcgcggc ggccgcgccc 74160
gcgcccgtct ggcctgtggc cttggcgtac gcgctatata agcccatgcg gcgttggatg 74220
agctcccgcg cgccccggaa ctcctccatc gcccatgggg ccaggtcccc ggccaccgcg 74280
tcgaattccg ccaacaggcc ccccagggta tcaaagttca tctcccaggc cacccttggc 74340
accacctcgt cccgcagccg ggcgctcagg tcggcgtgtt gggccacgcg ccccccgagc 74400
tcctccacgg ccccggcccg ctcggcgctc ttggcgccca ggacgccctg gtacttggcg 74460
ggaaggcgct cgtagtcccg ctgggctcgc agccccgaca cagtgttggt ggtgtcctgc 74520
agggcgcgaa gctgctcgca tgccgcgcga aatccctcgg gcgatttcca ggcccccccg 74580
cgaacgcggc cgaagcgacc ccatacctcg tcccactccg cctcggcctc ctcgagagac 74640
ctccgcaggg cctcgacgcg gcgacgggtg tcgaagagcg cctgcaggcg cgcgccctgt 74700
cgcgtcagga ggcccgggcc gtcgctgctg gccgcgctta gcgggtgcgt ctcaaaggta 74760
cgctgggcat gttccaacca ggcgaccgcc tgcacgtcga gctcgcgcgc cttctccgtc 74820
tggtccaaca gaatttcgac ctgatccgcg atctcctccg ccgagcgcgc ctggtccagc 74880
gtcttggcca cggtcgccgg gacggcgacc accttcagca gggtcttcag attggccaga 74940
ccctcggcct cgagctgggc ccggcgctcg cgcgcggcca gcacatcccg cagccccgcc 75000
gtgacccgct cggtggcttc ggcgcgctgc tgtttggcgc gcaccacggc gtccttggta 75060
tcggccaggt cctgtcgggt cacgaatgcg acgtagtcgg agtacgccgt gtccttcacg 75120
gggctctggt ccacgcgctc cagcgccgcc acgcacgcca ccagcgcgtc ctcgctcggg 75180
cagggcaggg tgacccctgc ccggacaagc tcggcggccg ccgccgggtc gttgcgcacc 75240
gcggatatct cctccgcggc ggcggccagg tccagcgcca cgcttccgat cgcgcgccgc 75300
gcgtcggccc ggagggcgtc caggcgatcg cggatatcca cgtactcggc gtagcccttt 75360
tgaaaaaacg gcacgtactg gcgcagggcc ggcacgcccc ccaagtcttc cgacaggtgt 75420
agtacggcct cgtggtagtc gataaacccg tcgttcgcct gggcccgctc cagcagcccc 75480
cccgcgagcc gcagaagccg cgccaggggc tcggtgtcca cccgaaacat gtcggcgtac 75540
gtgtcggccg cggccccaaa ggccgcgctc cagtcgatgc ggtgaatggc tgcgagcggg 75600
gggagcatgg ggtggcgctg gttctcgggg gtgtatgggt taaacgcaag ggccgtctcc 75660
agggcaaggg tcaccgcctt ggcgttggtt cccagcgcct gctcggcccg ctttcggaag 75720
tcccggggt tgtagccgtg cgtgcccgcc agcgcctgca ggcgacggag ctcgaccacg 75780
tcaaactcgg cactgctttc cacgcggtcc agcacggcct ccacgtcggc ggcccagcgc 75840
tcgtggctac tgcgggcgcg ctgggccgcc atcttctctc tgaggtcggc ggtggcggcc 75900
tcaagttcgt cggcgcggcg tcgcgtggcg ccgatgacct ttcccagctc ctgcagggcg 75960
cgcccgctgg gggagtggtc cccggccgtc ccttcggcgt gcaacaggcc cccgaacctg 76020
ccctcgtggc ccgcgaggct ttcccgcgcg ccggtggtcg cgcgcgtcgc ggcttggatc 76080
agggaggcat gctctccctt cggttggttg gcggcccggc gcacctggac gacaaggtcg 76140
gcggcagccg accctaaggt cgtgagctgg gcgatggccc cccgcgcgtc cagggccaac 76200
cgagtcgcct tgacgtatcc cgcggcgctg tcggccatgg ccgctaggaa ggccaggggg 76260
gaggccgggt cgctggcggc cgcgcccagg gccgtcaccg cgtcgaccag gacgcggtgc 76320
gcccgcacgg ccgcatccac cgtcgacgcg gggtctgccg tcgcgacggc ggcgctgccg 76380
gcgttgatgg cgttcgagac ggcgtgggct atgatcgggg cgtgatcggc gaagaactgc 76440
aagagaaacg gagtctcggg ggcgtcggcg aacaggttct tcagcaccac cacgaagctg 76500
ggatgcaagc cggacagagc cgtcgccgtg tccggagtcg ggtgctccag ggcatctcgg 76560
tactgcccca gcagccccca catgtccgcc cgcagcgccg ccgtaacctc agggggcgcc 76620
ccccgaacgg cctcggggag gtccgaccag cccgccggca gggaggcccg cagggtcgcc 76680
aggacggccg gacaggcctt tagccccaca aagtcaggga gggggcgcag gaccccctgg 76740
agtttgtgca agaacttctc ccgggcgtcg cgggccacct tcgcccgctc ccgcgctccc 76800
tcgagcattg cctccaggga gcgcgcgcgc tcccgcaaac ggacacgcgc atcgggggcg 76860
agctctgccg tcagcttggc ggcatccatg gcccgcgcct gccgcagcgc ttcctcggcc 76920
atgcgcgtgg cctctggcga cagcccgccg tcgtcggggt agggcgacgc gccgggcgca 76980
ggaacaaagg ccgcgtcgct gtccagctgc tggcccaggg ccgcatctag ggcgtcgaag 77040
cgccgcagct cggccagacc cgagctgcgg cgcgcctgct ggtcgttaat gtcgcggatg 77100
ctgcgcgcca gctcgtccag cggcttgcgt tctatcagcc cttggttggc ggcgtccgtc 77160
aggacggaga gccaggccgc caggtcctcg gggcgtcca gcgtctggcc ccgctgtatc 77220
agatcccgca acaggatggc cgtggggctg gtcgcgatcg ggggcggggc gggaatggcg 77280
gcgcgctgcg cgatgtcccg cgtgtgctgg tcgaagacag gcagggactc gagcagctgg 77340
accacgggca cgacggcggc cgaagccacg tgaaaccggc ggtcgttgtt gtcgctggcc 77400
tgtagagcct tggcgctgta tacggccccc cggtaaaagt actccttaac cgccccctcg 77460
atcgcccgac gggcctgggt ccgcacctcc tccagccgaa cctgaacggc ctcggggccc 77520
agggggggtg ggcgcggagc cccctgcggg gccgccccgg ccggggcggg cattacgccg 77580
aggggcccgg cgtgctgtga gaccgcgtcg accccgcgag cgagggcgtc gagggcctcg 77640
cgcatctggc gatcctccgc ctccacccta atctcttcgc cacgggcaaa tttggccaga 77700
gcctggactc tatacagaag cggttctggg tgcgtcgggg tggcgggggc aaaaagggtg 77760
tccgggtggg cctgcgagcg ctccagaagc cactcgccga ggcgtgtata cagattggcc 77820
ggcggggccg cgcgaagctg cagctccagg tccgcgagtt ccccgtaaaa ggcgtccgtc 77880
tcccgaatga catccctagc cacaaggatc agcttcgcca gcgccaggcg accgatcaga 77940
gagttttcgt ccagcacgtg ctggacgagg ggcagatggg cggccacgtc ggccaggctc 78000
aggcgcgtgg aggccagaaa gtcccccacg gccgttttcc ggggcagcat gctcagggta 78060
aactccaaca gggcggcggc cgggccggcc accccggcct gggtgtgcgt ccgggccccg 78120
ttctcgatga gaaaggcgag gacgcgttca aagaaaaaaa taacacagag ctccagcagc 78180
cccggagaag ccggatacgg cgaccgtaag gcgctgatgg tgagccgcga acacgcggcg 78240
acctcgcggg ccagggcggc ggagcacgcg gtgaacttaa ccgccgtggc ggccacgttt 78300
gggtgggcct cgaacagctg ggcaaggtct gcgcccgggg gctcgggtga gcggcgagtc 78360
ttcagcgcct cgagggcctg cgaggacgcc ggaaccgtgg gcccgtcgtc ctcgcccgcc 78420
tcggcgaccg gcggcccggc cgggtcgggg ggtgccgagg cgaggacagg ctccggaacg 78480
gaggcgggga ccgcggcccc gacgggggtt ttgcctttgg gggtggattt cttcttggtt 78540
ttggcagggg gggccgagcg tttcgttttc tcccccgaag tcaggtcttc gacgctggaa 78600
ggcggagtcc aggtgggtcg gcggcgcttg ggatggccgg ccgagtagcg tgcccggtgc 78660
cgaccaaccg ggacgacgcc catctccagg acccgcatgt cgtcgtcatc ttcttcggcc 78720
gcctctgcgg cgggggcctt gggggcggag ggaggcggtg gtgggatcgc ggagggtggg 78780
tcggcggagg ggggatccgt gggtggggta cccttcaggg ccaccgccca tacatcgtcg 78840
ggcgcccgat tcgggcgctt ggcctctggt tttgccgacg gaccggccgt cccccgggat 78900
gtctcggagg ccctgtcgtc gcgacgggcc cgggtcggtg gcggcgactg ggcggctgtg 78960
ggcgggtgtg gccccgtgcc ccctaccccc tcccgggggc ccacgccgac gcagggctcc 79020
cccaggcccg cgatctcgcc ccgcaggggg tgcgtgatgg ccacgcgccg ttcgctgaac 79080
gcttcgtcct gcaggtaagt ctcgctggcc ccgtaaagat gcagagccgc ggccgtcaag 79140
tccgcaggag ccgcgggttc cgggcccgac ggcacgaaaa acaccatggc tcccgcccac 79200
cgtacgtccg ggcgatcgcg ggtgtaatac gtcaggtatg gatacatgtc ccccgcccgc 79260
actttggcga tgaacgcggg ggtgccctcc ggaaggccgt gcgggtcaaa aaggtatgcg 79320
gtgtcgccgt ccctgaacag ccccatccct agggggccaa tggttaggag cgtgtacgac 79380
agggggcgca gggcccacgg gccggcgaag aacgtgtgtg cggggcattg tgtctccagc 79440
aggcccgccg cgggctcccc gaagaagccc acctcgccgt atacgcgcga gaagacacag 79500
cgcagtccgc cgcgcgcccc tgggtactcg aggaagttgg ggagctcgac gatcgaacac 79560
atgcgcggcg gcccagggcc cgcggtcgcg cgcgtccact cgcccccctc gaccaaacaa 79620
ccctcgatgg cctccgcgga cagaacgtcg cgagggccca catcaaatat gaggctgaga 79680
aaggacagcg acgagcgcat gcacgatacc gacccccccg gctccaggtc gggcgcgaac 79740
tggttccgag caccggtgac cacgatgtcg cgatcccccc cgcgttccat cgtggagtgc 79800
ggtggggtgc ccgcgatcat atgtgcccta ctggccagag acccggcctg tttatggacc 79860
ggacccccgg ggttagtgtt gtttccgcca cccatgcccc cgtaccatgg ccccggttcc 79920
cctgattagg ctacgagtcg cggtgatcgc ttcccaaaaa ccgagctgcg tttgtctgtc 79980
ttgatcttcc cccccccccc cgcccgcccg cccgcccgcc cgcccgcaca ccataacacc 80040
gagaacaaca cacgggggtg ggcgtaacat aataaagctt tattggtaac tagttaacgg 80100
caagtccgtg ggtggcgcga cggtgtcctc cgggctcatc tcgtcgtcct cgacgggggt 80160
gttggaatga ggcgcccccct cgcggtccgc ctggcgtggg ccgtgcccat aggcctccgg 80220
cttctgtgcg tccatgggca taggcgcggg gagactgttt ccggcgtcgc ggacctccag 80280
gtccctggga gactccggtc cggctaacgg acgaaacgcg gaagcgcgaa acacgccgtc 80340
ggtgacccgc aggagctcgt tcatcagtaa ccaatccata ctcagcgtaa cggccagccc 80400
ctggcgagac agatccacgg agtccggaac cgcggtcgtc tggcccaggg ggccgaggct 80460
gtagtccccc caggccccta ggtcgcgacg gctcgtaagc acgacgcggt cggccgcggg 80520
gctttgcggg ggggcgtcct cgggcgcatg cgccattacc tctcggatgg ccgcggcgcg 80580
ctggtcggcc gagctgacca agggcgccac gaccacggcg cgctccgtct gcaggccctt 80640
ccacgtgtcg tggagttcct ggacaaactc ggccacgggc tcgggtcccg cggccgcgcg 80700
cgcggcttga tagcaggccg agagacgccg ccagcgcgct agaaactgac ccatgaagca 80760
aaacccgggg acctggtctc ccgacagcag cttcgacgcc cgggtgtgaa tgccggacac 80820
aacggacaga aacccgtgaa tttcgcgccg gaccacggcc agcacgttgt cctcgtgcga 80880
cacctgggcc gccagctcgt cgcacacctc caggtgcgcc gtggtttcgg tgatgacgga 80940
acgcaggctc gcgagggacg cgaccagcgc gcgcttggcg tcgtgataca tgctgcagta 81000
ctgactcacc gcgtccccca tggcctcggg gggccagggc cccaggcggt cgggagtgtc 81060
cccgaccacc gcatacaggc ggcgcccgtc gctctcgaac cgacactcga aaaaggcgga 81120
gagcgtgcgc atgtgcagcc gcagcagcac gatggcgtcc tccagttggc gaatcagggg 81180
gtctgcgcgc tcggcgaggt cctgcagcac cccccgggcg gccagggcgt acatgctaat 81240
caacaggagg ctggtgccca cctcgggggg cggggggggc tgcagctgga ccaggggccg 81300
cagctgctcg acggcacccc tggagatcac gtacagctcc cggagcagct gctctatgtt 81360
gtcggccatc tgcatagtgg ggccgaggcc gccccgggcg gccggttcga ggagggtaat 81420
cagcgcgccc agtttggtgc gatggccctc gaccgtgggg agatagccca gcccaaagtc 81480
ccgggcccag gccaacacac gcagggcgaa ctcgaccggg cgtggaaggt aggccgcgct 81540
acacgtggcc cccaacgcgt ccccgaccac cagggccaga acgtagggga cgaagcccgg 81600
gtcggcgagg acgttggggt gaatgccctc gagggcgggg aagcggatct gggtcgccgc 81660
ggccaggtgg acagaggggg cgtggctggg ctgcccgacg gggagaagcg cggacagcgg 81720
cgtggccggg gtggtggggg tgatgtccca gtgggtctga ccatacacgt cgatccagat 81780
gagcgccgtc tcgcggagaa ggctgggttg accggaacta aagcggcgct cggccgtctc 81840
aaactccccc acgagcgccc gccgcaggct cgccagatgt tccgtcggca cggccggacc 81900
catgatacgc gccagtgtct ggctcagaac gccccccgac aggccgaccg cctcgcagag 81960
ccgcccgtgc gtgtgctcgc tggcgccctg gacccgcctg aaagttttta cgtagttggc 82020
atagtacccg tattcccgcg ccagaccaaa cacgttcgac cccgcgaggg caatgcaccc 82080
aaagagctgc tggacttcgc cgagtccgtg gccggcgggc gtccgcgcgg ggacgcccgc 82140
cgccagaaac ccctccaggg ccgaaaggta gtgcgtgcag tgcgagggcg tgaacccagc 82200
gtcgatcagg gtgttgatca ccacggaggg cgaattggta ttctggatca acgtccacgt 82260
ctgctgcagc agagccagca gccgctgctg ggcgccggcg gagggctgct ccccgagctg 82320
cagcaggctg gagacggcag gctggaagac tgccagtgcc gacgaactca ggaacggcac 82380
gtcgggatca aacacggcca cgtccgtccg cacgcgcgcc attagcgtcc ccgggggcgc 82440
acaggccgag cgcgggctga cgcggctgag ggccgtcgac acgcgcacct cctcgcggct 82500
gcgaaccatc ttgttggcct ccagtggcgg aatcattatg gccgggtcga tctcccgcac 82560
ggtgtgctga aactgcgcca acaggggcgg cgggaccaca gccccccgct cgggggtcgt 82620
caggtactcg tccaccaggg ccaacgtaaa gagggcccgt gtgaggggag tgagggtcgc 82680
gtcgtctatg cgctggaggt gcgccgagaa cagcgtcacc cgattactca ccagggccaa 82740
gaaccggagg ccctcttgca cgaacggggc ggggaagagc aggctgtacg ccggggtggt 82800
aaggttcgcg ctgggctgcc ccaacgggac cggcgccatc ttgagtgacg tctccccaag 82860
ggcctcgatg gaggtccgcg ggctcatggc caagcagctc ttggtgacgg tttgccagcg 82920
gtctatccac tccacggcgc actggcggac gcggaccggc cccagggccg ccgcggtgcg 82980
caggccggcg gaatccagcg catgggacgt gtcggagccg gtgaccgcga ggatggtgtc 83040
cttgatgacc tccatctccc ggaaggcctg gtcgggggcc tcggggagag ccaccaccaa 83100
gcggtgtacg agcaacccgg ggaggttctc ggccaagagc gccgtctccg gaagcccgtg 83160
ggcccggtgg agcgcgcaca ggtgttccag cagcggccgc cagcatgccc gcgcgtctac 83220
cggggcaatg gccgttcccg acaacagaaa cgccgccatg gcggcgcgca gcttggccgt 83280
ggccagaaac gccgggtcgt ccgccccgtt tgccgtctcg gccgtggggg ttggcggttg 83340
gcgaaggccg gctaggctcg ccaataggcg ctgcataggt ccgtccgagg gcggaccggc 83400
gggtgaggtc gtgacgacgg gggcctcgga cgggagaccg cggtctgcca tgacgcccgg 83460

-continued ctcgcgtggg tgggggacag cgtagaccaa cgacgagatc gggcgggaat gactgtcgtg 83520
cgctgtaggg agcggcgaat tatcgatccc ccgcggccct ccaggaaccc cgcaggcgtt 83580
gcgagtaccc cgcgtcttcg cggggtgtta tacggccact taagtcccgg catcccgttc 83640
gcggacccag gcccggggga ttgtccggat gtgcgggcag cccggacggc gtgggttgcg 83700
gactttctgc ggggcggccc aaatggccct ttaaacgtgt gtatacggac gcgccgggcc 83760
agtcggccaa cacaacccac cggaggcggt agccgcgttt ggctgtgggg tgggtggttc 83820
cgccttgcgt gagtgtcctt tcgacccccc tcccccgggt tttgttaggt cgcgatctgc 83880
agtcgcaatg aagaccaatc cgctacccgc aacccccttcc gtgtggggcg ggagtaccgt 83940
ggaactcccc cccaccacac gcgataccgc gggacagggc ctgcttcggc gcgtcctgcg 84000
ccccccgatc tctcgccgcg acggcccagt gctccccagg gggtcgggac cccggagggc 84060
ggccagcacg ctgtggttgc ttggcctgga cggcacagac gcgccccctg gggcgctgac 84120
ccccaacgac gataccgaac aggccctgga caagatcctg cggggcacca tgcgcggggg 84180
ggcggccctg atctgctccc cgcgccatca tctaacccgc caagtgatcc tgacggatct 84240
gtgccaaccc aacgcggatc gtgccgggac gctgcttctg gcgctgcggc accccgccga 84300
cctgcctcac ctggcccacc agcgcgcccc gccaggccgg cagaccgagc ggctgggcga 84360
ggcctggggc cagctgatgg aggcgaccgc cctggggtcg gggcgagccg agagcgggtg 84420
cacgcgcgcg ggcctcgtgt cgtttaactt cctggtggcg gcgtgtgccg cctcgtacga 84480
cgcgcgcgac gccgccgatg cggtacgggc ccacgtcacg gccaactacc gcgggacgcg 84540
ggtgggggcg cgcctggatc gtttttccga gtgtctgcgc gccatggttc acacgcacgt 84600
cttcccccac gaggtcatgc ggtttttcgg ggggctggtg tcgtgggtca cccaggacga 84660
gctagcgagc gtcaccgccg tgtgcgccgg gccacaggag gcggcgcaca ccggccaccc 84720
gggccggccc cgctcggccg tgatcctccc ggcgtgtgcg ttcgtggacc tggacgccga 84780
gctggggctg gggggcccgg gtgcggcgtt tctgtacctg gtattcactt accgccagcg 84840
ccgggaccag gagctgtgtt gtgtgtacgt gatcaagagc cagctccccc cgcgcgggtt 84900
ggagccggcc ctggagcggc tgtttgggcg cctccggatc accaacacga ttcacggcac 84960
cgaggacatg acgcccccgg ccccaaaccg aaaccccgac ttccccctcg cgggcctggc 85020
cgccaatccc caaaccccgc gttgctcggc tggccaggtc acgaaccccc agttcgccga 85080
caggctgtac cgctggcagc cggacctgcg gggcgccccc accgcacgca cctgtacgta 85140
cgccgccttt gcagagctcg gcatgatgcc cgaggatagt ccccgctgcc tgcaccgcac 85200
cgagcgcttt ggggcggtca gcgtccccgt tgtcatcctg gaaggcgtgg tgtggcgccc 85260
cggcgagtgg cgggcatgcg cgtgagcgta gcaaacgccc cgcccacaca acgctccgcc 85320
cccaacccct tccccgctgt cactcgtggt tcgttgaccc ggacgtccgc caaataaagc 85380
cactgaaacc cgaaacgcga gtgttgtaac gtcctttggg cgggaggaag ccacaaaatg 85440
caaatgggat acatggaagg aacacacccc cgtgactcag gacatcggcg tgtccttttg 85500
ggtttcactg aaactggccc gcgccccacc cctgcgcgat gtggataaaa agccagcgcg 85560
ggtggtttag ggtaccacag gtgggtgctt tggaaacttg tcggtcgccg tgctcctgtg 85620
agcttgcgtc cctccccggt ttcctttgcg ctcccgcctt ccggacctgc tcttgcctat 85680
cttctttggc tctcggtgcg attcgtcagg cagcggcctt gtcgaatctc gaccccacca 85740
ctcgccggac ccgccgacgt cccctctcga gcccaccgaa acccgccgcg tctgttgaaa 85800

-continued

```
tggccagccg cccagccgca tcctctcccg tcgaagcgcg ggccccggtt gggggacagg  85860
aggccggcgg ccccagcgca gccacccagg gggaggccgc cggggcccct ctcgcccacg  85920
gccaccacgt gtactgccag cgagtcaatg gcgtgatggt gctttccgac aagacgcccg  85980
ggtccgcgtc ctaccgcatc agcgatagca actttgtcca atgtggttcc aactgcacca  86040
tgatcatcga cggagacgtg gtgcgcgggc gcccccagga cccgggggcc gcggcatccc  86100
ccgctccctt cgttgcggtg acaaacatcg gagccggcag cgacggcggg accgccgtcg  86160
tggcattcgg gggaacccca cgtcgctcgg cggggacgtc taccggtacc cagacggccg  86220
acgtccccac cgaggccctt gggggccccc ctcctcctcc ccgcttcacc ctgggtggcg  86280
gctgttgttc ctgtcgcgac acacggcgcc gctctgcggt attcgggggg gagggggatc  86340
cagtcggccc cgcggagttc gtctcggacg accggtcgtc cgattccgac tcggatgact  86400
cggaggacac ggactcggag acgctgtcac acgcctcctc ggacgtgtcc ggcggggcca  86460
cgtacgacga cgcccttgac tccgattcgt catcggatga ctccctgcag atagatggcc  86520
ccgtgtgtcg cccgtggagc aatgacaccg cgcccctgga tgtttgcccc gggacccccg  86580
gcccgggcgc cgacgccggt ggtccctcag cggtagaccc acacgcgccg acgccagagg  86640
ccggcgctgg tcttgcggcc gatcccgccg tggcccggga cgacgcggag gggctttcgg  86700
acccccggcc acgtctggga acgggcacgg cctaccccgt ccccctggaa ctcacgcccg  86760
agaacgcgga ggccgtggcg cgctttctgg gagatgccgt gaaccgcgaa cccgcgctca  86820
tgctggagta cttttgccgg tgcgcccgcg aggaaaccaa gcgtgtcccc cccaggacat  86880
tcggcagccc ccctcgcctc acggaggacg actttgggct tctcaactac gcgctcgtgg  86940
agatgcagcg cctgtgtctg gacgttcctc cggtcccgcc gaacgcatac atgccctatt  87000
atctcaggga gtatgtgacg cggctggtca acgggttcaa gccgctggtg agccggtccg  87060
ctcgccttta ccgcatcctg ggggttctgg tgcacctgcg gatccggacc cgggaggcct  87120
cctttgagga gtggctgcga tccaaggaag tggccctgga ttttggcctg acggaaaggc  87180
ttcgcgagca cgaagcccag ctggtgatcc tggcccaggc tctggaccat tacgactgtc  87240
tgatccacag cacaccacac acgctggtcg agcgggggct gcaatcggcc ctgaagtatg  87300
aggagtttta cctaaagcgt tttggcgggc actacatgga gtccgtcttc cagatgtaca  87360
cccgcatcgc cggctttttg gcctgccggg ccacgcgcgg catgcgccac atcgccctgg  87420
ggcgagaggg gtcgtggtgg gaaatgttca agttcttttt ccaccgcctc tacgaccacc  87480
agatcgtacc gtcgaccccc gccatgctga acctggggac ccgcaactac tacacctcca  87540
gctgctacct ggtaaacccc caggccacca caaacaaggc gaccctgcgg gccatcacca  87600
gcaacgtcag tgccatcctc gcccgcaacg ggggcatcgg gctatgcgtg caggcgttta  87660
acgactccgg ccccgggacc gccagcgtca tgcccgccct caaggtcctt gactcgctgg  87720
tggcggcgca caacaaagag agcgcgcgtc cgaccggcgc gtgcgtgtac ctggagccgt  87780
ggcacaccga cgtgcgggcc gtgctccgga tgaagggggt cctcgccggc gaagaggccc  87840
agcgctgcga caatatcttc agcgccctct ggatgccaga cctgtttttc aagcgcctga  87900
ttcgccacct ggacggcgag aagaacgtca catggaccct gttcgaccgg gacaccagca  87960
tgtcgctcgc cgactttcac ggggaggagt tcgagaagct ctaccagcac ctcgaggtca  88020
tggggttcgg cgagcagata cccatccagg agctggccta tggcattgtg cgcagcgcgg  88080
ccacgaccgg gagccccttc gtcatgttca aagacgcggt gaaccgccac tacatctacg  88140
acacccaggg ggcggccatc gccggctcca acctctgcac cgagatcgtc catccggcct  88200
```

ccaagcgatc cagtggggtc tgcaacctgg gaagcgtgaa tctggcccga tgcgtctcca 88260
ggcagacgtt tgactttggg cggctccgcg acgccgtgca ggcgtgcgtg ctgatggtga 88320
acatcatgat cgacagcacg ctacaaccca cgccccagtg cacccgcggc aacgacaacc 88380
tgcggtccat gggaatcggc atgcagggcc tgcacacggc ctgcctgaag ctggggctgg 88440
atctggagtc tgccgaattt caggacctga acaaacacat cgccgaggtg atgctgctgt 88500
cggcgatgaa gaccagcaac gcgctgtgcg ttcgcggggc ccgtcccttc aaccacttta 88560
agcgcagcat gtatcgcgcc ggccgctttc actgggagcg ctttccggac gcccggccgc 88620
ggtacgaggg cgagtgggag atgctacgcc agagcatgat gaaacacggc ctgcgcaaca 88680
gccagtttgt cgcgctgatg cccaccgccg cctcggcgca gatctcggac gtcagcgagg 88740
gctttgcccc cctgttcacc aacctgttca gcaaggtgac ccgggacggc gagacgctgc 88800
gccccaacac gctcctgcta aaggaactgg aacgcacgtt tagcgggaag cgcctcctgg 88860
aggtgatgga cagtctcgac gccaagcagt ggtccgtggc gcaggcgctc ccgtgcctgg 88920
agcccaccca ccccctccgg cgattcaaga ccgcgtttga ctacgaccag aagttgttga 88980
tcgacctgtg tgcggaccgc gccccctacg tcgaccatag ccaatccatg accctgtatg 89040
tcacggagaa ggcggacggg accctcccag cctccaccct ggtccgcctt ctggtccacg 89100
catataagcg cggactaaaa acagggatgt actactgcaa ggttcgcaag gcgaccaaca 89160
gcggggtctt tggcggcgac gacaacattg tctgcacgag ctgcgcgctg tgaccgacaa 89220
accccctccg cgccaggccc gccgccactg tcgtcgccgt cccacgctct cccctgctgc 89280
catggattcc gcggccccag ccctctcccc cgctctgacg gcccttacgg gccagagcgc 89340
gacggcggac ctggcgatcc agattccaaa gtgccccgac cccgagaggt acttctacac 89400
ctcccagtgt cccgacatta accacctgcg ctccctcagc atccttaacc gctggctgga 89460
aaccgagctt gttttcgtgg gggacgagga ggacgtctcc aagctttccg agggcgagct 89520
cagcttttac cgcttcctct tcgctttcct gtcggccgcc gacgacctgg ttacggaaaa 89580
cctgggcggc ctctccggcc tgtttgagca gaaggacatt ctccactact acgtggagca 89640
ggaatgcatc gaagtcgtac actcgcgcgt gtacaacatc atccagctgg tgcttttcca 89700
caacaacgac caggcgcgcc gcgagtacgt ggccggcacc atcaaccacc cggccatccg 89760
cgccaaggtg gactggttgg aagcgcgggt gcgggaatgc gcctccgttc cggaaaagtt 89820
cattctcatg atcctcatcg agggcatctt ttttgccgcc tcgtttgccg ccatcgccta 89880
ccttcgcacc aacaaccttc tgcgggtcac ctgccagtca aacgacctca tcagccggga 89940
cgaggccgtg cacacgacgg cctcgtgtta catctacaac aactacctcg gcgggcacgc 90000
caagcccccg cccgaccgcg tgtacgggct gttccgccag gcggtcgaga tcgagatcgg 90060
atttatccga tcccaggcgc cgacggacag ccatatcctg agcccggcgg cgctggcggc 90120
catcgaaaac tacgtgcgat tcagcgcgga tcgcctgttg ggccttatcc acatgaagcc 90180
actgttttcc gccccacccc ccgacgccag ctttccgctg agcctcatgt ccaccgacaa 90240
acacaccaat tttttcgagt gtcgcagcac ctcctacgcc ggggcggtcg tcaacgatct 90300
gtgagtgtcg cggcgcgctt ctacccgtgt ttgcccataa taaacctctg aaccaaactt 90360
tgggtctcat tgtgattctt gtcagggacg cgggggtggg agaggataaa aggcggcgca 90420
aaaagcagta accaggtccg tccagattct gcgggcatag aataccataa ttttattggt 90480
gggtcgtttg ttcggggaca agcgcgctcg tctgacgttt gggctactcg tcccagaatt 90540

-continued

```
tggccaggac gtccttgtag aacgcgggtg ggggggcctg ggtccgcaac tgctccagaa  90600
acctgtcggc gatatcaggg gccgtgatat gccgggtcac gatagatcgc gccaggtttt  90660
cgtcgcggat gtcctggtag ataggcaggc gtttcagaag agtccacggc ccccgctcct  90720
tggggccgat aagcgatatg acgtacttaa tgtagcggtg ttccaccagc tcggtgatgg  90780
tcatgggatc ggggagccag tccagggact ctggggcgtc gtggatgacg tggcgtcgcc  90840
ggttggccac ataactgcgg tgctcttcca gcagctgcgc gttcgggacc tggacgagct  90900
cgggcggggt gagtatctcc gaggaggacg acctggggcc ggggtggccc ccggtaacgt  90960
cccggggatc cagggggagg tcctcgtcgt cttcgtatcc gccggcgatc tgttgggtta  91020
gaatttcggt ccacgagacg cgcgtctcgg tgccgccggc ggccggcggc agagggggcc  91080
tggtttccgt ggagcgcgag ctggtgtgtt cccggcggat ggcccgccgg gtctgagagc  91140
gactcggggg ggtccagtga cattcgcgca gcacatcctc cacggaggcg taggtgttat  91200
tgggatggag gtcggtgtgg cagcggacaa agagggccag gaactggggg tagctcatct  91260
taaagtactt cagtatatcg cgacagttga tcgtgggaat gtagcaggcg ctaatatcca  91320
acacaatatc acagcccatc aacaggaggt cagtgtccgt ggtgtacacg tacgcgaccg  91380
tgttggtgtg atagaggttg gcgcaggcat cgtccgcctc caactgaccc gagttaatgt  91440
aggcgtaccc cagggcccgg agaacgcgaa tacagaacag atgcgccaga cgcagggccg  91500
gcttcgaggg cgcggcggac ggcagcgcgg ctccggaccc ggccgtcccc cgggtccccg  91560
aggccagaga ggtgccgcgt cggcgcatgt tggaaaaggc agagctgggt ctggagtcgg  91620
tgatgggggga aggcggtgga gaggcgtcca cgtcactggc ctcctcgtcc gtccggcact  91680
gggccgtcgt gcgggccagg atggccttgg ctccaaacac aaccggctcc atacaattga  91740
ccccgcgatc ggtaacgaag atggggaaaa gggacttttg ggtaaacacc tttaataagc  91800
gacagaggca gtgtagcgta atggcctcgc ggtcgtaact ggggtatcgg cgctgatatt  91860
tgaccaccaa cgtgtacatg acgttccaca ggtccacggc aatgggggtg aagtacccgg  91920
ccggggcccc aaggccccgg cgcttgacca gatggtgtgt gtgggcaaac ttcatcatcc  91980
cgaacaaacc catgtcaggt cgattgtaac tgcggatcgg cctaactaag gcgtggttgg  92040
tgcgacggtc cgggacaccc gagcctgtct ctctgtgtat ggtgacccag acaacaacac  92100
cgacacaaga ggacaataat ccgttagggg acgctcttta taatttcgat ggcccaactc  92160
cacgcggatt ggtgcagcac cctgcatgcg ccggtgcggg ccaaccttcc ccccgctcat  92220
tgcctcttcc aaaagggtgt ggcctaacga gctgggggcg tatttaatca ggctagcgcg  92280
gcgggcctgc cgtagtttct ggctcggtga gcgacggtcc ggttgcttgg gtcccctggc  92340
tgccatcaaa accccaccct cgcagcggca tacgcccccct ccgcgtcccg cacccgagac  92400
cccggcccgg ctgccctcac caccgaagcc cacctcgtca ctgtggggtg ttcccagccc  92460
gcgttgggat gacggattcc cctggcggtg tggcccccgc ctcccacgtg gaggacgcgt  92520
cggacgcgtc cctcgggcag ccggaggagg gggcgccctg ccaggtggtc ctgcagggcg  92580
ccgaacttaa tggaatccta caggcgtttg ccccgctgcg cacgagcctt ctggactcgc  92640
ttctggttat gggcgaccgg ggcatcctta tccataacac gatctttggg gagcaggtgt  92700
tcctgcccct ggaacactcg caattcagtc ggtatcgctg gcgcggaccc acggcggcgt  92760
tcctgtctct cgtggaccag aagcgctccc tcctgagcgt gtttcgcgcc aaccagtacc  92820
cggacctacg tcgggtggag ttggcgatca cgggccaggc cccgtttcgc acgctggttc  92880
agcgcatatg gacgacgacg tccgacggcg aggccgttga gctagccagc gagacgctga  92940
```

-continued

```
tgaagcgcga actgacgagc tttgtggtgc tggttcccca gggaaccccc gacgttcagt  93000
tgcgcctgac gaggccgcag ctcaccaagg tccttaacgc gaccggggcc gatagtgcca  93060
cgcccaccac gttcgagctc ggggttaacg gcaaaatttc cgtgttcacc acgagtacct  93120
gcgtcacatt tgctgcccgc gaggagggcg tgtcgtccag caccagcacc caggtccaga  93180
tcctgtccaa cgcgctcacc aaggcgggcc aggcggccgc caacgccaag acggtgtacg  93240
gggaaaatac ccatcgcacc ttctctgtgg tcgtcgacga ttgcagcatg cgggcggtgc  93300
tccggcgact gcaggtcggc gggggcaccc tcaagttctt cctcacgacc cccgtcccca  93360
gtctgtgcgt caccgccacc ggtcccaacg ctgtatcggc ggtatttctc ctgaaacccc  93420
agaagatttg cctggactgg ctgggtcata gccaggggtc tccttcagcc gggagctcgg  93480
cctcccgggc ctctgggagc gagccaacag acagcaagga ctccgcgtcg gacgcggtca  93540
gccacggcga tccggaagac ctcgatggcg ctgcccgggc gggagaggcg ggggcctcgc  93600
acgcctgtcc gatgccgtcg tcgaccacgc gggtcactcc cacgaccaag cgggggcgct  93660
cggggggcga ggatgcgcgc gcggacacgg ccctaaagaa acctaagacg gggtcgccca  93720
ccgcaccccc gcccgcagat ccagtccccc tggacacgga ggacgactcc gatgcggcgg  93780
acgggacggc ggcccgtccc gccgctccag acgcccggag cggaagccgt tacgcgtgtt  93840
actttcgcga cctcccgacc ggagaagcaa gccccggcgc cttctccgcc ttccgggggg  93900
ggccccaaac cccgtatggt tttggattcc cctgacgggg cggggccttg gcggccgccc  93960
aactctcgca ccatcccggg ttaatgtaaa taaacttggt attgcccaac actctcccgc  94020
gtgtcgcgtg tggttcatgt gtgtgcctgg cgtcccccac cctcgggttc gtgtatttcc  94080
tttccctgtc cttataaaag ccgtatgtgg ggcgctgacg gaaccacccc gcgtgccatc  94140
acggccaagg cgcgggatgc tccgcaacga cagccaccgg gccgcgtccc cggaggacgg  94200
ccagggacgg gtcgacgacg gacggccaca cctcgcgtgc gtgggggccc tggcgcgggg  94260
gttcatgcat atctggcttc aggccgccac gctgggtttt gcgggatcgg tcgttatgtc  94320
gcgcgggccg tacgcgaatg ccgcgtctgg ggcgttcgcc gtcgggtgcg ccgtgctggg  94380
ctttatgcgc gcaccccctc ccctcgcgcg gcccaccgcg cggatatacg cctggctcaa  94440
actggcggcc ggtggagcgg cccttgttct gtggagtctc ggggagcccg gcacgcagcc  94500
gggggccccg gccccgggcc cggccaccca gtgcctggcg ctgggcgccg cctatgcggc  94560
gctcctggtg ctcgccgatg acgtctatcc gctctttctc ctcgccccgg ggcccctgtt  94620
cgtcggcacc ctggggatgg tcgtcggcgg gctgacgatc ggaggcagcg cgcgctactg  94680
gtggatcggt gggcccgccg cggccgcctt ggccgcggcg gtgttggcgg gcccgggggc  94740
gaccaccgcc agggactgct tctccagggc gtgccccgac caccgccgcg tctgcgtcat  94800
cgtcgcaggc gagtctgttt cccgccgccc ccccggaggac ccagagcgac ccggggaccc  94860
cgggccaccg tccccccccga caccccaacg atcccagggg ccgccggccg atgaggtcgc  94920
accggccggg gtagcgcggc ccgaaaacgt ctgggtgccc gtggtcacct ttctgggggc  94980
gggcgcgctc gccgtcaaga cggtgcgaga acatgcccgg ggaacgccgg gcccgggcct  95040
gccgctgtgg ccccaggtgt ttctcggagg ccatgtggcg gtggccctga cggagctgtg  95100
tcaggcgctt gcgccctggg accttacgga cccgctgctg tttgttcacg ccggactgca  95160
ggtcatcaac ctcgggttgg tgtttcggtt ttccgaggtt gtcgtgtatg cggcgctagg  95220
gggtgccgtg tggatttcgt tggcgcaggt gctggggctc cggcgtcgcc tgcgcaggaa  95280
```

ggaccccggg gacggggccc ggttggcggc gacgcttcgg ggcctcttct tctccgtgta 95340
cgcgctgggg tttggggtgg gggcgctgct gtgccctccg gggtcaacgg gcgggcggtc 95400
gggcgattga tatattttc aataaaaggc attagtcccg aagaccgccg gtgtgtgatg 95460
atttcgccat aacacccaaa ccccggatgg ggcccgggta taaattccgg aaggggacac 95520
gggctaccct cactaccgag ggcgcttggt cgggaggccg catcgaacgc acaccccat 95580
ccggtggtcc gtgtggaggt cgttttcagt gcccggtctc gctttgccgg gaacgctagc 95640
cgatccctcg cgagggggag gcgtagggca tggccccggg gcgggtgggc cttgccgtgg 95700
tcctgtggag cctgttgtgg ctcggggcgg gggtgtccgg gggctcggaa actgcctcca 95760
ccgggcccac gatcaccgcg ggagcggtga cgaacgcgag cgaggccccc acatcggggt 95820
cccccgggtc agccgccagc ccggaagtca cccccacatc gaccccaaac cccaacaatg 95880
tcacacaaaa caaaaccacc cccaccgagc cggccagccc cccaacaacc cccaagccca 95940
cctccacgcc caaaagcccc cccacgtcca cccccgaccc caaacccaag aacaacacca 96000
cccccgccaa gtcgggccgc cccactaaac cccccgggcc cgtgtggtgc gaccgccgcg 96060
acccattggc ccggtacggc tcgcgggtgc agatccgatg ccggtttcgg aattccaccc 96120
gcatggagtt ccgcctccag atatggcgtt actccatggg tccgtccccc ccaatcgctc 96180
cggctcccga cctagaggag gtcctgacga acatcaccgc cccacccggg ggactcctgg 96240
tgtacgacag cgcccccaac ctgacggacc cccacgtgct ctgggcggag ggggccggcc 96300
cgggtgccga ccctccgttg tattctgtca ccgggccgct gccgacccag cggctgatta 96360
tcggcgaggt gacgcccgcg acccagggaa tgtattactt ggcctggggc cggatggaca 96420
gcccgcacga gtacgggacg tggtgcgcg tccgcatgtt ccgccccccg tctctgaccc 96480
tccagcccca cgcggtgatg gagggtcagc cgttcaaggc gacgtgcacg gccgacgcct 96540
actacccgcg taaccccgtg gagttggtct ggttcgagga cgaccgccag gtgtttaacc 96600
cgggccagat cgacacgcag acgcacgagc accccgacgg gttcaccacc gtctctaccg 96660
tgacctccga ggctgtcggc ggccaggtcc ccccgcggac cttcacctgc cagatgacgt 96720
ggcaccgcga ctccgtgaca ttctcgcgac gcaatgccac cgggctggcc ctggtgctgc 96780
cgcggccaac catcaccatg gaatttgggg tccggcatgt ggtctgcacg gccggctgcg 96840
tccccgaggg cgtgacgttt gcctggttcc tgggggacga cccctcaccg gcggctaagt 96900
cggccgttac ggcccaggag tcatgcgacc accccgggct ggctacggtc cggtccaccc 96960
tgcccatttc gtacgactac agcgagtaca tctgtcggtt gaccggatat ccggccggga 97020
ttcccgttct agaacaccac ggcagtcacc agcccccacc cagggacccc accgagcggc 97080
aggtgatcga ggcgatcgag tgggtgggga ttggaatcgg ggttctcgcg gcgggggtcc 97140
tggtcgtaac ggcgatcgtg tacgtcgtcc gcacatcaca gtcgcggcag cgtcatcggc 97200
ggtaacgcga gacccccccg ttaccttttt aatatctata tagtttggtc ccccctctat 97260
cccgcccacc gctgggcgct ataaagccgc caccctctct tccctcaggt catccttggt 97320
cgatcccgaa cgacacacgg cgtggagcaa aacgcctccc cctgagccgc tttcctacca 97380
acacaccggc atgcctctgc gggcatcgga acacgcctac cggcccctgg gccccgggac 97440
acccccccatg cgggctcggc tccccgccgc ggcctgggtt ggcgtcggga ccatcatcgg 97500
gggagttgtg atcattgccg cgttggtcct cgtgccctcg cgggcctcgt gggcactttc 97560
cccatgcgac agcggatggc acgagttcaa cctcgggtgc atatcctggg atccgacccc 97620
catggagcac gagcaggcgg tcggcggctg tagcgccccg gcgaccctga tcccccgcgc 97680

```
ggctgccaaa cagctggccg ccgtcgcacg cgtccagtcg gcaagatcct cgggctactg  97740
gtgggtgagc ggagacggca ttcgggcctg cctgcggctc gtcgacggcg tcggcggtat  97800
tgaccagttt tgcgaggagc ccgcccttcg catatgctac tatccccgca gtcccggggg  97860
ctttgttcag tttgtaactt cgacccgcaa cgcgctgggg ctgccgtgag gcgcgtgtac  97920
tgcggtctgt ctcgtctcct cttctcccct tccctccccc tccgcatccc aggatcacac  97980
cggccaacga gggttggggg gtccggcacg gacccaaaat aataaacaca caatcacgtg  98040
cgataaaaag aacacgcggt cccctgtggt gtttttggtt atttttatta aatctcgtcg  98100
acaaacaggg ggaaaggggc gtggtctagc gacggcagca cgggcggagg cgttcaccgg  98160
ctccggcgtc cttcgcgttt aagcttggtc aggagggcgc tcagggcggc gacgttggtc  98220
gggccgtcgt tggtcagggc gttggctcga tggcgggcga ggacgggcga ggggctcaac  98280
ggcgggggcg ggggcccggt gcggcccggg ggggaaaata gggcggatcc cccccagtcg  98340
tacaggggat tttccgcctc aatgtacggg gaggccggcg ctgcattcgc cgtgttcacg  98400
cagacgtttt cgtagacccg catccatggt atttcctcgt agacacgccc cccgtcctcg  98460
cgcaccgtct cgtatattga ctcgtcgtcc tcgtaggggg cgtgccgttc gcgggccgag  98520
gcggcgtggg tggctttgcg gcgggcgtcg tcgtcgtcgt cgtcggccgt cagatacgtg  98580
gcttccatct ggtcgggttc tccctccggg gcgggtcccc acacccgtgg ccgatcgagg  98640
ctccccagag acgcgcgccg gacgaggagg gggcacgtcg ccgccggcgg tcgcctgtcg  98700
ggtcccgcga cgttacgggc cgggaggcgc gggggcacct cccccatgtg cgtgtaatac  98760
gtggccggct gtgcggccgc agcgggggc tcggcgaccg ggtcgttcgc atccggaagc  98820
gggggccccg cgccgtccgc gcggcgcctc cggaacctcc gggtggacgc gggggtcgag  98880
tgtaggcgag gtcgggggag gggcgggggc tcgttgtcgc gccgcgcccg ctgaatcttt  98940
tcccgacagg tcccaccccc cgcgcgatgc ccccccgggc cgctggccat gtcgtccggg  99000
ggaggccccg cggaccacgt cgtccggcga gacgccacga gccgcaggat ggactcgtag  99060
tggagcgacg gcgccccgct gcggagcaga tccgcggcca gggcggcccc gaaccaagcc  99120
ttgatgctca actccatccg ggcccagctg gggcggtca tcgtggggaa caggggggcg  99180
gtggtccgac agaaacgctc ctggctgtcc accgcggccc gcagatactc gttgttcagg  99240
ctgtcggtgg cccagacgcc gtacccggtg agggtcgcgt tgatgatata ctgggcgtgg  99300
tgatggacga tcgacagaac ctccaccgtg gatacgacgg tatccacggt cccgtacgta  99360
ccgccgctcc gcttgccggt ctgccacagg ttggctaggc gcgtcaggtg gcccaggacg  99420
tcgctgaccg ccgccctgag cgccatgcac tgcatggagc cggttgtgcc gctgggaccc  99480
cggtccagat ggcgcgcgaa cgtttccgcg ggcgcctccg ggctgccgcc gagcgggagg  99540
aaccggcgat tggagggact cagccggtga catacgtgct tgtctgtcgt ccacagcatc  99600
caggacgccc accggtacag cacggagacg taggccagga gctcgttgag ccgcagtgcg  99660
gtgtcggtgc tggggcggct tgggtccgcc gggcgcataa agaacatgta ctgctgaatc  99720
cgatggaggg cgtcgcgcag gccggccacg gtggcggcgt acttggccgc cacggccccg  99780
ctcttgaacg gggtgcgcgc cagcagcttt ggcgccaggg tgggccgcag cagcacgtga  99840
aggctggggt cgcagtcgcc cacggggtcc tcggggacgt ccaggccgct gggcaccacc  99900
gtctgcaggt acttccagta ctgcgtgagg atggcgcggc tcaactggcc gccgggcagc  99960
tccacctcgc ccagcgcctg ggtggcggcc gaagcgtagt gccggatgta ctcgtagtgc 100020
```

-continued gggtcgctgg cgagcccgtc cacgatcaaa ctctcgggaa ccgtgttgtg ttgccgcgcg 100080
gccaaccgga cgctgcgatc ggtgcaggtc agaaacgccg gctgcgcgtc gtcggagcgc 100140
tgccgcaagg cgcccacggc cgcgctaagg agcccctccg gggtggggag cagacacccg 100200
ccgaagatgc gccgctcggg aacgcccgcg ttgtcgccgc ggatcaggtt ggcaggcgtc 100260
aggcaccgcg ccagccgcag ggagctcgcg ccgcgcgtcc ggcgctgcat ggtgacgccc 100320
gttcggtcgg gacccgccgg tcggagttat gccgcgtcca gggccatcgg ggcgcttttt 100380
atcgggagga gcttatgggc gtggcgggcc tcccagcccg gtcgcgcgcc tccccgacac 100440
gtgcgcccgc agggcggcgg ccccctcgtc tcccatcagc agtttcctaa actgggacat 100500
gatgtccacc acgcggaccc gcgggcccaa cacggacccg ccgcttacgg gggcgggggg 100560
gaagggctcc aggtccttga gaagaaaggc ggggtctgcc gtcccggaca cgggggcccg 100620
gggcgctgag gaggcggggc gcagatccac gtgctccgcg gccgcgcgga cgtccgccca 100680
gaacttggcg ggggtggtgc gcgcgtacag gggctgggtc gctcggagga cgcacgcgta 100740
gcgcaggggg gtgtacgtgc ccacctcggg ggccgtgaat cccccgtcaa acgcggccag 100800
tgtcacgcac gccaccacgg tgtcggcaaa gcccagcagc cgctgcagga cgagcccggc 100860
ggccagaatg gcgcgcgtgg ccgccgcgtc gtcccggcgc cggtgcgcgt ccccgcacgc 100920
ccgggcgtac tttaaggtca cggtcgccag ggccgtgtgc agcgcgtaca ccgcagcgcc 100980
cagcacggcg ttgagcccgc tgttggcgag cagccggcgc gctgcggtgt cgcccagcgc 101040
ctcgtgctcg gcccccacga ccgcggggct tcccaggggc agggcgcgaa acagctcctc 101100
ccgcgccacg tccgcaaagg cggggtggtg cacgtgcggg tgcaggcgcg cccccacgac 101160
caccgagagc cactggaccg tctgctccgc catcaccgcc agcacatcca gcacgcgccc 101220
caggaaggcg gcctcccgcg tcaaaacgca ccggacggcg tcgggattga agcgggcgag 101280
cagggccccg gtggccaggt acgtcatgcg gccggcatag cgggcggcca cgcgacagtc 101340
gcggtccagc agcgcgcgca ccccgggcca gtacagcagg gaccccagcg agctgcggaa 101400
caccgcggcg tcggggccgg attgggggga cactaacccc cccgcgctca gtaacggcac 101460
ggccgcggcc ccgacgggac gcaacgccgt gaggctcgcg aactgccgcc tcagctcggc 101520
cgccctgtcg tccaggtcag acccgcgcgc ctccgcgtga aggcgcgtcc cgcacaccca 101580
cccgttgatg gccagccgca cgacggcatc cgccaaaaag ctcatcgcct gggcggggct 101640
ggtttttgtt cgacgatccg tcaggtcaag aatcccatcg cccgtgatat accaggccaa 101700
cgcctcgccc tgctgcaggg tttggcggaa aaacaccgcg gggttgtcgg gggaggcgaa 101760
gtgcatgacc cccacgcgcg ataacccgaa cgcgctatcc ggacacgggt aaaacccggc 101820
cggatgcccc agggctaggg cggagcgcac ggactcgtcc cacacggcaa cctgaggggc 101880
cagtcgatcc aacgggaatg ccgcccggag ctccgggccc ggcacgcgtc cctccagaac 101940
ctccaccttg ggcggggaac gggccccgcc gccgtcctcc ggcccgacgg cttccgggta 102000
gtcgtcctcc tcgtactgca gctcctctag gaacagcggc gacggcgcca cccgcgaacc 102060
gccgacccgc cccaaaatag cccgcgcgtc gacgggaccc aggtatcccc cctgccgggc 102120
ctgcggagga ccgcggggaa cctcatcatc atcgtccagg cgaccgcgca ccgactggct 102180
acgggccgca tcgggcccgg ggcgctgccg ggacgctcgg cgatgggatg tgggcggggc 102240
ttccgacgcg cgccgtcgtc gggctcgcgg gccttcccgt cgacggcgca cgggcggctc 102300
gtcgcccgcc atctcctcca gagcctctag ctcgctgtcg tcatccccgc ggaacaccgc 102360
acgcaggtac cccatgaacc ccaccccatc gcccgctggc tcgtccgcca cgggcgaggc 102420
gcgggggcgg gtggatgcgc gcctcctgcg ccccgcgggt tcgcgagccg acatggtggc 102480
gatagacgcg ggttatcgga tgtccgctac cccccaaaaa agaaaaagac cccacagcgc 102540
ggatggaggc cggggtaggt gccgccggac cccctcgcga tgggaatgga cgggagcgac 102600
ggggccggcg caaaaaaacg cagtatctcc cgcgaaggct acccgccgcc ccagcccccg 102660
gccaaatgcg gaaacggtcc cgcgctctcg cctttatacg cgggccgccc tgcgacacaa 102720
tcacccgtcc gtggtttcga atctacacga caggcccgca gacgcggcta acacacacgc 102780
cggcaaccca gaccccagtg ggttggttgc gcggtcccgt ctcctggcta gttctttccc 102840
ccaccaccaa ataatcagac gacaaccgca ggttttgtaa tgtatgtgct cgtgtttatt 102900
gtggatacga accggtgacg ggaggggaaa acccagacgg gggatgcggg tccggtcgcg 102960
ccccctaccc accgtactcg tcaattccaa gggcatcggt aaacatctgc tcaaactcga 103020
agtcggccat atccagagcg ccgtaggggg cggagtcgtg gggggtaaat cccggccccg 103080
gggaatcccc gtcccccaac atgtccagat cgaaatcgtc tagcgcgtcg gcatgcgcca 103140
tcgccacgtc ctcgccgtct aagtggagct cgtcccccag gctgacatcg gtcggggggg 103200
ccgtcgacag tctgcgcgtg tgtcccgcgg ggagaaagga caggcgcgga gccgccagcc 103260
ccgcctcttc gggggcgtcg tcgtccggga gatcgagcag gccctcgatg gtagacccgt 103320
aattgttttt cgtacgcgcg cggctgtacg cgtgttcccg catgaccgcc tcggagggcg 103380
aggtcgtgaa gctggaatac gagtccaact tcgcccgaat caacaccata aagtacccag 103440
aggcgcgggc ctgggtgcca tgcagggtgg gaggggtcgt caacggcgcc cctggctcct 103500
ccgtagccgc gctgcgcacc agcgggaggt taaggtgctc gcgaatgtgg tttagctccc 103560
gcagccggcg ggcctcgatt ggcactcccc ggacggtgag cgctccgttg acgaacatga 103620
agggctggaa cagacccgcc aactgacgcc agctctccag gtcgcaacag aggcagtcaa 103680
acaggtcggg ccgcatcatc tgctcggcgt acgcggccca taggatctcg cgggtcaaaa 103740
atagatacaa atgcaaaaac agaacacgcg ccagacgagc ggtctctcgg tagtacctgt 103800
ccgcgatcgt ggcgcgcagc atttctccca ggtcgcgatc gcgtccgcgc atgtgcgcct 103860
ggcggtgcag ctgccggacg ctggcgcgca ggtaccggta cagggccgag cagaagttgg 103920
ccaacacggt tcgatagctc tcctcccgcg cccgtagctc ggcgtggaag aaacgagaga 103980
gcgcttcgta gtagagcccg aggccgtcgc gggtggccgg aagcgtcggg aaggccacgt 104040
cgccgtgggc gcgaatgtcg atttgggcgc gttcggggac gtacgcgtcc ccccattcca 104100
ccacatcgct gggcagcgtt gataggaatt tacactcccg gtacaggtcg gcgttggtcg 104160
gtagcgccga aaacagatcc tcgttccagg tatcgagcat ggtacatagc gcggggcccg 104220
cgctaaagcc caagtcgtcg aggagacggt taaagagggc ggcggggggg acgggcatgg 104280
gtggggaggg catgagctgg gcctggctca ggcgccccgt tgcgtacagc gggggggccg 104340
ccggggtgtt tttgggaccc ccggctgggc gggggggcgg tggcgaagcg ccgtccgcgt 104400
tcatgtcggc aaacagctcg tcgaccaaga ggtccattgg gtggggttga tacgggaaag 104460
acgatatcgg gcttttgatg cgatcgtccc cgcccgccca gagagtgtgg gacgcccgac 104520
ggcgcgggaa gagaaaaacc cccaaacgcg ttagaggacc ggacggacct tatgggggga 104580
agtgggcagc gggaaccccg tccgttcccg aggaatgaca gcccgtggtc gccaccacgc 104640
atttaagcaa cccgcacggg ccgccccgta cctcgtgact tccccccaca ttggctcctg 104700
tcacgtgaag gcgaaccgag ggcggctgtc caacccaccc cccgccaccc agtcccggtc 104760

-continued cccgtcggat tgggaaacaa aggcacgcaa cgccaacacc gaatgaaccc ctgttggtgc 104820
tttattgtct gggtacggaa gttttcactc gacgggccgt ctggggcgag aagcggagcg 104880
ggctggggct cgaggtcgct cggtggggcg cgacgccgca gaacgccctc gagtcgccgt 104940
ggccgcgtcg acgtcctgca ccacgtctgg attcaccaac tcgttggcgc gctgaagcag 105000
gtttttgccc tcgcagaccg tcacgcggat ggtggtgatg ccaaggagtt cgttgaggtc 105060
ttcgtctgtg cgcggacgcg acatgtccca gagctggacc gccgccatcc gggcatgcat 105120
ggccgccagg cgcccgaccg cggcgcagaa gacgcgcttg ttaaagccgg ccacccgggg 105180
ggtccatggc gcgtcggggt ttgggggggc ggtgctaaag tgcagctttc tggccagccc 105240
ctgcgcgggt gtcttggatc gggttggcgc cgtcgacgcg ggggcgtctg ggagtgcggc 105300
ggattctggc tgggccgatt tcctgccgcg ggtggtctcc gccgccgggg ccgcgggggc 105360
cttagtcgcc acccgctggg ttcgggggggc ccgggggggcg gtggtgggtg tgcgtccggc 105420
ccctccggac ccagcgggtg gcggaggtgc ccgcgcaggc cccgggccgg acaaaaccgc 105480
cccggaaacg ggacgccgcg tccgggggac ctccgggtgt tcgtcgtctt cggatgacga 105540
gcccccgtag agggcataat ccgactcgtc gtactggacg aaacggacct cgcccctctg 105600
gcgcgagcgt gtctgtaggg cgccacggcg ggaggtgtca ggcggactat cgggactcgc 105660
catacctgaa gacggggtgt agtacagatc ctcgtactca tcgcgcggaa cctcccgcgg 105720
acccgacttc acggagcggc gagaggtcat ggttccacga acacgctagg gtcggatgcg 105780
cggacaatta ggcctgggtt cggacggcgg gggtggtgca ggtgtggaga ggtcgagcga 105840
taggggcggc ccgggagaga agagagggtc cgcaaaaccc actggggatg cgtgagtggc 105900
cctctgtggg cggtggggga gagtcttata ggaagtgcat ataaccacaa cccatgggtc 105960
taaccaatcc ccaggggcca agaaacagac acgccccaaa cggtctcggt ttccgcgagg 106020
aaggggaagt cctgggacac cctccacccc cacccctcac cccacacagg gcgggttcag 106080
gcgtgcccgg cagccagtag cctctggcag atctgacaga cgtgtgcgat aatacacacg 106140
cccatcgagg ccatgcctac ataaaagggc accagggccc ccggggcaga catttggcca 106200
gtgttttggg tctcgcaccg cgcgcccccg atcccatcgc gcccgccctc ctcgccgggc 106260
ggctccccgt gcgggcccgc gtctcccgcc gctaaggcga cgagcaagac aaacaacagg 106320
cccgcccgac agacccttct ggggggggccc atcgtcccta acaggaagat gagtcagtgg 106380
ggatccgggg cgatccttgt ccagccggac agcttgggtc gggggtacga tggcgactgg 106440
cacacggccg tcgctactcg cgggggcgga gtcgtgcaac tgaacctggt caacaggcgc 106500
gcggtggctt ttatgccgaa ggttagcggg gactccggat gggccgtcgg gcgcgtctct 106560
ctggacctgc gaatggctat gccggctgac ttttgcgcga ttattcacgc ccccgcgcta 106620
gccagccccg ggcaccacgt aatactgggt cttatcgact cggggtaccg cggaaccgtt 106680
atggccgtgg tcgtagcgcc taaaaggacg cgggaatttg cccccgggac cctgtgggtc 106740
gacgtgacgt tcctggacat cctggcgacc cccccggccc tcaccgagcc gatttccctg 106800
cggcagttcc cgcaactggc gcccccccct ccaaccgggg ccgggatacg cgaagatcct 106860
tggttggagg gggcgctcgg ggccccaagc gtgactacgg ccctaccggc gcgacgccga 106920
gggcggtccc tcgtctatgc cggcgagctg acgccggttc agacggaaca cggggacggc 106980
gtacgagaag ccatcgcctt ccttccaaaa cgcgaggagg atgccggttt cgacattgtc 107040
gtccgtcgcc cggtcaccgt cccggcaaac ggcaccacgg tcgtgcagcc atccctccgc 107100
atgctccacg cggacgccgg gcccgcggcc tgctatgtgt tggggcggtc gtcgctcaac 107160
gcccgcggcc tcctggtcgt tcctacgcgc tggctccccg ggcacgtatg tgcgtttgtt 107220
gtttacaacc ttacgggggt tcctgtgacc ctcgaggccg gcgccaaggt cgcccagctc 107280
ctggttgcgg gggcggacgc tcttccttgg atcccccccgg acaactttca cgggaccaaa 107340
gcgcttcgaa actaccccag gggtgttccg gactcaaccg ccgaacccag gaacccgccg 107400
ctcctggtgt ttacgaacga gtttgacgcg gaggcccccc cgagcgagcg cgggaccggg 107460
ggttttggct ctaccggtat ttagcccaca gctttgggtt cgttccgggc aataaaaaac 107520
gtttgtatcg catctttcct gtgtgtagtt gtttatgttg gatgcctgtg ggtctatcac 107580
acccgcccct ccatcccaca aacacaaaac acacgggttg gatgaaaaca cgcatttatt 107640
gacccaaaac acacggagct gctcgagatg ggccagggcg aggtgcggtt ggggaggctg 107700
taggtctggg aacggacacg cggggacacg attccggttt ggggtccggg agggcgtcgc 107760
cgtttcgggc ggcaggcgcc agcgtaacct ccgggggcgg cgtgtggggg tgccccaagg 107820
agggcgcctc ggtcacccca atcccccccg accgggttcc cccggcaacc ccgaaggcgg 107880
agaggccaag ggcccgttcg gcgatggcca catcctccat gaccacgtca ctctcggcca 107940
tgctccgaat agcctgggag acgagcacat ccgcggactt gtcagccgcc cccacggaca 108000
tgtacatctg caggatggtg gccatacacg tgtccgccag gcgccgcatc ttgtcctgat 108060
gggccgccac ggccccgtcg atcgtggggg cctcgagccc ggggtggtgg cgcgccagtc 108120
gttctaggtt caccatgcag gcgtggtacg tgcgggccaa ggcgcgggcc ttcacgaggc 108180
gtcgggtgtc gtccagggac cccagggcgt catcgagcgt gatgggggcg ggaagtagcg 108240
cgttaacgac cgccagggcc tcctgcagcc gcggctccgc ctccgagggc ggaacggccg 108300
cgcggatcat ctcatattgt tcctcggggc gcgctcccca gccacatata gccccgagaa 108360
gagaagccat cgcgggcggg tactggccct tgggcgcgcg gacgcaatgg ggcaggaaga 108420
cgggaaccgc ggggagaggc gggcggccgg gactcccgtg gaggtgaccg cgctttatgc 108480
gaccgacggg tgcgttatta cctcttcgat cgccctcctc acaaactctc tactgggggc 108540
cgagccggtt tatatattca gctacgacgc atacacgcac gatggccgtg ctgacgggcc 108600
cacggagcaa gacaggttcg aagagagtcg ggcgctctac caagcgtcgg gcgggctaaa 108660
tggcgactcc ttccgagtaa ccttttgttt attggggacg gaagtgggtg ggacccacca 108720
ggcccgcggg cgaacccgac ccatgttcgt ctgtcgcttc gagcgagcgg acgacgtcgc 108780
cgcgctacag gacgccctgg cgcacgggac cccgctacaa ccggaccaca tcgccgccac 108840
cctggacgcg gaggccacgt tcgcgctgca tgcgaacatg atcctggctc tcaccgtggc 108900
catcaacaac gccagccccc gcaccggacg cgacgccgcc gcggcgcagt atgatcaggg 108960
cgcgtcccta cgctcgctcg tggggcgcac gtccctggga caacgcggcc ttaccacgct 109020
atacgtccac cacgaggcgc gcgtgcttgc cgcgtaccgc agggcgtatt atggaagcgc 109080
gcagagtccc ttctggtttc ttagcaaatt cgggccggac gaaaaaagcc tggtgctcac 109140
cactcggtac tacctgcttc aggcccagcg tctgggggc gcgggggcca cgtacgacct 109200
gcaggccatc aaggacatct gcgccaccta cgcgattccc cacgcccccc gccccgacac 109260
cgtcagcgct gcgtccctga cctcgtttgc cgccatcacg cggttctgtt gcacgagcca 109320
gtacgcccgc ggggccgcgg cggccgggtt tccgctttac gtggagcgcc gtattgcggc 109380
cgacgtccgc gagaccagtg cgctggagaa gttcataacc cacgatcgca gttgcctgcg 109440
cgtgtccgac cgtgaattca ttacgtacat ctacctggcc cattttgagt gtttcagccc 109500

-continued cccgcgccta gccacgcatc ttcgggccgt gacgacccac gaccccaacc ccgcggccag 109560
cacggagcag ccctcgcccc tgggcaggga ggccgtggaa caattttttt gtcacgtgcg 109620
cgcccaactg aatatcgggg agtacgtcaa acacaacgtg accccccggg agaccgtcct 109680
ggatggcgat acggccaagg cctacctgcg cgctcgcacg tacgcgcccg gggccctgac 109740
gcccgccccc gcgtattgcg gggccgtgga ctccgccacc aaaatgatgg ggcgtttggc 109800
ggacgccgaa aagctcctgg tcccccgcgg gtggcccgcg tttgcgcccg ccagtcccgg 109860
ggaggacacg gcgggcggca cgccgccccc acagacctgc ggaattgtca agcgcctcct 109920
gagactggcc gccacggaac agcagggcac cacacccccg gcgatcgcgg cgcttatccg 109980
taatgcggcg gtgcagactc ccctgcccgt ctaccggata tccatggtcc ccacgggaca 110040
ggcatttgcc gcgctggcct gggacgactg ggcccgcata acgcgggacg ctcgcctggc 110100
cgaagcggtc gtgtccgccg aagcggcggc gcaccccgac cacggcgcgc tgggcaggcg 110160
gctcacggat cgcatccgcg cccagggccc cgtgatgccc cctggcggcc tggatgccgg 110220
ggggcagatg tacgtgaatc gcaacgagat attcaacggc gcgctggcaa tcacaaacat 110280
catcctggat ctcgacatcg ccctgaagga gcccgtcccc tttcgccggc tccacgaggc 110340
cctgggccac tttaggcgcg gggctctggc tgcggttcag ctcctgtttc ccgcggcccg 110400
cgtggacccc gacgcatatc cctgttattt tttcaaaagc gcatgtcggc ccggcccggc 110460
gtccgtgggt tccggcagcg gactcggcaa cgacgacgac ggggactggt ttccctgcta 110520
cgacgacgcc ggtgatgagg agtgggcgga ggacccgggc gccatggaca catcccacga 110580
tcccccggac gacgaggttg cctactttga cctgtgccac gaagtcggcc ccacggcgga 110640
acctcgcgaa acggattcgc ccgtgtgttc ctgcaccgac aagatcggac tgcgggtgtg 110700
catgcccgtc cccgccccgt acgtcgtcca cggttctcta acgatgcggg gggtggcacg 110760
ggtcatccag caggcggtgc tgttggaccg agattttgtg gaggccatcg ggagctacgt 110820
aaaaaacttc ctgttgatcg atacgggagt gtacgcccac ggccacagcc tgcgcttgcc 110880
gtattttgcc aaaatcgccc ccgacgggcc tgcgtgcgga aggctgctgc cagtgtttgt 110940
gatccccccc gcctgcaaag acgttccggc gtttgtcgcc gcgcacgccg acccgcggcg 111000
cttccatttt cacgccccgc ccacctatct cgcttccccc cgggagatcc gtgtcctgca 111060
cagcctgggt ggggactatg tgagcttctt tgaaaggaag gcgtcccgca acgcgctgga 111120
acactttggg cgacgcgaga ccctgacgga ggtcctgggt cggtacaacg tacagccgga 111180
tgcgggaggg accgtcgagg ggttcgcatc ggaactgctg ggcggatag tcgcgtgcat 111240 cgaaacccac tttcccgaac acgccggcga atatcaggcc gtatccgtcc ggcgggccgt 111300
cagtaaggac gactgggtcc tcctacagct agtccccgtt cgcggtaccc tgcagcaaag 111360
cctgtcgtgt ctgcgcttta agcacggccg ggcgagtcgc gccacggcgc ggacattcgt 111420
cgcgctgagc gtcggggcca acaaccgcct gtgcgtgtcc ttgtgtcagc agtgctttgc 111480
cgccaaatgc gacagcaacc gcctgcacac gctgtttacc attgacgccg gtacgccatg 111540
ctcgccgtcc gttccctgca gcacctctca accgtcgtct tgataacggc gtacggcctc 111600
gtgctcgtgt ggtacaccgt cttcggtgcc agtccgctgc accgatgtat ttacgcggta 111660
cgccccaccg gcaccaacaa cgacaccgcc ctcgtgtgga tgaaaatgaa ccagacccta 111720
ttgtttctgg gggccccgac gcaccccccc aacgggggct ggcgcaacca cgcccatatc 111780
tgctacgcca atcttatcgc gggtagggtc gtgcccttcc aggtcccacc cgacgccatg 111840
aatcgtcgga tcatgaacgt ccacgaggca gttaactgtc tggagaccct atggtacaca 111900
cgggtgcgtc tggtggtcgt agggtggttc ctgtatctgg cgttcgtcgc cctccaccaa 111960
cgccgatgta tgtttggtgt cgtgagtccc gcccacaaga tggtggcccc ggccacctac 112020
ctcttgaact acgcaggccg catcgtatcg agcgtgttcc tgcagtaccc ctacacgaaa 112080
attacccgcc tgctctgcga gctgtcggtc cagcggcaaa acctggttca gttgtttgag 112140
acggacccgg tcaccttctt gtaccaccgc cccgccatcg ggtcatcgt aggctgcgag 112200
ttgatgctac gctttgtggc cgtgggtctc atcgtcggca ccgctttcat atcccggggg 112260
gcatgtgcga tcacataccc cctgtttctg accatcacca cctggtgttt tgtctccacc 112320
atcggcctga cagagctgta ttgtattctg cggcggggcc cggcccccaa gaacgcagac 112380
aaggccgccg ccccggggcg atccaagggg ctgtctggcg tctgcgggcg ctgttgttcc 112440
atcatcctct cgggcatcgc agtgcgattg tgttatatcg ccgtggtggc cggggtggtg 112500
ctcgtggcgc ttcactacga gcaggagatc cagaggcgcc tgtttgatgt atgacgtcac 112560
atccaggccg gcggaaaccg gaacggcata tgcaaattgg aaactgtcct gtcttggggc 112620
ccacccaccc gacgcgtcat atgcaaatga aaatcggtcc cccgaggcca cgtgtagcct 112680
ggatcccaac gaccccgccc atgggtccca attggccgtc ccgttaccaa gaccaaccca 112740
gccagcgtat ccacccccgc ccgggtcccc gcggaagcgg aacggtgtat gtgatatgct 112800
aattaaatac atgccacgta cttatggtgt ctgattggtc cttgtctgtg ccggaggtgg 112860
ggcggggccc ccgcccgggg ggcggaacga ggaggggttt gggagagccg gccccggcac 112920
cacgggtata aggacatcca ccacccggcc ggtggtggtg tgcagccgtg ttccaaccac 112980
ggtcacgctt ctgtgcctct ccccgattcg ggcccggtcg ctcgctaccg gtgcaccacc 113040
accagaggcc atatccgaca ccccagcccc gacggcagcc gacagcccgg tcatggcgac 113100
tgacattgat atgctaattg acctcggcct ggacctctcc gacagcgatc tggacgagga 113160
ccccccccgag ccggcggaga gccgccgcga cgacctggca tcggacagca gcggggagtg 113220
ttcctcgtcg gacgaggaca tggaagaccc ccacggagag gacggaccgg agccgatact 113280
cgacgccgct cgcccggcgg tccgcccgtc tcgtccagaa gaccccggcg tacccagcac 113340
ccagacgcct cgtccgacgg agcggcaggg ccccaacgat cctcaaccag cgccccacag 113400
tgtgtggtcg cgcctcgggg cccggcgacc gtcttgctcc cccgagcagc acgggggcaa 113460
ggtggcccgc ctccaacccc caccgaccaa agcccagcct gcccgcggcg gacgccgtgg 113520
gcgtcgcagg ggtcggggtc gcggtggtcc cggggccgcc gatggtttgt cggacccccg 113580
ccggcgtgcc cccagaacca atcgcaaccc ggggggaccc cgccccgggg cggggtggac 113640
ggacggcccc ggcgcccccc atggcgaggc gtggcgcgga agtgagcagc ccgacccacc 113700
cggaggcccg cggacacggg gcgtgcgcca agcacccccc ccgctaatga cgctggcgat 113760
tgcccccccg cccgcggacc cccgcgcccc ggccccggag cgaaaggcgc ccgccgccga 113820
caccatcgac gccaccacgc ggttggtcct gcgctccatc tccgagcgcg cggcggtcga 113880
ccgcatcagc gagagctttg gccgcagcgc acaggtcatg cacgacccct ttggggggca 113940
gccgtttccc gccgcgaata gcccctgggc cccggtgttg gcgggccaag gagggccctt 114000
tgacgccgag accagacggg tctcctggga aaccttggtc gcccacggcc cgagcctcta 114060
tcgcactttt gccggcaatc ctcgggccgc atcgaccgcc aaggccatgc gcgactgcgt 114120
gctgcgccaa gaaaatttca tcgaggcgct ggcctccgcc gacgagacgc tggcgtggtg 114180
caagatgtgc atccaccaca acctgccgct gcgcccccag gaccccatta tcgggacggc 114240
cgcggctgtg ctggataacc tcgccacgcg cctgcggccc tttctccagt gctacctgaa 114300
ggcgcgaggc ctgtgcggcc tggacgaact gtgttcgcgg cggcgtctgg cggacattaa 114360
ggacattgca tccttcgtgt ttgtcattct ggccaggctc gccaaccgcg tcgagcgtgg 114420
cgtcgcggag atcgactacg cgacccttgg tgtcggggtc ggagagaaga tgcatttcta 114480
cctccccggg gcctgcatgg cgggcctgat cgaaatccta gacacgcacc gccaggagtg 114540
ttcgagtcgt gtctgcgagt tgacggccag tcacatcgtc gcccccccgt acgtgcacgg 114600
caaatatttt tattgcaact ccctgtttta ggtacaataa aaacaaaaca tttcaaacaa 114660
atcgccccac gtgttgtcct tctttgctca tggccggcgg ggcgtgggtc acggcagatg 114720
gcgggggtgg gcccggcgta cggcctgggt gggcggaggg aactaaccca acgtataaat 114780
ccgtccccgc tccaaggccg gtgtcatagt gcccttagga gcttcccgcc cgggcgcatc 114840 ccccctttg cactatgaca gcgacccccc tcaccaacct gttcttacgg gccccggaca 114900
taacccacgt tgcccccct tactgcctca acgccacctg gcaggccgaa acggccatgc 114960
acaccagcaa aactgactcc gcttgcgtgg ccgtgtggag ttacctggtc cgcgcctcct 115020
gtgagaccag cggcacaatc cactgctttt tctttgtggt atacaaggac acccaccata 115080
cccctccgct gattaccgag ctccgcaact ttgcggacct ggttaaccac ccgccggtcc 115140
tacgcgaact ggaggataag cgcggggtgc ggctgcggtg tgcgcggccg tttagcgtcg 115200
ggacgattaa ggacgtctct gggtccggcg cgtcctcggc gggagagtac acgataaacg 115260
ggatcgtgta ccactgccac tgtcggtatc cgttctcaaa aacatgctgg atgggggcct 115320
ccgcggccct acagcacctg cgctccatca gctccagcgg catggccgcc cgcgcggcag 115380
agcatcgacg cgtcaagatt aaaattaagg cgtgatttcc aaccccccat gaatgtgtgt 115440 aaccccccc aaaaaaataa agagccgtaa cccaaccaaa ccaggcgtgg tgtgagtttg 115500
tggacccaaa gccctcagag acaacgcgac aggccagtat ggaccgtgag acttttattt 115560
attaactcac aggggcgctt accgccacag gaataccaga ataatgacca ccacaatcgc 115620
gaccacccca aatacagcat ggcgccccac cacgccacaa cagccctgtc gccggtatgg 115680
ggcatgatca gacgagccgc gagccgcgcg ttgggccctg tacagctcgc gcgaattgac 115740
cctaggaggc cgccacgcgc ccgagttttg cgttcgtcgc tggtcgtcgg gcaccaaagc 115800
cccggacggc tgttcggtcg aacgaacggc cacgacagtg gcataggttg gggggtggtc 115860
cgacatagcc tcggcgtacg tcgggaggcc cgacaagagg tcccttgtga tgtcgggtgg 115920
ggccacaagc ctggtttccg gaagaaacag gggggttgcc aataacccgc cagggccaaa 115980
actccggccc tggcgcacgt cgttcggcgc ggcgccgggc gcgccgagcg gctcgctggg 116040
cggcttggcg tgagcggccc cgctccgacg cctcgccctc tccggaggag gttggtggaa 116100
ttggcacgga cgacaggggc ccagcagagt acggtggagg tgggtccgtg ggggtgtcca 116160
gatcaataac gacaaacggc ccctcgttcc taccagacaa gctatcgtag gggggcgggg 116220
gatcaacaaa cgcgttcccc gcgctccata gacccgcgtc gggttgcgcc gcctccgaag 116280
ccatggatgc gccccaaagc cacgactccc gcgcgctagg tccttggggt aagggaaaag 116340
gccctactcc ccatccaagc cagccaagtt aacgggctac gccttcgggg atgggactgg 116400
caccccggcg gattttgttg ggctggcatg cgtcgcccaa ccgagggccg cgtccacggg 116460
acgcgccttt tataaccccg ggggtcattc ccaacgatca catgcaatct aactggctcc 116520
cctctcctcc cctctcccct ctcccctctc ccctctcccc tctcccctct cccctcttag 116580
gttggggggt ggtccgacat agcctcggcg tacgtcggga ggcccgacaa gaggtccctt 116640

-continued gtgatgtcgg gtggggccac aagcctggtt tccggaagaa acagggggt tgccaagcgg 116700
cccggcccgc gctccccccc ccccggggcc gtgtccttgc tttcccccg tctcccccc 116760
cctcctcctc cttctcctcc tcctcgtttt tccaaacccc gcccacccgg cccggcccgg 116820
cccggccacc gccgcccacc cacccaccgc gggagaccca gccccggtcc cccgttcccc 116880
gggggccgtt atctccagcg ccccgtccgg cgcgccgccc cccgccgcta aaccccatcc 116940
cgcccccggg accccacata taagccccca gccacacgca agaacagaca cgcagaacgg 117000
ctgtgtttat ttaaataaac cgatgtcgga ataaacaaac acaaacaccc gcgacggggg 117060
gacggaggga ggggggtgac gggggacggg aacagacaca aaaaacaacc acaaaaaaac 117120
agccaccccc gacacccccc accccagtct cctcgccttt tcccacccac cccacgcccc 117180
cactgagccc ggtcgatcga cgagcacccc cgcccccgcc cctgccccgg cgacccccgg 117240
cccgcacgat cccgacaaca ataacaaccc caacggaaag cggcggggtg ttgggggagg 117300
cgaggaacaa ccgaggggaa cgggggatgg aaggacggga agtggaagtc ctgataccca 117360
tcctacaccc ccctgccttc caccctccgg ccccccgcga gtccacccgc cggccggcta 117420
ccgagaccga acacggcggc cgccgcagcc gccgcagccg ccgccgacac cgcagagccg 117480
gcgcgcgcac acacaagcgg cagaggcaga aaggccccga gtcattgttt atgtggccgc 117540
gggccagcag acggcccgcg acaccccccc gcccgtgtgg gtatccggcc ccccgccccg 117600
cgccggtcca ttaagggcgc gcgtgcccgc gagatatcaa tccgttaagt gctctgcaga 117660
caggggcacc gcgcccggaa atccattagg ccgcagacga ggaaaataaa attacatcac 117720
ctacccacgt ggtgctgtgg cctgtttttg ctgcgtcatc tgagccttta taaaagcggg 117780
ggcgcggccg tgccgatcgc gggtggtgcg aaagactttc cgggcgcgtc cgggtgccgc 117840
ggctctccgg gcccccctgc agccggggcg gccaaggggc gtcggcgaca tcctcccccct 117900
aagcgccggc cggccgctgg tctgtttttt gttttccccg tttcgggggt gggggggtt 117960
acggtttctg ttttttaaac ccgtctgggg tgtttttcgt tccgtcgccg ggatgtttcg 118020
ttcgttcggc ccctcacggg gcgaaggccg cgtacggccc gggacgaggg gcccccgacc 118080
gcggcggtcc gggccccgtc cgggcccgct cgccggcacg cgacgcgaaa aaggcccccc 118140
ggaggctttt ccgggttccc ggcccggggc ctgagataaa caatcggggt taccgccaac 118200
ggccggcccc cgtggcggcc cggcccgggg ccccggcgga cccaaggggc cccggcccgg 118260
ggccccacaa cggcccggcg catgcgctgt gtttttttt tcctcggtgt tctgccgggc 118320
tccgtcgcct ttcctgttct cgcttcttcc cccccccctt cttcaccccc agtaccctcc 118380
tccctccctt cctcccccgt tatcccactc gtcgagggcg ccccggtgtc gttcaacaaa 118440
gacgccgcgt ttccaggtag gttagacacc tgcttctccc caatagaggg ggggggaccc 118500
aaacgacagg gggcgcccca gaggctaagg tcggccacgc cactcgcggg tgggctcgtg 118560
ttacagcaca ccagcccgtt cttttccccc cctcccaccc ttagtcagac tctgttactt 118620
acccgtccga ccaccaactg ccccccttatc taagggccgg ctggaagacc gccagggggt 118680
cggccggtgt cgctgtaacc ccccacgcca atgacccacg tactccaaga aggcatgtgt 118740
cccaccccgc ctgtgttttt gtgcctggct ctctatgctt gggtcttact gcctgggggg 118800
ggggatgcgg gggaggggg gtgtggaagg aaatgcacgg cgcgtgtgta cccccccccc 118860
aaagttgttc ctaaagcgag gatatggagg agtggcgggt gccgggggac gggggtgatc 118920
tctggcacgc ggggggggaa gggtcggggg aggggggat ggggtaccgg cccacctggc 118980
cgacgcgggt gcgcgtgcct ttgcacacca accccacgtc ccccggcggt ctctaagaag 119040
caccgccccc cctccttcat accaccgagc atgcctgggt gtgggttggt aaccaacacg 119100
cccatcccct cgtctcctgt gattctctgg ctgcaccgca ttcttgtttt ctaactatgt 119160
tcctgtttct gtctccccc cacccctccg ccccaccccc caacacccac gtctgtggtg 119220
tggccgaccc ccttttgggc gccccgtccc gccacccctc ccgtcctttg ttgccctata 119280
gtgtagttaa cccccccccc gccctttgtg gcggccagag gccaggtcag tccgggcggg 119340
caggcgctcg cggaaactta acacccacac ccagcccact gtggttctgg ctccatgcca 119400
gtggcaggat gctttcgggg atcggtggtc aggcagcccg ggccgcggct ctgtggttaa 119460
caccagagcc tgcccaacat ggcacccccca ctcccacgca cccccactcc cacgcacccc 119520
cactcccacg cacccccact cccacgcacc cccactccca cgcaccccca ctcccacgca 119580
cccccactcc cacgcacccc cactcccacg cacccccact cccacgcacc cccactccca 119640
cgcaccccca ctcccacgca cccccactcc cacgcacccc cactcccacg cacccccaag 119700
atccatccaa cacagacagg gaaaagatac aaaagtaaac ctttatttcc caatagacag 119760
caaaaatccc ctgagttttt tattagggcc aacactaaag acccgctggt gtgtggtgcc 119820
cgtgtctttc actttcccct ccccgacacg gattggctgg tgtagtgggc gcggccagag 119880
accacccagc acccgacccc cctccccaca aacacggggg gcgtccctta ttgttttccc 119940
tcgtcccggg tcgacgcccc ctgctccccg gaccacgggt gccgagaccg caggctgcgg 120000
aagtccaggg cgcccactag ggtgccctgg tcgaacagca tgttccccac gggggtcatc 120060
cagaggctgt tccactccga cgcgggggcc gtcgggtact cgggggggcat cacgtggtta 120120 cccgcggtct cggggagcag ggtgcggcgg ctccagccgg ggaccgcggc ccgcagccgg 120180
gtcgccatgt ttcccgtctg gtccaccagg accacgtacg ccccgatgtt ccccgtctcc 120240
atgtccagga tgggcaggca gtcccccgtg atagtcttgt tcacgtaagg cgacagggcg 120300
accacgctag agacccccga gatgggcagg tagcgcgtga ggccgcccgc ggggacggcc 120360
ccggaagtct ccgcgtggcg cgtcttccgg gcacacttcc tcggccccg cggcccagaa 120420 gcagcgcggg ggccgaggga ggtttcctct tgtctccctc ccagggcacc gacggccccg 120480
cccgaggagg cggaagcgga ggaggacgcg gccccggcgg cggaagaggc ggcccccgcg 120540
ggggtcgggg ccgaggagga agaggcagag gaggaagagg cggaggccgc cgaggacgtc 120600
aggggggtcc cgggcccacc ctggccgcgc ccccccggcc ctgagtcgga gggggggtgc 120660
gtcgccgccc tcttggcccc tgccggcgcg aggggggggac gcgtggactg gggggagggg 120720
ttttcctggc ccgacccgcg cctcttcctc ggacgcaccg ccgcctcctg ctcgacagag 120780
acggcggagg ggagcggggc ggcgccggag ggggtgcggc cgcgggaggg cccgtgccca 120840
ccctccacgc ccggcccccc cgagccgcgc gccaccgtcg cacgcgcccg gcacagactc 120900
tgttcttggt tcgcggcctg agccagggac gagtgcgact ggggcacacg gcgcgcgtcc 120960
gcggggcggg cggccggctc cgccccgggg gccggggcgc gggggccggg ccccggaggc 121020
ggcgctcgca cgcacggggc cacggccgcg cgggggcgcg cgggtcccga cgcggccgag 121080
gacgcggggg gcccggggcg gggggcggag cctggcatgg gcgccgcggg gggcctgtgg 121140
ggagaggccg ggggggagtc gctgatcact atggggtctc tgttgtttgc aaggggggcg 121200
ggtctgttga caagggggcc cgtccggccc ctcggccgcc ccgcctccgc ttcaacaacc 121260
ccaaccccaa ccccaacccc cccggagggg ccagacgccc cccgcggcgc cgcggctcgc 121320
gactggcggg agccgccgcc gccgctgctg ttggtggtgg tgttggtgtt actgctgccg 121380
tgtggcccga tgggcgccga ggggggcgct gtccgagccg cggccggctg gggggctgcg 121440
ttagacgccc cgcccgtcac ggggggcgcg gcggtgcctc tgcgtggggg ggcgcggggc 121500
gtccggcggg gggcgggcgg gacgtagtct gctgcaagag acaacggggg gcgcgatcag 121560
gttacgcccc ctccccggcc cgccctttcc tcgcccgccc gcccattcct ccctcctcct 121620
cctcccccag ggtccttgcc gccccccgcc tcaccgtcgt ccaggtcgtc gtcatcctcg 121680
tccgtggtgg gctccgggtg ggtgggcgac agggccctca ccgtgtgccc ccccagggtc 121740
aggtaccgcg gggcgaaccg ctgattgccc gtccagataa agtccacggc cgtgcccgcc 121800
ctgacggcct cctcggcctc catgcgggtc tgggggtcgt tcacgatcgg gatggtgctg 121860
aacgacccgc tgggcgtcac gcccactatc aggtacacca gcttggcgtt gcacagcggg 121920
caggtgttgc gcaattgcat ccaggttttc atgcacggga tgcagaagcg gtgcatgcac 121980
gggaaggtgt cgcagcgcag gtggggcgcg atctcatccg tgcacacggc gcacacgtcg 122040
ccctcgtcgc tccccccgtc ctctcgaggg ggggcgcccc cgcaactgcc ggggtcttcc 122100
tcgcgggggg ggctcccccc cgagaccgcc cccccatcca cgccctgcgg ccccagcagc 122160
cccgtctcga acagttccgt gtccgtgctg tccgcctcgg aggcggagtc gtcgtcatgg 122220
tggtcggcgt ccccccgccc ccccacttcg gtctccgcct cagagtcgct gctgtccggc 122280
aggtctcggt cgcagggaaa cacccagaca tccggggcgg gctaagggga aaaaaggggg 122340
gcgggtaaga atgggggggg atttcccgcg tcaatcagcg cccacgagtt ccccctctcc 122400
ccccccgcct cacaaagtcc tgccccccctg ctggcctcgg aagagggggg agaaaggggt 122460
ctgcaaccaa aggtggtctg ggtccgtcct ttggatcccg acccctcttc ttccctcttc 122520
tcccgccctc cagacgcacc ggagtcgggg gtcccacggc gtcccccaaa tatggcgggc 122580
ggctcctccc caccccccta gatgcgtgtg agtaaggggg gcctgcgtat gagtcagtgg 122640
ggaccacgcc cccaacacgg cgaccccggt ccctgtgtgt ttgttgtggg ggcgtgtctc 122700
tgtgtatgag tcagggggtc ccacggcgac cccgggccct gcgtctgagt caaaggggcc 122760
atgtgtatgt gttgggggtc tgtatatata aagtcagggg gtcacatggc gacccccaac 122820
agggcgaccc cggtccctgt atatataggg tcagggggtt ccgcgccccc taacatggcg 122880
cccccggtcc ctgtatatat agtgtcacgg ggttccacgc cccctaacat ggcgccccaa 122940
catggcgccc ggctcccgtg tatgagtggg ggtcccccaa catgggggcc ggttccaggg 123000
taagggtcgg gggtccccca acatggcgcc ccccaatatg gcgccccaga catggcgccc 123060
ggcccctcac ctcgcgctgg gggcggccct caggccggcg ggtactcgct ccggggcggg 123120
gctccatggg ggtcgtatgc ggctggaggg tcgcggacgg agggtccctg ggggtcgcaa 123180
cgtaggcggg gcttctgtgg tgatgcggag agggggcggc ccgagtctgc ctggctgctg 123240
cgtctcgctc cgagtgccga ggtgcaaatg cgaccagacc gtcgggccag ggctaactta 123300
taccccacgc ctttcccctc cccaaagggg cggcagtgac gattccccca atggccgcgc 123360
gtcccagggg aggcaggccc accgcggggc ggccccgtcc ccggggacca acccggcgcc 123420
cccaaagaat atcattagca tgcacggccc ggcccccgat ttgggggacc aacccggtgt 123480
cccccaaaga accccattag catgcccctc ccgccgacgc aacaggggct tggcctgcgt 123540
cggtgccccg gggcttcccg ccttcccgaa gaaactcatt accatacccg gaaccccagg 123600
ggaccaatgc gggttcattg agcgacccgc gggccaatgc gcgaggggcc gtgtgttccg 123660
ccaaaaaagc aattagcata acccggaacc ccaggggagt ggttacgcgc ggcgcgggag 123720

-continued gcggggaata ccggggttgc ccattaaggg ccgcgggaat tgccggaagc gggaagggcg 123780
gccggggccg cccattaatg agtttctaat taccataccg ggaagcggaa caaggcctct 123840
tgcaagtttt taattaccat accgggaagt gggcggcccg gcccattggg cggtaactcc 123900
cgcccaatgg gccgggcccc gaagactcgg cggacgctgg ttggccgggc cccgccgcgc 123960
tggcggccgc cgattggcca gtcccgcccc cgaggcgggc ccgccttggg ggcggaccgg 124020
ctcccagcgt atatatgcgc ggctcctgcc atcgtctctc cggagagcgg cttggtgcgg 124080
agctcccggg agctccgcgg aagacccagg cgcctcgggt gtaacgttag accgagttcg 124140
ccgggccggc tccgcgggcc agggcccggg cacgggcctc gggccccagg cacggcccga 124200
tgaccgcctc ggcctccgcc acccggcgcc ggaaccgagc ccggtcggcc cgctcgcggg 124260
cccacgagcc gcggcgcgcc aggcgggcgg ccgaggccca gaccaccagg tggcgcaccc 124320
ggacgtgggg cgagaagcgc acccgcgcgg gggtcgcggg ggtcgcgggg gtcgcggggg 124380
tcgcgggggt cgcgggggtc gcgggggtcg cgggggtcgc ggggggctcc ggcgcccccct 124440
ccccgcccgc gcgtcgcagg cgcaggcgcg ccaggtgctc cgcggtgacg cgcaggcgga 124500
gggcgaggcg cggcggaagg cggaaggggc gcgagggggg gtgggagggg tcagccccgc 124560
cccccgggcc cacgccgggc ggtggggacc ggggccgggg ggcggcggcg gtgggccggg 124620
cctctggcgc cggctcgggc ggggggctgt ccggccagtc gtcgtcatcg tcgtcgtcgg 124680
acgcggactc gggaacgtgg agccactggc gcagcagcag cgaacaagaa ggcgggggcc 124740
caccggcggg gggcggcggc ggggcggccg cgggcgcgct cctgaccgcg ggttccgagt 124800
tgggcgtgga ggttacctgg gactgtgcgg ttgggacggc gcccgtgggc ccgggcggcc 124860
gggggcggcg ggggccgcga tggcggcggc ggcgggccat ggagacagag agcgtgccgg 124920
ggtggtagag tttgacaggc aagcatgtgc gtgcagaggc gagtagtgct tgcctgtcta 124980
actcgctagt ctcggccgcg gggggcccgg gctgcccgcc gccgcgcttt aaagggccgc 125040
gcgcgacccc cggggggtgt gtttcggggg ggcccgtttt tggggtctgg ccgctcctcc 125100
cccgctcctc cccgtctgtg ggtggggctc ctcccccgct cctcccccgc tcctcccccg 125160
ctcctccccg tctgtgggtg gggctcctcc cccgctcccg cggccccgcc ccccacgccc 125220
gccgcgcgcg cgcacgccgc ccggaccgcc gcccgccttt tttgcgcgcc gccccgcgcg 125280
cgggggggccc gggctgccac aggtgtaaca acaccaacag aacaccaaca gcacggcgca 125340
ccggcgactc cggttcctca tccacacgtc acgtcatcca acacacctgc ccaacaacac 125400
aactcacagc gacaactcac cgcgcaacaa ctcctgttcc tcatccacac gtcaccgcgc 125460
acccccgct cctccagacg tcccccagcg caacacgccg ctcctgtcac acaccacagc 125520
cccagccctc cccagcccca gccctcccca gccccagccc tccccagccc cagccctccc 125580
cagccccagc cctccccagc cccagccctc cccagcccca gccctcccca gccccagccc 125640
tccccagccc cagccctccc cagccccagc cctccccagc cccagccctc cccagcccca 125700
gccctcccca gccgcgtccc gcgctccctc ggggggggttc gggcatctct acctcagtgc 125760
cgccaatctc aggtcagaga tccaaaccct ccgggggcgc ccgcgcacca ccaccgcccc 125820
tcgccccctc ccgcccctcg ccccctcccg cccctcgccc cctcccgccc ctcgccccct 125880
cccgccccctc gccccctccc gcccctcgcc ccctcccgcc cctcgccccc tcccgcccct 125940
cgccccctcc cgcccctcga ataaacaacg ctactgcaaa acttaatcag gtcgttgccg 126000
tttattgcgt cttcgggttt cacaagcgcc ccgccccgtc ccggcccgtt acagcacccc 126060
gtccccctcg aacgcgccgc cgtcgtcttc gtcccaggcg ccttcccagt ccacaacgtc 126120

-continued ccgtcgcggg ggcgtggcca agcccgcctc cgcccccagc acctccacgg cccccgccgc 126180
cgccagcacg gtgccgctgc ggcccgtggc cgaggcccag cgaatcccgg gcggcgccgg 126240
cggcagggcc cccgggccgt cgtcgtcgcc gcgcagcacc agcggggggg cgtcgtcgtc 126300
gggctccagc agggcgcggg cgcaaaagtc cctccgcggc ccgcgccacc gggccgggcc 126360
ggcgcgcacc gcctcgcgcc ccagcgccac gtacacgggc cgcagcggcg cgcccaggcc 126420
ccagcgcgcg caggcgcggt gcgagtgggc ctcctcctcg cagaagtccg gcgcgccggg 126480
cgccatggcg tcggtggtcc ccgaggccgc cgcccggccg tccagcgccg gcagcacggc 126540
ccggcggtac tcgcgcgggg acatgggcac cggcgtgtcc gggccgaagc gcgtgcgcac 126600
gcggtagcgc acgttgccgc cgcggcacag gcgcagcggc ggcgcgtcgg ggtacaggcg 126660
cgcgtgcgcg gcctccacgc gcgcgaagac ccccgggccg aacacgcggc ccgaggccag 126720
caccgtgcgg cgcaggtcgc gcgccgccgg ccagcgcacg gcgcactgca cggcgggcag 126780
caggtcgcac gccaggtagg cgtgctgccg cgacaccgcg ggcccgtcgg cgggccagtc 126840
gcaggcgcgc acggtgttga ccacgatgag ccgccggtcg ccggcgctgg cgagcagccc 126900
cagaaactcc acggccccgg cgaaggccag gtcccgcgtg gacagcagca gcacgccctg 126960
cgcgcccagc gccgacacgt cgggggcgcc ggtccagttg cccgcccagg cggccgtgtc 127020
cggcccgcac agccggttgg ccagggccgc cagcaggcag gacagcccgc cgcgctcggc 127080
ggaccactcc ggcggccccc ccgaggcccc gccgccggcc aggtcctcgc ccggcagcgg 127140
cgagtacagc accaccacgc gcacgtcctc ggggtcgggg atctggcgca tccaggccgc 127200
catgcggcgc agcgggcccg aggcgcgcag ggggccaaag aggcggcccc cggcggcccc 127260
gtgggggtgg gggttctcgt cgtcgtcgcc gccgccgcac gcggcctggg cggcgggggc 127320
gggcccggcg caccgcgcgg cgatcgaggc cagggcccgc gggtcaaaca tgagggccgg 127380
tcgccagggg acggggaaca gcgggtggtc cgtgagctcg gccacggcgc gcggggagca 127440
gtaggcctcc agggcggcgg ccgcgggcgc cgccgtgtgg ctgggccccg ggggctgccg 127500
ccgccagccg cccagggggt cggggccctc ggcgggccgg cgcgacagcg ccacggggcg 127560
cgggcgggcc tgcgccgcgg cggcccgggg cgccgcgggc tgggcggggg cgggctcggg 127620
ccccgggggc gtggaggggg gcgcgggcgc ggggaggggg gcgcgggcgt ccgagccggg 127680
ggcgtccgcg ccgctcttct tcgtcttcgg gggtcgcggg ccgccgcctc cgggcggccg 127740
ggccgggccg ggactcttgc gcttgcgccc ctcccgcggc gcggcggagg cggcggccgc 127800
gacccccgaa gacgaagaag agcggcgcgg acccgccgcc agcagggggc gcaggctctg 127860
gttctcaaac agcaggtccg cggcggcggc ggccgcggag ctcggcaggc gcgggtcccg 127920
cggcagcgcg ggacccaggg ccccggcgac caggctcacg gcgcgcacgg cggccacggc 127980
ggcctcgctg ccgccggcca cgcgcaggtc cccgcgcagg cgcatgagca ccagcgcgtc 128040
gcgcacgaac cgcagctcgc gcagccacgc gcgcaggcgg ggcgcgtcgg cgtgcggcgg 128100
cggcggggaa gcggggcccg cgggtccctc cggccgcggg gggctggcgg gccgggcccc 128160
ggccagcccc gggacggccg ccaggtcgcc gtcgaagccc tcggccagcg cctccaggat 128220
cccgcggcag gcggccaggc actccacggc cacgcggccg gcctgggcgc ggcgcccggc 128280
gtcgtcgtcg gcgtcggcgt ggcgggcggc gtcggggtcg tcgccccccg cgggggaggc 128340
gggcgcggcg gacagccgcc ccagggcggc gaggatcccc gcggcgccgt acccggcggg 128400
caccgcgcgc tcgcccggtg cggcggcggc ggcgacgacg gcggcggcga ccccctcgtc 128460

-continued atctgcgccg gcgccggggc tccccgcggc ccccgtcagc gccgcgttct cgcgcgccaa 128520
caggggcgcg taggcgcggc gcaggctggt cagcaggaag cccttctgcg cgcggtcgta 128580
tcggcggctc atggccacgg cggccgccgc gtgcgccagg ccccagccga agcggccggc 128640
cgccatggcg tagcccaggt ggggcacggc ccgcgccacg ctgccggtga tgaaggagct 128700
gctgttgcgc gcggcgcccg agatccggaa gcaggcctgg tccagcgcca cgtccccggg 128760
gaccacgcgc gggttctgga gccaccccat ggcctccgcg tccggggtgt acagcagccg 128820
cgtgatcagg gcgtactgct gcgcggcgtc gcccagctcg ggcgcccaca cggccgccgg 128880
ggcgcccgag gcctcgaacc ggcgtcgcgc ctcctccgcc tcgggcgccc cccagaggcc 128940
cgggcggctg tcgcccaggc cgccgtacag cacccgcccc gggggcgggg gcccggcgcc 129000
gggccacggc tccccgctga cgtacccgtc gcgatagcgc gcgtagaagg cgccggaggc 129060
cgcgtcggcg tccagctcga cccgccgggg ctgcccggcc gtgaagcggc ccgtggcgtc 129120
gcggccggcc accgccgcgc gggcccggcg gcgctcgatg cggcccgcgg aggccgcggg 129180
ggtcctcgcc gccgcccggg gcttgggcgc ggcctcggag aggggggggtg gcccgggcgg 129240 gggcggcgtc cgcccggggg cttccggcgc cgcgctcgac ggaccccgcc cgacggcccg 129300
cgcctcgcgt gcgtggtcgg ccgcgtcgtt gccgtcgtcg tcctcgtcct cgtcggacga 129360
cgaggacgaa gaggatgcgg acgacgagga cgaggacccg gagtccgacg aggtcgatga 129420
cgccgatggc cgccgccggc cgtgacgacg tctctgcggc ggctgggccg gcgggcgcgg 129480
cgacaggcgg tccgtggggt ccggatacgc gccgcgtagc ggggcctccc gtgcgcggcc 129540
ccgggccggg gcccggtcgc cggcggcgtc ggctgcgtcg tcgtactcgt ccccgtcatc 129600
gtcgtcggct cgaaaggcgg gggtccgggg cggcgaggcc gcggggtcgg gcgtcgggat 129660
cgtccggacg gcctcctcta ccatggaggc cagcagggcc agctgtcgcg gcgagacggc 129720
gtccccggcg tcctcgccgg cgtcggtgcc cgccgcgggg gccctcccgt cccgccgggc 129780
gtcgtcgagg tcgtgggggt ggtcggggtc gtggtcgggg tcgtccccgc cctcctccgt 129840
ctccgcgccc cacccgaggg ccccccgctc gtcgcggtct gggctcgggg tgggcggcgg 129900
cccgtcggtg gggcccgggg agccggggcg ctgcttgttc tccgacgcca tcgccgatgc 129960
ggggcgatcc tccggggata cgactgcgac ggcggacgta gcacggtagg tcacctacgg 130020
actctcgatg gggagggggc gagacccacg gaccccgacg acccccgccg tcgacgcgga 130080
actagcgcgg accggtcgat gcttgggtgg gaaaaaggac agggacggcc gatccccctc 130140
ccgcgcttcg tccgcgtatc ggcgtcccgg cgcggcgagc gtctgacggt ctgtctctgg 130200
cggtcccgcg tcgggtcgtg gatccgtgtc ggcagccgcg ctccgtgtgg acgatcgggg 130260
cgtcctcggg ctcatatagt cccaggggcc ggcgggaagg aggagcagcg gaggccgccg 130320
gccccccgcc cccacggcgg gcccgccccg aacggaattc cattatgcac gaccccgccc 130380
cgacgccggc acgccggggg cccgtggccg cggcccgttg gtcgaacccc cggccccgcc 130440
catccgcgcc atctgccatg ggcggggcgc tagggcgggt gggcccgcgc cccgccccgc 130500
atggcatctc attaccgccc gatccggcgg tttccgcttc cgttccgcat gctaacgagg 130560
aacgggcagg gggcggggcc cgggccccga cttcccggtt cggcggtaat gagatacgag 130620
ccccgcgcgc ccgttggccg tccccgggcc cccggtcccg cccgccggac gccgggacca 130680
acgggacggc gggcggccca agggccgccc gccttgccgc ccccccattg gccggcgggc 130740
gggaccgccc caagggggcg gggccgccgg gtaaaagaag tgagaacgcg aagcgttcgc 130800
acttcgtccc aatatatata tattattagg gcgaagtgcg agcactggcg ccgtgcccga 130860
ctccgcgccg gccccggggg cgggcccggg cggcgggggg cgggtctctc cggcgcacat 130920
aaaggcccgg cgcgaccgac gcccgcagac ggcgccggcc acgaacgacg ggagctgctg 130980
cggagcacgc ggaccgggag cgggactcgc agagggccgt cggagcggac ggcgtcggca 131040
tcgcgacgcc ccggctcggg atcgggatcg catcggaaag ggacacgcgg aaagacccac 131100
ccaccccacc cacgaaacac aggggacgca ccccgggggc ctccgacgac agaaacccac 131160
cggtccgcct ttttgcacgg gtaagcacct tgggtgggcg gaggagggcg gaggaggggg 131220
gacgcggggg cggaggaggg gggacgcggg ggcggaggag gggggacgcg ggggcggagg 131280 agggggggacg cgggggcgga ggaggggggct cacccgcgtt cgtgccttcc cgcaggagga 131340
acgtcctcgt cgaggcgacc ggcggcgacc gttgcgtgga ccgcttcctg ctcgtcgggg 131400
cgaccggcgg cgaccgttgc gtggaccgct tcctgctcgt cggggcgacc ggcggcgacc 131460
gttgcgtgga ccgcttcctg ctcgtcgggg gggggggggg gaagccactg tggtcctccg 131520
ggacgttttc tggatggccg acatttcccc aggcgctttt gcgccttgtg taaaagcgcg 131580
gcgtcccgct ctccgatccc cgcccctggg cacgcgcaag cgcaagcgcc ctgcccgccc 131640
cctctcatcg gagtctgagg tcgaaaccga tacagccttg gagtctgagg tcgaatccga 131700
gacagcatcg gattcgaccg agtctgggga ccaggaggaa gccccccgca tcggtggccg 131760
tagggccccc cggaggcttg gggggcggtt ttttctggac atgtcggcgg aatccaccac 131820
ggggacggaa acggatacgg cggtgtcgga cgaccccgac gacacgtccg actggtctta 131880
tgacgacatt cccccacgac ccaagcgggc ccgggtaaac ctgcggctca cgagctctcc 131940
cgatcggcgg gatggggtta tttttcctaa gatggggcgg gtccggtcta cccgggaaac 132000
gcagccccgg gccccaaccc cgtcggcccc aagcccaaat gcaatgctac ggcgctcggt 132060
gcgccaggcc cagaggcgga gcagcgcacg atggaccccc gacctgggct acatgcgcca 132120
gtgtatcaat cagctgtttc gggtcctgcg ggtcgcccgg gacccccacg gcagtgccaa 132180
ccgcctgcgc cacctgatac gcgactgtta cctgatggga tactgccgag cccgtctggc 132240
cccgcgcacg tggtgccgct tgctgcaggt gtccggcgga acctggggca tgcacctgcg 132300
caacaccata cgggaggtgg aggctcgatt cgacgccacc gcggaacccg tgtgcaaact 132360
tccttgtttg gaggccagac ggtacggccc ggagtgtgat cttagtaatc tcgagattca 132420
tctcagcgcg acaagcgatg atgaaatctc cgatgccacc gatctggagg ccgccggttc 132480
ggaccacacg ctcgcgtccc agtccgacac ggaggatgcc ccctcccccg ttacgctgga 132540
aaccccagaa ccccgcgggt ccctcgctgt gcgtctggag gatgagtttg gggagtttga 132600
ctggaccccc caggagggct cccagccctg gctgtctgcg gtcgtggccg ataccagctc 132660
cgtggaacgc ccgggcccat ccgattctgg ggcgggtcgc gccgcagaag accgcaagtg 132720
tctggacggc tgccggaaaa tgcgcttctc caccgcctgc ccctatccgt gtagcgacac 132780
gtttctccgg ccgtgagtcc ggtcgccccg accccttttgt atgtcaccaa aataaaagac 132840
caaaatcaaa gcgtttgtcc cagcgtctta atggcgggaa gggcggagag aaacagacca 132900
cgcggacatg gggggtgttt gggggtttat tggcaccggg ggctaaaggg tggtaaccgg 132960
atagcagatg tgaggaagtc ggggccgttc gccgcgaacg gcgatcagag ggtcagtttc 133020
ttgcggacca cggcccggcg atgtgggttg ctcgtctggg acctcgggca tgcccataca 133080
cgcacaacac ggacgccgca ccggatggga cgtcgtaagg gggcctgggg tagctgggtg 133140
gggtttgtgc agagcaatca gggaccgcag ccagcgcata caatcgcgct cccgtccgtt 133200

-continued tgtcccgggc agtaccacgc cgtactggta ttcgtaccgg ctgagcaggg tctccagggg 133260
gtggttgggg gccgcgggga acggggtcca cgccacggtc cactcgggca aaaaccgagt 133320
cggcacggcc cacggttctc ccacccacgc gtctggggtc ttgatggcga taaatcttac 133380
cccgagccgg attttttggg cgtattcgag aaacggcaca cacagatccg ccgcgcctac 133440
cacccacaag tggtagatgc gagggggct gggttggtct cggtgcagca gtcggaagca 133500
cgccacggcg tccacgacct cggtgctctc caaggggctg tcctccgcaa acaggcccgt 133560
ggtggtgttt ggggggcagc gacaggacct agtgcgcacg atcgggcggg tgggtttggg 133620
taagtccatc agcggctcgg ccaaccgtcg aaggttggcc ggacgaacga cgaccggggt 133680
acccaggggt tctgatgcca aaatgcggca ctgcctaagc aggaagctcc acagggccgg 133740
gcttgcgtcg acggaagtcc ggggcagggc gttgttctgg tcaaggaggg tcattacgtt 133800
gacgacaaca acgcccatgt tggtatatta caggcccgtg tccgatttgg ggcacttgca 133860
gatttgtaag gccacgcacg gcggggagac aggccgacgc gggggctgct ctaaaaattt 133920
aagggcccta cggtccacag acccgccttc ccgggggggg ggcccttgga gcgaccggca 133980
gcgtaggcgt ccgggggagg ggagggtgat ttacgggggg gtaggtcagg gggtgggtcg 134040
tcaaactgcc gctccttaaa accccggggc ccgtcgttcg gggtgctcgt tggttggcac 134100
tcacggtgcg gcgaatggcc tgtcgtaagt tttgtcgcgt ttacggggga cagggcagga 134160
ggaaggagga ggccgtcccg ccggagacaa agccgtcccg ggtgtttcct catggcccct 134220
tttatacccc agccgaggac gcgtgcctgg actccccgcc cccggagacc cccaaacctt 134280
cccacaccac accacccagc gaggccgagc gcctgtttca tctgcaggag atccttgccc 134340
agatgtacgg aaaccaggac taccccatag aggacgaccc cagcgcggat gccgcggacg 134400
atgtcgacga ggacgccccg gacgacgtgg cctatccgga ggaatacgca gaggagcttt 134460
ttctgcccgg ggacgcgacc ggtcccctta tcggggccaa cgaccacatc cctcccccgt 134520
gtggcgcatc tccccccggt atacgacgac gcagccggga tgagattggg gccacgggat 134580
ttaccgcgga agagctggac gccatggaca gggaggcggc tcgagccatc agccgcggcg 134640
gcaagccccc ctcgaccatg gccaagctgg tgactggcat gggctttacg atccacggag 134700
cgctcacccc aggatcggag gggtgtgtct ttgatagcag ccacccagat tacccccaac 134760
gggtaatcgt gaaggcgggg tggtacacga gcacgagcca cgaggcgcga ctgctgaggc 134820
gactggacca ccccgcgatc ctgcccctcc tggacctgca tgtcgtctcc ggggtcacgt 134880
gtctggtcct ccccaagtac caggccgacc tgtataccta tctgagtagg cgcctgaacc 134940
cgctgggacg cccgcagatc gcagcggtct cccggcagct cctaagcgcc gttgactaca 135000
ttcaccgcca gggcattatc caccgcgaca ttaagaccga aaatattttt attaacaccc 135060
ccgaggacat ttgcctgggg gactttggtg ccgcgtgctt cgtgcagggt tcccgatcaa 135120
gccccttccc ctacggaatc gccggaacca tcgacaccaa cgcccccgag gtcctggccg 135180
gggatccgta taccacgacc gtcgacattt ggagcgccgg tctggtgatc ttcgagactg 135240
ccgtccacaa cgcgtccttg ttctcggccc cccgcggccc caaaaggggc ccgtgtgaca 135300
gtcagatcac ccgcatcatc cgacaggccc aggtccacgt tgacgagttt tccccgcatc 135360
cagaatcgcg cctcacctcg cgctaccgct cccgcgcggc cgggaacaat cgcccgcctt 135420
acacccgacc ggcctggacc cgctactaca agatggacat agacgtcgaa tatctggttt 135480
gcaaagccct caccttcgac ggcgcgcttc gccccagcgc cgcagagctg ctttgtttgc 135540
cgctgtttca acagaaatga ccgcccccgg ggggcggtgc tgtttgcggg ttggcacaaa 135600

-continued aagaccccga cccgcgtctg tggtgttttt ggcatcatgt cgccgggcgc catgcgtgcc 135660
gttgttccca ttatcccatt ccttttggtt cttgtcggtg tatcgggggt tcccaccaac 135720
gtctcctcca ccacccaacc ccaactccag accaccggtc gtccctcgca tgaagccccc 135780
aacatgaccc agaccggcac caccgactct cccaccgcca tcagccttac cacgcccgac 135840
cacacacccc ccatgccaag tatcggactg gaggaggagg aggaagagga ggagggggcc 135900
ggggatggcg aacatcttaa ggggggagat gggacccgtg acaccctacc ccagtccccg 135960
ggtccagccg tcccgttggc cggggatgac gagaaggaca aacccaaccg tcccgtagtc 136020
ccaccccccg gtcccaacaa ctcccccgcg cgcccccgaga ccagtcgacc gaagacaccc 136080
cccaccagta tcgggccgct ggcaactcga cccacgaccc aactcccctc aaaggggcga 136140
cccttggttc cgacgcctca acatacccccg ctgttctcgt tcctcactgc ctcccccgcc 136200
ctggacaccc tcttcgtcgt cagcaccgtc atccacacct tatcgttttt gtgtattggt 136260
gcgatggcga cacacctgtg tggcggttgg tccagacgcg ggcgacgcac acaccctagc 136320
gtgcgttacg tgtgcctgcc gtccgaacgc gggtagggta tggggcgggg gatggggaga 136380
gcccacatgc ggaaagcaag aacaataaag gcggtggtat ctagttgata tgcatctctg 136440
ggtgtttttg gggtgtggcg gacgcggggc ggtcattgga cggggtgcag ttaaatacat 136500
gcccgggacc catgaagcat gcgcgacttc cgggcctcgg aacccacccg aaacggccaa 136560
cggacgtctg agccaggcct ggctatccgg agaaacagca cacgacttgg cgttctgtgt 136620
gtcgcgatgt ctctgcgcgc agtctggcat ctggggcttt tgggaagcct cgtgggggct 136680
gttcttgccg ccacccatcg gggacctgcg gccaacacaa cggacccctt aacgcacgcc 136740
ccagtgtccc ctcaccccag ccccctgggg ggctttgccg tccccctcgt agtcggtggg 136800
ctgtgcgccg tagtcctggg ggcggcgtgt ctgcttgagc tcctgcgtcg tacgtgccgc 136860
gggtgggggc gttaccatcc ctacatggac ccagttgtcg tataattccc ccccccccctt 136920
ctccgcatgg gtgatgtcgg gtccaaactc ccgacaccac cagctggcat ggtataaatc 136980
accggtgcgc cccccaaacc atgtccggca gggggatggg ggggcgaatg cggagggcac 137040
ccaacaacac cgggctaacc aggaaatccg tggccccggc ccccaataaa gatcgcggta 137100
gcccggccgt gtgacactat cgtccatacc gaccacaccg acgaatcccc taagggggag 137160
gggccatttt acgaggagga ggggtataac aaagtctgtc tttaaaaagc aggggttagg 137220
gagttgttcg gtcataagct tcagcgcgaa cgaccaacta ccccgatcat cagttatcct 137280
taaggtctct tttgtgtggt gcgttccggt atgggggggg ctgccgccag gttgggggcc 137340
gtgattttgt ttgtcgtcat agtgggcctc catggggtcc gcggcaaata tgccttggcg 137400
gatgcctctc tcaagatggc cgaccccaat cgctttcgcg gcaaagacct tccggtcctg 137460
gaccagctga ccgaccctcc gggggtccgg cgcgtgtacc acatccaggc gggcctaccg 137520
gacccgttcc agccccccag cctcccgatc acggtttact acgccgtgtt ggagcgcgcc 137580
tgccgcagcg tgctcctaaa cgcaccgtcg gaggccccccc agattgtccg cggggcctcc 137640
gaagacgtcc ggaaacaacc ctacaacctg accatcgctt ggtttcggat gggaggcaac 137700
tgtgctatcc ccatcacggt catggagtac accgaatgct cctacaacaa gtctctgggg 137760
gcctgtccca tccgaacgca gccccgctgg aactactatg acagcttcag cgccgtcagc 137820
gaggataacc tggggttcct gatgcacgcc cccgcgtttg agaccgccgg cacgtacctg 137880
cggctcgtga agataaacga ctggacggag attacacagt ttatcctgga gcaccgagcc 137940

-continued

```
aagggctcct gtaagtacgc cctcccgctg cgcatccccc cgtcagcctg cctgtccccc 138000
caggcctacc agcagggggt gacggtggac agcatcggga tgctgccccg cttcatcccc 138060
gagaaccagc gcaccgtcgc cgtatacagc ttgaagatcg ccgggtggca cgggcccaag 138120
gccccataca cgagcaccct gctgccccg gagctgtccg agaccccaa cgccacgcag 138180
ccagaactcg ccccggaaga ccccgaggat tcggccctct tggaggaccc cgtggggacg 138240
gtggcgccgc aaatcccacc aaactggcac ataccgtcga tccaggacgc cgcgacgcct 138300
taccatcccc cggccacccc gaacaacatg ggcctgatcg ccggcgcggt gggcggcagt 138360
ctcctggcag ccctggtcat ttgcggaatt gtgtactgga tgcgccgccg cactcaaaaa 138420
gccccaaagc gcatacgcct cccccacatc cgggaagacg accagccgtc ctcgcaccag 138480
cccttgtttt actagatacc ccccttaat gggtgcgggg gggtcaggtc tgcggggttg 138540
ggatgggacc ttaactccat ataaagcgag tctggaaggg gggaaaggcg gacagtcgat 138600
aagtcggtag cgggggacgc gcacctgttc cgcctgtcgc acccacagct tttttgcga 138660
accgtcccgt tccgggatgc cgtgccgccc gttgcagggc ctggtgctcg tgggcctctg 138720
ggtctgtgcc accagcctgg ttgtccgtgg ccccacggtc agtctggtat caaactcatt 138780
tgtggacgcc ggggccttgg ggcccgacgg cgtagtggag gaagacctgc ttattctcgg 138840
ggagcttcgc tttgtggggg accaggtccc ccacaccacc tactacgatg ggtcgtaga 138900
gctgtggcac taccccatgg gacacaaatg cccacgggtc gtgcatgtcg tcacggtgac 138960
cgcgtgccca cgtcgccccg ccgtggcttt cgccctgtgt cgcgcgaccg acaacactca 139020
cagccccgca tatcccaccc tggagctgaa tctggcccaa cagccgcttt tgcgggtccg 139080
gagggcgacg cgtgactatg ccggggtgta cgtgttacgc gtatgggtcg tggacgcacc 139140
aaacgccagc ctgtttgtcc tggggatggc catagccgcc gaagggactc tggcgtacaa 139200
cggctcggcc catggctcct gcgacccgaa actgcttccg tattcggccc cgcgtctggc 139260
cccggcgagc gtataccaac ccgcccctaa cccggcctcc accccctcga ccaccacctc 139320
cacccctcg accaccacct ccacccctc gaccaccacc tccaccccct cgaccaccac 139380
ctccacccc tcgaccacca cctccacccc ctcgaccacc acctccaccc cctcgaccac 139440
catccccgct ccccaagcat cgaccacacc cttccccacg ggagacccaa aaccccaacc 139500
tcacggggtc aaccacgaac ccccatcgaa tgccacgcga gcgacccgcg actcgcgata 139560
cgcgctaacg gtgacccaga taatccagat agccatcccc gcgtccatta tagccctggt 139620
gtttctgggg agctgtattt gctttataca cagatgtcaa cgccgctacc gacgctcccg 139680
ccgcccgatt tacaaccccc agatacccac gggcatctca tgcgcggtga acgaagcggc 139740
catggcccgc ctcggagccg agctcaaatc gcatccgagc accccccca aatcccggcg 139800
ccggtcgtca cgcacgccaa tgccctccct gacggccatc gccgaagagt cggagcccgc 139860
gggggcggct gggcttccga cgccccccgt ggaccccacg acatccaccc caacgcctcc 139920
cctgttggta taggtccacg gccactggcc gggggcacca cataaccgac cgcagtcact 139980
gagttgggaa taaaccggta ttatttacct atatccgtgt atgtccattt ctttccccc 140040
cccccccccc cggaaaccca aagaaggaag caaagaatgg atgggaggag ttcaggaagc 140100
cggggagagg gcccgcggcg catttaaggc gttgttgtgt tgactttggc tcttctggcg 140160
ggttggtgcg gtgctgtttg ttgggctccc attttacccg aagatcggct gctatccccg 140220
ggacatggat cgcggggcgg tggtggggtt tcttctcggt gtttgtgttg tatcgtgctt 140280
ggcgggaatg cccaaaaacgt cctggagacg ggtgagtgtc ggcgaggacg tttcgttgct 140340
```

-continued tccagctccg gggcctacgg ggcgcggccc gacccagaaa ctactatggg ccgtggaacc 140400
cctggatggg tgcggcccct tacacccgtc gtgggtctcg ctgatgcccc ccaagcaggt 140460
gcccgagacg gtcgtggatg cggcgtgcat gcgcgctccg gtcccgctgg cgatggcgta 140520
cgcccccccg gccccatctg cgaccggggg tctacgaacg gacttcgtgt ggcaggagcg 140580
cgcggccgtg gttaaccgga gtctggttat tcacggggtc cgagagacgg acagcggcct 140640
gtataccctg tccgtgggcg acataaagga cccggctcgc caagtggcct cggtggtcct 140700
ggtggtgcaa ccggccccag ttccgacccc acccccgacc ccagccgatt acgacgagga 140760
tgacaatgac gagggcgagg gcgaggacga aagtctagcc ggcactcccg ccagcgggac 140820
cccccggctc ccgcctcccc ccgccccccc gaggtcttgg cccagcgccc ccgaagtctc 140880
acacgtgcgt ggggtgaccg tgcgtatgga gactccggaa gctatcctgt tttcccccgg 140940
ggaggcgttt agcacgaacg tctccatcca tgccatcgcc cacgacgacc agacctacac 141000
catggacgtc gtctggttga ggttcgacgt gccgacctcg tgtgccgaga tgcgaatata 141060
cgaatcgtgt ctgtatcacc cgcagctccc agagtgtctg tccccggccg acgctccgtg 141120
cgccgcgagt acgtggacgt ctcgcctggc cgtccgcagc tacgcggggt gttccagaac 141180
aaaccccccg ccgcgctgtt cggccgaggc tcacatggag cccttcccgg ggctggcgtg 141240
gcaggcggcc tccgtcaatc tggagttccg ggacgcgtcc ccacaacact ccggcctgta 141300
tctgtgcgtg gtgtacgtca acgaccatat tcacgcatgg ggccacatta ccatcagcac 141360
cgcggcgcag taccggaacg cggtggtgga acagcccctc ccacagcgcg gcgcggattt 141420
ggccgagccc acccacccgc acgtcggggc ccctccccac gcgcccccaa cccacggcgc 141480
cctgcggtta ggggcggtga tgggggccgc cctgctgctg tctgcgctgg ggttgtcggt 141540
gtgggcgtgt atgacctgtt ggcgcaggcg tgcctggcgg gcggttaaaa gcagggcctc 141600
gggtaagggg cccacgtaca ttcgcgtggc cgacagcgag ctgtacgcgg actggagctc 141660
ggacagcgag ggagaacgcg accaggtccc gtggctggcc cccccggaga gacccgactc 141720
tccctccacc aatggatccg gctttgagat cttatcacca acggctccgt ctgtataccc 141780
ccgtagcgat gggcatcaat ctcgccgcca gctcacaacc tttggatccg gaaggcccga 141840
tcgccgttac tcccaggcct ccgattcgtc cgtcttctgg taaggcgccc catcccgagg 141900
ccccacgtcg gtcgccgaac tgggcgaccg ccggcgaggt ggacgtcgga gacgagctaa 141960
tcgcgatttc cgacgaacgc ggaccccccc gacatgaccg cccgcccctc gccacgtcga 142020
ccgcgccctc gccacacccg cgacccccgg gctacacggc cgttgtctcc ccgatggccc 142080
tccaggctgt cgacgccccc tccctgtttg tcgcctggct ggccgctcgg tggctccggg 142140
gggcttccgg cctgggggcc gtcttgtgtg ggattgcgtg gtatgtgacg tcaattgccc 142200
gaggcgcata aagggccggt ggtccgccta gccgcagcaa attaaaaatc gtgagtcact 142260
gcgaccgcaa cttcccaccc ggagctttct tccggcctcg atgacgtccc ggctctccga 142320
tcccaactcc tcagcgcgat ccgacatgtc cgtgccgctt tatcccacgg cctcgccagt 142380
ttcggtcgaa gcctactact cggaaagcga agacgaggcg gccaacgact tcctcgtacg 142440
catgggccgc caacagtcgg tattaaggcg tcgacgcaga cgcacccgct gcgtcggcat 142500
ggtgatcgcc tgtctcctcg tggccgttct gtcgggcgga tttggggcgc tcctgatgtg 142560
gctgctccgc taaaagaccg catcgacacg cgcgtccttc ttgtcgtctc tcttccccc 142620
atcaccccgc aatttgcacc cagcctttaa ctacattaaa ttgggttcga ttggcaatgt 142680

-continued tgtctcccgg ttgatttttg ggtgggtggg gagtgggtgg gtggggagtg ggtgggtggg 142740
gagtgggtgg gtggggagtg ggtgggtggg gagtgggtgg gtggggagtg ggtgggtggg 142800
gagtgggtgg gtggggagtg ggtgggtggg gagtgggtgg gtggggagtg ggtgggtggg 142860
gagtgggtgg gtggggagtg ggtgggtggg gagtgggtgg gtggggagtg ggtgggtggg 142920
gagtgggtgg gtggggagtg gcaaggaaga aacaagcccg accaccagac agaaaatgta 142980
accataccca aaccgactct gggggctgtt tgtggggtcg gaaccatagg atgaacaaac 143040
caccccgtac ctcccgcacc cttgggtgcg ggtggctcat cggcatctgt ccggtatggg 143100
ttgttcccca cccactcgcg ttcggacgtc ttagaatcat ggcggtttct atgccgacat 143160
cggtttctcc cccgcaataa gacacgatgc gataaaatct gtttgtgaaa tttattaagg 143220
gtacaaattg ccctagcaca ggggtggggt tagggccggg tccccacacc caaacgcacc 143280
aaacagatgc aggcagtggg tcgagtacag ccccgcgtac gaacacgtcg atgcgtgtgt 143340
cagacagcac cagaaagcac aggccatcaa caggtcgtgc atgtgtcggt gggtttggac 143400
gcgggggcc atggtgggtg ataaagttaa tggccgccgt ccgccagggc cacaggggcg 143460
acgtctcttg gttggcccgg agccactggg tgtggaccag ccgcgcgtgg cggcccaaca 143520
tggcccctgt agccgggggc gggggatcgc gcacgtttgc agcgcacatg cgagacacct 143580
cgaccacggt tcggaagaag gcccggtggt ccgcgggcaa catcaccagg tgcgcaagcg 143640
cccgggcgtc cagagggtag agccctgagt catccgaggt tggctcatcg cccgggtcat 143700
gccgcaagtg cgtgtgggtt gggcttccgg tgggcgggac gcgaaccgcg gtgtggagcc 143760
cgacgcgggc ccgagcgtac gctccatctt gtggggagaa ggggtctggg ctcgccaggg 143820
gggcatactt gcccgggcta tacagacccg cgagccgtac gtggttcgcg gggggtgcgt 143880
ggggtccggg gctcccgggg aggccggggc tcccggggtt gtcgtggatc cctggggtca 143940
cgcggtaccc tggggtctct gggagctcgc ggtactctgg gttccctagg ttctcggggt 144000
ggtcgcggaa cccggggctc ccggggaaca cgcggtgtcc tggggattgt tggcggtcgg 144060
acggcttcag atggcttcga gatcgtagtg tccgcaccga ctcgtagtag acccgaatct 144120
ccacattgcc ctgccgcttg atcattatca ccccgttgcg ggggtccgga gatcatgcgc 144180
gggtgtcctc gaggtgcgtg aacacctctg gggtgcatgc cggcggacgg cacgcctttt 144240
aagtaaacat ctgggtcgcc cggcccaact ggggccgggg gttgggtctg gctcatctcg 144300
agagccacgg ggggaaccac cctccgccca gaaacttggg cgatggtcgt acccgggact 144360
caacgggtta ccggattacg gggactgtcg gtcacggtcc cgccggttct tcgatgtgcc 144420
acacccaagg atgcgttggg ggcgattttg ggcagcagcc cgggagagcg cagcagagga 144480
cgctccgggt cgtgcacggc ggttctggcc gcctcccggt cctcacgccc ccttttattg 144540
atctcatcgc gtacgtcggc gtacgtcctg ggcccaaccc gcatgttgtc caggaaggtg 144600
tccgccattt ccagggccca cgacatgctc cccccccccc ccccgacgag caggaagcgg 144660
tccacgcaac ggtcgccgcc ggtcgccccg acgagcagga agcggtccac gcaacggtcg 144720
ccgccggtcg ccccgacgag caggaagcgg tccacgcaac ggtcgccgcc ggtcgcctcg 144780
acgaggacgt tcctcctgcg ggaaggcacg aacgcgggtg agccccctcc tccgccccg 144840
cgtcccccct cctccgcccc cgcgtccccc ctcctccgcc cccgcgtccc ccctcctccg 144900
cccccgcgtc ccccctcctc cgccctcctc cgcccaccca aggtgcttac ccgtgcaaaa 144960
aggcggaccg gtgggtttct gtcgtcggag gcccccgggg tgcgtcccct gtgtttcgtg 145020
ggtggggtgg gtgggtcttt ccgcgtgtcc ctttccgatg cgatcccgat cccgagccgg 145080
ggcgtcgcga tgccgacgcc gtccgctccg acggccctct gcgagtcccg ctcccggtcc 145140
gcgtgctccg cagcagctcc cgtcgttcgt ggccggcgcc gtctgcgggc gtcggtcgcg 145200
ccgggccttt atgtgcgccg gagagacccg ccccccgccg cccgggcccg cccccggggc 145260
cggcgcggag tcgggcacgg cgccagtgct cgcacttcgc cctaataata tatatatatt 145320
gggacgaagt gcgaacgctt cgcgttctca cttcttttac ccggcggccc cgcccccttg 145380
gggcggtccc gcccgccggc caatgggggg gcggcaaggc gggcggccct tgggccgccc 145440
gccgtcccgt tggtcccggc gtccggcggg cgggaccggg ggcccgggga cggccaacgg 145500
gcgcgcgggg ctcgtatctc attaccgccg aaccgggaag tcggggcccg ggccccgccc 145560
cctgcccgtt cctcgttagc atgcggaacg gaagcggaaa ccgccggatc gggcggtaat 145620
gagatgccat gcggggcggg gcgcgggccc acccgcccta gcgccccgcc catggcagat 145680
ggcgcggatg ggcggggccg ggggttcgac caacgggccg cggccacggg cccccggcgt 145740
gccggcgtcg gggcggggtc gtgcataatg gaattccgtt cggggcgggc ccgccgtggg 145800
ggcggggggc cggcggcctc cgctgctcct ccttcccgcc ggcccctggg actatatgag 145860
cccgaggacg ccccgatcgt ccacacggag cgcggctgcc gacacggatc cacgacccga 145920
cgcgggaccg ccagagacag accgtcagac gctcgccgcg ccgggacgcc gatacgcgga 145980
cgaagcgcgg gagggggatc ggccgtccct gtcctttttc ccacccaagc atcgaccggt 146040
ccgcgctagt tccgcgtcga cggcgggggt cgtcggggtc cgtgggtctc gccccctccc 146100
catcgagagt ccgtaggtga cctaccgtgc tacgtccgcc gtcgcagtcg tatccccgga 146160
ggatcgcccc gcatcggcga tggcgtcgga gaacaagcag cgccccggct ccccgggccc 146220
caccgacggg ccgccgccca ccccgagccc agaccgcgac gagcgggggg ccctcgggtg 146280
gggcgcggag acggaggagg gcggggacga ccccgaccac gaccccgacc acccccacga 146340
cctcgacgac gcccggcggg acgggagggc ccccgcggcg ggcaccgacg ccggcgagga 146400
cgccggggac gccgtctcgc cgcgacagct ggccctgctg gcctccatgg tagaggaggc 146460
cgtccggacg atcccgacgc ccgaccccgc ggcctcgccg ccccggaccc ccgcctttcg 146520
agccgacgac gatgacgggg acgagtacga cgacgcagcc gacgccgccg gcgaccgggc 146580
cccggcccgg ggccgcgcac gggaggcccc gctacgcggc gcgtatccgg accccacgga 146640
ccgcctgtcg ccgcgcccgc cggcccagcc gccgcagaga cgtcgtcacg gccggcggcg 146700
gccatcggcg tcatcgacct cgtcggactc cgggtcctcg tcctcgtcgt ccgcatcctc 146760
ttcgtcctcg tcgtccgacg aggacgagga cgacgacggc aacgacgcgg ccgaccacgc 146820
acgcgaggcg cgggccgtcg ggcggggtcc gtcgagcgcg gcgccggaag cccccgggcg 146880
gacgccgccc ccgcccgggc caccccccct ctccgaggcc gcgcccaagc cccgggcggc 146940
ggcgaggacc ccccgcggcct ccgcgggccg catcgagcgc cgccgggccc gcgcggcggt 147000
ggccggccgc gacgccacgg gccgcttcac ggccgggcag ccccggcggg tcgagctgga 147060
cgccgacgcg gcctccggcg ccttctacgc gcgctatcgc gacgggtacg tcagcgggga 147120
gccgtggccc ggcgccgggc cccgcccccc ggggcgggtg ctgtacggcg gcctgggcga 147180
cagccgcccg ggcctctggg gggcgcccga ggcggaggag gcgcgacgcc ggttcgaggc 147240
ctcgggcgcc ccggcggccg tgtgggcgcc cgagctgggc gacgccgcgc agcagtacgc 147300
cctgatcacg cggctgctgt acaccccgga cgcggaggcc atggggtggc tccagaaccc 147360
gcgcgtggtc cccggggacg tggcgctgga ccaggcctgc ttccggatct cgggcgccgc 147420

-continued

```
gcgcaacagc agctccttca tcaccggcag cgtggcgcgg gccgtgcccc acctgggcta 147480
cgccatggcg gccggccgct tcggctgggg cctggcgcac gcggcggccg ccgtggccat 147540
gagccgccga tacgaccgcg cgcagaaggg cttcctgctg accagcctgc gccgcgccta 147600
cgcgcccctg ttggcgcgcg agaacgcggc gctgacgggg gccgcgggga gccccggcgc 147660
cggcgcagat gacgaggggg tcgccgccgc cgtcgtcgcc gccgccgccg caccgggcga 147720
gcgcgcggtg cccgccgggt acggcgccgc ggggatcctc gccgccctgg ggcggctgtc 147780
cgccgcgccc gcctccccg cgggggcga cgaccccgac gccgcccgcc acgccgacgc 147840
cgacgacgac gccgggcgcc gcgcccaggc cggccgcgtg gccgtggagt gcctggccgc 147900
ctgccgcggg atcctggagg cgctggccga gggcttcgac ggcgacctgg cggccgtccc 147960
ggggctggcc ggggcccggc ccgccagccc cccgcggccg gagggacccg cgggccccgc 148020
ttccccgccg ccgccgcacg ccgacgcgcc ccgcctgcgc gcgtggctgc gcgagctgcg 148080
gttcgtgcgc gacgcgctgg tgctcatgcg cctgcgcggg gacctgcgcg tggccggcgg 148140
cagcgaggcc gccgtggccg ccgtgcgcgc cgtgagcctg gtcgccgggg ccctgggtcc 148200
cgcgctgccg cgggacccgc gcctgccgag ctccgcggcc gccgccgccg cggacctgct 148260
gtttgagaac cagagcctgc gccccctgct ggcggcgggt ccgcgccgct cttcttcgtc 148320
ttcgggggtc gcggccgccg cctccgccgc gccgcgggag gggcgcaagc gcaagagtcc 148380
cggcccggcc cggccgcccg gaggcggcgg cccgcgaccc ccgaagacga agaagagcgg 148440
cgcggacgcc cccggctcgg acgcccgcgc ccccctcccc gcgcccgcgc ccccctccac 148500
gcccccgggg cccgagcccg cccccgccca gcccgcggcg ccccgggccg ccgcggcgca 148560
ggcccgcccg cgccccgtgg cgctgtcgcg ccggcccgcc gagggccccg acccccctggg 148620
cggctggcgg cggcagcccc cggggcccag ccacacggcg gcgcccgcgg ccgccgccct 148680
ggaggcctac tgctccccgc gcgccgtggc cgagctcacg gaccacccgc tgttccccgt 148740
cccctggcga ccggccctca tgtttgaccc gcgggccctg gcctcgatcg ccgcgcggtg 148800
cgccgggccc gcccccgccg cccaggccgc gtgcggcggc ggcgacgacg acgagaaccc 148860
ccacccccac ggggccgccg ggggccgcct ctttggcccc ctgcgcgcct cgggcccgct 148920
gcgccgcatg gcggcctgga tgcgccagat ccccgacccc gaggacgtgc gcgtggtggt 148980
gctgtactcg ccgctgccgg gcgaggacct ggccggcggc ggggcctcgg gggggccgcc 149040
ggagtggtcc gccgagcgcg gcgggctgtc ctgcctgctg gcggccctgg ccaaccggct 149100
gtgcgggccg gacacggccg cctgggcggg caactggacc ggcgccccccg acgtgtcggc 149160
gctgggcgcg cagggcgtgc tgctgctgtc cacgcgggac ctggccttcg ccggggccgt 149220
ggagtttctg gggctgctcg ccagcgccgg cgaccggcgg ctcatcgtgg tcaacaccgt 149280
gcgcgcctgc gactggcccg ccgacgggcc cgcggtgtcg cggcagcacg cctacctggc 149340
gtgcgacctg ctgcccgccg tgcagtgcgc cgtgcgctgg ccggcggcgc gcgacctgcg 149400
ccgcacggtg ctggcctcgg gccgcgtgtt cggcccgggg gtcttcgcgc gcgtggaggc 149460
cgcgcacgcg cgcctgtacc ccgacgcgcc gccgctgcgc ctgtgccgcg gcggcaacgt 149520
gcgctaccgc gtgcgcacgc gcttcggccc ggacacgccg gtgcccatgt ccccgcgcga 149580
gtaccgccgg gccgtgctgc cggcgctgga cggccgggcg gcggcctcgg ggaccaccga 149640
cgccatggcg cccggcgcgc cggacttctg cgaggaggag gcccactcgc accgcgcctg 149700
cgcgcgctgg ggcctgggcg cgccgctgcg gcccgtgtac gtggcgctgg ggcgcgaggc 149760
ggtgcgcgcc ggcccggccc ggtggcgcgg gccgcggagg gacttttgcg cccgcgccct 149820
```

-continued gctggagccc gacgacgacg cccccccgct ggtgctgcgc ggcgacgacg acggcccggg 149880
ggccctgccg ccggcgccgc ccgggattcg ctgggcctcg gccacgggcc gcagcggcac 149940
cgtgctggcg gcggcggggg ccgtggaggt gctgggggcg gaggcgggct tggccacgcc 150000
cccgcgacgg gacgttgtgg actgggaagg cgcctgggac gaagacgacg gcggcgcgtt 150060
cgagggggac ggggtgctgt aacgggccgg gacggggcgg ggcgcttgtg aaacccgaag 150120
acgcaataaa cggcaacgac ctgattaagt tttgcagtag cgttgtttat tcgaggggcg 150180
ggagggggcg aggggcggga gggggcgagg ggcgggaggg ggcgaggggc gggagggggc 150240
gaggggcggg agggggcgag gggcgggagg gggcgagggg cgggaggggg cgaggggcgg 150300
gagggggcga ggggcggtgg tggtgcgcgg gcgcccccgg agggtttgga tctctgacct 150360
gagattggcg gcactgaggt agagatgccc gaaccccccc gagggagcgc gggacgcggc 150420
tggggagggc tggggctggg gagggctggg gctggggagg gctggggctg gggagggctg 150480
gggctgggga gggctggggc tggggagggc tggggctggg gagggctggg gctggggagg 150540
gctggggctg gggagggctg gggctgggga gggctggggc tggggagggc tggggctggg 150600
gagggctggg gctgtggtgt gtgacaggag cggcgtgttg cgctggggga cgtctggagg 150660 agcgggggt gcgcggtgac gtgtggatga ggaacaggag ttgttgcgcg gtgagttgtc 150720
gctgtgagtt gtgttgttgg gcaggtgtgt tggatgacgt gacgtgtgga tgaggaaccg 150780
gagtcgccgg tgcgccgtgc tgttggtgtt ctgttggtgt tgttacacct gtggcagccc 150840 gggcccccg cgcgcggggc ggcgcgcaaa aaaggcgggc ggcggtccgg gcggcgtgcg 150900
cgcgcgcggc gggcgtgggg ggcggggccg cgggagcggg ggaggagccc cacccacaga 150960
cggggaggag cgggggagga gcgggggagg agcgggggag gagccccacc cacagacggg 151020
gaggagcggg ggaggagcgg ccagacccca aaaacgggcc cccccgaaac acaccccccg 151080
ggggtcgcgc gcggcccttt aaagcgcggc ggcgggcagc ccgggccccc cgcgg 151135

<210> SEQ ID NO 2
<211> LENGTH: 1300
<212> TYPE: PRT
<213> ORGANISM: human herpesvirus 1 strain McKrae ICP4

<400> SEQUENCE: 2

Met Ala Ser Glu Asn Lys Gln Arg Pro Gly Ser Pro Gly Pro Thr Asp
1 5 10 15

Gly Pro Pro Pro Thr Pro Ser Pro Asp Arg Asp Glu Arg Gly Ala Leu
20 25 30

Gly Trp Gly Ala Glu Thr Glu Glu Gly Gly Asp Asp Pro Asp His Asp
35 40 45

Pro Asp His Pro His Asp Leu Asp Asp Ala Arg Arg Asp Gly Arg Ala
50 55 60

Pro Ala Ala Gly Thr Asp Ala Gly Glu Asp Ala Gly Asp Ala Val Ser
65 70 75 80

Pro Arg Gln Leu Ala Leu Leu Ala Ser Met Val Glu Glu Ala Val Arg
85 90 95

Thr Ile Pro Thr Pro Asp Pro Ala Ala Ser Pro Pro Arg Thr Pro Ala
100 105 110

Phe Arg Ala Asp Asp Asp Asp Gly Asp Glu Tyr Asp Asp Ala Ala Asp
115 120 125

Ala Ala Gly Asp Arg Ala Pro Ala Arg Gly Arg Ala Arg Glu Ala Pro
130 135 140

Leu Arg Gly Ala Tyr Pro Asp Pro Thr Asp Arg Leu Ser Pro Arg Pro
145 150 155 160

Pro Ala Gln Pro Pro Gln Arg Arg Arg His Gly Arg Arg Arg Pro Ser
165 170 175

Ala Ser Ser Thr Ser Ser Asp Ser Gly Ser Ser Ser Ser Ser Ser Ala
180 185 190

Ser Ser Ser Ser Ser Ser Ser Asp Glu Asp Glu Asp Asp Asp Gly Asn
195 200 205

Asp Ala Ala Asp His Ala Arg Glu Ala Arg Ala Val Gly Arg Gly Pro
210 215 220

Ser Ser Ala Ala Pro Glu Ala Pro Gly Arg Thr Pro Pro Pro Pro Gly
225 230 235 240

Pro Pro Pro Leu Ser Glu Ala Ala Pro Lys Pro Arg Ala Ala Ala Arg
245 250 255

Thr Pro Ala Ala Ser Ala Gly Arg Ile Glu Arg Arg Arg Ala Arg Ala
260 265 270

Ala Val Ala Gly Arg Asp Ala Thr Gly Arg Phe Thr Ala Gly Gln Pro
275 280 285

Arg Arg Val Glu Leu Asp Ala Asp Ala Ala Ser Gly Ala Phe Tyr Ala
290 295 300

Arg Tyr Arg Asp Gly Tyr Val Ser Gly Glu Pro Trp Pro Gly Ala Gly
305 310 315 320

Pro Pro Pro Pro Gly Arg Val Leu Tyr Gly Gly Leu Gly Asp Ser Arg
325 330 335

Pro Gly Leu Trp Gly Ala Pro Glu Ala Glu Glu Ala Arg Arg Arg Phe
340 345 350

Glu Ala Ser Gly Ala Pro Ala Ala Val Trp Ala Pro Glu Leu Gly Asp
355 360 365

Ala Ala Gln Gln Tyr Ala Leu Ile Thr Arg Leu Leu Tyr Thr Pro Asp
370 375 380

Ala Glu Ala Met Gly Trp Leu Gln Asn Pro Arg Val Val Pro Gly Asp
385 390 395 400

Val Ala Leu Asp Gln Ala Cys Phe Arg Ile Ser Gly Ala Ala Arg Asn
405 410 415

Ser Ser Ser Phe Ile Thr Gly Ser Val Ala Arg Ala Val Pro His Leu
420 425 430

Gly Tyr Ala Met Ala Ala Gly Arg Phe Gly Trp Gly Leu Ala His Ala
435 440 445

Ala Ala Ala Val Ala Met Ser Arg Arg Tyr Asp Arg Ala Gln Lys Gly
450 455 460

Phe Leu Leu Thr Ser Leu Arg Arg Ala Tyr Ala Pro Leu Leu Ala Arg
465 470 475 480

Glu Asn Ala Ala Leu Thr Gly Ala Ala Gly Ser Pro Gly Ala Gly Ala
485 490 495

Asp Asp Glu Gly Val Ala Ala Ala Val Val Ala Ala Ala Ala Ala Pro
500 505 510

Gly Glu Arg Ala Val Pro Ala Gly Tyr Gly Ala Ala Gly Ile Leu Ala
515 520 525

Ala Leu Gly Arg Leu Ser Ala Ala Pro Ala Ser Pro Ala Gly Gly Asp
530 535 540

Asp Pro Asp Ala Ala Arg His Ala Asp Ala Asp Asp Asp Ala Gly Arg
545 550 555 560

-continued

```
Arg Ala Gln Ala Gly Arg Val Ala Val Glu Cys Leu Ala Ala Cys Arg
                565                 570                 575

Gly Ile Leu Glu Ala Leu Ala Glu Gly Phe Asp Gly Asp Leu Ala Ala
            580                 585                 590

Val Pro Gly Leu Ala Gly Ala Arg Pro Ala Ser Pro Pro Arg Pro Glu
        595                 600                 605

Gly Pro Ala Gly Pro Ala Ser Pro Pro Pro Pro His Ala Asp Ala Pro
    610                 615                 620

Arg Leu Arg Ala Trp Leu Arg Glu Leu Arg Phe Val Arg Asp Ala Leu
625                 630                 635                 640

Val Leu Met Arg Leu Arg Gly Asp Leu Arg Val Ala Gly Gly Ser Glu
                645                 650                 655

Ala Ala Val Ala Ala Val Arg Ala Val Ser Leu Val Ala Gly Ala Leu
            660                 665                 670

Gly Pro Ala Leu Pro Arg Asp Pro Arg Leu Pro Ser Ser Ala Ala Ala
        675                 680                 685

Ala Ala Ala Asp Leu Leu Phe Glu Asn Gln Ser Leu Arg Pro Leu Leu
    690                 695                 700

Ala Ala Gly Pro Arg Arg Ser Ser Ser Ser Ser Gly Val Ala Ala Ala
705                 710                 715                 720

Ala Ser Ala Ala Pro Arg Glu Gly Arg Lys Arg Lys Ser Pro Gly Pro
                725                 730                 735

Ala Arg Pro Pro Gly Gly Gly Gly Pro Arg Pro Pro Lys Thr Lys Lys
            740                 745                 750

Ser Gly Ala Asp Ala Pro Gly Ser Asp Ala Arg Ala Pro Leu Pro Ala
        755                 760                 765

Pro Ala Pro Pro Ser Thr Pro Pro Gly Pro Glu Pro Ala Pro Ala Gln
    770                 775                 780

Pro Ala Ala Pro Arg Ala Ala Ala Ala Gln Ala Arg Pro Arg Pro Val
785                 790                 795                 800

Ala Leu Ser Arg Arg Pro Ala Glu Gly Pro Asp Pro Leu Gly Gly Trp
                805                 810                 815

Arg Arg Gln Pro Pro Gly Pro Ser His Thr Ala Ala Pro Ala Ala Ala
            820                 825                 830

Ala Leu Glu Ala Tyr Cys Ser Pro Arg Ala Val Ala Glu Leu Thr Asp
        835                 840                 845

His Pro Leu Phe Pro Val Pro Trp Arg Pro Ala Leu Met Phe Asp Pro
    850                 855                 860

Arg Ala Leu Ala Ser Ile Ala Ala Arg Cys Ala Gly Pro Ala Pro Ala
865                 870                 875                 880

Ala Gln Ala Ala Cys Gly Gly Gly Asp Asp Asp Glu Asn Pro His Pro
                885                 890                 895

His Gly Ala Ala Gly Gly Arg Leu Phe Gly Pro Leu Arg Ala Ser Gly
            900                 905                 910

Pro Leu Arg Arg Met Ala Ala Trp Met Arg Gln Ile Pro Asp Pro Glu
        915                 920                 925

Asp Val Arg Val Val Val Leu Tyr Ser Pro Leu Pro Gly Glu Asp Leu
    930                 935                 940

Ala Gly Gly Gly Ala Ser Gly Gly Pro Pro Glu Trp Ser Ala Glu Arg
945                 950                 955                 960

Gly Gly Leu Ser Cys Leu Leu Ala Ala Leu Ala Asn Arg Leu Cys Gly
                965                 970                 975

Pro Asp Thr Ala Ala Trp Ala Gly Asn Trp Thr Gly Ala Pro Asp Val
```

-continued

```
            980                 985                 990

Ser Ala Leu Gly Ala Gln Gly Val  Leu Leu Leu Ser Thr  Arg Asp Leu
        995                 1000                1005

Ala Phe  Ala Gly Ala Val Glu  Phe Leu Gly Leu Leu  Ala Ser Ala
    1010                 1015                 1020

Gly Asp  Arg Arg Leu Ile Val  Val Asn Thr Val Arg  Ala Cys Asp
    1025                 1030                 1035

Trp Pro  Ala Asp Gly Pro Ala  Val Ser Arg Gln His  Ala Tyr Leu
    1040                 1045                 1050

Ala Cys  Asp Leu Leu Pro Ala  Val Gln Cys Ala Val  Arg Trp Pro
    1055                 1060                 1065

Ala Ala  Arg Asp Leu Arg Arg  Thr Val Leu Ala Ser  Gly Arg Val
    1070                 1075                 1080

Phe Gly  Pro Gly Val Phe Ala  Arg Val Glu Ala Ala  His Ala Arg
    1085                 1090                 1095

Leu Tyr  Pro Asp Ala Pro Pro  Leu Arg Leu Cys Arg  Gly Gly Asn
    1100                 1105                 1110

Val Arg  Tyr Arg Val Arg Thr  Arg Phe Gly Pro Asp  Thr Pro Val
    1115                 1120                 1125

Pro Met  Ser Pro Arg Glu Tyr  Arg Arg Ala Val Leu  Pro Ala Leu
    1130                 1135                 1140

Asp Gly  Arg Ala Ala Ala Ser  Gly Thr Thr Asp Ala  Met Ala Pro
    1145                 1150                 1155

Gly Ala  Pro Asp Phe Cys Glu  Glu Glu Ala His Ser  His Arg Ala
    1160                 1165                 1170

Cys Ala  Arg Trp Gly Leu Gly  Ala Pro Leu Arg Pro  Val Tyr Val
    1175                 1180                 1185

Ala Leu  Gly Arg Glu Ala Val  Arg Ala Gly Pro Ala  Arg Trp Arg
    1190                 1195                 1200

Gly Pro  Arg Arg Asp Phe Cys  Ala Arg Ala Leu Leu  Glu Pro Asp
    1205                 1210                 1215

Asp Asp  Ala Pro Pro Leu Val  Leu Arg Gly Asp Asp  Asp Gly Pro
    1220                 1225                 1230

Gly Ala  Leu Pro Pro Ala Pro  Pro Gly Ile Arg Trp  Ala Ser Ala
    1235                 1240                 1245

Thr Gly  Arg Ser Gly Thr Val  Leu Ala Ala Ala Gly  Ala Val Glu
    1250                 1255                 1260

Val Leu  Gly Ala Glu Ala Gly  Leu Ala Thr Pro Pro  Arg Arg Asp
    1265                 1270                 1275

Val Val  Asp Trp Glu Gly Ala  Trp Asp Glu Asp Asp  Gly Gly Ala
    1280                 1285                 1290

Phe Glu  Gly Asp Gly Val Leu
    1295                 1300


<210> SEQ ID NO 3
<211> LENGTH: 420
<212> TYPE: PRT
<213> ORGANISM: human herpesvirus 1 strain McKrae ICP22

<400> SEQUENCE: 3

Met Ala Asp Ile Ser Pro Gly Ala Phe Ala Pro Cys Val Lys Ala Arg
1               5                   10                  15

Arg Pro Ala Leu Arg Ser Pro Pro Leu Gly Thr Arg Lys Arg Lys Arg
            20                  25                  30
```

```
Pro Ala Arg Pro Leu Ser Ser Glu Ser Glu Val Glu Thr Asp Thr Ala
        35                  40                  45

Leu Glu Ser Glu Val Glu Ser Glu Thr Ala Ser Asp Ser Thr Glu Ser
    50                  55                  60

Gly Asp Gln Glu Glu Ala Pro Arg Ile Gly Gly Arg Arg Ala Pro Arg
65                  70                  75                  80

Arg Leu Gly Gly Arg Phe Phe Leu Asp Met Ser Ala Glu Ser Thr Thr
                85                  90                  95

Gly Thr Glu Thr Asp Thr Ala Val Ser Asp Asp Pro Asp Asp Thr Ser
            100                 105                 110

Asp Trp Ser Tyr Asp Asp Ile Pro Pro Arg Pro Lys Arg Ala Arg Val
        115                 120                 125

Asn Leu Arg Leu Thr Ser Ser Pro Asp Arg Arg Asp Gly Val Ile Phe
    130                 135                 140

Pro Lys Met Gly Arg Val Arg Ser Thr Arg Glu Thr Gln Pro Arg Ala
145                 150                 155                 160

Pro Thr Pro Ser Ala Pro Ser Pro Asn Ala Met Leu Arg Arg Ser Val
                165                 170                 175

Arg Gln Ala Gln Arg Arg Ser Ser Ala Arg Trp Thr Pro Asp Leu Gly
            180                 185                 190

Tyr Met Arg Gln Cys Ile Asn Gln Leu Phe Arg Val Leu Arg Val Ala
        195                 200                 205

Arg Asp Pro His Gly Ser Ala Asn Arg Leu Arg His Leu Ile Arg Asp
    210                 215                 220

Cys Tyr Leu Met Gly Tyr Cys Arg Ala Arg Leu Ala Pro Arg Thr Trp
225                 230                 235                 240

Cys Arg Leu Leu Gln Val Ser Gly Gly Thr Trp Gly Met His Leu Arg
                245                 250                 255

Asn Thr Ile Arg Glu Val Glu Ala Arg Phe Asp Ala Thr Ala Glu Pro
            260                 265                 270

Val Cys Lys Leu Pro Cys Leu Glu Ala Arg Arg Tyr Gly Pro Glu Cys
        275                 280                 285

Asp Leu Ser Asn Leu Glu Ile His Leu Ser Ala Thr Ser Asp Asp Glu
    290                 295                 300

Ile Ser Asp Ala Thr Asp Leu Glu Ala Ala Gly Ser Asp His Thr Leu
305                 310                 315                 320

Ala Ser Gln Ser Asp Thr Glu Asp Ala Pro Ser Pro Val Thr Leu Glu
                325                 330                 335

Thr Pro Glu Pro Arg Gly Ser Leu Ala Val Arg Leu Glu Asp Glu Phe
            340                 345                 350

Gly Glu Phe Asp Trp Thr Pro Gln Glu Gly Ser Gln Pro Trp Leu Ser
        355                 360                 365

Ala Val Val Ala Asp Thr Ser Ser Val Glu Arg Pro Gly Pro Ser Asp
    370                 375                 380

Ser Gly Ala Gly Arg Ala Ala Glu Asp Arg Lys Cys Leu Asp Gly Cys
385                 390                 395                 400

Arg Lys Met Arg Phe Ser Thr Ala Cys Pro Tyr Pro Cys Ser Asp Thr
                405                 410                 415

Phe Leu Arg Pro
            420
```

<210> SEQ ID NO 4
<211> LENGTH: 88
<212> TYPE: PRT

<213> ORGANISM: human herpesvirus 1 strain McKrae ICP47

<400> SEQUENCE: 4

Met Ser Trp Ala Leu Glu Met Ala Asp Thr Phe Leu Asp Asn Met Arg
1 5 10 15

Val Gly Pro Arg Thr Tyr Ala Asp Val Arg Asp Glu Ile Asn Lys Arg
20 25 30

Gly Arg Glu Asp Arg Glu Ala Ala Arg Thr Ala Val His Asp Pro Glu
35 40 45

Arg Pro Leu Leu Arg Ser Pro Gly Leu Leu Pro Lys Ile Ala Pro Asn
50 55 60

Ala Ser Leu Gly Val Ala His Arg Arg Thr Gly Gly Thr Val Thr Asp
65 70 75 80

Ser Pro Arg Asn Pro Val Thr Arg
85

<210> SEQ ID NO 5
<211> LENGTH: 4020
<212> TYPE: DNA
<213> ORGANISM: human herpesvirus 1 strain McKrae ICP4

<400> SEQUENCE: 5
tttattgcgt cttcgggttt cacaagcgcc ccgccccgtc ccggcccgtt acagcacccc 60
gtccccctcg aacgcgccgc cgtcgtcttc gtcccaggcg ccttcccagt ccacaacgtc 120
ccgtcgcggg ggcgtggcca agcccgcctc cgcccccagc acctccacgg cccccgccgc 180
cgccagcacg gtgccgctgc ggcccgtggc cgaggcccag cgaatcccgg gcggcgccgg 240
cggcagggcc cccgggccgt cgtcgtcgcc gcgcagcacc agcggggggg cgtcgtcgtc 300
gggctccagc agggcgcggg cgcaaaagtc cctccgcggc ccgcgccacc gggccgggcc 360
ggcgcgcacc gcctcgcgcc ccagcgccac gtacacgggc cgcagcggcg cgcccaggcc 420
ccagcgcgcg caggcgcggt gcgagtgggc ctcctcctcg cagaagtccg gcgcgccggg 480
cgccatggcg tcggtggtcc ccgaggccgc cgcccggccg tccagcgccg gcagcacggc 540
ccggcggtac tcgcgcgggg acatgggcac cggcgtgtcc gggccgaagc gcgtgcgcac 600
gcggtagcgc acgttgccgc cgcggcacag gcgcagcggc ggcgcgtcgg ggtacaggcg 660
cgcgtgcgcg gcctccacgc gcgcgaagac ccccgggccg aacacgcggc ccgaggccag 720
caccgtgcgg cgcaggtcgc gcgccgccgg ccagcgcacg gcgcactgca cggcgggcag 780
caggtcgcac gccaggtagg cgtgctgccg cgacaccgcg ggcccgtcgg cgggccagtc 840
gcaggcgcgc acggtgttga ccacgatgag ccgccggtcg ccggcgctgg cgagcagccc 900
cagaaactcc acggccccgg cgaaggccag gtcccgcgtg gacagcagca gcacgccctg 960
cgcgcccagc gccgacacgt cgggggcgcc ggtccagttg cccgcccagg cggccgtgtc 1020
cggcccgcac agccggttgg ccagggccgc cagcaggcag gacagcccgc cgcgctcggc 1080
ggaccactcc ggcggccccc ccgaggcccc gccgccggcc aggtcctcgc ccggcagcgg 1140
cgagtacagc accaccacgc gcacgtcctc ggggtcgggg atctggcgca tccaggccgc 1200
catgcggcgc agcgggcccg aggcgcgcag ggggccaaag aggcggcccc cggcggcccc 1260
gtgggggtgg gggttctcgt cgtcgtcgcc gccgccgcac gcggcctggg cggcgggggc 1320
gggcccggcg caccgcgcgg cgatcgaggc cagggcccgc gggtcaaaca tgagggccgg 1380
tcgccagggg acggggaaca gcgggtggtc cgtgagctcg gccacggcgc gcggggagca 1440
gtaggcctcc agggcggcgg ccgcgggcgc cgccgtgtgg ctgggccccg ggggctgccg 1500

-continued

```
ccgccagccg cccagggggt cggggccctc ggcgggccgg cgcgacagcg ccacggggcg   1560
cgggcgggcc tgcgccgcgg cggcccgggg cgccgcgggc tgggcggggg cgggctcggg   1620
ccccgggggc gtggaggggg gcgcgggcgc ggggaggggg gcgcgggcgt ccgagccggg   1680
ggcgtccgcg ccgctcttct tcgtcttcgg gggtcgcggg ccgccgcctc cgggcggccg   1740
ggccgggccg ggactcttgc gcttgcgccc ctcccgcggc gcggcggagg cggcggccgc   1800
gacccccgaa gacgaagaag agcggcgcgg acccgccgcc agcagggggc gcaggctctg   1860
gttctcaaac agcaggtccg cggcggcggc ggccgcggag ctcggcaggc gcgggtcccg   1920
cggcagcgcg ggacccaggg ccccggcgac caggctcacg gcgcgcacgg cggccacggc   1980
ggcctcgctg ccgccggcca cgcgcaggtc cccgcgcagg cgcatgagca ccagcgcgtc   2040
gcgcacgaac cgcagctcgc gcagccacgc gcgcaggcgg ggcgcgtcgg cgtgcggcgg   2100
cggcggggaa gcggggcccg cgggtccctc cggccgcggg gggctggcgg gccgggcccc   2160
ggccagcccc gggacggccg ccaggtcgcc gtcgaagccc tcggccagcg cctccaggat   2220
cccgcggcag gcggccaggc actccacggc cacgcggccg gcctgggcgc ggcgcccggc   2280
gtcgtcgtcg gcgtcggcgt ggcgggcggc gtcggggtcg tcgccccccg cgggggaggc   2340
gggcgcggcg gacagccgcc ccagggcggc gaggatcccc gcggcgccgt acccggcggg   2400
caccgcgcgc tcgcccggtg cggcggcggc ggcgacgacg gcggcggcga ccccctcgtc   2460
atctgcgccg gcgccggggc tccccgcggc ccccgtcagc gccgcgttct cgcgcgccaa   2520
caggggcgcg taggcgcggc gcaggctggt cagcaggaag cccttctgcg cgcggtcgta   2580
tcggcggctc atggccacgg cggccgccgc gtgcgccagg ccccagccga agcggccggc   2640
cgccatggcg tagcccaggt ggggcacggc ccgcgccacg ctgccggtga tgaaggagct   2700
gctgttgcgc gcggcgcccg agatccggaa gcaggcctgg tccagcgcca cgtccccggg   2760
gaccacgcgc gggttctgga gccaccccat ggcctccgcg tccggggtgt acagcagccg   2820
cgtgatcagg gcgtactgct gcgcggcgtc gcccagctcg ggcgcccaca cggccgccgg   2880
ggcgcccgag gcctcgaacc ggcgtcgcgc ctcctccgcc tcgggcgccc cccagaggcc   2940
cgggcggctg tcgcccaggc cgccgtacag cacccgcccc gggggcgggg gcccggcgcc   3000
gggccacggc tccccgctga cgtacccgtc gcgatagcgc gcgtagaagg cgccggaggc   3060
cgcgtcggcg tccagctcga cccgccgggg ctgcccggcc gtgaagcggc ccgtggcgtc   3120
gcggccggcc accgccgcgc gggcccggcg gcgctcgatg cggcccgcgg aggccgcggg   3180
ggtcctcgcc gccgcccggg gcttgggcgc ggcctcggag agggggggtg gcccgggcgg   3240
gggcggcgtc cgcccggggg cttccggcgc cgcgctcgac ggaccccgcc cgacggcccg   3300
cgcctcgcgt gcgtggtcgg ccgcgtcgtt gccgtcgtcg tcctcgtcct cgtcggacga   3360
cgaggacgaa gaggatgcgg acgacgagga cgaggacccg gagtccgacg aggtcgatga   3420
cgccgatggc cgccgccggc cgtgacgacg tctctgcggc ggctgggccg gcgggcgcgg   3480
cgacaggcgg tccgtggggt ccggatacgc gccgcgtagc ggggcctccc gtgcgcggcc   3540
ccgggccggg gcccggtcgc cggcggcgtc ggctgcgtcg tcgtactcgt ccccgtcatc   3600
gtcgtcggct cgaaaggcgg gggtccgggg cggcgaggcc gcggggtcgg gcgtcgggat   3660
cgtccggacg gcctcctcta ccatggaggc cagcagggcc agctgtcgcg gcgagacggc   3720
gtccccggcg tcctcgccgg cgtcggtgcc cgccgcgggg gccctcccgt cccgccgggc   3780
gtcgtcgagg tcgtgggggt ggtcggggtc gtggtcgggg tcgtccccgc cctcctccgt   3840
```

```
ctccgcgccc cacccgaggg ccccccgctc gtcgcggtct gggctcgggg tgggcggcgg   3900

cccgtcggtg gggcccgggg agccggggcg ctgcttgttc tccgacgcca tcgccgatgc   3960

ggggcgatcc tccggggata cgactgcgac ggcggacgta gcacggtagg tcacctacgg   4020


<210> SEQ ID NO 6
<211> LENGTH: 1320
<212> TYPE: DNA
<213> ORGANISM: human herpesvirus 1 strain McKrae ICP22

<400> SEQUENCE: 6

ggtcctccgg gacgttttct ggatggccga catttcccca ggcgcttttg tgccttgtgt     60

aaaagcgcgg cgtcccgctc tccgatcccc gcccctgggc acgcgcaagc gcaagcgccc    120

tgcccgcccc ctctcatcgg agtctgaggt cgaatccgag acagccttgg agtctgaggt    180

cgaatccgag acagcatcgg attcgaccga gtctggggac caggaggaag ccccccgcat    240

cggtggccgt agggcccccc ggaggcttgg ggggcggttt tttctggaca tgtcggcgga    300

atccaccacg gggacggaaa cggatgcgtc ggtgtcggac gaccccgacg acacgtccga    360

ctggtcttgt gacgacattc cccacgacc caagcgggcc cgggtaaacc tgcggctcac    420

tagctctccc gatcggcggg atggggttat ttttcctaag atggggcggg tccggtctac    480

ccgggaaacg cagccccggg cccccacccc gtcggcccca agcccaaatg caatgctccg    540

gcgctcggtg cgccaggccc agaggcggag cagcgcacga tggacccccg acctgggcta    600

catgcgccag tgtatcaatc agctgtttcg ggtcctgcgg gtcgcccggg acccccacgg    660

cagtgccaac cgcctgcgcc acctgatacg cgactgttac ctgatgggat actgccgagc    720

ccgtctggcc ccgcgcacgt ggtgccgctt gctgcaggtg tccggcggaa cctggggcat    780

gcacctgcgc aacaccatac gggaggtgga ggctcgattc gacgccaccg cagaacccgt    840

gtgcaagctt ccttgtttgg aggccagacg gtacggcccg gagtgtgatc ttagtaatct    900

cgagattcat ctcagcgcga caagcgatga tgaaatctcc gatgccaccg atctggaggc    960

cgccggttcg gaccacacgc tcgcgtccca gtccgacacg gaggatgccc cctcccccgt   1020

tacgctggaa accccagaac cccgcgggtc cctcgctgtg cgtctggagg atgagtttgg   1080

ggagtttgac tggacccccc aggagggctc ccagccctgg ctgtctgcgg tcgtggccga   1140

taccagctcc gtggaacgcc cgggcccatc cgattctggg gcgggtcgcg cagcagaaga   1200

ccgcaagtgt ctggacggct gccggaaaat gcgcttctcc accgcctgcc cctatccgtg   1260

cagcgacacg tttctccggc cgtgagtccg gtcgccccga ccccttgta tgtccccaaa    1320


<210> SEQ ID NO 7
<211> LENGTH: 360
<212> TYPE: DNA
<213> ORGANISM: human herpesvirus 1 strain McKrae ICP47

<400> SEQUENCE: 7

tccgcccaga gactcgggtg atggtcgtac ccgggactca acgggttacc ggattacggg     60

gactgtcggt cacggtcccg ccggttcttc gatgtgccac acccaaggat gcgttggggg    120

cgatttcggg cagcagcccg ggagagcgca gcaggggacg ctccgggtcg tgcacggcgg    180

ttctggccgc ctcccggtcc tcacgccccc ttttattgat ctcatcgcgt acgtcggcgt    240

acgtcctggg cccaacccgc atgttgtcca ggaaggtgtc cgccatttcc agggcccacg    300

acatgctttt ccccccgacg agcaggaagc ggtccacgca acggtcgccg ccggtcgcct    360
```

-continued

<210> SEQ ID NO 8
<211> LENGTH: 523
<212> TYPE: DNA
<213> ORGANISM: Human cytomegalovirus

<400> SEQUENCE: 8
gaagatcttt ggttatatag cataaatcaa tattggctat tggccattgc atacgttgta 60
tccatatcat aatatgtaca tttatattgg ctcatgtcca acattaccgc catgttgaca 120
ttgattattg actagttatt aatagtaatc aattacgggg tcattagttc atagcccata 180
tatggagttc cgcgttacat aacttacggt aaatggcccg cctggctgac cgcccaacga 240
cccccgccca ttgacgtcaa taatgacgta tgttcccata gtaacgccaa tagggacttt 300
ccattgacgt caatgggtgg agtatttacg gtaaactgcc cacttggcag tacatcaagt 360
gtatcatatg ccaagtacgc cccctattga cgtcaatgac ggtaaatggc ccgcctggca 420
ttatgcccag tacatgacct tatgggactt tcctacttgg cagtacatct acgtattagt 480
catcgctatt accatggtga tgcggttttg gcagtacatc aat 523

<210> SEQ ID NO 9
<211> LENGTH: 1199
<212> TYPE: DNA
<213> ORGANISM: Homo sapiens

<400> SEQUENCE: 9
aatgggtttg ggtgtgtgta aatgagtgtg accggaagcg agtgtgagct tgatctaggc 60
agggaccaca cagcactgtc acacctgcct gctctttagt agaggactga agtgcggggg 120
tgggggtacg gggccggaat agaatgtctc tgggacatct tggcaaacag cagccggaag 180
caaaggggca gctgtgcaaa cggctcaggc aggtgatgga tggcagggta ggaaggggga 240
ggtccagagg tctggatgga ggcttccgca tctgtacctt gcaactcacc cctcaggccc 300
agcaggtcat cggccccctc ctcacacatg taatgacgta gaagagtacc ccgggacagt 360
ccggggagat ggagattcgg aaagtatcca tggagctctt acagaatccc ctgtgcggac 420
caggaaactc ttgtagatcc ctgcctatct gaggcccagg cgctgggctg tttctcacaa 480
tattccttca agatgagatt gtggtcccca tttcaaagat gagtacactg agcctctgtg 540
aagttacttg cccatgatca cacaaccagg aattgggcca actgtaattg aactcctgtc 600
taacaaagtt cttgctccca gctccgtctc ttgtttccca cgagccctgg ccctctgtgg 660
gtaataccag ctactggagt cagatttctt gggcccagaa cccaccctta ggggcattaa 720
cctttaaaat ctcacttggg caggggtctg ggatcagagt tggaagagtc cctacaatcc 780
tggacccttt ccgccaaatc gtgaaaccag gggtggagtg gggcgagggt tcaaaaccag 840
gccggactga gaggtgaaat tcaccatgac gtcaaactgc cctcaaattc ccgctcactt 900
taagggcgtt acttgttggt gcccccacca tcccccacca tttccatcaa tgacctcaat 960
gcaaatacaa gtgggacggt cctgctgacg cctccaggtt ctggaagcat gagggtgacg 1020
cacccagggg caaaggaccc ctccgcccat tggttgctgt gcactggcgg aactttcccg 1080
acccacagcg gcgggaataa gagcagtcgc tggcgctggg aggcatcaga gacactgccc 1140
agcccaagtg tcgccgccgc ttccacaggg ctctggctgg acgccgccgc cgccgctgc 1199

<210> SEQ ID NO 10
<211> LENGTH: 225
<212> TYPE: DNA
<213> ORGANISM: Artificial Sequence
<220> FEATURE:

<223> OTHER INFORMATION: bovine growth hormone polyadenylation signal

<400> SEQUENCE: 10

```
ggatcccgac tgtgccttct agttgccagc catctgttgt ttgcccctcc cccgtgcctt     60

ccttgaccct ggaaggtgcc actcccactg tcctttccta ataaaatgag gaaattgcat    120

cgcattgtct gagtaggtgt cattctattc tggggggtgg ggtggggcag gacagcaagg    180

gggaggattg ggaagacaat agcaggcatg ctggggaaga tcttc                    225
```

<210> SEQ ID NO 11
<211> LENGTH: 7
<212> TYPE: PRT
<213> ORGANISM: human herpesvirus 1 strain McKrae

<400> SEQUENCE: 11

```
Ser Thr Pro Ser Thr Thr Thr
1               5
```

<210> SEQ ID NO 12
<211> LENGTH: 16
<212> TYPE: DNA
<213> ORGANISM: human herpesvirus 1 strain McKrae

<400> SEQUENCE: 12

```
gcacccccac tcccac                                                     16
```

<210> SEQ ID NO 13
<211> LENGTH: 16
<212> TYPE: DNA
<213> ORGANISM: human herpesvirus 1 strain McKrae

<400> SEQUENCE: 13

```
ccccagccct ccccag                                                     16
```

<210> SEQ ID NO 14
<211> LENGTH: 17
<212> TYPE: DNA
<213> ORGANISM: human herpesvirus 1 strain McKrae

<400> SEQUENCE: 14

```
cccctcgccc cctcccg                                                    17
```

<210> SEQ ID NO 15
<211> LENGTH: 14
<212> TYPE: PRT
<213> ORGANISM: human herpesvirus 1 strain KOS

<400> SEQUENCE: 15

```
Ala Ala Ser Ala Pro Asp Ala Ala Asp Ala Leu Ala Ala Ala
1               5                   10
```

<210> SEQ ID NO 16
<211> LENGTH: 13
<212> TYPE: PRT
<213> ORGANISM: human herpesvirus 1 strain McKrae

<400> SEQUENCE: 16

```
Gly Pro Arg Arg Ser Ser Ser Ser Ser Gly Val Ala Ala
1               5                   10
```

<210> SEQ ID NO 17

<400> SEQUENCE: 17

-continued

```
000


<210> SEQ ID NO 18

<400> SEQUENCE: 18

000


<210> SEQ ID NO 19
<211> LENGTH: 9
<212> TYPE: PRT
<213> ORGANISM: human herpesvirus 1

<400> SEQUENCE: 19

Thr Ala Ala Thr Gly Ala Arg Ala Thr
1               5
```